US012643944B2

(12) United States Patent
Lee et al.

(10) Patent No.: US 12,643,944 B2
(45) Date of Patent: Jun. 2, 2026

---

(54) ANTIBODY-PAYLOAD CONJUGATES WITH ENHANCED DELIVERY DOMAIN AND USES THEREOF

(71) Applicant: IPROGEN BIOTECH INC., Burnaby (CA)

(72) Inventors: Keun Ho Lee, Coquitlam (CA); Leo Yen-Cheng Lin, Surrey (CA); Ranjani Vaidyanathan, Vancouver (CA); Paula Lario, Vancouver (CA)

(73) Assignee: IPROGEN BIOTECH INC., Burnaby (CA)

( * ) Notice: Subject to any disclaimer, the term of this patent is extended or adjusted under 35 U.S.C. 154(b) by 1060 days.

(21) Appl. No.: 17/775,574

(22) PCT Filed: Nov. 12, 2019

(86) PCT No.: PCT/CA2019/051612
§ 371 (c)(1),
(2) Date: May 9, 2022

(87) PCT Pub. No.: WO2021/092672
PCT Pub. Date: May 20, 2021

(65) Prior Publication Data
US 2023/0227547 A1     Jul. 20, 2023

(51) Int. Cl.
C07K 16/28        (2006.01)
A61K 47/64        (2017.01)
A61K 47/68        (2017.01)
A61P 37/02        (2006.01)

(52) U.S. Cl.
CPC ............. *C07K 16/28* (2013.01); *A61K 47/64* (2017.08); *A61K 47/68* (2017.08); *A61P 37/02* (2018.01); *C07K 2317/64* (2013.01)

(58) Field of Classification Search
None
See application file for complete search history.

(56) References Cited

U.S. PATENT DOCUMENTS

| | | | |
|---|---|---|---|
| 4,946,778 | A | 8/1990 | Ladner et al. |
| 7,238,489 | B2 | 7/2007 | Schneewind et al. |
| 8,410,250 | B2 | 4/2013 | Ashkenazi et al. |
| 9,809,645 | B2 | 11/2017 | Ohsawa et al. |
| 2003/0143234 | A1 | 7/2003 | Shi et al. |
| 2019/0248902 | A1 | 8/2019 | Nioi et al. |
| 2019/0248917 | A1 | 8/2019 | Chang et al. |

FOREIGN PATENT DOCUMENTS

| | | |
|---|---|---|
| AU | 2013231851 A1 | 9/2013 |
| CA | 2695385 A1 | 2/2009 |
| WO | 2009/018500 A1 | 2/2009 |
| WO | 2010129033 A2 | 11/2010 |
| WO | 2013/081463 A2 | 6/2013 |

| | | |
|---|---|---|
| WO | 2013/095091 A2 | 6/2013 |
| WO | 2013/134880 A1 | 9/2013 |
| WO | 2015/037992 A1 | 3/2015 |
| WO | 2017/189432 A1 | 11/2017 |
| WO | 2018/136626 A1 | 7/2018 |
| WO | 2018/169953 A1 | 9/2018 |
| WO | 2018/213335 A1 | 11/2018 |
| WO | 2018/218004 A1 | 11/2018 |

OTHER PUBLICATIONS

Agerberth et al. "The human antimicrobial and chemotactic peptides LL-37 and a-defensins are expressed by specific lymphocyte and monocyte populations." Blood. 96(9):3086-3093 (Nov. 1, 2000).
Armstrong et al. "EpCAM: A New Therapeutic Target for an Old Cancer Antigen." Cancer Biol. Ther. 2(4):320-325 (Jul./Aug. 2003).
Austin et al. "Endocytosis and Sorting of ErbB2 and the Site of Action of Cancer Therapeutics Trastuzumab and Geldanamycin." Mol. Biol. Cell. 15:5268-5282 (Dec. 2004).
Banerjee et al. "Anti-NaPi2b antibody-drug conjugate lifastuzumab vedotin (DNIB0600A) compared with pegylated liposomal doxorubicin in patients with platinum-resistant ovarian cancer in a randomized, open-label, phase II study." Ann. Oncol., 29:917-923 (2018).
Battaglin et al. "Anti-EGFR monoclonal antibody panitumumab for the treatment of patients with metastatic colorectal cancer: an overview of current practice and future perspectives." Expert Opin. Biol. Ther. 17:1297 (2017).
Beerli et al. "Sortase Enzyme-Mediated Generation of Site-Specifically Conjugated Antibody Drug Conjugates with High In Vitro and In Vivo Potency." 2015, Plos One 10(7):e0131177.
Boeggeman et al. "Site specific conjugation of fluoroprobes to the remodeled Fc Nglycans of monoclonal antibodies using mutant glycosyltransferases: Application for cell surface antigen detection." 2009 Bioconjugate Chem., 20, 1228.
Boku N. "HER2-positive gastric cancer." (2014), Gastric Cancer, 17,1.
Bonucci et al. "A Spectroscopic Study of the Aggregation State of the Human Antimicrobial Peptide LL-37 in Bacterial versus Host Cell Model Membranes." (2015) Biochemistry, 54, 6760.
Bowdish et al. "A Re-evaluation of the Role of Host Defence Peptides in Mammalian Immunity." (2005), Curr. Protein Pept. Sci., 6, 35.
Buza et al. "HER2/neu in Endometrial Cancer: A Promising Therapeutic Target With Diagnostic Challenges." (2014), Arch. Pathol. Lab. Med., 138, 343.

(Continued)

*Primary Examiner* — Ruixiang Li
(74) *Attorney, Agent, or Firm* — Haynes and Boone, LLP

(57)        ABSTRACT

The present invention provides a covalent conjugate. The conjugate includes an antibody or antibody derivative, at least two LL37-derived polypeptides, and a payload. The antibody or antibody derivative targets a cell that has phosphatidylserine in its outer leaflet. The payload includes: a small molecule cytotoxic drug of less than 3 kDa, or a plurality thereof; or a peptide or protein of less than 100 kDa. Uses and methods of using these covalent conjugates are also provided, related to enhancing delivery of the antibody/derivative or the payload, e.g. to enhance therapeutic or diagnostic effectiveness.

13 Claims, 47 Drawing Sheets

Specification includes a Sequence Listing.

(56) References Cited

OTHER PUBLICATIONS

Carden et al. "From Darkness to Light With Biomarkers in Early Clinical Trials of Cancer Drugs." (2009), Clin. Pharmacol. Ther., 85, 131.

Carvajal-Vallejos et al. "Unprecedented Rates and Efficiencies Revealed for New Natural Split Inteins from Metagenomic Sources." 2012, J. Biol. Chem. 287: 28686.

Chan and Stanners. "Recent advances in the tumour biology of the GPI-anchored carcinoembryonic antigen family members CEACAM5 and CEACAM6." 2007, Curr. Oncol., 14, 70.

Chen et al. "Fusion Protein Linkers: Property, Design and Functionality." Adv Drug Deliv Rev. 2013; 65(10):1357-1369.

Collin and Olsen, "EndoS, a novel secreted protein from *Streptococcus pyogenes* with endoglycosidase activity on human IgG." 2001, EMBO J., 20, 3046.

Davidson et al. "The Cationic Antimicrobial Peptide LL-37 Modulates Dendritic Cell Differentiation and Dendritic Cell-Induced T Cell Polarization." (2004), J. Immunol. 172, 1146.

De et al. "A Novel Therapeutic Strategy for Cancer Using Phosphatidylserine Targeting Stearylamine-Bearing Cationic Liposomes." 2018, Mol. Ther. Nucleic Acids., 10, 9.

Delves and Roitt, 2011, Roitt's Essential Immunology. Chichester, West Sussex: Wiley-Blackwell at 114.

Deyev and Lebedenko. "Multivalency: the hallmark of antibodies used for optimization of tumor targeting by design." (2008, BioEssays 30:904-918).

Doronina et al. "Development of potent monoclonal antibody auristatin conjugates for cancer therapy." (2003) Nat. Biotechnol., 21, 778.

Dorr et al. "Reprogramming the specificity of sortase enzymes." 2014, Proc Natl Acad Sci U S A 111: 13343-13348.

Dorschner et al. "Cutaneous Injury Induces the Release of Cathelicidin Anti-Microbial Peptides Active Against Group A Streptococcus." (2001) J. Invest. Dermatol. 117, 91.

Duplantier and van Hoek. "The human cathelicidin antimicrobial peptide LL-37 as a potential treatment for polymicrobial infected wounds." (2013), Frontiers in Immunology, 4, article 143.

Durr et al. "LL-37, the only human member of the cathelicidin family of antimicrobial peptides." (2006), Biochim. Biophys. Acta, 1758, 1408.

Eyvazi et al. "Antibody Based EpCAM Targeted Therapy of Cancer, Review and Update." 2018, Curr. Cancer Drug Targets 18, 857.

Fierer et al. "SpyLigase peptide-peptide ligation polymerizes affibodies to enhance magnetic cancer cell capture." 2014, Proc. Natl. Acad. Sci. U.S.A. 111: E1176.

Frohm et al. "The Expression of the Gene Coding for the Antibacterial Peptide LL-37 Is Induced in Human Keratinocytes during Inflammatory Disorders." (1997), J. Biol. Chem. 272, 15258.

Gust et al. "Fibroblast Growth Factor Receptor 3 is a Rational Therapeutic Target in Bladder Cancer." 2013, Mol. Cancer Ther. 12, 1245.

Harper et al. "Selecting an Optimal Antibody for Antibody-Drug Conjugate Therapy: Internalization and Intracellular Localization." (2013) Methods Mol. Biol., 1045, 41.

Hase et al. "Expression of LL-37 by Human Gastric Epithelial Cells as a Potential Host Defense Mechanism Against Helicobacter pylori." (2003), Gastroenterology, 125, 1613.

Johansson et al. "Conformation-dependent Antibacterial Activity of the Naturally Occurring Human Peptide LL-37." (1998) J. Biol. Chem., 273, 3718.

Jones et al. "Replacing the complementarity determining regions in a human antibody with those from a mouse." Nature 1986; 321:522-525.

Kaufmann et al. "Analysis of Her2/neu membrane protein clusters in different types of breast cancer cells using localization microscopy." (2011), J. Microsc., 242, 46.

Kim and Kim. "Diallyl Disulfide Prevents Cyclophosphamide-Induced Hemorrhagic Cystitis in Rats through the Inhibition of Oxidative Damage, MAPKs, and NF-κB Pathways." 2015, Biomol Ther (Seoul) 23: 493-509.

Kohler & Milstein. "Continuous cultures of fused cells secreting antibody of predefined specificity." Nature 256:495-497 (1975).

Kozbor et al. "The production of monoclonal antibodies from human lymphocytes." Immunology Today 4:72 (1983).

Kuroda, K. et al., "The human cathelicidin antimicrobial peptide LL-37 and MillliCS are 1-47 potential anticancer drugs". Frontiers in Oncology, Jun. 30, 2015 (Jun. 30, 2015), vol. 5(Article potential anticancer drugs. Frontiers in Oncology, Jun. 30, 2015 (Jun. 30, 2015), vol. 5(Article 144), pp. 1-10, ISSN 2234943X.

Levan et al. "Immunohistochemical evaluation of epithelial ovarian carcinomas identifies three different expression patterns of the MX35 antigen, NaPi2b." 2017, BMC Cancer, 17, 303.

Lutje et al. "Characterization of Site-Specifically Conjugated Monomethyl Auristatin E- and Duocarmycin-Based Anti-PSMA Antibody—Drug Conjugates for Treatment of PSMA-Expressing Tumors." 2018, J. Nucl. Med. 59, 494.

Mao et al. "Sortase-Mediated Protein Ligation: A New Method for Protein Engineering." 2004, J. Am. Chem. Soc., 126: 2670.

Marks et al. "By-passing Immunization: Building High Affinity Human Antibodies by Chain Shuffling." Biotechnology, 10:779-783, (1992).

McCafferty et al. "Phage antibodies: filamentous phage displaying antibody variable domains.", Nature 348:552-554 (1990).

Mitri et al. "The HER2 Receptor in Breast Cancer: Pathophysiology, Clinical Use, and New Advances in Therapy." (2012), Chemother. Res. Pract., 2012, 743193.

Morrison and Oi. "Genetically Engineered Antibody Molecules." Adv. Immunol. 1988; 44:65-92.

Morrison et al. "Chimeric human antibody molecules: Mouse antigen-binding domains with human constant region domains." Proc. Natl. Acad. Sci. USA 1984; 81:6851-6855.

Padlan. "A Possible Procedure for Reducing the Immunogenicity of Antibody Variable Domains While Preserving Their Ligand-Binding Properties" Molec. Immun. 1991; 28:489-498.

Padlan. "Anatomy of the Antibody Molecule." Molec. Immun. 1994; 31(3):169-217.

Presta. "Antibody engineering." Curr. Op. Struct. Biol. 1992; 2:593-596.

Ramakrishnan and Qasba. "Structure-based Design of 1,4-Galactosyltransferase I (4Gal-T1) with Equally Efficient N-Acetylgalactosaminyltransferase Activity." 2002, J. Biol. Chem. 277, 20833.

Rashidian et al. "Enzymatic Labeling of Proteins: Techniques and Approaches." 2013, Bioconjug. Chem. 24: 1277.

Riechmann et al. "Reshaping human antibodies for therapy." Nature 1988; 332:323-327.

Rose et al. "Hydrophobicity of Amino Acid Residues in Globular Proteins." 1995, Science, 229:834-838.

Rossi et al. "Complex and defined biostructures with the dock-and-lock method." 2012, Trends Pharmacol. Sci. 33: 474.

Sancho-Vaello et al. "Structural remodeling and oligomerization of human cathelicidin on membranes suggest fibril-like structures as active species." (2017) Sci. Rep. 7, 15371.

Shah and Muir. "Inteins: nature's gift to protein chemists." 2014, Chem. Sci. 5: 446.

Shahmiri et al. "Membrane Core-Specific Antimicrobial Action of Cathelicidin LL-37 Peptide Switches Between Pore and Nanofibre Formation." (2016), Sci. rep. 6, article 38184.

Sharkey et al. "Selective and Concentrated Accretion of SN-38 with a CEACAM5-Targeting Antibody-Drug Conjugate (ADC), Labetuzumab Govitecan (IMMU-130)." 2018, Mol. Cancer Ther. 17, 196.

Stech and Kubich. "Cell-Free Synthesis Meets Antibody Production: A Review." 2015, Antibodies 4: 12-33.

Swee et al. "Sortase-mediated modification of αDEC205 affords optimization of antigen presentation and immunization against a set of viral epitopes." 2013, Proc. Natl. Acad. Sci. U.S.A. 110:1428-1433.

(56) References Cited

OTHER PUBLICATIONS

Tarcic and Tarden (2013), Vesicle Trafficking in Cancer (Springer publishing, ISBN 978-1-4614-6528-7), 361.

Teplinsky and Muggia. "Targeting HER2 in ovarian and uterine cancers: Challenges and future directions." (2014), Gynecol. Oncol., 135, 364.

Veggiani et al. "Superglue from Bacteria: Unbreakable Bridges for Protein Nanotechnology." 2014, Trends Biotechnol. 32: 506.

Venugopal et al. "Anti-EGFR anchored paclitaxel loaded PLGA nanoparticles for the treatment of triple negative breast cancer. In-vitro and in-vivo anticancer activities." 2018, PLoS One, 13, e0206109.

Verhoeyen et al. "Reshaping Human Antibodies: Grafting an Antilysozyme Activity." Science 1988; 239:1534-1536.

Vezina et al. "Antibody—Drug Conjugates as Cancer Therapeutics: Past, Present, and Future." (2017) J. Clin. Pharmacol., 57, S11.

Von Eyben et al. "PSMA diagnostics and treatments of prostate cancer become mature." 2018, Clin. Transl. Imaging 6, 145.

Woo et al. "Expression of Cathelicidin in Human Salivary Glands." (2003), Arch. Otolaryngol. Head Neck Surg. 129, 211.

Yao, X. et al., "A novel humanized anti-HER2 antibody conjugated with MIME exerts potent 36 anti-tumor activity". Breast Cancer Research and Treatment, Aug. 18, 2015 (Aug. 18, 2015), vol. 153(1), pp. 123-133, ISSN 01676806.

Young and Schultz. "Beyond the Canonical 20 Amino Acids: Expanding the Genetic Lexicon." 2010, J. Biol. Chem. 285: 11039-11044.

Yurkovetskiy et al. "A Polymer-Based Antibody—VincaDrugConjugate Platform: Characterization and Preclinical Efficacy." Cancer Res; 75(16), 2015).

Zakeri and Howarth. "Spontaneous Intermolecular Amide Bond Formation between Side Chains for Irreversible Peptide Targeting." 2010, J. Am. Chem. Soc. 132: 4526.

Zhang M, Qiu Z, Li Y, Yang Y, Zhang Q, Xiang Q, Su Z, Huang Y. "Construction and characterization of a recombinant human beta defensin 2 fusion protein targeting the epidermal growth factor receptor: in vitro study." Appl Microbiol Biotechnol. May 2013;97(9):3913-23. doi: 10.1007/s00253-012-4257-z. Epub Aug. 5, 2012. PMID: 22903275.

International Search Report and Written Opinion for PCT/CA2019/051612 dated Jul. 13, 2020, 9 pages.

Li, X., et al., Solution structures of human LL-37 fragments and NMR-based identification of a minimal membrane-targeting antimicrobial and anticancer region, Journal of the American Chemical Society, American Chemical Society, (May 3, 2006), vol. 128, No. 17, doi: 10.1021/JA0584875, ISSN 0002-7863, pp. 5776-5785.

Kuroda, Kengo, et al., The Human Cathelicidin Antimicrobial Peptide LL-37 and Mimics are Potential Anticancer Drugs, Frontiers in Oncology, (Jun. 30, 2015), vol. 5, doi: 10.3389/fonc.2015.00144, XP055822431, 10 pgs.

Tang, Xiao, et al., P2X7 Receptor Regulates Internalization of Antimicrobial Peptide LL-37 by Human Macrophages That Promotes Intracellular Pathogen Clearance, The Journal of Immunology, US, (Aug. 1, 2015), vol. 195, No. 3, doi:10.4049/jimmunol.1402845, ISSN 0022-1767, pp. 1191-1201, XP093059920.

Extended European Search Report for EP Application No. 19952147.7 dated Jul. 17, 2023, 9 pgs.

E

A

B

A

B

A

B

A

B

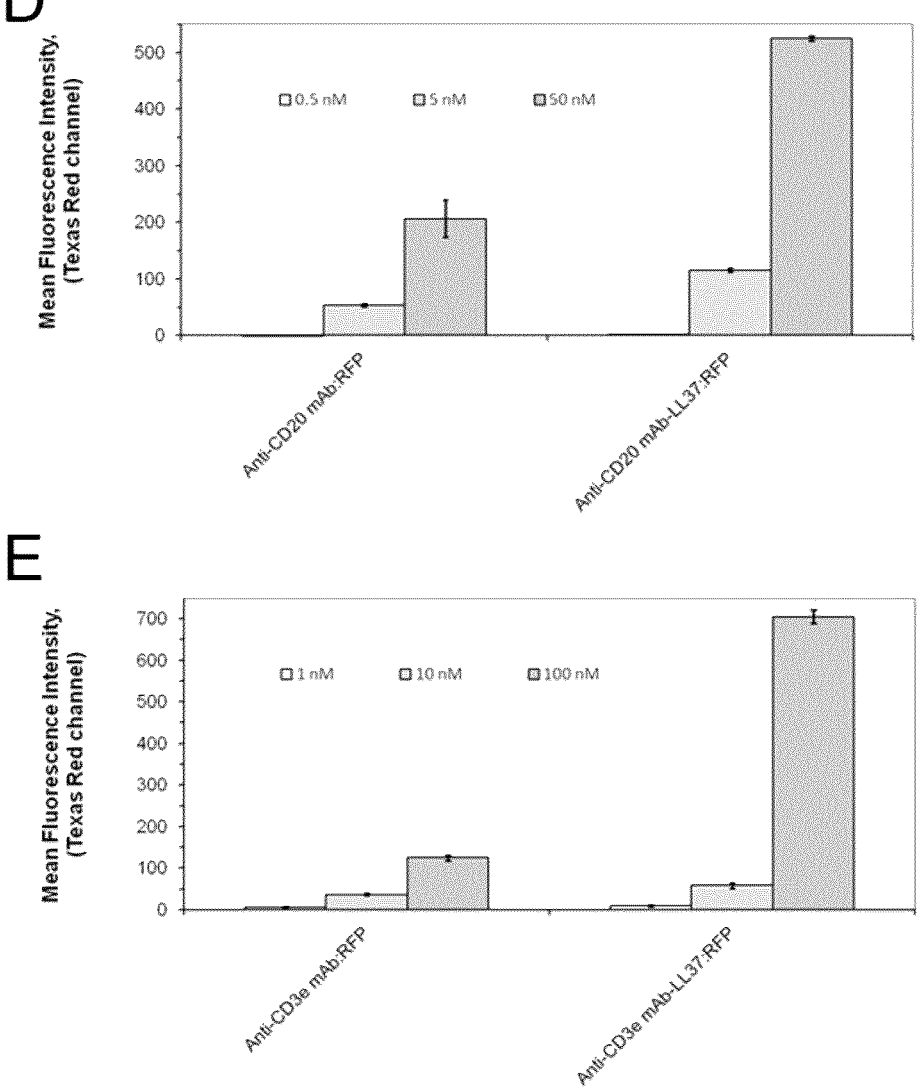

A

Non-biniding
(JIMT1)

B

Low HER2
(RT4v6)

C cell surface

Antigenic receptor

Receptor-specific antibody

Multimerization domain (such as LL37)

Anti-HER2 mAb                    Anti-HER2 mAb-LL37

ANTIBODY-PAYLOAD CONJUGATES WITH ENHANCED DELIVERY DOMAIN AND USES THEREOF

CROSS-REFERENCE TO RELATED APPLICATION

This application is a U.S. national stage entry under 35 U.S.C. § 371 of International Application No. PCT/CA2019/051612 filed Nov. 12, 2019, entitled "ANTIBODY-PAYLOAD CONJUGATES WITH ENHANCED DELIVERY DOMAIN AND USES THEREOF". The foregoing application is hereby incorporated by reference in its entirety (except for any subject matter disclaimers or disavowals, and except to the extent of any conflict with the disclosure of the present application, in which case the disclosure of the present application shall control).

SEQUENCE LISTING

The present application is filed with a Sequence Listing in electronic format. The Sequence Listing is provided as a file entitled "V814150US_amended_SL_24Oct2022.txt" created on Oct. 24, 2022, which is 145 kilobytes in size. The information in the electronic format of the sequence listing is incorporated herein by reference in its entirety.

FIELD OF INVENTION

The present invention relates to increasing the delivery of antibody-payload conjugates to cells. In particular, the present invention relates to antibody-payload conjugates further conjugated with LL37-derived polypeptides to enhance antibody directed delivery of the payload to human cells.

BACKGROUND OF THE INVENTION

Antibody-drug conjugates (ADCs) combine the specific targeting of a target cell (e.g. a cancer cell), through antibody-antigen binding of a specifically-expressed cell surface antigen, with delivery of a payload (e.g. a therapeutic drug) conjugated to the antibody. In some cases, the payload is conjugated to the antibody using a releasable linker. This maintains the payload in an inactive state when circulating (reducing side effects) and releases the active payload only after the ADC-bound surface antigen is internalized into the target cell.

ADCs are limited by the availability of target-specific cell surface antigens that are both (1) highly expressed and (2) sufficiently internalized upon ADC-binding. There is therefore a need for technologies that increase the delivery of antibody-payload conjugates to target-specific cell surface antigens, e.g. to increase the effectiveness of existing ADC therapies and to produce new ADCs that target poorly expressed cell-surface antigens. There is also a need for technologies that increase internalization of antibody-payload conjugates by target cells.

SUMMARY

Various embodiments of this disclosure relate to utilizing the ability of LL37 to form a multimer to produce new ADCs that multimerize at target cells expressing the ADC target antigen, thereby enhancing specific antibody delivery and ADC payload effectiveness (e.g. therapeutic effect). LL37 is a naturally found human peptide that preferentially forms stable dimers in solution and polymers on mammalian outer cellular membranes rich in phosphatidylserine, such as cancer cells, diseased or dying cells, pathogen infected cells and immune cells involved in autoimmune conditions/disease. This disclosure shows that covalently adding at least two or more LL37-derived polypeptides to an ADC forms a stable protein conjugate suitable for therapeutic applications, and that this conjugate causes the formation of ADC multimers on the target cell surface, leading to increased delivery of the ADC payload(s).

Various embodiments of this disclosure relate to a covalent conjugate comprising: an antibody that specifically binds to a cell surface epitope of a human cell that has outer leaflet phosphatidylserine, or an antibody derivative, the antibody derivative comprising: an antibody variable domain that specifically binds to the cell surface epitope of the human cell, and a hinge region coupling two heavy chains or two heavy chain fragments; a payload comprising: a small molecule drug of less than 3 kDa that is toxic to human cells, or a plurality of small molecule drugs that are each less than 3 kDa and which are toxic to human cells; or a peptide or protein of less than 100 kDa; and a first LL37-derived polypeptide and a second LL37-derived polypeptide, the first LL37-derived polypeptide, the first LL37-derived polypeptide and the second LL37-derived polypeptide each comprising an LL37-derived amino acid sequence or sequences, wherein each of the LL37-derived amino acid sequence or sequences independently comprise: SEQ ID NO: 14 (IGKEFKRIVQRIKDFLRNLVPRTES); or SEQ ID NO: 111 (SETRPVLNRLFDKIRQVIRKFEKGI); or a fragment of SEQ ID NO: 14 or 111 having consecutive deletions at either or both of the N- and C-termini up to a total deletion of at most 8 amino acids; or a plurality of fragments of SEQ ID NO: 14 and/or SEQ ID NO: 111, each fragment of the plurality of fragments independently having consecutive deletions at either or both of the N- and C-termini up to a total deletion of at most 10 amino acids; wherein each Lys and Arg residue in each fragment is independently substituted or not substituted with a conservative substitute amino acid residue selected from the group consisting of: Lys, Orn (ornithine), DBu (2,4-diaminobutanoate), Dpr (2,3-diaminopropionate), Hyl (hydroxylysine), aHyl (allo-hydroxylysine), MeLys (6-N-methyllysine), Arg, Cit (citrulline), and 2-amino-3-guanidinopropionate; wherein 0, 1, 2, 3, 4 or 5 amino acid residues, selected from the group consisting of Gly, Asp, Glu, Asn, Gln, Ile, Leu, Val, Phe, Ser, Thr, Pro, and a combination thereof, in each fragment are each independently substituted with a conservative substitute amino acid residue selected from within its Group, $X^1$, $X^2$, $X^3$, $X^4$, $X^5$, or $X^6$ as defined below: (Group $X^1$) Ala, Gly; (Group $X^2$) Asp, Glu, bAad (3-aminoadipic acid), Apm (2-aminopimelic acid); (Group $X^3$) Asn, Gln; (Group $X^4$) Ile, Leu, Met, Val, Phe, Tyr, Trp, Abu (2-aminobutyric acid), Ahe (2-aminoheptanoic acid), aIle (allo-isoleucine), Nva (norvaline), Nle (norleucine); (Group $X^5$) Ser, Thr, Tyr; (Group $X^6$) Pro, 3Hyp (3-hydroxyproline), 4Hyp (4-hydroxyproline); and wherein 0, 1 or 2 amino acid residues, selected from the group consisting of Lys, Arg, Gly, Asp, Glu, Asn, Gln, Ile, Leu, Val, Phe, Ser, Thr, Pro, and a combination thereof, in each fragment are each independently substituted with a non-conservative substitute amino acid residue.

Various embodiments of this disclosure relate to a covalent conjugate comprising: an antibody that specifically binds to a cell surface epitope of a human cell, or an antibody derivative, the antibody derivative comprising: an antibody variable domain that specifically binds to the cell surface epitope of the human cell, and a hinge region coupling two heavy chains or two heavy chain fragments; a payload comprising: a small molecule drug of less than 3 kDa that is toxic to human cells, or a plurality of small molecule drugs that are each less than 3 kDa and which are toxic to human cells; or a peptide or protein of less than 100 kDa; and a first LL37-derived polypeptide and a second LL37-derived polypeptide, the first LL37-derived polypeptide, the first LL37-derived polypeptide and the second LL37-derived polypeptide each comprising an LL37-derived amino acid sequence or sequences, wherein each of the LL37-derived amino acid sequence or sequences independently comprise: SEQ ID NO: 14 (IGKEFKRIVQRIKD-FLRNLVPRTES); or SEQ ID NO: 111 (SETRPVLNRLFD-KIRQVIRKFEKGI); or a fragment of SEQ ID NO: 14 or 111 having consecutive deletions at either or both of the N- and C-termini up to a total deletion of at most 8 amino acids; or a plurality of fragments of SEQ ID NO: 14 and/or SEQ ID NO: 111, each fragment of the plurality of fragments independently having consecutive deletions at either or both of the N- and C-termini up to a total deletion of at most 10 amino acids; wherein each Lys and Arg residue in each fragment is independently substituted or not substituted with a conservative substitute amino acid residue selected from the group consisting of: Lys, Orn (ornithine), DBu (2,4-diaminobutanoate), Dpr (2,3-diaminopropionate), Hyl (hydroxylysine), aHyl (allo-hydroxylysine), MeLys (6-N-methyllysine), Arg, Cit (citrulline), and 2-amino-3-guanidinopropionate; wherein 0, 1, 2, 3, 4 or 5 amino acid residues, selected from the group consisting of Gly, Asp, Glu, Asn, Gln, Ile, Leu, Val, Phe, Ser, Thr, Pro, and a combination thereof, in each fragment are each independently substituted with a conservative substitute amino acid residue selected from within its Group, $X^1$, $X^2$, $X^3$, $X^4$, $X^5$, or $X^6$ as defined below: (Group $X^1$) Ala, Gly; (Group $X^2$) Asp, Glu, bAad (3-aminoadipic acid), Apm (2-aminopimelic acid); (Group $X^3$) Asn, Gln; (Group $X^4$) Ile, Leu, Met, Val, Phe, Tyr, Trp, Abu (2-aminobutyric acid), Ahe (2-amino-heptanoic acid), aIle (allo-isoleucine), Nva (norvaline), Nle (norleucine); (Group $X^5$) Ser, Thr, Tyr; (Group $X^6$) Pro, 3Hyp (3-hydroxyproline), 4Hyp (4-hydroxyproline); wherein 0, 1 or 2 amino acid residues, selected from the group consisting of Lys, Arg, Gly, Asp, Glu, Asn, Gln, Ile, Leu, Val, Phe, Ser, Thr, Pro, and a combination thereof, in each fragment are each independently substituted with a non-conservative substitute amino acid residue; and wherein the human cell is: a cancer cell; a pathogen-infected cell; or an immune cell responsible for an autoimmune condition or disease.

Various embodiments of this disclosure relate to a covalent conjugate comprising: an antibody that specifically binds to a cell surface epitope of a human cell, or an antibody derivative, the antibody derivative comprising: an antibody variable domain that specifically binds to the cell surface epitope of the human cell, and a hinge region coupling two heavy chains or two heavy chain fragments; a payload comprising: a small molecule drug of less than 3 kDa that is toxic to human cells, or a plurality of small molecule drugs that are each less than 3 kDa and which are toxic to human cells; or a peptide or protein of less than 100 kDa; and a first LL37-derived polypeptide and a second LL37-derived polypeptide, the first LL37-derived polypeptide, the first LL37-derived polypeptide and the second LL37-derived polypeptide each comprising an LL37-derived amino acid sequence or sequences, wherein each of the LL37-derived amino acid sequence or sequences independently comprise: SEQ ID NO: 14 (IGKEFKRIVQRIKD-FLRNLVPRTES); or SEQ ID NO: 111 (SETRPVLNRLFD-KIRQVIRKFEKGI); or a fragment of SEQ ID NO: 14 or 111 having consecutive deletions at either or both of the N- and C-termini up to a total deletion of at most 8 amino acids; or a plurality of fragments of SEQ ID NO: 14 and/or SEQ ID NO: 111, each fragment of the plurality of fragments independently having consecutive deletions at either or both of the N- and C-termini up to a total deletion of at most 10 amino acids; wherein each Lys and Arg residue in each fragment is independently substituted or not substituted with a conservative substitute amino acid residue selected from the group consisting of: Lys, Orn (ornithine), DBu (2,4-diaminobutanoate), Dpr (2,3-diaminopropionate), Hyl (hydroxylysine), aHyl (allo-hydroxylysine), MeLys (6-N-methyllysine), Arg, Cit (citrulline), and 2-amino-3-guanidinopropionate; wherein 0, 1, 2, 3, 4 or 5 amino acid residues, selected from the group consisting of Gly, Asp, Glu, Asn, Gln, Ile, Leu, Val, Phe, Ser, Thr, Pro, and a combination thereof, in each fragment are each independently substituted with a conservative substitute amino acid residue selected from within its Group, $X^1$, $X^2$, $X^3$, $X^4$, $X^5$, or $X^6$ as defined below: (Group $X^1$) Ala, Gly; (Group $X^2$) Asp, Glu, bAad (3-aminoadipic acid), Apm (2-aminopimelic acid); (Group $X^3$) Asn, Gln; (Group $X^4$) Ile, Leu, Met, Val, Phe, Tyr, Trp, Abu (2-aminobutyric acid), Ahe (2-amino-heptanoic acid), aIle (allo-isoleucine), Nva (norvaline), Nle (norleucine); (Group $X^5$) Ser, Thr, Tyr; (Group $X^6$) Pro, 3Hyp (3-hydroxyproline), 4Hyp (4-hydroxyproline); and wherein 0, 1 or 2 amino acid residues, selected from the group consisting of Lys, Arg, Gly, Asp, Glu, Asn, Gln, Ile, Leu, Val, Phe, Ser, Thr, Pro, and a combination thereof, in each fragment are each independently substituted with a non-conservative substitute amino acid residue.

In some embodiments, the LL37-derived amino acid sequence or sequences may comprise SEQ ID NO: 16 (PEP #38) or SEQ ID NO: 74 (PEP #48). In some embodiments, each fragment of the plurality of fragments may independently comprise SEQ ID NO: 51 or the inverse sequence of SEQ ID NO: 51. In some embodiments, the plurality of fragments may comprise a pair of palindromic sequences. In some embodiments, the LL37-derived amino acid sequence or sequences may have a total calculated standard state surface area of hydrophobic residues ($sssA_H$) of at least 1400 Å². In some embodiments, the LL37-derived amino acid sequence or sequences may have a total calculated $sssA_H$ of at least 1900 Å².

In some embodiments: the antibody or the antibody derivative may comprise a first heavy chain constant region and a second heavy chain constant region, wherein the first LL37-derived polypeptide is coupled directly or indirectly to the first heavy chain constant region and the second LL37-derived polypeptide is coupled directly or indirectly to the same amino acid residue in the second heavy chain constant region; or the antibody or the antibody derivative may comprise a first light chain constant region and a second light chain constant region, wherein the first LL37-derived polypeptide is coupled directly or indirectly to the first light chain constant region and the second LL37-derived polypeptide is coupled directly or indirectly to the same amino acid residue in the second light chain constant region.

In some embodiments: the antibody or the antibody derivative may comprise a first heavy chain constant region and a second heavy chain constant region, wherein the first LL37-derived polypeptide is coupled directly or indirectly to a C-terminus of the first heavy chain constant region and the second LL37-derived polypeptide is coupled directly or indirectly to a C-terminus of the second heavy chain constant region; or the antibody or the antibody derivative may comprise a first light chain constant region and a second light chain constant region, wherein the first LL37-derived polypeptide is coupled directly or indirectly to a C-terminus of the first light chain constant region and the second LL37-derived polypeptide is coupled directly or indirectly to a C-terminus of the second light chain constant region.

In some embodiments, a ratio of LL37-derived polypeptides per antibody monomer in the covalent conjugate may be exactly 2:1. In other embodiments, a ratio of LL37-derived polypeptides per antibody monomer in the covalent conjugate may be exactly 4:1, exactly 6:1 or exactly 8:1.

In some embodiments, the first LL37-derived polypeptide and the second LL37-derived polypeptide may form a covalent conjugate with the antibody or with the antibody derivative through: peptide bonds; disulfide linkages; isopeptide bonds; and/or 1,2,3-triazole linkages. In some embodiments, the first LL37-derived polypeptide may be coupled to the antibody or to the antibody derivative through a first peptide linker and the second LL37-derived polypeptide is coupled to the antibody or to the antibody derivative through a second peptide linker, wherein the first peptide linker and the second peptide linker are the same or different.

In some embodiments, the covalent conjugate may comprise: 18V4F, 4R34.1.19, A-803, Abagovomab, Abciximab, Abituzumab, Abrezekimab, Abrilumab, Adalimumab, ADCPF-06688992, Adecatumumab, Ado-trastuzumab, Afelimomab, Afutuzumab, AGS16F, Alacizumab, Alemtuzumab, Alirocumab, ALKS4230, Altumomab, Amatuximab, AMG191, AMG531, Anatumomab, Andecaliximab, Anetumab, Anifrolumab, Anti-HM1.24, Apolizumab, Aprutumab, Arcitumomab, ARD5, Aselizumab, ASG-15ME, Atezolizumab, Atinumab, AUTO2, Avelumab, Azintuxizumab, B-701, Basiliximab, Bavituximab, BAY1179470, Bectumomab, Begelomab, Belantamab, Belimumab, Bemarituzumab, Benralizumab, Bersanlimab, Bertilimumab, Bevacizumab, BI-505, Biciromab, BIIB023, Bimagrumab, Bimekizumab, BION-1301, Bivatuzumab, Bleselumab, Blinatumomab, Blontuvetmab, Blosozumab, BMS-986148, BMS-986156, BMS-986179, Brentuximab, Brodalumab, Brolucizumab, Brontictuzumab, BTH1704, Burosumab, C7-FcDT, Cabiralizumab, Camidanlumab, Camrelizumab, CAN04, Canakinumab, Cantuzumab, CAP-100, Caplacizumab, capromab, Carotuximab, Catumaxomab, CC-90002, CD133KDEL, CD147-CART, CD96-S32F, CDX-1401, Cedelizumab, Cemiplimab, Cergutuzumab, Cetrelimab, Cetuximab, Cibisatamab, Citatuzumab, Cixutumumab, Claudiximab, Clenoliximab, Clivatuzumab, Codrituzumab, Cofetuzumab, Coltuximab, COM701, COM902, Conatumumab, Crizanlizumab, Crotedumab, CSL324, Cusatuzumab, Dacetuzumab, Daclizumab, Dalotuzumab, Dapirolizumab, Daratumumab, Darleukin, DCR2, Dectrekumab, Demcizumab, Denintuzumab, Denosumab, Depatuxizumab, Derlotuximab, Detumomab, Dinutuximab, Dorlimomab, Drozitumab, Duligotuzumab, Dupilumab, Durvalumab, Duvortuxizumab, Ecromeximab, Eculizumab, Edrecolomab, Efalizumab, EGFR806, EJ212_007-C12-5, ELB01101, Elgemtumab, Elotuzumab, Elsilimomab, Emactuzumab, Emapalumab, EMD525797, Emibetuzumab, Enapotamab, Enavatuzumab, Enfortumab, Enoblituzumab, Enoticumab, EOL4G8, Epratuzumab, Ertumaxomab, Etaracizumab, Evolocumab, Fanolesomab, Faralimomab, Farletuzumab, Fezakinumab, Fibatuzumab, Ficlatuzumab, Flanvotumab, Flotetuzumab, FLYSYN, Foralumab, Galiximab, Gancotamab, Ganitumab, Gatipotuzumab, Gavilimomab, GD2Bi-aATC, Gemtuzumab, GI-270384, Gilvetmab, Girentuximab, Glembatumumab, Golimumab, Gomiliximab, GSK2849330, Guselkumab, HB-n1, HFE7A, HLX20, HS-110, Hu3ST93, Ibalizumab, Ibritumomab, Icrucumab, Ifabotuzumab, Igovomab, Imalumab, Imaprelimab, IMC-CS4, Imgatuzumab, Inclacumab, Indatuximab, Indusatumab, Inebilizumab, Infliximab, Inotuzumab, Intetumumab, Iomab-B, iPH5401, Ipilimumab, Iratumumab, Isatuximab, Iscalimab, Istiratumab, Itolizumab, Ixekizumab, Keliximab, KH7B9, KTN0182A, KU42.33C, Labetuzumab, Ladiratuzumab, Lanadelumab, Lanalumab, Laprituximab, Lemalesomab, Leronlimab, Letolizumab, Lexatumumab, Lifastuzumab, Lilotomab, Lintuzumab, Lirilumab, Lokivetmab, Loncastuximab, Lorvotuzumab, Losatuxizumab, Lucatumumab, Lulizumab, Lumretuzumab, Lupartumab, Lutikizumab, LY3321367, LY3435151, M290, Mapatumumab, Margetuximab, Maslimomab, Matuzumab, Mavrilimumab, MBG453, MCLA-117, MEDI3617, MEDI3622, MEN1112, Mepolizumab, Milatuzumab, Minretumomab, Mirvetuximab, Mitumomab, MLS102, MM-111, MMP9, MNRP1685A, Modotuximab, Mogamulizumab, Monalizumab, Moxetumomab, MOXR0916, Muromonab, MVT-5873, Nacolomab, Naptumomab, Naratuximab, Narnatumab, Natalizumab, Navicixizumab, Necitumumab, Nerelimomab, Nesvacumab, Netakimab, NI-0101, Nimotuzumab, Nivolumab, NNC0151-00000000, Nofetumomab, Obinutuzumab, Ocaratuzumab, Ocrelizumab, Odulimomab, Ofatumumab, Olaratumab, Oleclumab, olokizumab, Omalizumab, Onartuzumab, Ontuxizumab, Onvatilimab, Opicinumab, Oportuzumab, Oregovomab, Otelixizumab, Otlertuzumab, Oxelumab, Pamrevlumab, Panitumumab, Pankomab, Parsatuzumab, Pasotuxizumab, Patritumab, PD-0360324, PDR001, Pembrolizumab, Pemtumomab, Pertuzumab, PF-00547659, PF-03446962, PF-04518600, PF-06650808, Pidilizumab, Pinatuzumab, Pintumomab, Plozalizumab, Polatuzumab, Prezalumab, Priliximab, Pritumumab, PTK7-ADC, Quilizumab, Radretumab, Ramucirumab, Ranibizumab, Ravagalimab, Refanezumab, REGN2176, Relatlimab, Reslizumab, RG7287, Rilotumumab, Rinucumab, Risankizumab, Rituximab, RO-001, RO6958688, Robatumumab, Romilkimab, Romosozumab, Rovalpituzumabtesirine, Rovelizumab, Rozanolixizumab, Ruplizumab, Sacituzumab, Samalizumab, Samrotamab, SAR252067, SAR408701, Sarilumab, Satralizumab, Satumomab, Secukinumab, Selicrelumab, Seribantumab, Setrusumab, SGN-15, SGN-CD123A, SGN-CD228A, SGN-CD352A, SGN-CD47M, SGN-CD48A, SGN-CD70A, SGN-LIV1A, SHP647, Siamab.com, Sibrotuzumab, Siltuximab, Simtuzumab, Sirtratumab, SL-279252, Sofituzumab, Solitomab, Sonepcizumab, Sontuzumab, Spartalizumab, Sphingomab, SS1 (dsFv) PE38 (CAT-5001), Sulesomab, TAB004, Tabalumab, Tacatuzumab, Tadocizumab, Talacotuzumab, Tamtuvetmab, Taplitumomab, Tarextumab, Telimomab, Telisotuzumab, Tenatumomab, Teneliximab, Teplizumab, Tepoditamab, Teprotumumab, Theralizumab, Tigatuzumab, Tildrakizumab, Timigutuzumab, Timolumab, Tiragotumab, Tislelizumab, Tisotumab, TKH2, Tocilizumab, Tomuzotuximab, Tositumomab, Trastuzumab, Tregalizumab, Tremelimumab, TSR-022, TTX-030, Tucotuzumab, Ublituximab, Ulocuplumab, Urelumab, Ustekinumab, Ustekinumab, Vadastuximab, Vanalimab, Vapaliximab, Varlilumab, Vatelizumab, Vedolizumab, Vepalimomab, Vesencumab, Visilizumab, Vobarilizumab, Vofatamab, Vociximab, Vonrolizumab, Vopratelimab, Vorsetuzumab, Votumumab, Vunakizumab, VX15/2503, Y-443, Zalutumumab, Zanolimumab, Zenocutuzumab, Ziralimumab, or Zolbetuximab.

In some embodiments, the covalent conjugate may comprise: A-803, ADCPF-06688992, Afutuzumab, Alemtuzumab, AMG191, AMG531, Anti-HM1.24, Apolizumab, Atezolizumab, AUTO2, Avelumab, Azintuxizumab, Basiliximab, Bectumomab, Belantamab, Bersanlimab, BI-505, BION-1301, Bleselumab, Blinatumomab, Blontuvetmab, Brentuximab, Cabiralizumab, Camidanlumab, Camrelizumab, CAN04, CAP-100, CC-90002, CD133KDEL, CD96-S32F, CDX-1401, Cedelizumab, Cemiplimab, Cetrelimab, Cixutumumab, Clenoliximab, Codrituzumab, Coltuximab, Com902, Conatumumab, Crotedumab, Cusatuzumab, Dacetuzumab, Daclizumab, Dalotuzumab, Dapirolizumab, Daratumumab, Darleukin, DCR2, Dectrekumab, Denintuzumab, Detumomab, Drozitumab, Durvalumab, Duvortuxizumab, Efalizumab, EJ212_007-C12-5, ELB01101, Elotuzumab, Elsilimomab, Emactuzumab, Emibetuzumab, Enapotamab, Epratuzumab, Fanolesomab, Fibatuzumab, Ficlatuzumab, Flotetuzumab, FLYSYN, Foralumab, Galiximab, Ganitumab, Gemtuzumab, GI-270384, Gilvetmab, Gomiliximab, HFE7A, Hu3S193, Ibalizumab, Ibritumomab, Ifabotuzumab, IMC-CS4, Inebilizumab, Inotuzumab, Iomab-B, Ipilimumab, Iratumumab, Isatuximab, Iscalimab, Istiratumab, Itolizumab, Keliximab, KTN0182A, Leronlimab, Letolizumab, Lexatumumab, Lilotomab, Lintuzumab, Lirilumab, Loncastuximab, Lucatumumab, Lulizumab, Lutikizumab, Maslimomab, MCLA-117, MEN1112, Milatuzumab, Mitumomab, Mogamulizumab, Monalizumab, Moxetumomab, Muromonab, Nacolomab, Naratuximab, Natalizumab, NI-0101, Nivolumab, Nofetumomab, Obinutuzumab, Ocaratuzumab, Ocrelizumab, Odulimomab, Ofatumumab, Olokizumab, Onartuzumab, Otelixizumab, Otlertuzumab, Oxelumab, PD-0360324, PDR001, Pembrolizumab, Pidilizumab, Pinatuzumab, Polatuzumab, Priliximab, Radretumab, Ravagalimab, REGN2176, Relatlimab, Rilotumumab, Rinucumab, Rituximab, RO-001, Robatumumab, Romilkimab, Rovelizumab, Ruplizumab, Samalizumab, Sarilumab, Satralizumab, Selicrelumab, SGN-15, SGN-CD123A, SGN-CD352A, SGN-CD47M, SGN-CD48A, SGN-CD70A, Siltuximab, SL-279252, Sontuzumab, Spartalizumab, Tabalumab, Talacotuzumab, Tamtuvetmab, Taplitumomab, Telimomab, Telisotuzumab, Teneliximab, Teplizumab, Tepoditamab, Teprotumumab, Theralizumab, Tigatuzumab, Tiragotumab, Tislelizumab, Tocilizumab, Tositumomab, Tregalizumab, Tremelimumab, TTX-030, Ublituximab, Ulocuplumab, Vadastuximab, Vanalimab, Varlilumab, Visilizumab, Vobarilizumab, Vorsetuzumab, or Zanolimumab.

In some embodiments, the covalent conjugate may comprise: 5B1(MVT-5873), Abagovomab, Abituzumab, Abrezekimab, ADCPF-06688992, Adecatumumab, AGS16F, Alacizumab, ALKS4230, Altumomab, Amatuximab, AMG191, Anatumomab, Andecaliximab, Anetumab, Anti-HM1.24, Aprutumab, Arcitumomab, ASG-15ME, Atezolizumab, Atinumab, Avelumab, B-701, Bavituximab, BAY1179470, Bemarituzumab, Bersanlimab, Bevacizumab, BI-505, Bivatuzumab, Bleselumab, BMS-986148SS1, BMS-986156, BMS-986179, Brolucizumab, Brontictuzumab, BTH1704Pemtumomab, Cabiralizumab, Camrelizumab, CAN04, Cantuzumab, Carotuximab, Catumaxomab, CC-90002, CD133KDEL, CD147-CART, CDX-1401, Cemiplimab, Cergutuzumab, Cetrelimab, Cetuximab, Cibisatamab, Citatuzumab, Cixutumumab, Claudiximab, Clivatuzumab, Codrituzumab, Cofetuzumab, COM701, Com902, Conatumumab, Crizanlizumab, Crotedumab, Cusatuzumab, Dacetuzumab, Dalotuzumab, Dectrekumab, Demcizumab, Depatuxizumab, Derlotuximab, dinutuximab, Drozitumab, Duligotuzumab, Durvalumab, Ecromeximab, Edrecolomab, EGFR806, Elgemtumab, Emactuzumab, EMD525797, Emibetuzumab, Enapotamab, Enavatuzumab, Enfortumab, Enoblituzumab, Enoticumab, EOL4G8, Ertumaxomab, Etaracizumab, Fanolesomab, Farletuzumab, Fibatuzumab, Ficlatuzumab, Flanvotumab, Gancotamab, Ganitumab, Gatipotuzumab, Gavilimomab, GD2Bi-aATC, GI-270384, Gilvetmab, Girentuximab, Glembatumumab, GSK2849330, HLX20, HS-110, Hu3S193, Icrucumab, Ifabotuzumab, Igovomab, Imalumab, Imaprelimab, IMC-CS4, Imgatuzumab, Inclacumab, Indatuximab, Indusatumab, Intetumumab, iPH5401, Ipilimumab, Iscalimab, Istiratumab, KH7B9, KTN0182A, KU42.33C, Labetuzumab, Ladiratuzumab, Laprituximab, Leronlimab, Lexatumumab, Lifastuzumab, Lirilumab, Lorvotuzumab, Losatuxizumab, Lucatumumab, Lulizumab, Lumretuzumab, Lupartumab, Lutikizumab, LY3321367, LY3435151, Mapatumumab, Margetuximab, C7-FcDT, Matuzumab, MBG453, MEDI3617, MEDI3622, Milatuzumab, Minretumomab, Mirvetuximab, Mitumomab, MLS102, MM-111, MMP9, MNRP1685A, Modotuximab, Monalizumab, MOXR0916, Nacolomab, Naptumomab, Narnatumab, Navicixizumab, Necitumumab, Nesvacumab, Nimotuzumab, Nivolumab, NNC0151-00000000, Nofetumomab, Olaratumab, Oleclumab, Onartuzumab, Ontuxizumab, Onvatilimab, Oportuzumab, Oregovomab, Oxelumab, Pamrevlumab, Panitumumab, Pankomab, Parsatuzumab, Pasotuxizumab, Patritumab, PD-0360324, PDR001, PE38 (CAT-5001), Pembrolizumab, Pertuzumab, PF-03446962, PF-04518600, PF-06650808, Pidilizumab, Pintumomab, Pritumumab, PTK7-ADC, Ramucirumab, Ranibizumab, Ravagalimab, Relatlimab, RG7287, Rilotumumab, RO-001, R06958688, Robatumumab, Romilkimab, Rovalpituzumab, Sacituzumab, Samrotamab, SAR408701, Sarilumab, Satralizumab, Satumomab, Selicrelumab, Seribantumab, SGN-15, SGN-CD228A, SGN-CD47M, SGN-CD70A, SGN-LIV1A, Sibrotuzumab, Sirtratumab, SL-279252, Sofituzumab, Solitomab, Sonepcizumab, Sontuzumab, Spartalizumab, Sphingomab, TAB004, Tacatuzumab, Tarextumab, Telisotuzumab, Tenatumomab, Teneliximab, Teprotumumab, Theralizumab, Tigatuzumab, Timigutuzumab, Timolumab, Tiragotumab, Tislelizumab, Tisotumab, TKH2HB-n1, Tocilizumab, Tomuzotuximab, Trastuzumab, Tremelimumab, TSR-022, TTX-030, Tucotuzumab, Urelumab, Vanalimab, Vapaliximab, Varlilumab, Vatelizumab, Vepalimomab, Vesencumab, Vobarilizumab, Vofatamab, Volociximab, Volociximab, Vonlerolizumab, Vopratelimab, Vorsetuzumab, Votumumab, VX15/2503, Y-443, Zalutumumab, Zenocutuzumab, Ziralimumab, or Zolbetuximab.

In some embodiments, the covalent conjugate may comprise: ALKS4230, Atezolizumab, Avelumab, Bleselumab, Cabiralizumab, Camrelizumab, CDX-1401, Cemiplimab, Cetrelimab, COM701, Com902, Dacetuzumab, Durvalumab, EGFR806, Elsilimomab, Emactuzumab, Enoblituzumab, Gilvetmab, HLX20, HS-110, Imalumab, IMC-CS4, Ipilimumab, Iscalimab, Lucatumumab, Lulizumab, MEDI3622, Monalizumab, MOXR0916, Nivolumab, Olokizumab, Oxelumab, PD-0360324, PDR001, Pembrolizumab, PF-04518600, Pidilizumab, Ravagalimab, Relatlimab, Samalizumab, Selicrelumab, Siltuximab, SL-279252, Spartalizumab, TAB004, Teneliximab, Theralizumab, Tiragotumab, Tislelizumab, Tremelimumab, Urelumab, Vanalimab, Varlilumab, Vonlerolizumab, or Vopratelimab.

In some embodiments, the covalent conjugate may comprise: Adalimumab, Afelimomab, ARD5, BIIB023, Cedelizumab, Clenoliximab, Com902, CSL324, Faralimomab, Golimumab, Ibalizumab, Infliximab, Iomab-B, Keliximab, Nerelimomab, Priliximab, SAR252067, Tenatumomab, Tiragotumab, Tregalizumab, Ustekinumab, Y-443, or Zanolimumab In some embodiments, the covalent conjugate may comprise: 18V4F, 4R34.1.19, Abciximab, Abrilumab, Adalimumab, ADF-06688992, Afelimomab, Alirocumab, Andecaliximab, Anifrolumab, Aselizumab, Basiliximab, Begelomab, Belimumab, Benralizumab, Bersanlimab, Bertilimumab, BI-505, BIIB023, Bimagrumab, Bimekizumab, Bleselumab, Blosozumab, Brodalumab, Burosumab, Camidanlumab, Canakinumab, CD147-CART, Cedelizumab, Clenoliximab, Crotedumab, Dacetuzumab, Daclizumab, Dapirolizumab, Daratumumab, Dectrekumab, Denosumab, Dorlimomab, Dupilumab, Efalizumab, Emapalumab, Etaracizumab, Evolocumab, Fezakinumab, Flotetuzumab, Gavilimomab, GI-270384, Glembatumumab, Golimumab, Guselkumab, HFE7A, Hu3S193, Ibalizumab, Infliximab, iPH5401, Isatuximab, Iscalimab, Ixekizumab, Keliximab, Lanalumab, Lemalesomab, Letolizumab, Lokivetmab, Lucatumumab, Lutikizumab, LY3321367, M290, Mavrilimumab, MBG453, Mepolizumab, Milatuzumab, Mitumomab, MMP9, Natalizumab, Nerelimomab, Netakimab, NI-0101, NNC0151-00000000, Odulimomab, Omalizumab, Opicinumab, Oxelumab, Pamrevlumab, PF-00547659, Plozalizumab, Prezalumab, Priliximab, Quilizumab, Ravagalimab, REGN2176, Reslizumab, Rinucumab, Risankizumab, RO-001, Romilkimab, Romosozumab, Rozanolixizumab, Ruplizumab, SAR252067, Sarilumab, Satralizumab, Secukinumab, Selicrelumab, Setrusumab, SGN-15, SGN-CD123A, SHP647, Simtuzumab, SL-279252, Sonepcizumab, Sulesomab, Tabalumab, Tadocizumab, Talacotuzumab, Tamtuvetmab, Telimomab, Tenatumomab, Teneliximab, Tildrakizumab, Timolumab, Tisotumab, Tocilizumab, Tregalizumab, TSR-022, Ustekinumab, Ustekinumab, Vanalimab, Vapaliximab, Vatelizumab, Vedolizumab, Vepalimomab, Vobarilizumab, Vunakizumab, VX15/2503, Zanolimumab, or Ziralimumab.

In some embodiments, the covalent conjugate may comprise: Trastuzumab, Mirvetuximab, Panitumumab, Lifastuzumab, Labetuzumab, Citatuzumab, Foralumab, Brentuximab, Rituximab, Ofatumumab, Vadastuximab, Vofatamab, or hj591. In some embodiments, the covalent conjugate may comprise Trastuzumab.

In some embodiments, the cell surface epitope may form part of: 5AC (Mucin 5AC), 5T4, activin receptor-like kinase 1, ACVR2B, adenocarcinoma antigen, alpha-fetoprotein, AOC3, AXL, c-Met, C242 antigen (CanAg) novel glycoform of MUC1, CA-125, *Canis lupus familiaris* IL31, tumor-associated glycoprotein 72 antigen, Addressin, Angiopoietin-2, C5, CA19-9, Carbonic anhydrase 9 (CA-IX), CCL11, CD3, CD1a, CD1b, CD1c, CD1d, CD1e, CD2, CD3d, CD3e, CD3g, CD4, CD5, CD6, CD7, CD8a, CD8b, CD9, CD10, CD11a, CD11b, CD11c, CD11d, CD13, CD14, CD15s, CD15su, CD15u, CD16a, CD16b, CD17, CD18, CD19, CD20, CD21, CD22, CD23, CD24, CD25, CD26, CD27, CD28, CD29, CD30, CD31, CD32A, CD32B, CD32C, CD33, CD34, CD35, CD36, CD37, CD38, CD39, CD40, CD41, CD42a, CD42b, CD42c, CD42d, CD43, CD44, CD44v6, CD45, CD46, CD47, CD48, CD49a, CD49b, CD49c, CD49d, CD49e, CD49f, CD50, CD51, CD52, CD53, CD54, CD55, CD56, CD57, CD58, CD59, CD60a, CD60b, CD60c, CD61, CD62E, CD62L, CD62P, CD63, CD64a, CD65, CD65s, CD66a, CD66b, CD66c, CD66d, CD66e, CD66f, CD68, CD69, CD70, CD71, CD72, CD73, CD74, CD75, CD75s, CD77, CD79A, CD79B, CD80, CD81, CD82, CD83, CD84, CD85A, CD85B, CD85C, CD85D, CD85F, CD85G, CD85H, CD85I, CD85J, CD85K, CD85M, CD86, CD87, CD88, CD89, CD90, CD91, CD92, CD93, CD94, CD95, CD96, CD97, CD97B, CD98, CD99, CD99R, CD100, CD101, CD102, CD103, CD104, CD105, CD106, CD107a, CD107b, CD108, CD109, CD110, CD111, CD112, CD112R, CD113, CD114, CD115, CD116, CD117, CD118, CD119, CD120a, CD120b, CD121a, CD121b, CD122, CD123, CD124, CD125, CD126, CD127, CD129, CD130, CD131, CD132, CD133, CD134, CD135, CD136, CD137, CD138, CD140A, CD140B, CD141, CD142, CD143, CD144, CD146, CD147, CD148, CD150, CD151, CD152, CD153, CD154, CD155, CD156a, CD156b, CD156c, CD157, CD158a, CD158B1, CD158B2, CD158C, CD158D, CD158E1, CD158E2, CD158F1, CD158F2, CD158G, CD158H, CD158I, CD158J, CD158K, CD159a, CD159c, CD160, CD161, CD162, CD163, CD164, CD165, CD166, CD167a, CD167b, CD168, CD169, CD170, CD171, CD172a, CD172b, CD172g, CD173, CD174, CD175, CD175s, CD176, CD177, CD178, CD179a, CD179b, CD180, CD181, CD182, CD183, CD184, CD185, CD186, CD191, CD192, CD193, CD194, CD195, CD196, CD197, CD198w, CD199, CD200, CD201, CD202b, CD203c, CD204, CD205, CD206, CD207, CD208, CD209, CD210, CD212, CD213a1, CD213a2, CD215, CD217, CD218a, CD218b, CD220, CD221, CD222, CD223, CD224, CD225, CD226, CD227, CD228, CD229, CD230, CD231, CD232, CD233, CD234, CD235a, CD235b, CD236, CD236R, CD238, CD239, CD240CE, CD240D, CD241, CD242, CD243, CD244, CD246, CD247, CD248, CD249, CD252, CD253, CD254, CD256, CD257, CD258, CD261, CD262, CD263, CD264, CD265, CD266, CD267, CD268, CD269, CD270, CD271, CD272, CD273, CD274, CD275, CD276, CD277, CD278, CD279, CD280, CD281, CD282, CD283, CD284, CD286, CD288, CD289, CD290, CD292, CD293w, CD294, CD295, CD296, CD297, CD298, CD299, CD300A, CD300C, CD300E, CD300F, CD301, CD302, CD303, CD304, CD305, CD306, CD307a, CD307b, CD307c, CD307d, CD307e, CD309, CD312, CD314, CD315, CD316, CD317, CD318, CD319, CD320, CD321, CD322, CD324, CD325, CD326, CD327, CD328, CD329, CD331, CD332, CD333, CD334, CD335, CD336, CD337, CD338, CD339, CD340, CD344, CD349, CD350, CD351, CD352, CD353, CD354, CD355, CD357, CD358, CD360, CD361, CD362, CD363, CD364, CD365, CD366, CD367, CD368, CD369, CD370, CD371, CD66, CTGF, Cytokeratin, DLL1, DLL3, DLL4, EGFL7, EGFR, EPHA3, FAP, FcRn, FGF23, Fibrin, Fibronectin, FRalpha, Ganglioside D2, gp75, GPC3, Guanylate cyclase 2C, Hematopoietin 1, Hepatocyte growth factor, Her3, Histone H1, HLA-DR, IgE, IL-13, IL-17, IL-18, IL-2, IL-22, IL-31, IL-5, IL-6, IL1RAP, IL23, INFA1, Integrin beta-7, Interferon receptor, IL-1, Interleukin 23, KLKB1, LEC, Leucine-rich repeat-containing protein 15, LINGO-1, LIV1A, Lysyl oxidase homolog 2, Mesothelin, MIF, MMP9, Myelin-associated glycoprotein, Nectin-4, NOTCH1, NOTCH2, Notch3, PCSK9, PS, PSMA (GCPII), PTK7, Reticulon 4 (NOGO), Sclerostin, SLITRK6, Sodium-dependent phosphate transport protein 2B (NaPi2b), Sphingosine-1-phosphate (SIP), STEAP1, TcRa, Tenascin C (TN-C), TIGIT, TROP-2, Tumor necrosis factor, TWEAK, VEGFA, VEGFR1, VEGFR2, VEGRF1, Vimentin, VISTA, or von Willebrand factor.

In some embodiments, the cell surface epitope may form part of: AXL, c-Met, C242 antigen (CanAg) novel glycoform of MUC1, *Canis lupus familiaris* IL31, CD3, CD1a, CD1b, CD1c, CD1d, CD1e, CD2, CD3d, CD3e, CD3g, CD4, CD5, CD6, CD8a, CD8b, CD9, CD11a, CD11b, CD11c, CD11d, CD13, CD15s, CD15u, CD16a, CD16b, CD17, CD18, CD19, CD20, CD21, CD22, CD23, CD24, CD25, CD27, CD28, CD30, CD32A, CD32B, CD32C, CD33, CD34, CD37, CD38, CD39, CD40, CD43, CD44, CD45, CD47, CD48, CD49d, CD50, CD52, CD53, CD54, CD60a, CD62E, CD63, CD64a, CD65, CD65s, CD68, CD69, CD70, CD71, CD72, CD74, CD75, CD77, CD79A, CD79B, CD80, CD83, CD84, CD85A, CD85B, CD85C, CD85D, CD85F, CD85G, CD85H, CD85I, CD85J, CD85K, CD85M, CD86, CD90, CD92, CD93, CD94, CD95, CD96, CD97B, CD99, CD99R, CD106, CD108, CD110, CD115, CD117, CD123, CD126, CD130, CD131, CD132, CD133, CD135, CD140B, CD143, CD148, CD150, CD152, CD153, CD154, CD157, CD158a, CD158B1, CD158B2, CD158C, CD158D, CD158E1, CD158E2, CD158F1, CD158F2, CD158G, CD158H, CD158I, CD158J, CD158K, CD159a, CD159c, CD160, CD161, CD162, CD164, CD165, CD166, CD169, CD170, CD172a, CD174, CD175, CD177, CD178, CD179a, CD179b, CD180, CD181, CD182, CD183, CD184, CD185, CD194, CD195, CD197, CD198w, CD200, CD204, CD205, CD206, CD207, CD209, CD210, CD212, CD213a1, CD215, CD218a, CD218b, CD221, CD223, CD229, CD231, CD233, CD236R, CD244, CD247, CD252, CD256, CD262, CD267, CD268, CD269, CD273, CD279, CD280, CD281, CD282, CD283, CD284, CD286, CD288, CD289, CD290, CD296, CD300A, CD300C, CD300E, CD300F, CD303, CD305, CD306, CD307a, CD307b, CD307c, CD307d, CD307e, CD312, CD314, CD317, CD319, CD320, CD321, CD322, CD325, CD327, CD328, CD329, CD334, CD335, CD336, CD337, CD352, CD353, CD355, CD361, CD367, CD368, CD369, CD370, CD371, DLL1, EPHA3, Fibronectin, GPC3, Hepatocyte growth factor, HLA-DR, IL-13, IL-6, IL1RAP, TcRa, or TIGIT.

In some embodiments, the cell surface epitope may form part of: 5AC (Mucin 5AC), 5T4, activin receptor-like kinase 1, adenocarcinoma antigen, alpha-fetoprotein, AOC3, AXL, c-Met, C242 antigen (CanAg) novel glycoform of MUC1, CA-125, *Canis lupus familiaris* IL31, tumor-associated glycoprotein 72 antigen, Angiopoietin-2, CA19-9, Carbonic anhydrase 9 (CA-IX), CD1d, CD5, CD7, CD9, CD10, CD13, CD14, CD15s, CD15su, CD15u, CD24, CD27, CD29, CD39, CD40, CD44, CD44v6, CD46, CD47, CD49b, CD49e, CD49f, CD50, CD51, CD54, CD56, CD57, CD58, CD60a, CD60b, CD60c, CD61, CD62P, CD66a, CD66c, CD66e, CD68, CD70, CD73, CD81, CD87, CD88, CD91, CD99, CD99R, CD100, CD102, CD105, CD106, CD109, CD112, CD112R, CD115, CD117, CD126, CD133, CD134, CD136, CD137, CD138, CD140A, CD141, CD142, CD144, CD146, CD147, CD151, CD152, CD156a, CD156b, CD158a, CD159a, CD164, CD167a, CD168, CD171, CD174, CD175, CD175s, CD176, CD178, CD195, CD201, CD203c, CD205, CD206, CD213a2, CD220, CD221, CD223, CD224, CD225, CD226, CD227, CD228, CD233, CD239, CD243, CD243, CD246, CD248, CD252, CD253, CD254, CD261, CD262, CD266, CD271, CD272, CD274, CD276, CD278, CD279, CD280, CD295, CD299, CD301, CD302, CD304, CD309, CD317, CD318, CD324, CD326, CD331, CD332, CD333, CD334, CD338, CD339, CD340, CD344, CD349, CD350, CD354, CD357, CD358, CD360, CD363, CD366, CD66, CTGF, Cytokeratin, DLL1, DLL3, DLL4, EGFL7, EGFR, EPHA3, FAP, FRalpha, Ganglioside D2, gp75, GPC3, Guanylate cyclase 2C, Hematopoietin 1, Hepatocyte growth factor, Her3, Histone H1, IL-13, IL1RAP, Leucine-rich repeat-containing protein 15, LIV1A, Mesothelin, MIF, MMP9, Nectin-4, NOTCH1, NOTCH2, Notch3, PS, PSMA (GCPII), PTK7, Reticulon 4 (NOGO), SLITRK6, Sodium-dependent phosphate transport protein 2B (NaPi2b), Sphingosine-1-phosphate (SiP), STEAP1, Tenascin C (TN-C), TIGIT, TROP-2, VEGFA, VEGFR1, VEGFR2, VEGRF1, Vimentin, or VISTA.

In some embodiments, the cell surface epitope may form part of: CD27, CD40, CD81, CD86, CD90, CD112R, CD115, CD134, CD137, CD152, CD153, CD156b, CD159a, CD162, CD178, CD200, CD205, CD223, CD252, CD272, CD274, CD276, CD278, CD279, CD360, CD369, IL-6, MIF, PSMA (GCPII), or TIGIT.

In some embodiments, the cell surface epitope may form part of: CD4, CD31, CD32A, CD32B, CD32C, CD34, CD45, CD55, CD59, CD66d, CD81, CD111, CD112, CD113, CD114, CD155, CD178, CD212, CD232, CD234, CD258, CD270, CD289, CD321, CD365, Interferon receptor, Tenascin C (TN-C), TIGIT, or Tumor necrosis factor.

In some embodiments, the cell surface epitope may form part of: ACVR2B, AOC3, Addressin, CCL11, CD4, CD5, CD11a, CD11b, CD25, CD26, CD31, CD35, CD36, CD38, CD40, CD41, CD49b, CD49c, CD49d, CD54, CD60a, CD61, CD62L, CD66b, CD66d, CD74, CD83, CD86, CD88, CD89, CD90, CD95, CD97, CD100, CD103, CD104, CD106, CD107a, CD107b, CD116, CD119, CD122, CD123, CD124, CD125, CD126, CD127, CD140B, CD142, CD147, CD154, CD162, CD174, CD178, CD191, CD192, CD193, CD196, CD202b, CD208, CD210, CD217, CD220, CD252, CD254, CD257, CD258, CD265, CD268, CD270, CD275, CD284, CD294, CD295, CD329, CD363, CD366, CTGF, FcRn, FGF23, Hematopoietin 1, IgE, IL-13, IL-17, IL-18, IL-22, IL-31, IL-5, IL23, INFA1, Integrin beta-7, IL-1, Interleukin 23, LEC, LINGO-1, Lysyl oxidase homolog 2, MMP9, PCSK9, Sclerostin, Tenascin C (TN-C), Tumor necrosis factor, or TWEAK.

In some embodiments, the cell surface epitope may form part of: HER2, folate receptor, EGFR, CD20, CD30, CD3e, FGFR3, *Napi*2b, CD33A, CEACAM5, EPCAM, or PSMA. In some embodiments, the cell surface epitope may form part of HER2.

In some embodiments, the payload may comprise the small molecule drug, wherein the small molecule drug is a V-ATPase inhibitor, a HSP90 inhibitor, an ion channel inhibitor, an IAP inhibitor, an mTor inhibitor, a microtubule stabilizer, a microtubule destabilizer, a dolastatin, a methionine aminopeptidase, an inhibitor of nuclear export of proteins, a DPPIV inhibitor, an inhibitor of phosphoryl transfer reactions in mitochondria, a protein synthesis inhibitor, a kinase inhibitor, a CDK2 inhibitor, a CDK9 inhibitor, a proteasome inhibitor, a kinesin inhibitor, an HDAC inhibitor, a DNA damaging agent, a DNA alkylating agent, a DNA intercalator, a DNA minor groove binder or a DHFR inhibitor, a radionuclide-containing compound, a chemotherapeutic moiety, an anti-cancer drug, an antimitotic compound, an inhibitor of DNA replication, an inhibitor of protein synthesis, cyclophosphamide, vincristine, prednisolone, cyclophosphamide, methotrexate, 5-fluorouracil, a DNA cleaving compound, a chalicheamicin, SN-38, irinotecan, camptothecin, D6.5, a duocarmycin, an auristatin, a maytansine, a maytansinoid, an amatoxin, durcomycin, doxorubicin, a pyrrolbenzodiazepine (PBD), an anthracycline, paclitaxel, a fungal toxin, or a derivative, analogue or prodrug thereof. In some embodiments, the payload may comprise the small molecule drug, wherein the small molecule drug is MMAE, MMAF, DM1, DM2, DM3, DM4, SN38, doxorubicin, pyrrolbenzodiazepine (PBD), duocarmycin, tubulysin, chalicheamicin, anthracycline, paclitaxel, vinblastine, alpha-amanitin, or a derivative, analogue or prodrug thereof. In some embodiments, the payload may comprise the small molecule drug, wherein the small molecule drug is MMAE, DM1, doxorubicin, duocarmycin, paclitaxel or a derivative, analogue or prodrug thereof.

In some embodiments, the payload may comprise the peptide or protein. In some embodiments, the payload may comprise the peptide or protein, wherein the peptide or protein comprises: a transcription factor, a bacterial toxin, a viral toxin, a protease, an RNAse, a DNAse, a proteolysis targeting chimera (PROTAC), or a fluorescent or colorimetric marker.

In some embodiments, the covalent conjugate may comprise the antibody. In some embodiments, the covalent conjugate may comprise the antibody derivative.

In some embodiments, the covalent conjugate may comprise an anti-HER2 antibody and the payload may be MMAE.

In some embodiments, the human cell has outer leaflet phosphatidylserine. In some embodiments, the human cell is a cancer cell. In some embodiments, the human cell is a pathogen-infected cell. In some embodiments, the human cell is an immune cell responsible for an autoimmune condition or disease.

Various embodiments of this disclosure relate to a method of increasing delivery of a payload to a human cell that has outer leaflet phosphatidylserine, the method comprising contacting the human cell with a covalent conjugate as defined herein, wherein the human cell expresses the cell surface epitope that the antibody or the antibody derivative specifically binds. Various embodiments of this disclosure relate to use of a covalent conjugate as defined herein for increasing delivery of a payload to a human cell that has outer leaflet phosphatidylserine, wherein the human cell expresses the cell surface epitope that the antibody or the antibody derivative specifically binds. The human cell may have outer leaflet phosphatidylserine. The human cell may be a cancer cell. The human cell may be a pathogen-infected cell. The human cell may be an immune cell responsible for an autoimmune condition or disease.

Various embodiments of this disclosure relate to a method of treating cancer in a human subject comprising administering to the human subject a covalent conjugate as defined herein, wherein the antibody or the antibody derivative of the covalent conjugate selectively binds tumor cells of the cancer, and wherein the payload of the covalent conjugate is toxic to human cells. Various embodiments of this disclosure relate to use of a covalent conjugate as defined herein for treatment of, or for manufacturing a medicament for treatment of, cancer in a human subject, wherein the antibody or the antibody derivative of the covalent conjugate selectively binds tumor cells of the cancer, and wherein the payload of the covalent conjugate is toxic to human cells. In some embodiments, the covalent conjugate may comprise an antibody or antibody-drug conjugate (ADC) selected from Table 2 or 3 and the cancer may be the cancer indicated in Table 2 or 3 as being treated by the antibody or ADC selected from Table 2 or 3.

Various embodiments of this disclosure relate to a method of treating an infection in a human subject, the method comprising administering to the human subject a covalent conjugate as defined herein, wherein the antibody or the antibody derivative of the covalent conjugate selectively binds pathogen-infected human cells, and wherein the payload of the covalent conjugate is toxic to human cells. Various embodiments of this disclosure are relate to use of a covalent conjugate as defined herein for treatment of, or for manufacture of a medicament for treatment of, an infection in a human subject, wherein the antibody or the antibody derivative of the covalent conjugate selectively binds pathogen-infected human cells, and wherein the payload of the covalent conjugate is toxic to human cells.

Various embodiments of this disclosure are related to a method of treating an autoimmune disease or condition in a human subject comprising administering to the human subject a covalent conjugate as defined herein, wherein the antibody or the antibody derivative of the covalent conjugate selectively binds immune cells causing the autoimmune disease or condition, and wherein the payload of the covalent conjugate is toxic to human cells. Various embodiments of this disclosure relate to use of a covalent conjugate as defined herein for treatment of, or for manufacture of a medicament for treatment of, an autoimmune disease or condition in a human subject, wherein the antibody or the antibody derivative of the covalent conjugate selectively binds immune cells causing the autoimmune disease or condition, and wherein the payload of the covalent conjugate is toxic to human cells.

This summary of the invention does not necessarily describe all features of the invention.

BRIEF DESCRIPTION OF THE DRAWINGS

These and other features of the invention will become more apparent from the following description in which reference is made to the appended drawings, as briefly described below.

FIG. 23 (Panel B) shows a graph comparing the viability of HL60 cells (human peripheral blood promyeloblast with CD33A on the cell surface) after 72 hrs treatment with anti-CD33A (Vadastuximab) ADC (MMAE) either linked to LL37 (i.e., anti-CD33A mAb-LL37-MMAE) or without LL37 (i.e., anti-CD33A mAb-MMAE).

FIG. 26A) or OVCAR3 (human ovary epithelial adenocarcinoma cell line with medium-to-high level of HER2+; FIG. 26B) after 72 hrs treatment with anti-HER2 ADC (MMAE) (i.e. anti-HER2 mAb-MMAE), or anti-HER2 ADC (MMAE) conjugated to either LL37 (i.e. anti-HER2 mAb-LL37-MMAE) or LL37 derivative PEP55 (i.e. anti-HER2 mAb-PEP55-MMAE).

(LC)2]), and compared to the HER2-specific ADCs that have two LL37 peptides covalently linked in a mAb (i.e., ant-HER2 mAb [(HC-MMAE)2; (LC-LL37)2]). The HER2-specific ADCs without LL37 (i.e., anti-HER2 mAb [(HC-MMAE)2; (LC)2], and anti-HER2 mAb [(HC)2; (LC)2]-MMAE4]) are included in the study for comparison and to highlight the LL37 enhancement.

Figure 28:
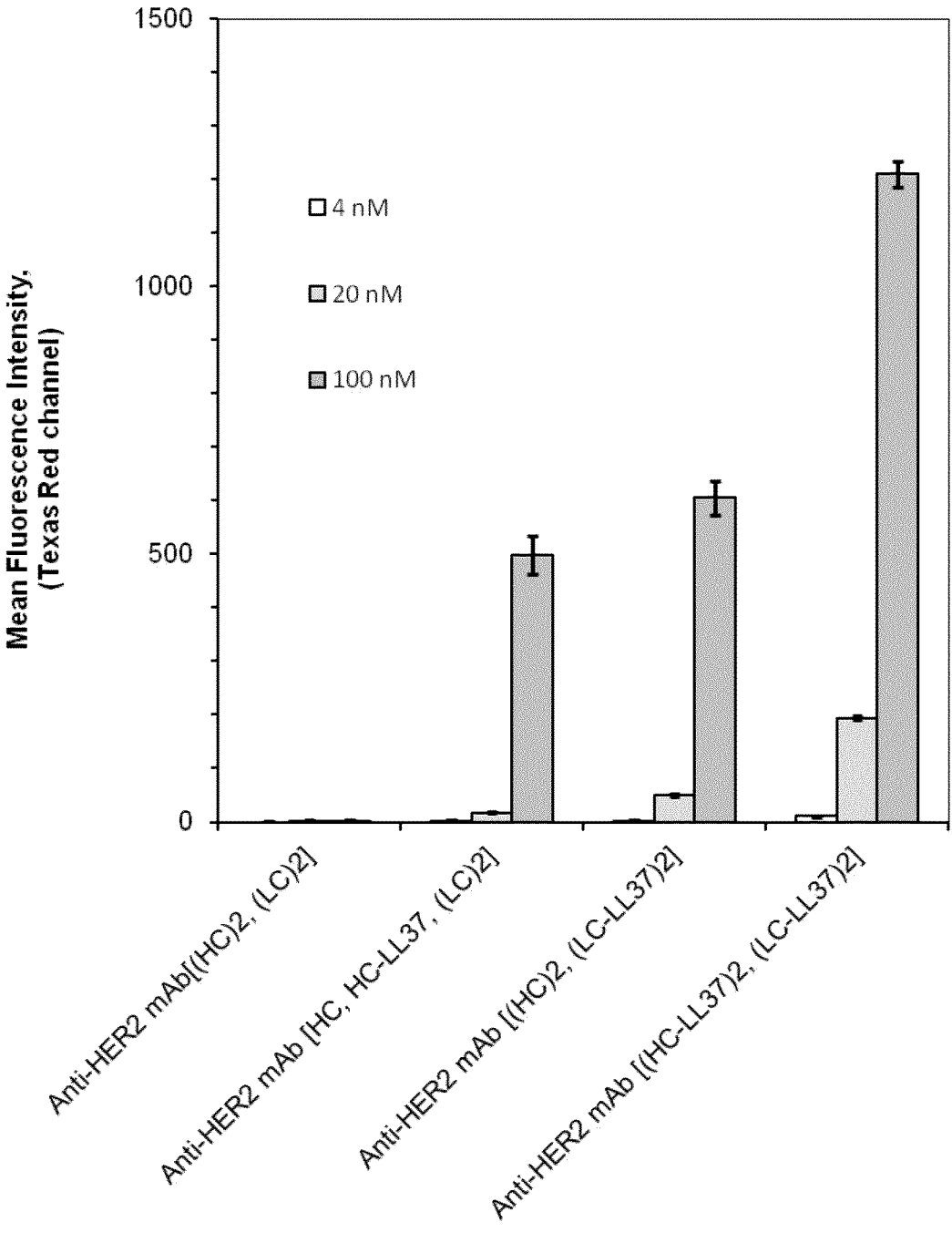

FIG. 28 shows a graph comparing various covalently linked mAb-LL37 protein-peptide conjugates. The anti-HER2 mAb with one covalently linked LL37 peptide per monomer (i.e., anti-HER2 mAB [(HC, HC-LL37); (LC)2]), the anti-HER2 mAb with two covalently linked LL37 peptides per monomer (i.e., anti-HER2 mAb [(HC)2; (LC-LL37)2)), and the anti-HER2 mAb with four covalently linked LL37 peptides per monomer (i.e., anti-HER2 mAb [(HC-LL37)2; (LC-LL37)2]).

Figure 29:
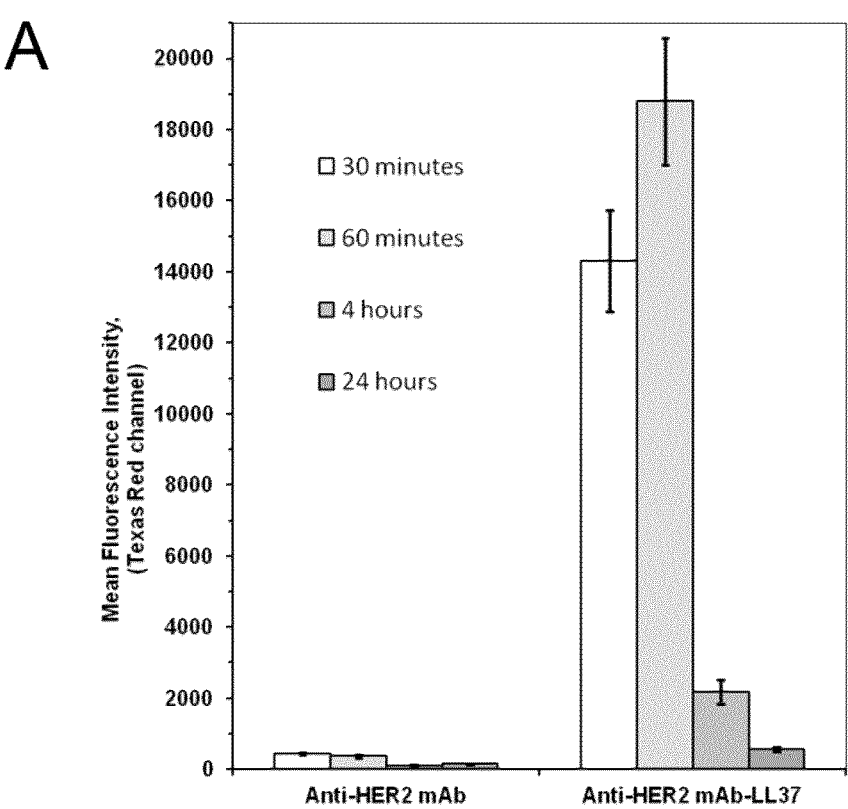
Figure 29:
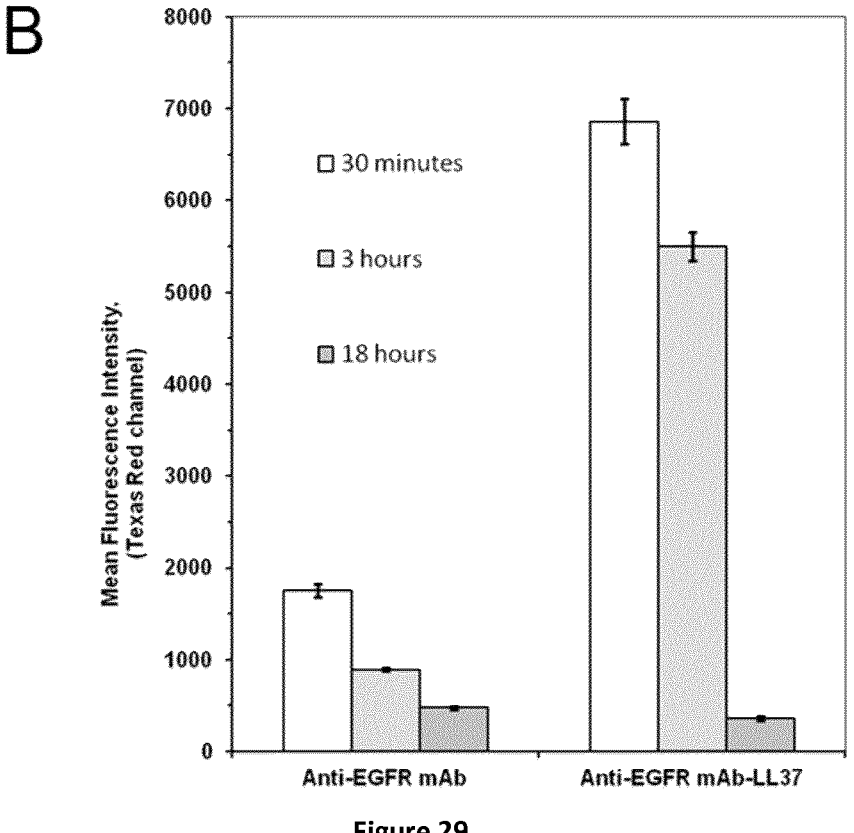

FIG. 29 shows two graphs comparing fluorescence of Z-RFP-bound antibodies overtime. In Panel A, anti-HER2 mAb is compared with LL37-conjugated anti-HER2 mAb (i.e. anti-HER2 mAb-LL37). In Panel B, anti-EGFR mAb is compared with LL37-conjugated anti-EGFR mAb (i.e. anti-EGFR mAb-LL37).

Figure 30:
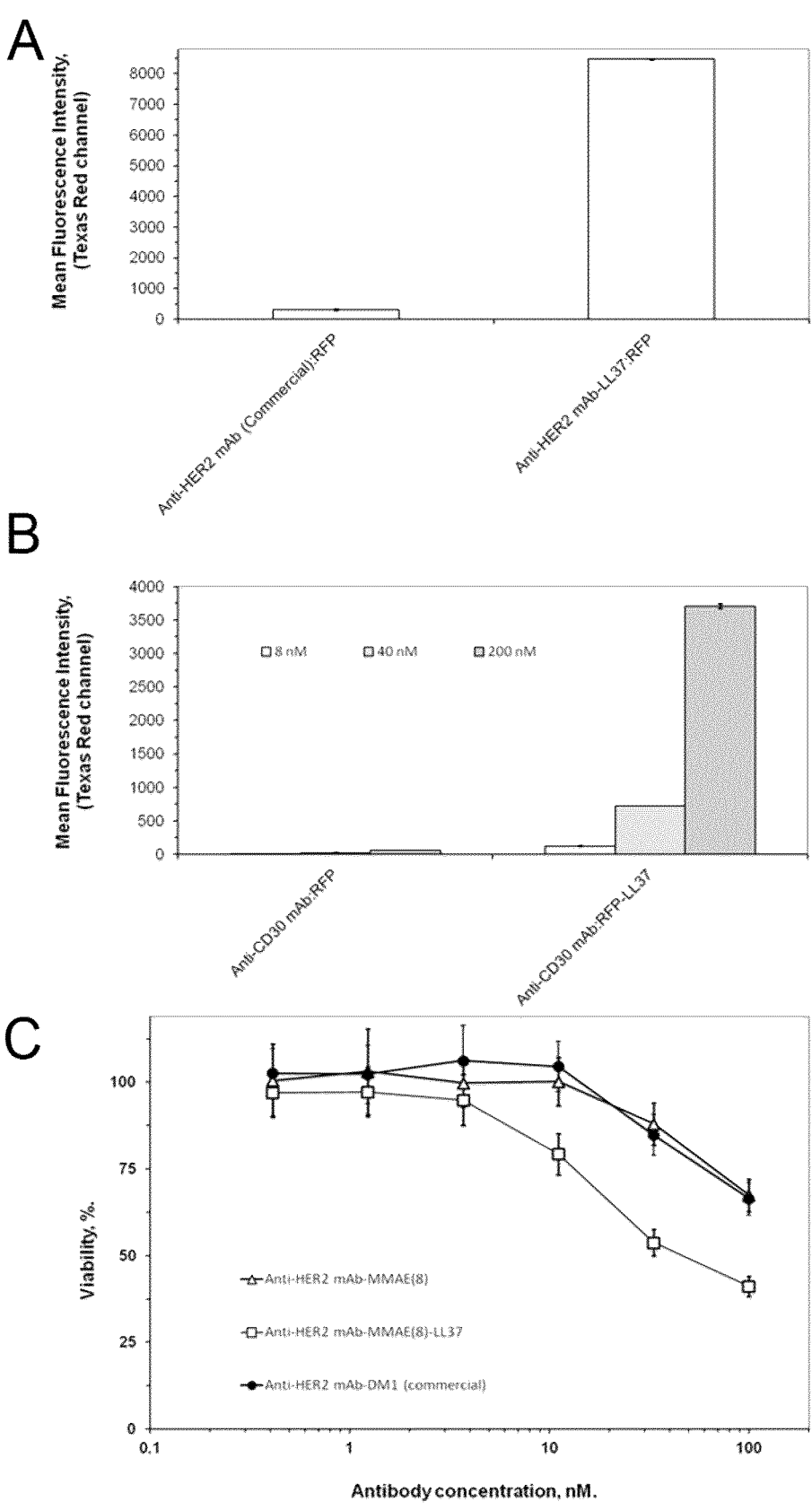

FIG. 30 shows five graphs highlighting the LL37-enhanced delivery of receptor-specific antibodies to the target cells displaying the antigenic receptors. In Panel A, LL37 enhances delivery of anti-HER2 mAb (i.e., comparison of anti-HER2 mAb to the anti-HER2 mAb-LL37 covalent conjugate) to the HEK293 that displays the recombinantly expressed HER2 extracellular domain. In Panel B, LL37 enhances delivery of an anti-CD30 mAb (Brentuximab) (i.e., comparison of anti-CD30 mAb to the anti-CD30 mAb: Z-RFP-LL37 complex) to the human iPSC. In Panel C, LL37 enhances delivery of anti-HER2 mAb to the human skin fibroblast cells. In Panel D, LL37 enhances delivery of anti-CD20 mAb (Ofatumumab) to RL, a CD20+ liquid tumor cell. In Panel E, LL37 enhances delivery of anti-CD3e mAb (Foralumab) to Jurkat, a CD3+ cell.

Figure 31:
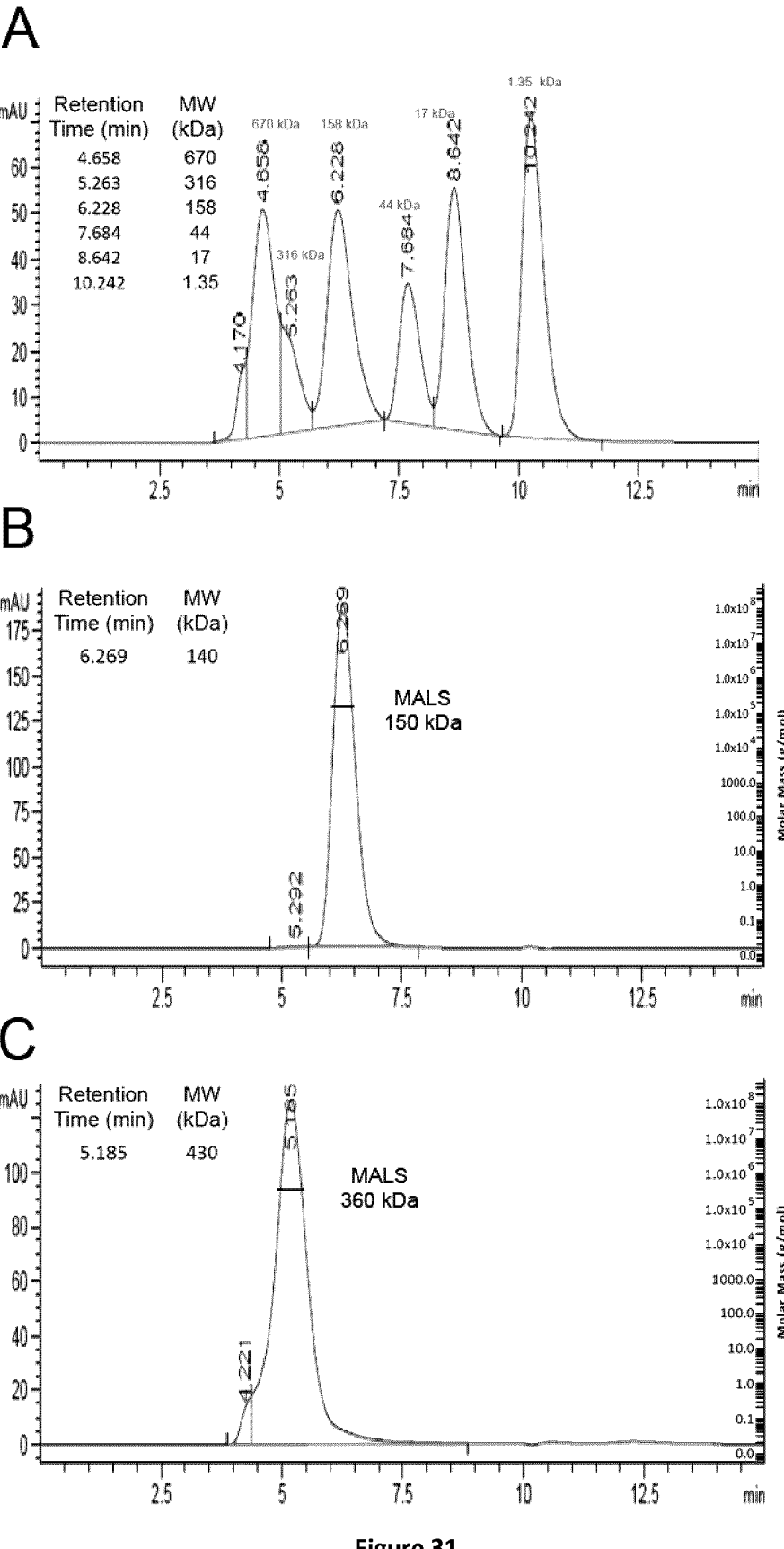

FIG. 31 shows three graphs. Panel A shows the size exclusion chromatography (SEC) calibration with reference protein standards. Panel B shows the SEC-MALS of anti-HER2 mAb. Panel C shows the SEC-MALS of anti-HER2 mAb-LL37.

Figure 32:
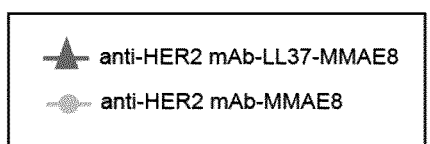
Figure 32:
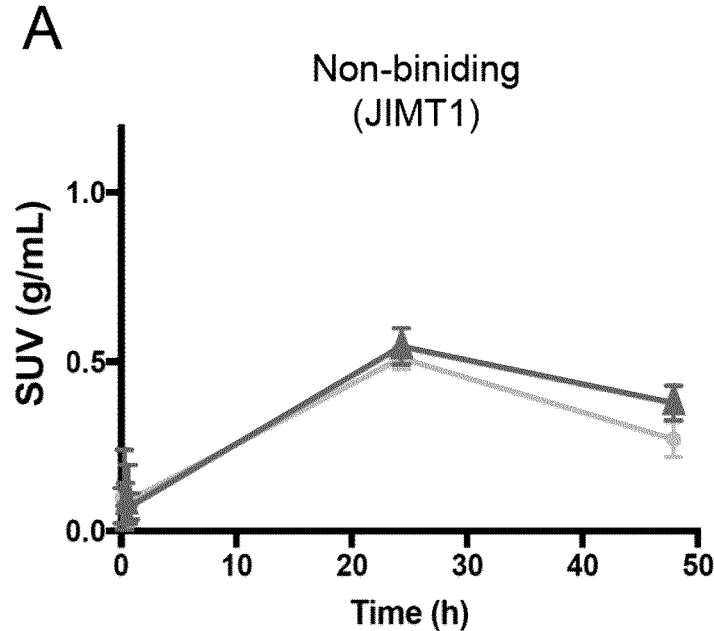
Figure 32:
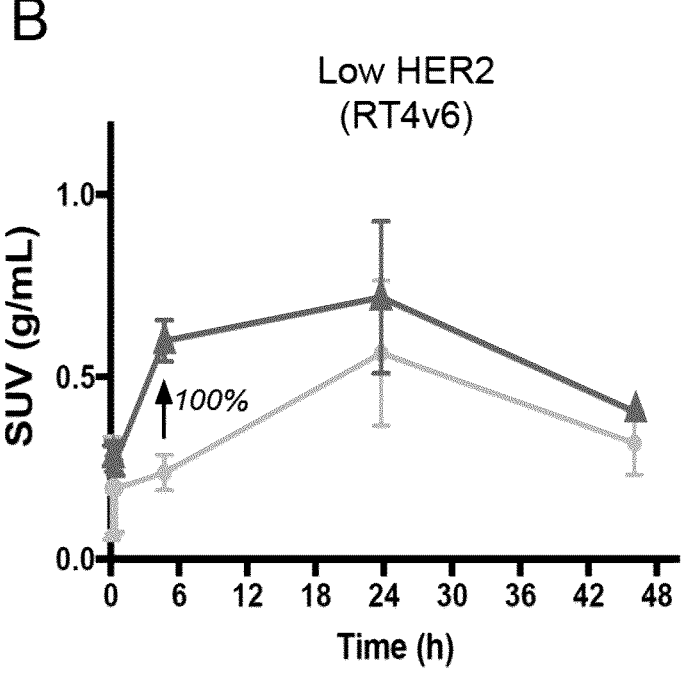
Figure 33:
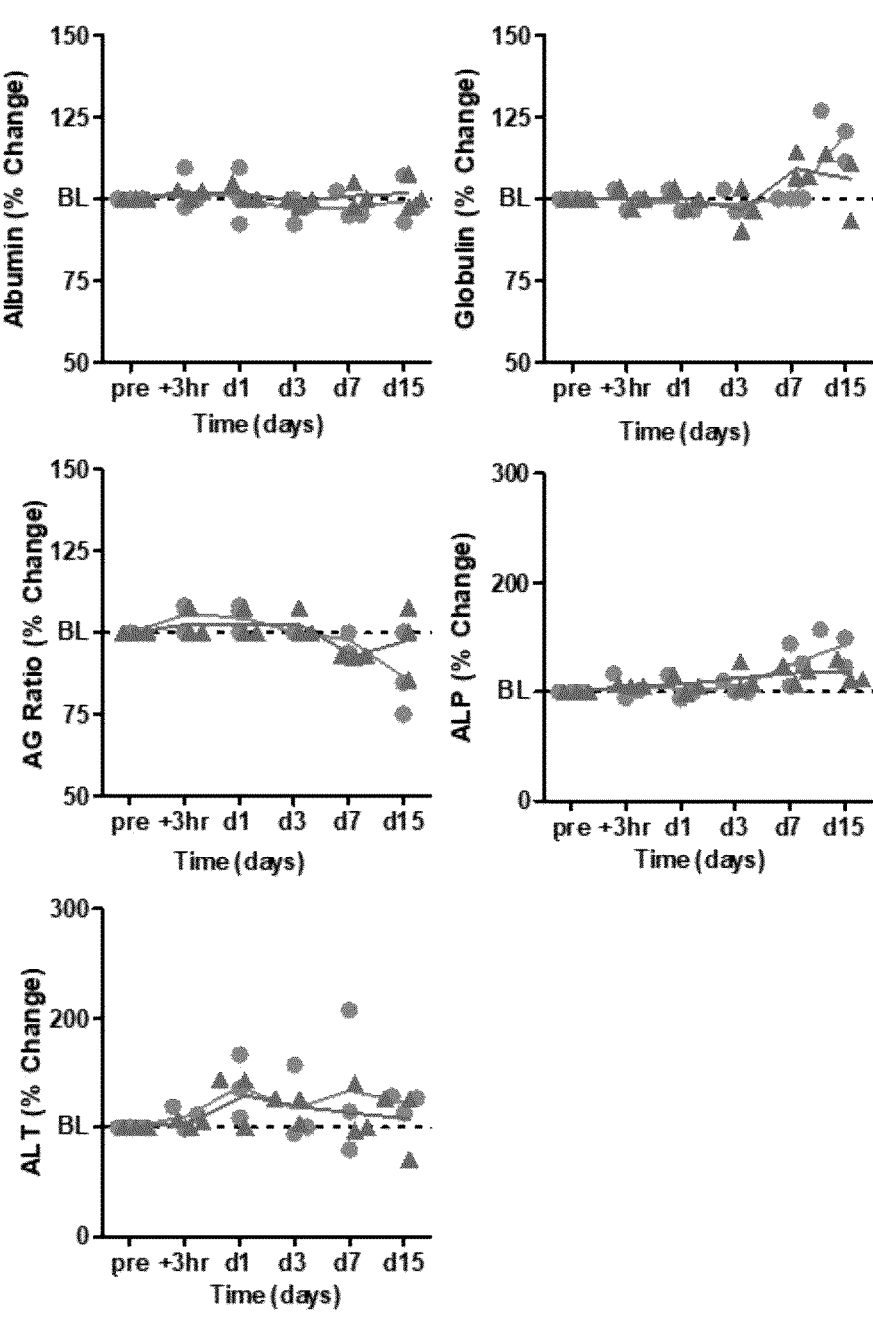
Figure 34:
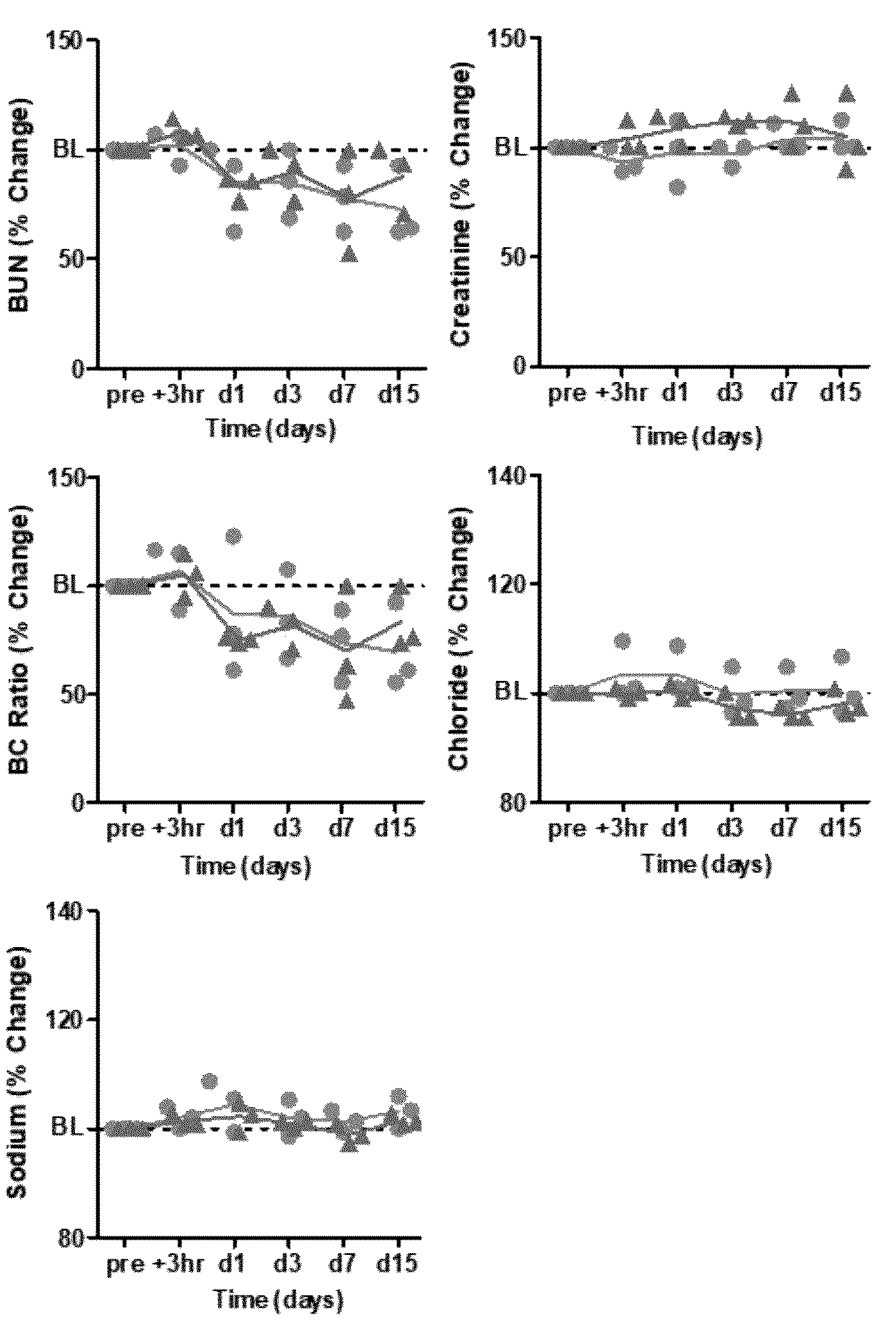
Figure 35:
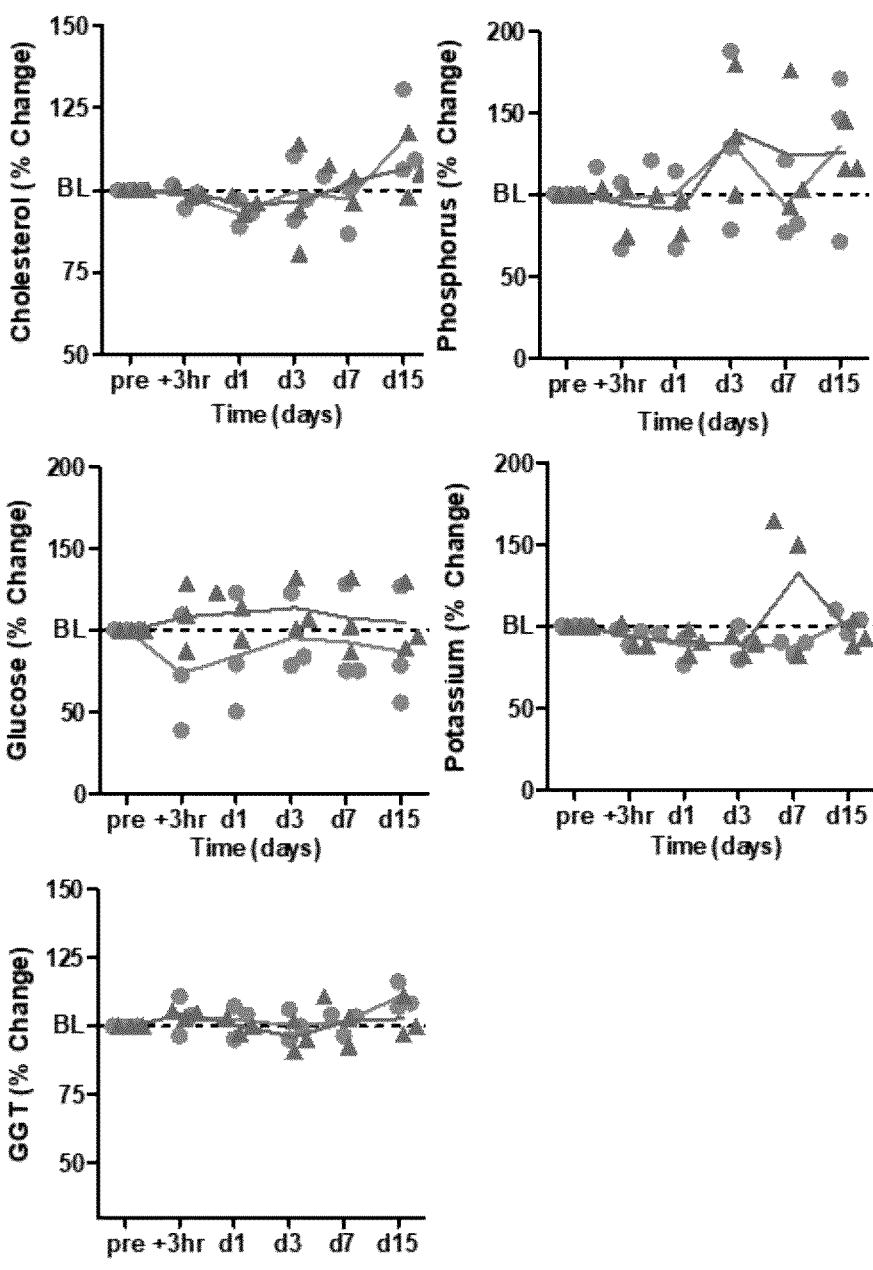
Figure 36:
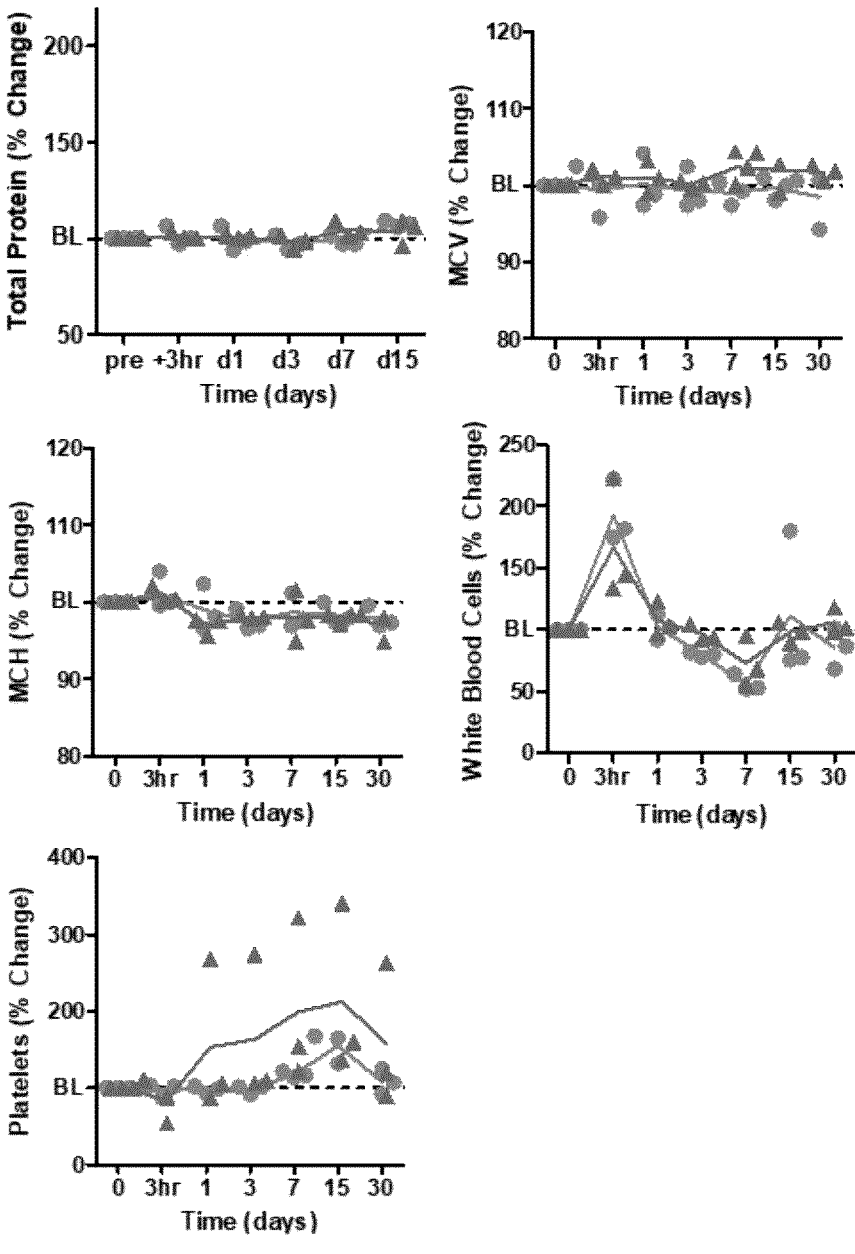
Figure 37:
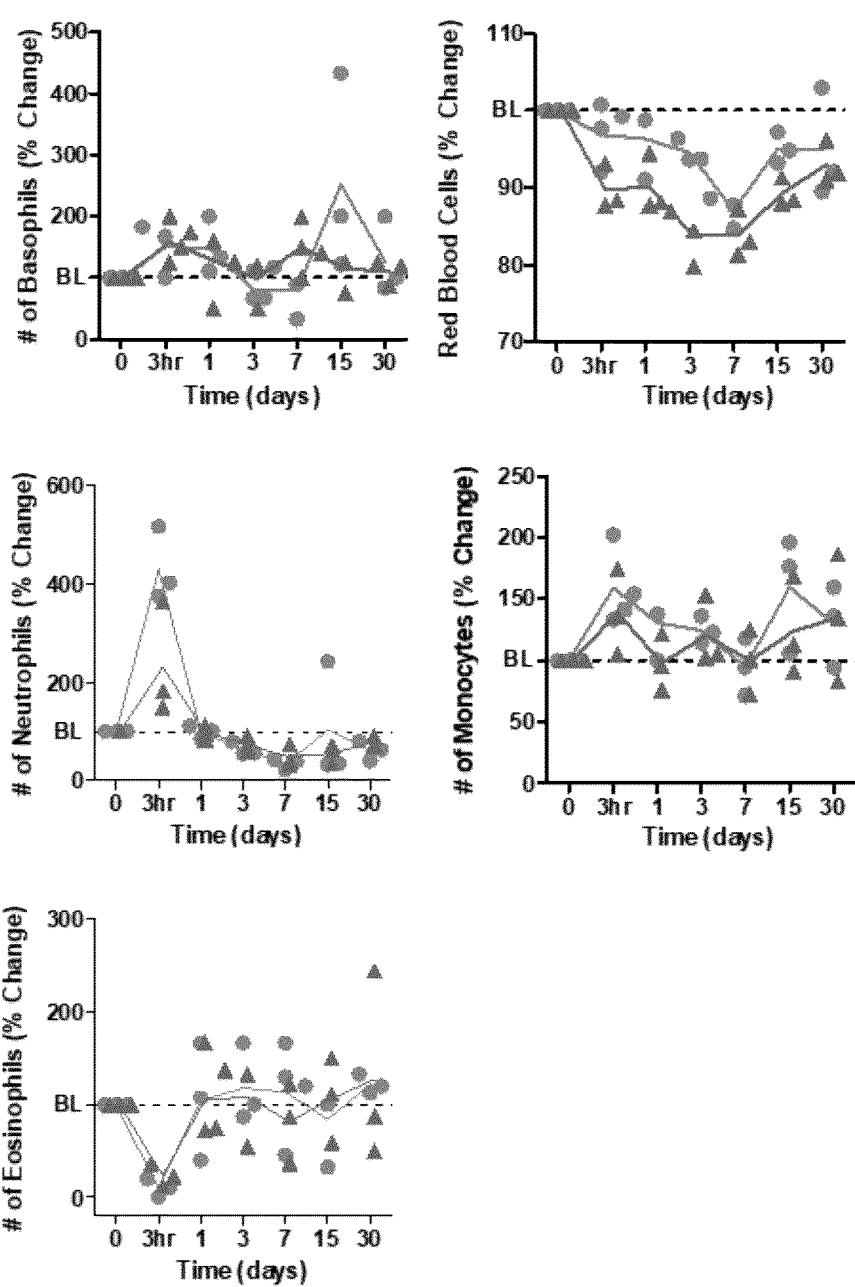

FIG. 32 shows two graphs. Panel A shows in vivo safety with LL37-enhanced antibody delivery in mice, and the absence of non-specific delivery enhancement of LL37. Panel B shows the enhanced in-vivo efficacy with LL37, and LL37 doubles (i.e., increases by 100%) the delivery and retainment of anti-HER2 mAb to the mice bearing the human RT4v6 xenograft tumor.

FIGS. 33-37 are composite graphs showing that LL37-linked ADC [anti-HER2 mAb-LL37-(MMAE)s, MMAE DAR 8] and conventional ADC [anti-HER2 mAb-(MMAE)s, MMAE DAR 8] have very similar safety and toxicology profiles with respect to their pharmacokinetic endpoints, biochemistry, hematology, and cell differentials in monkeys.

Figure 38:
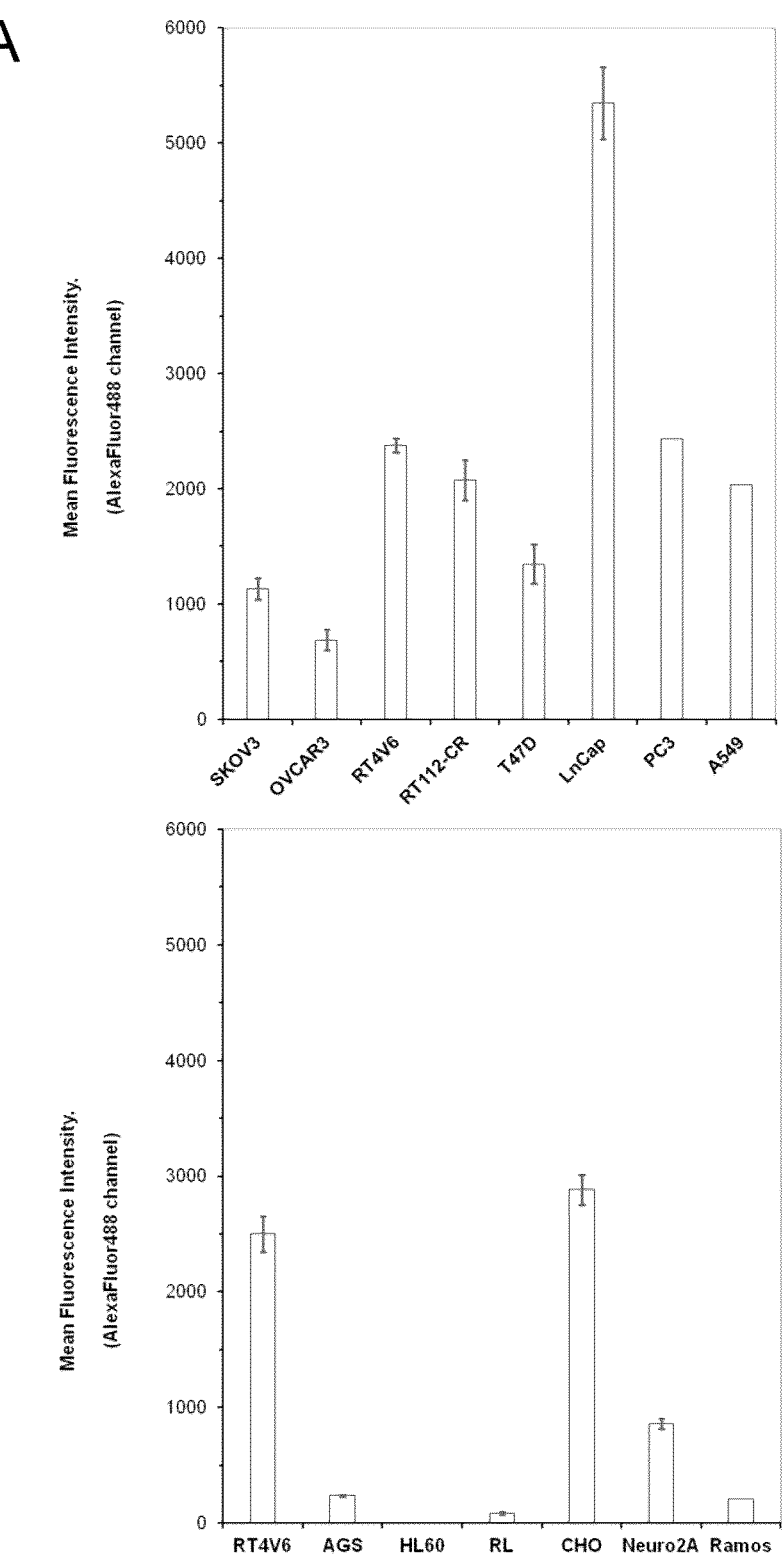
Figure 38:
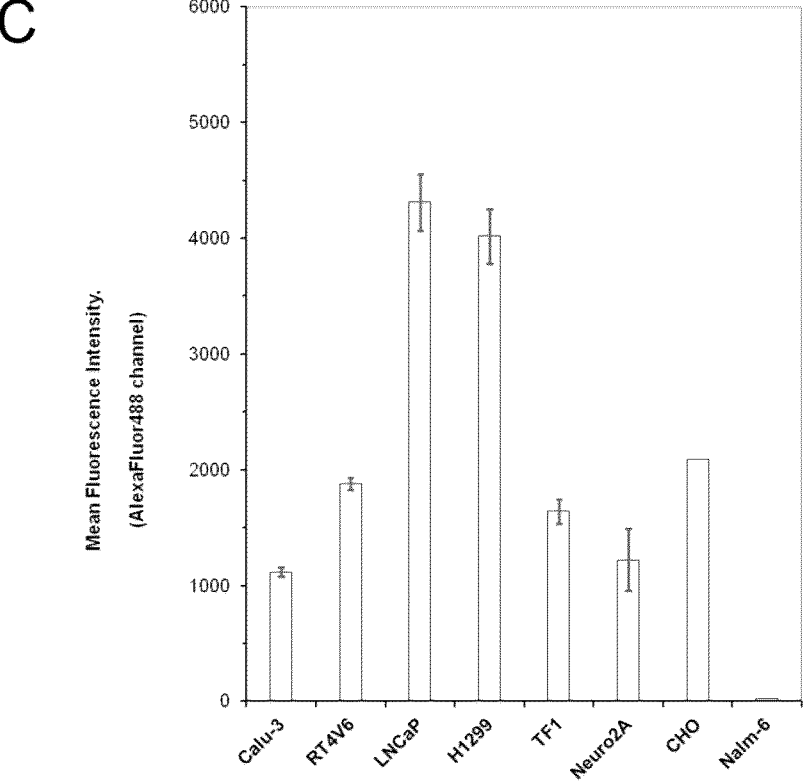

FIG. 38 shows three graphs (Panels A, B and C) comparing the relative level of phosphatidylserine (PS) on various cell types (high, medium or low PS-expressing cell lines or undetectable, i.e., HL60), measured using the fluorescent labeled PS-binding protein, Annexin V-AlexaFluor488, in a fluorescence-activated cell sorting (FACS) instrument.

Figure 39A:
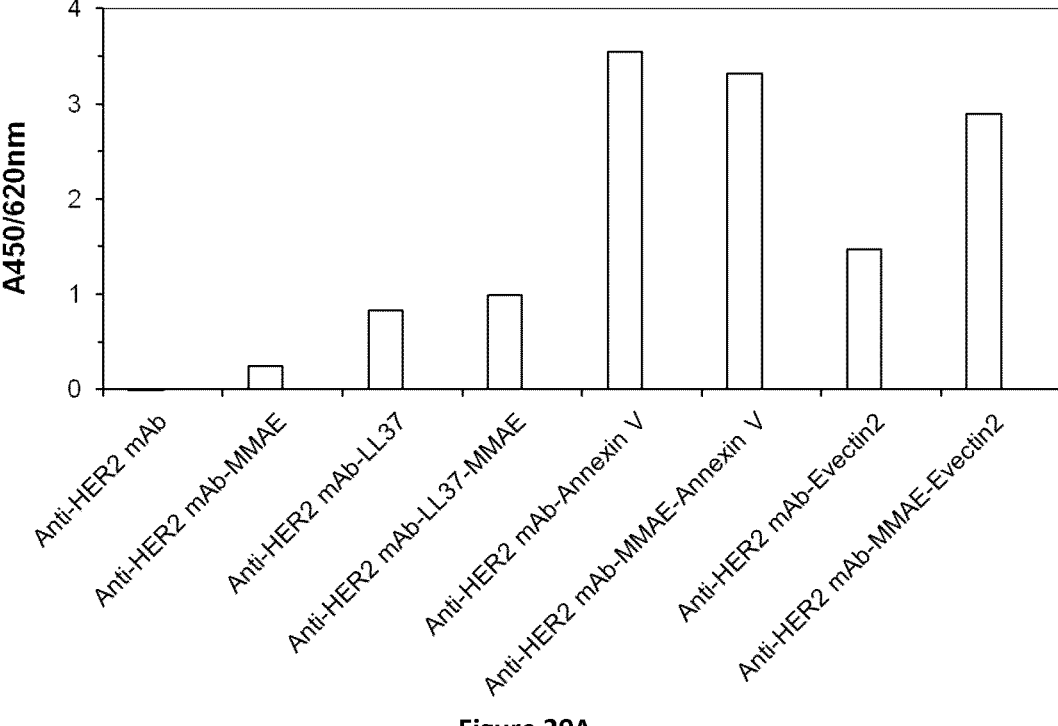
Figure 39B:
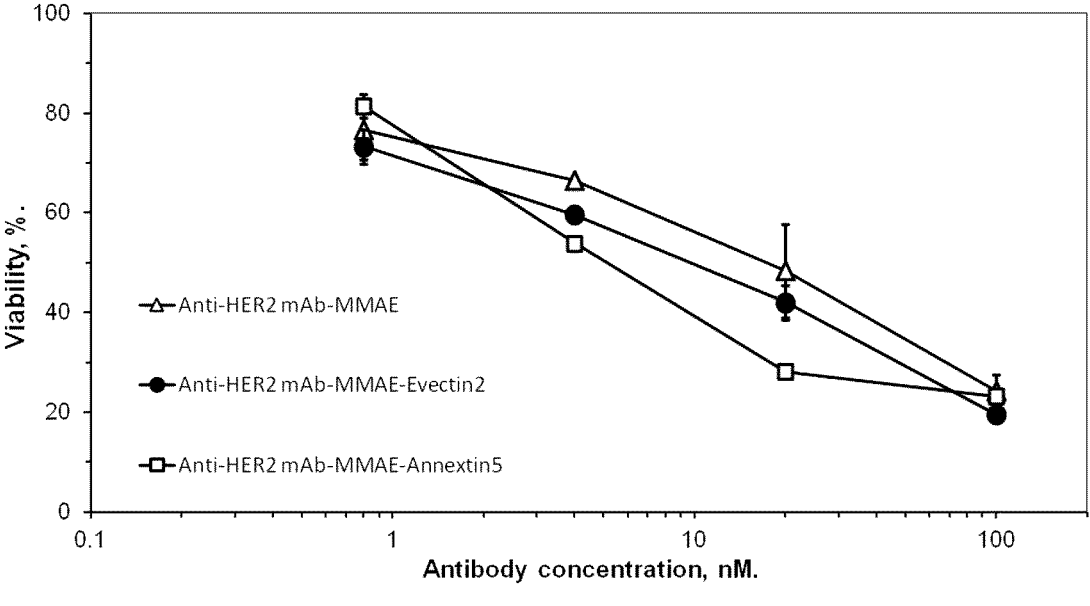

FIG. 39 shows two graphs. Panel A shows that covalent conjugates of phosphatidylserine (PS)-binding proteins (i.e., Annexin V, Evectin2) to anti-HER2 mAb and its ADC have enhanced binding to phosphatidylserine. Panel B shows that covalent conjugates ADC (anti-HER2 mAb-MMAE8)

linked to PS-binding protein has only minimally improved (i.e., comparable) drug efficacy when compared to the same ADC not linked to PS-binding protein.

Figure 40A:
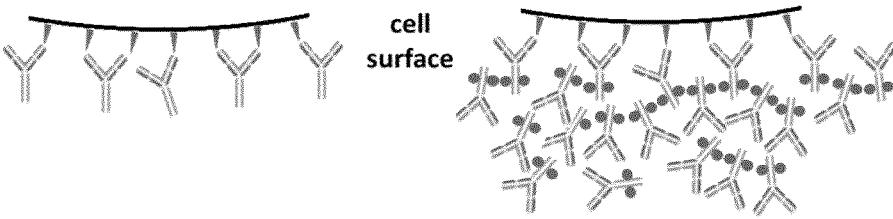

FIG. 40A is a conceptual schematic showing a mechanism of action for the enhancement in antibody/payload delivery to the target cell due to conjugation with LL37 or LL37-derived polypeptides. These conjugated polypeptides promote the multimerization of antibody (or antibody derivatives) on the target cell surface (i.e., beyond the saturation limit of receptors). FIG. 40B shows fluorescent microscope images of the graph in FIG. 8, demonstrating that intense antibody decoration on cell surface can be visualized.

DETAILED DESCRIPTION

I. General Definitions

As used herein, the terms "comprising," "having", "including" and "containing," and grammatical variations thereof, are inclusive or open-ended and do not exclude additional, unrecited elements and/or method steps. The term "consisting essentially of" when used herein in connection with a composition, use or method, denotes that additional elements and/or method steps may be present, but that these additions do not materially affect the manner in which the recited composition, method or use functions. The term "consisting of" (when used) herein in connection with a composition, use or method, excludes the presence of additional elements and/or method steps. A composition, use or method described herein as comprising certain elements and/or steps may also, in certain embodiments consist essentially of those elements and/or steps, and in other embodiments consist of those elements and/or steps, whether or not these embodiments are specifically referred to. A use or method described herein as comprising certain elements and/or steps may also, in certain embodiments consist essentially of those elements and/or steps, and in other embodiments consist of those elements and/or steps, whether or not these embodiments are specifically referred to.

A reference to an element by the indefinite article "a" does not exclude the possibility that more than one of the elements is present, unless the context clearly requires that there be one and only one of the elements. The singular forms "a", "an", and "the" include plural referents unless the content clearly dictates otherwise. The use of the word "a" or "an" when used herein in conjunction with the term "comprising" may mean "one," but it is also consistent with the meaning of "one or more," "at least one" and "one or more than one."

Unless indicated to be further limited, the term "plurality" as used herein means more than one, for example, two or more, three or more, four or more, and the like.

As used herein, the term "about" refers to an approximately +/-10% variation from a given value.

As used herein, the recitation of numerical ranges by endpoints includes all numbers subsumed within that range including all whole numbers, all integers and all fractional intermediates (e.g., 1 to 5 includes 1, 1.5, 2, 2.75, 3, 3.80, 4, and 5 etc.).

Unless otherwise specified, "certain embodiments", "various embodiments", "an embodiment" and similar terms includes the particular feature(s) described for that embodiment either alone or in combination with any other embodiment or embodiments described herein, whether or not the other embodiments are directly or indirectly referenced and regardless of whether the feature or embodiment is described in the context of a method, product, use, composition, protein, cell surface binding conjugate, nucleic acid, plasmid, cell, etcetera. None of Sections I, II, III and IV should be viewed as independent of the other Sections, but instead should be interpreted as a whole. Unless otherwise indicated, embodiments described in individual sections may further include any combination of features described in the other sections. Definitions presented for terms in any section(s) may be incorporated into other section(s) as a substitute or alternative definition.

As used herein, a "polypeptide" is a chain of two or more amino acid residues (e.g. 2, 10, 50, 100, 200 or any other number of residues) linked by peptide bonds, including a peptide or a protein chain. A "peptide", "polypeptide" or "protein" may refer to a naturally occurring amino acid polymer (or polymers in the case of multichain proteins) or may refer to amino acid polymer(s) in which one or more of the amino acid residues is an artificial chemical analogue of a corresponding naturally occurring amino acid or is a completely artificial amino acid with no obvious natural analogue. Naturally occurring amino acids are those encoded by the genetic code (i.e. alanine, arginine, glycine, asparagine, aspartic acid, cysteine, glutamine, glutamic acid, serine, threonine, histidine, lysine, methionine, proline, valine, isoleucine, leucine, tyrosine, tryptophan and phenylalanine), as well as those amino acids that are later modified (e.g. hydroxyproline, γ-carboxyglutamate, 0-phosphoserine and the like). The artificial amino acid can be a close analogue of one of the twenty natural amino acids, an amino acid mimetic, or a compound that introduces a completely new functionality and chemistry. Amino acid analogues have the same general chemical structure as a naturally occurring amino acid, i.e. a carbon bound to a hydrogen, a carboxyl group (or carbonyl), an amino group (or amide), and an R group (e.g., homoserine, ornithine, 2,4-diaminobutanoic acid, 2,3-diaminopropionic acid, norvaline, norleucine, methionine sulfoxide, methionine methyl sulfonium, methylated R-groups, and the like). Such analogues have modified R groups (e.g., norleucine) or modified peptide backbones (e.g. β-amino acid instead of α-amino acid, or replacement of carbonyl and/or amide groups with esters, sulfides or alkyls/alkylenyls), but otherwise retain the same basic chemical structure as a naturally occurring amino acid. Amino acid mimetics refer to chemical compounds that have a structure that is different from the general chemical structure of an amino acid, but that functions in a manner similar to a naturally occurring amino acid. The incorporation of non-natural amino acids can be accomplished by known chemical methods including without limitation solid-phase peptide synthesis or native chemical ligation, or by biological methods such as, but not limited to, in vivo incorporation of the non-natural amino acid by expression of the cloned gene in a suitable host (e.g. see Young and Schultz, 2010, *J. Biol. Chem.* 285: 11039-11044). In some cases (and in some embodiments) a polypeptide defined herein (including peptides and longer polypeptides) may incorporate one or more (e.g. 1, 2, 4, 5, 6, 7, 8, 9, 10, or more than 10) non-peptide bonds (e.g. an isopeptide bond, a —C—C(O)— bond, or the like) or may have one or more peptide-bonds replaced with non-peptide bonds (e.g. a —C—C(O)— bond or the like). As used herein, a "peptide" may comprise 100 amino acids or less than 100 amino acids, e.g. 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids.

As used herein, a "protein" comprises one or more polypeptides and may or may not further comprise non-polypeptide elements, including covalently or non-covalently attached co-factors, metals, organic compounds, lipids, carbohydrates, nucleic acids and/or other biomolecules or molecular entities. As such, a "region", "portion" or "domain" of a protein may consist or comprise of such non-polypeptide elements. For example, a "protein" as used herein includes protein-containing molecular complexes, antibody-drug conjugates and the like. A protein may comprise 1, 2, 3, 4, 5, 6, 7, 8, 9, 10 or more than 10 polypeptide chains in covalent and/or non-covalent association. Non-limiting examples of non-covalent interaction include hydrogen bonds, hydrophobic interactions and/or electrostatic interactions. A non-limiting example of a covalent bond between polypeptides is a disulfide bridge.

"Conservatively modified variants", "conservative substitute", and similar phrases apply to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations", which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As for amino acid sequences, one of skill in the art will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. The term "substituted" or "substitute" in the context of peptides and polypeptides (e.g. in the term "conservative substitute amino acid") means replacement of one amino acid in the peptide/polypeptide chain for another. Conservative substitution tables providing functionally similar amino acids are well known in the art. Such conservatively modified variants are in addition to and do not exclude polymorphic variants, interspecies homologues and alleles.

Furthermore, any substitution of a natural amino acid with a non-natural amino acid that maintains approximate size, charge and hydrophobicity/polarity would be considered a conservative substitution, particularly for non-conserved residues or when the substituted residue is in a non-structured region or when the non-natural amino acid would be expected to maintain integrity of a secondary structural element (e.g. alpha helix, beta sheet, etc.). Particular conservative amino acid substitutions are listed elsewhere in this document.

There are many cases where D-amino acids may be substituted for L-amino acids without destroying the function of a peptide or polypeptide, particularly where the function does not require binding with a chiral binding partner. Indeed, for a right-handed alpha helix made up of 100% L-amino acids, replacement of 100% of the L-amino acids with their D-amino acid counterparts would produce a left-handed alpha helix (its mirror image) and retain all of the physico-chemical properties of the right-handed alpha helix, e.g. charge, size, polarity/hydrophobicity, aromaticity. Substitution of L-amino acids at known proteolytic sites within a peptide/polypeptide with D-amino acids has been shown to increase stability by reducing the ability of pro-teolytic enzymes to recognize the D-substituted cleavage site. Accordingly, substitution of L-amino acid(s) in prote-olytic sites with D-amino acid(s), substitution of L-amino acid(s) within non-structured regions with D-amino acid(s), substitution of L-amino acid(s) at termini of secondary structural regions with D-amino acid(s), and 100% substi-tution of L-amino acid(s) with D-amino acid(s), and the like, would be considered conservative substitutions.

An amino acid sequence which comprises at least 50, 60, 70, 75, 80, 81, 82, 83, 84, 85, 86, 87, 88, 89, 90, 91, 92, 93, 94, 95, 96, 97, 98, 99 or 100% amino acid sequence identity to a specified reference sequence (e.g. a full-length reference sequence) is also a "conservatively modified variant" so long as it retains a specified activity or fraction of said activity. Sequence identity can be determined using the methods described herein, for example, aligning two sequences using BLAST, ALIGN, or another alignment software or algorithm known in the art using default param-eters.

A "non-conservative substitute" amino acid refers to any substituted (i.e. replaced) amino acid that is not a conser-vative substitution as specified above or as alternatively or further specified.

II. Covalent Antibody-Payload Conjugates Further Comprising LL37-Derived Polypeptides The present disclosure relates to novel covalent conju-gates comprising an antibody or an antibody derivative, a payload, and LL37-derived polypeptides. The antibody or antibody derivative specifically binds to a cell surface epitope of a human cell. The payload comprises a small molecule drug or a peptide or protein (other than the LL37-derived polypeptide). The LL37-derived polypeptides comprise a first LL37-derived polypeptide and a second LL37-derived polypeptide.

When excluding LL37 itself, i.e. a peptide found in nature, the present disclosure also relates to novel peptides or proteins comprising LL37-derived polypeptides as dis-closed herein.

As used herein, the term "conjugate" includes covalent attachment, whether directly, e.g. without a linker, or indi-rectly attached, such as through a linker and/or an interme-diary domain or domains. The term "covalent conjugate" means that that each component of the conjugate is cova-lently attached to at least one other component of the conjugate. As used herein, the terms "linked", "conjugated", "coupled" and similar terms are used interchangeably to refer to covalent attachment, including both direct covalent attachment (i.e. without an intermediary domain(s)) and indirect covalent attachment (i.e. through an intermediary domain(s) covalently connected to the molecules/domains that are indirectly linked, conjugated or coupled; e.g. a linker or spacer). Without limitation, in some embodiments, the first LL37-derived polypeptide and the second LL37-de-rived polypeptide form a covalent conjugate with the anti-body or the antibody derivative through: peptide bonds; disulfide linkages; isopeptide bonds; and/or 1,2,3-triazole linkages. In some embodiments, both of the first LL37-derived polypeptide and the second LL37-derived polypep-tide are conjugated to the antibody or the antibody derivative through: peptide bonds; disulfide linkages; isopeptide bonds; or 1,2,3-triazole linkages. In other embodiments, one or both of the first LL37-derived polypeptide and the second LL37-derived polypeptide may be conjugated to a payload (s) conjugated to the antibody or the antibody derivative, or the payload may be conjugated to LL37-derived polypep-tides conjugated to the antibody or antibody derivative.

LL37 is a human alpha defensin derived from the active portion of hCAP-18 protein, and is the only cathelicidin-derived antimicrobial peptide found in humans (see, Durr et al. (2006), *Biochim. Biophys. Acta,* 1758, 1408). LL37 is produced mainly by phagocytic leukocytes and epithelial cells in high concentration during the inflammatory process (see, Agerberth et al. (2000), *Blood,* 96, 3086; Bowdish et al. (2005), *Curr. Protein Pept. Sci.,* 6, 35; Hase et al. (2003), *Gastroenterology,* 125, 1613; Woo et al. (2003), *Arch Oto-laryngol. Head NeckSurg.* 129, 211). During an infection or inflammatory processes, phagocytic leukocytes and epithe-lial cells secrete LL37, resulting in a very high local con-centration of LL37 (see, Davidson et al. (2004), *J. Immunol.* 172, 1146; Frohm et al. (1997), *J. Biol. Chem.* 272, 15258; Dorschner et al. (2001) *J. Invest. Dermatol.* 117, 91), which is effective to kill a variety of microbes by destabilizing the bacterial membrane (see, Duplantier and van Hoek (2013), *Frontiers in Immunology,* 4, article 143). This antimicrobial activity is thought to occur initially through weak membrane interactions and, eventually, through the formation of fibrils as the concentration of LL37 increases (see, Sancho-Vaello et al. (2017) *Sci. Rep.* 7, 15371; Shahmiri et al. (2016), *Sci. rep.* 6, article 38184). The structure and biochemical prop-erties of LL37 favors interaction with the bacterial mem-brane over the human cell membrane. The nature of the mammalian cell membrane (including a relatively higher cholesterol content) limits interaction with LL37 (see, Bonucci et al. (2015) *Biochemistry,* 54, 6760) at a low concentration. LL37 is therefore nontoxic to mammalian cells unless present in very high concentrations (see, Johan-sson et al. (1998) *J. Biol. Chem.,* 273, 3718). LL37 has an alpha helical structure (see, Sancho-Vaello et al. (2017) *Sci. Rep.* 7, 15371). Full-length LL37 is a 37 residue peptide (SEQ ID NO:1) having a core alpha helical region of residues 13-29.

In some embodiments, the first LL37-derived polypeptide and the second LL37-derived polypeptide each comprises an LL37-derived amino acid sequence or sequences, wherein each of the LL37-derived amino acid sequence or sequences independently comprise the following, or substitution vari-ants thereof (defined further below):

residues 13-37 of full length LL37 (i.e. residues 13-37 of SEQ ID NO: 1, or the full length of SEQ ID NO: 14); or SEQ ID NO: 111 (i.e. the inverse sequence of SEQ ID NO: 14); or a fragment of SEQ ID NO: 14 or 111 having consecutive deletions at either or both of the N- and C-termini up to a total deletion of at most 8 amino acids (e.g.: deletion of 1, 2, 3, 4, 5, 6, 7 or 8 amino acids from the N-terminus; or deletion of 1, 2, 3, 4, 5, 6, 7 or 8 amino acids from the C-terminus; or deletion of a total of 1, 2, 3, 4, 5, 6, 7, or 8 amino acids from a combination of deletions to both the N- and C-termini, including ratios of N-terminal:C-terminal deletions of 1:1, 1:2, 1:3, 1:4, 1:5, 1:6, 1:7, 2:1, 2:2, 2:3, 2:4, 2:5, 2:6, 3:1, 3:2, 3:3, 3:4, 3:5, 4:1, 4:2, 4:3, 4:4, 5:1, 5:2, 5:3, 6:1, 6:2, and 7:1); or a plurality (e.g. 2, 3, 4, 5, or more than 5) of fragments of SEQ ID NO: 14 and/or SEQ ID NO: 111, each fragment of the plurality of fragments independently having consecutive deletions at either or both of the N- and C-termini up to a total deletion of at most 10 amino acids (e.g.: deletion of 1, 2, 3, 4, 5, 6, 7, 8, 9 or 10 amino acids from the N-terminus; or deletion of 1, 2, 3, 4, 5, 6, 7, 8, 9 or 10 amino acids from the C-terminus; or deletion of a total of 1, 2, 3, 4, 5, 6, 7, 8, 9 or 10 amino acids from a combination of deletions to both the N- and C-termini, including ratios of N-terminal:C-terminal deletions of 1:1, 1:2, 1:3, 1:4, 1:5, 1:6, 1:7, 1:8, 1:9, 2:1, 2:2, 2:3, 2:4, 2:5, 2:6, 2:7, 2:8, 3:1, 3:2, 3:3, 3:4, 3:5, 3:6, 3:7, 4:1, 4:2, 4:3, 4:4, 4:5, 4:6, 5:1, 5:2, 5:3, 5:4, 5:5, 6:1, 6:2, 6:3, 6:4, 7:1, 7:2, 7:3, 8:1, 8:2, and 9:1; each fragment in the plurality may have the same or a different pattern of deletions).

In some embodiments, the first LL37-derived polypeptide and the second LL37-derived polypeptide each comprises an LL37-derived amino acid sequence or sequences, wherein each of the LL37-derived amino acid sequence or sequences independently comprise the following, or substitution variants thereof (defined further below):

residues 13-37 of full length LL37 (i.e. residues 13-37 of SEQ ID NO: 1, or the full length of SEQ ID NO: 14); or a fragment of SEQ ID NO: 14 having consecutive deletions at either or both of the N- and C-termini up to a total deletion of at most 8 amino acids (e.g.: deletion of 1, 2, 3, 4, 5, 6, 7 or 8 amino acids from the N-terminus; or deletion of 1, 2, 3, 4, 5, 6, 7 or 8 amino acids from the C-terminus; or deletion of a total of 1, 2, 3, 4, 5, 6, 7, or 8 amino acids from a combination of deletions to both the N- and C-termini, including ratios of N-terminal:C-terminal deletions of 1:1, 1:2, 1:3, 1:4, 1:5, 1:6, 1:7, 2:1, 2:2, 2:3, 2:4, 2:5, 2:6, 3:1, 3:2, 3:3, 3:4, 3:5, 4:1, 4:2, 4:3, 4:4, 5:1, 5:2, 5:3, 6:1, 6:2, and 7:1); or a plurality (e.g. 2, 3, 4, 5, or more than 5) of fragments of SEQ ID NO: 14, or a plurality of fragments comprising at least one fragment of SEQ ID NO: 14 plus at least one fragment of SEQ ID NO: 111, each fragment of the plurality of fragments independently having consecutive deletions at either or both of the N- and C-termini up to a total deletion of at most 10 amino acids (e.g.: deletion of 1, 2, 3, 4, 5, 6, 7, 8, 9 or 10 amino acids from the N-terminus; or deletion of 1, 2, 3, 4, 5, 6, 7, 8, 9 or 10 amino acids from the C-terminus; or deletion of a total of 1, 2, 3, 4, 5, 6, 7, 8, 9 or 10 amino acids from a combination of deletions to both the N- and C-termini, including ratios of N-terminal:C-terminal deletions of 1:1, 1:2, 1:3, 1:4, 1:5, 1:6, 1:7, 1:8, 1:9, 2:1, 2:2, 2:3, 2:4, 2:5, 2:6, 2:7, 2:8, 3:1, 3:2, 3:3, 3:4, 3:5, 3:6, 3:7, 4:1, 4:2, 4:3, 4:4, 4:5, 4:6, 5:1, 5:2, 5:3, 5:4, 5:5, 6:1, 6:2, 6:3, 6:4, 7:1, 7:2, 7:3, 8:1, 8:2, and 9:1; each fragment in the plurality may have the same or a different pattern of deletions).

The first LL37-derived polypeptide and the second-LL37 derived polypeptide may be the same or different.

In some embodiments, the LL37-derived amino acid sequence or sequences comprise SEQ ID NO: 16 (PEP #38). In some embodiments, the LL37-derived amino acid sequence or sequences comprise SEQ ID NO: 74 (PEP #48). In some embodiments, the LL37-derived amino acid sequence or sequences comprise SEQ ID NO: 14 (PEP #36). In some embodiments, the LL37-derived amino acid sequence or sequences comprise an inverse of the foregoing sequences (i.e. the inverse of SEQ ID NO: 14, 16 or 74).

In some embodiments, the LL37-derived sequence or sequences comprises a plurality of the fragments defined herein. For example, the LL37-derived polypeptide may comprise 2, 3, 4, 5 or more than 5 LL37-derived amino acid sequences, optionally separated by a spacer. Each fragment may be the same or different. The spacer may be any spacer (e.g. without limitation, a peptide spacer comprising natural and/or artificial amino acids, a peptoid linker, a non-peptide chemical/polymer linker, and the like, all of which would be straightforward to synthesize or purchase from a commercial vendor). In some embodiments, the spacer is a peptide spacer of 1, 2, 3, 4, 5, 6, 7, 8, 9, 10 or more than 10 residues, wherein each residue in the peptide may independently be Gly, Ser, Glu, Gln, Ala, Leu, Iso, Lys, Arg, Pro, or another amino acid. In some embodiments, the spacer is $X_{1-3}$, wherein each X is independently Gly, Ser or Ala. In some embodiments, the LL37-derived sequence or sequences comprises a plurality of fragments, and each fragment of the plurality of fragments independently comprises SEQ ID NO: 51 or the inverse sequence of SEQ ID NO: 51. In some embodiments, the LL37-derived sequence or sequences comprises a plurality of fragments, and the plurality of fragments comprises a pair of palindromic sequences (e.g. SEQ ID NO: 51 and the inverse sequence of SEQ ID NO: 51).

In some embodiments, each Lys and Arg residue in each fragment is independently substituted or not substituted with a conservative substitute amino acid residue selected from other positively charged amino acids, including proteinogenic amino acids, non-proteinogenic amino acids, and amino acid analogues. In some embodiments, the conservative substitutions for Lys and Arg are selected from the group consisting of: Lys, Orn (ornithine), DBu (2,4-diaminobutanoate), Dpr (2,3-diaminopropionate), Hyl (hydroxylysine), aHyl (allo-hydroxylysine), MeLys (6-N-methyllysine), Arg, Cit (citrulline), and 2-amino-3-guanidinopropionate. In some embodiments, the conservative substitutions for Lys and Arg are selected from the group consisting of Lys and Arg.

In some embodiments, 0, 1, 2, 3, 4 or 5 amino acid residues, selected from the group consisting of Gly, Asp, Glu, Asn, Gln, Ile, Leu, Val, Phe, Ser, Thr, Pro, and a combination thereof, in each fragment are each independently substituted with a conservative substitute amino acid residue selected from within its Group, $X^1$, $X^2$, $X^3$, $X^4$, $X^5$, or $X^6$ as defined below:

(Group $X^1$) Ala, Gly;

(Group $X^2$) Asp, Glu, bAad (3-aminoadipic acid), Apm (2-aminopimelic acid);

(Group $X^3$) Asn, Gln;

(Group $X^4$) Ile, Leu, Met, Val, Phe, Tyr, Trp, Abu (2-aminobutyric acid), Ahe (2-aminoheptanoic acid), aIle (allo-isoleucine), Nva (norvaline), Nle (norleucine);

(Group $X^5$) Ser, Thr, Tyr;

(Group $X^6$) Pro, 3Hyp (3-hydroxyproline), 4Hyp (4-hydroxyproline).

In some embodiments, 5 amino acid residues (as defined above) in each fragment are each independently substituted with a conservative substitute amino acid residue selected from within its Group, $X^1$, $X^2$, $X^3$, $X^4$, $X^5$, or $X^6$. In some embodiments, 4 amino acid residues (as defined above) in each fragment are each independently substituted with a conservative substitute amino acid residue selected from within its Group, $X^1$, $X^2$, $X^3$, $X^4$, $X^5$, or $X^6$. In some embodiments, 3 amino acid residues (as defined above) in each fragment are each independently substituted with a conservative substitute amino acid residue selected from within its Group, $X^1$, $X^2$, $X^3$, $X^4$, $X^5$, or $X^6$. In some embodiments, 2 amino acid residues (as defined above) in each fragment are each independently substituted with a conservative substitute amino acid residue selected from within its Group, $X^1$, $X^2$, $X^3$, $X^4$, $X^5$, or $X^6$. In some embodiments, 1 amino acid residues (as defined above) in each fragment are each independently substituted with a conservative substitute amino acid residue selected from within its Group, $X^1$, $X^2$, $X^3$, $X^4$, $X^5$, or $X^6$. In some embodiments, none of the non-Lys/Arg amino acid residues in each fragment is substituted. In some embodiments, some fragments have substituted non-Lys/Arg residues (e.g. 1, 2, 3, 4, 5) and other fragments are not substituted or have a different number of substituted residues. In some embodiments, each Group is limited to proteinogenic amino acids.

In some embodiments, 0, 1 or 2 amino acid residues, selected from the group consisting of Lys, Arg, Gly, Asp, Glu, Asn, Gln, Ile, Leu, Val, Phe, Ser, Thr, Pro, and a combination thereof, in each fragment are independently substituted with a non-conservative substitute amino acid residue. Exemplary, but non-limiting, non-conservative amino acid substitutions include substituting Lys or Arg with any of the other 18 proteinogenic amino acids or any of the non-proteinogenic amino acids in Groups $X^1$, $X^2$, $X^3$, $X^4$, $X^5$, and $X^6$. Exemplary, but non-limiting, non-conservative amino acid substitutions for Group $X^1$ amino acids would be any of the proteinogenic amino acids other than those defined in Group $X^1$ above, or any of the non-proteinogenic amino acids in Groups $X^2$, $X^3$, $X^4$, and $X^6$. Exemplary, but non-limiting, non-conservative amino acid substitutions for Group $X^2$ amino acids would be any of the proteinogenic amino acids other than those defined in Group $X^2$ above, or any of the non-proteinogenic amino acids in Groups $X^3$, $X^4$, and $X^6$. Exemplary, but non-limiting, non-conservative amino acid substitutions for Group $X^3$ amino acids would be any of the proteinogenic amino acids other than those defined in Group $X^3$ above, or any of the non-proteinogenic amino acids in Groups $X^2$, $X^4$, and $X^6$. Exemplary, but non-limiting, non-conservative amino acid substitutions for Group $X^4$ amino acids would be any of the proteinogenic amino acids other than those defined in Group $X^4$ above, or any of the non-proteinogenic amino acids in Groups $X^2$, $X^3$, and $X^6$. Exemplary, but non-limiting, non-conservative amino acid substitutions for Group $X^5$ amino acids would be any of the proteinogenic amino acids other than those defined in Group $X^5$ above, or any of the non-proteinogenic amino acids in Groups $X^2$, $X^3$, $X^4$, and $X^6$. Exemplary, but non-limiting, non-conservative amino acid substitutions for Group $X^6$ amino acids would be any of the proteinogenic amino acids other than Pro or any of the non-proteinogenic amino acids in Groups $X^2$, $X^3$, and $X^4$. In some embodiments, 2 amino acid residues in each fragment are substituted with non-conservative amino acids. In some embodiments, 1 amino acid residue is substituted in each fragment with a non-conservative amino acid. In some embodiments, no amino acids are substituted. The fragments may have a different number or the same number of non-conservatively substituted amino acid residues, or some fragment(s) may have conservatively substituted amino acid(s) while others have no conservatively substituted amino acids.

The structure of LL37 forms an amphipathic alpha helix with a net positive charge and a hydrophobic patch. In some embodiments, the standard state surface area of hydrophobic residues ($sssA_H$) calculated as the sum of the per residue standard state surface area for each hydrophobic residue within the LL37-derived amino acid sequence(s) (i.e. calculated for the fragment defined by SEQ ID NO: 14 and/or its inverse sequence SEQ ID NO: 111) is at least 1400 $Å^2$, at least 1500 $Å^2$, at least 1600 $Å^2$, at least 1700 $Å^2$, at least 1800 $Å^2$, at least 1900 $Å^2$ at least 2000 $Å^2$, at least 2100 $Å^2$, at least 2200 $Å^2$, at least 2300 $Å^2$, at least 2400 $Å^2$, or at least 2500 $Å^2$. For further clarity, the $sssA_H$ is calculated as in Rose et al., 1995, Science, 229:834-838, including only the hydrophobic residues within SEQ ID NO: 14 or 111, or within the fragments of these sequences or substituted variants thereof.

In some embodiments, the LL37-derived polypeptide sequence(s) consists of 100% L-amino acids. In some embodiments, the LL37-derived polypeptide sequence(s) comprises D-amino acid(s), e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 or 37 D-amino acids. In some embodiments, the LL37-derived polypeptide sequence comprises at least 2%, 3%, 5%, 8%, 13%, 16%, 19%, 22%, 25%, 27%, 30%, 32%, 35%, 38%, 41%, 43%, 46%, 49%, 51%, 54%, 57%, 59%, 62%, 65%, 68%, 70%, 73%, 76%, 78%, 81%, 84%, 86%, 89%, 92%, 95%, 97% or 100% D-amino acid(s), or any decimal therebetween. Each fragment in the plurality of fragments may have the same or different percentage of D-amino acid(s).

In some embodiments, the LL37-derived amino acid sequence(s) consists of 100% natural amino acids or D-enantiomers of natural amino acids. In some embodiments, the LL37-derived amino acid sequence(s) comprise unnatural amino acids.

Inclusion of the LL37-derived polypeptides serves to selectively increase delivery of the antibody or antibody derivative and its conjugated payload to a target human cell displaying the cell surface epitope compared to delivery of the same antibody/derivative (or antibody-payload conjugate) absent the LL37-derived polypeptides. In this context, the term "delivery" refers to the sum of the concentration of the antibody/derivative (as part of the conjugate) both at the cell surface of the target cell and internalized within the target human cell. As such, an "increase" in delivery means that the total amount/concentration of the antibody/derivative, associated with the cell surface and that which is internalized (i.e. not only the internalized amount or the surface-bound amount, but the combination of the two amounts), has increased as compared to the same antibody/derivative (or antibody-payload conjugate) in the absence of the LL37-derived polypeptide(s). In alternative embodiments, the inclusion of the LL37-derived polypeptides selectively increases delivery of the antibody/derivative (or the antibody-payload conjugate) to the target cell by at least 2-fold, at least 3-fold, at least 4-fold, at least 5-fold, at least 6-fold, at least 7-fold, at least 8-fold, at least 9-fold, at least 10-fold, at least 11-fold, at least 12-fold, at least 13-fold, at least 14-fold, at least 15-fold, at least 16-fold, at least 17-fold, at least 18-fold, at least 19-fold or at least 20-fold, e.g. when delivery is measured in vitro (as described in the Examples herein) at a concentration of 100 nM conjugate or antibody/derivative. An increase in "selective" delivery means an increase in delivery to the target human cell (i.e. the cell expressing the epitope on its cell surface) as opposed to merely increasing delivery to any cell (including those which do not significantly express the cell surface epitope), i.e. non-specific or non-selective delivery. An increase in selective delivery is not intended to mean that non-specific delivery is not also increased, but an increase in "selective delivery" refers to the increase in delivery minus any non-specific increase that may also result. In some embodiments, the increase in delivery is to the extent that it exceeds the level of delivery possible when the target epitope is saturated by bound antibodies/derivatives. As used herein, "antibody-payload conjugate" refers to the covalent conjugates of the present disclosure, including conjugates that comprise an antibody as well as conjugates that comprise an antibody derivative as defined herein.

The phrase "specifically binds" or "selectively binds," when used in the context of describing the interaction between the antibody or antibody derivative and a cell surface epitope (i.e. between an epitope and an antibody variable domain) refers to a preferred association (e.g. formation of a non-covalent complex, including a transitory complex) as compared to a background association with a heterogeneous population of proteins and/or other macromolecules. Thus, under designated conditions (e.g. immunoassay conditions), the specified antibody/derivative "specifically binds" to the cell surface eptiope when they associate at least two times the background level of association with other macromolecules present in a sample, organism, cell or cell environment. A variety of immunoassay formats may be used to select antibodies which specifically bind with a particular protein or ligand. For example, solid-phase ELISA immunoassays are routinely used to select antibodies which specifically bind with a protein (see, e.g., Harlow & Lane, Using Antibodies, A Laboratory Manual (1998), Cold Spring Harbor Laboratory (N.Y.), for a description of immunoassay formats and conditions that can be used to determine specific binding). Typically a specific or selective binding reaction will produce a signal at least twice over the background signal and in some cases at least 10 to 100 times over the background. Unless otherwise specified, the association of the antibody with the cell surface epitope (e.g. a cell surface protein or receptor) will, in certain embodiments, generally have an equilibrium dissociation constant ($K_D$) of about $10^{-4}$ M to $10^{-15}$ M, i.e. less than about $10^{-4}$ M, less than about $10^{-5}$ M, less than about $10^{-6}$ M, less than about $10^{-7}$ M, less than about $10^{-8}$ M, less than about $10^{-9}$ M, less than about $10^{-10}$ M, less than about $10^{-11}$ M, less than about $10^{-12}$ M, less than about $10^{-13}$ M, or less than about $10^{-14}$ M. Equilibrium dissociation constants can be measured using any known method in the art.

The cell surface epitope is specifically bound by the variable domain of the antibody. In general, an "epitope" may be a peptide, protein, nucleic acid, carbohydrate, polysaccharide, lipid, organic compound, and the like, as well as complexes thereof, which forms contacts with an antibody variable domain. An epitope forms at least a part of, without limitation, a hapten, an antigen, an immunogen, a major histocompatibility complex (MHC)-peptide complex (including class I and class II MHC), a CD1-antigen complex, as well as any fragment, portion or analogue thereof which is specifically bound by the antibody variable domain. The area of an epitope that contacts the antibody variable domain is typically between about 4 and 10 $nm^2$ (Delves and Roitt, 2011, *Roitt's Essential Immunology*. Chichester, West Sussex: Wiley-Blackwell at 114). An epitope may be continuous or discontinuous.

The heavy chain of an antibody is composed of a variable domain ($V_H$) and multiple constant domains (e.g. for IgG1: $C_H^1$, $C_H^2$ and $C_H^3$). The "Fc region", "Fc domain", or "fragment crystallizable" region/domain refers to the dimerized constant portion of an antibody which remains after papain digestion of an antibody, i.e. excluding the Fab fragments. For example, the Fc domain of IgG1 is essentially composed of $C_H^2$ and $C_H^3$. The light chain of an antibody is composed of a variable domain ($V_L$) and a constant domain ($C_L$). There are two isotypes of light chains in humans and other mammals, i.e. kappa (κ) and lambda (λ), whereas tetrapods additionally have a sigma (σ) isotype. The endogenous $V_L$ is encoded by the gene segments V (variable) and J (junctional), and the endogenous $V_H$ is encoded by V, D (diversity), and J. Each of $V_L$ and $V_H$ includes three complementarity determining regions (CDRs) apiece as well as framework regions. The six CDRs may all contribute to epitope binding, but their relative contributions vary, and in certain cases, not all six CDRs are necessary for binding. For example, the CDR3 of the heavy chain tends to contribute disproportionately more to epitope binding. Furthermore, single domain antibodies, nanobodies, and the like are known which only have three CDRs (e.g. a single domain antibody obtained or derived from the heavy chain variable domain of dromedaries, camels, llamas, alpacas, sharks, or similar animals, or engineered from the heavy chain of conventional antibodies, including but not limited to human and murine antibodies). As used herein, unless otherwise specified the term "antibody" includes antibodies having both heavy and light chains, and also includes heavy-chain only antibodies Unless otherwise specified, the phrase "antibody variable domain" as used herein refers to comprising $V_H$ (if capable of epitope-binding without $V_L$; e.g. as found in $V_H$H, $V_{NAR}$, or engineered from $V_H$ of conventional antibodies), both $V_H$ and $V_L$ (e.g. scFv), the variable domain of a single domain antibody (e.g. $V_H$H, $V_{NAR}$), the variable domain of a nanobody (derived from $V_H$ or $V_L$), or any antibody-derived protein domain which suitably positions the required CDRs (e.g. 1, 2, 3, 4, 5 or 6 CDRs) for specific binding of the epitope portion of an antigen.

Methods for producing proteins comprising an antibody variable domain (such as antibodies, antibody-drug conjugates, antibody derivatives, and the like) which bind a particular epitope are known, including (without limitation): isolation of antibodies from an immunized animal or production of proteins comprising antibody variable domains by in vitro recombination of CDRs (e.g. Stech and Kubich, 2015, Antibodies 4: 12-33; WO/2013/134880), from the modification of antibodies, from de novo synthesis using recombinant DNA methodologies or solid phase peptide/polypeptide synthesis, or selected from display libraries (see, e.g., McCafferty et al., Nature 348:552-554 (1990)) and the like. For preparation of monoclonal or polyclonal antibodies, any technique known in the art may be used (for non-limiting examples, see: Kohler & Milstein, Nature 256:495-497 (1975); Kozbor et al., *Immunology Today* 4:72 (1983); Cole et al., Monoclonal Antibodies and Cancer Therapy, pp. 77-96. Alan R. Liss, Inc. 1985). Techniques for the production of single chain antibodies are also known (for non-limiting examples, see U.S. Pat. No. 4,946,778). Alternatively, phage display (or another display technology) can be used to identify antibodies and heteromeric Fab fragments that specifically bind to selected antigens (see, e.g., McCafferty et al., Nature 348:552-554 (1990); Marks et al., *Biotechnology*, 10:779-783, (1992)).

In some embodiments, the covalent conjugate comprises an antibody. The antibody may be of any species or may be chimeric or artificial. For example, but without limitation, the antibody may be non-human (e.g.: a camelid, such as dromedary, camel, llama, alpaca, and the like; cartilaginous fish, such as shark and the like; mouse, rat, monkey or other), primatized, humanized or fully human. A chimeric antibody contains amino acid sequences from multiple species, e.g. from human and non-human or from two non-human species. Methods for humanizing or primatizing non-human antibodies are well known in the art, e.g. by substituting non-human (or non-primate) constant domains for those of a human antibody (creating a chimeric antibody) or by substituting one or more (e.g. 1, 2, 3, 4, 5 or 6) of the Complementarity Determining Regions (CDRs) of a human (or primate) antibody with a non-human antibody (see, e.g.: Jones et al. Nature 1986; 321:522-525; Riechmann et al. Nature 1988; 332:323-327; Verhoeyen et al. Science 1988; 239:1534-1536; Presta. Curr. Op. Struct. Biol. 1995; 2:593-596; Morrison et al. Proc. Natl. Acad. Sci. USA 1984; 81:6851-6855; Morrison and Oi. Adv. Immunol. 1988; 44:65-92; Padlan. Molec. Immun. 1991; 28:489-498; and Padlan. Molec. Immun. 1994; 31(3):169-217). In some embodiments, the antibody is comprised of two heavy chains and two light chains. In some embodiments, the antibody is a heavy chain only antibody (e.g. an dromedary, camel, llama, alpaca or shark antibody which lacks light chains, or a human heavy chain). In some embodiments, the antibody is bispecific. In some embodiments, the antibody is monospecific. In some embodiments, the antibody is an IgA, an IgM, an IgG, an IgE, or an IgD. In some embodiments, the antibody is an IgG antibody.

In some embodiments, the covalent conjugate comprises an antibody derivative. The antibody derivative comprises an antibody variable domain that specifically binds to the cell surface epitope of the human cell, and further comprises a hinge region coupling two heavy chains or two heavy chain fragments. Such derivatives include antibody fragments which retain antigen binding functionality as well as artificial antibodies. The hinge region may be wild-type or may be modified (e.g. by substitution, deletion and/or insertion of amino acids) so long as there is sufficient intermolecular disulfide bridging to retain coupling of the heavy chains or heavy chain fragments.

In some embodiments, the antibody variable domain of the antibody derivative comprises $V_H$ and $V_L$. In some embodiments, the antibody variable domain comprises $V_H$ without $V_L$. In some embodiments, the antibody variable domain is a single chain Fv (scFv). In some embodiments, the antibody variable domain is a $V_H H$ or $V_{NAR}$ (i.e. a nanobody, e.g. from or derived from dromedaries, camels, llamas, alpacas, sharks, and the like). In some embodiments, the antibody variable domain is a single domain antibody (sdAb). In some embodiments, the antibody derivative comprises a single antibody variable domain per antibody monomer. In some embodiments, the antibody derivative comprises two antibody variable domains per antibody monomer. In some embodiments, the two antibody variable domains are the same. In other embodiments, the two antibody variable domains are different. In some embodiments, the different antibody variable domains bind different epitopes (e.g. bispecific antibodies/derivatives). In some embodiments, the antibody derivative comprises a an ScFv and a conventional Fv.

In some embodiments, the antibody derivative comprises full-length heavy chains (e.g. $V_H$-$C_H1$-$C_H2$-$C_H3$) coupled together by the hinge region. In other embodiments, the hinge region couples two heavy chain fragments. In some embodiments, the heavy chain fragment is an Fc (e.g. the fragment is a $C_H2$-$C_H3$ fragment, and the like) or otherwise excludes the CHI domain (e.g. a $C_H2$-$C_H3$-$C_H4$ fragment, a $C_H2$-$C_H3$-$C_H4$ fragment, and the like). In some embodiments, the antibody derivative consists of only a heavy chain (e.g. a fragment of heavy chain only antibody from or derived from dromedaries, camels, llamas, alpacas, sharks, and the like). In some embodiments, the antibody derivative includes both heavy chains and light chains. In some embodiments, the antibody derivative is a F(ab')2 fragment, and in other embodiments the antibody is a Fd fragment (i.e. lacking F(ab')2 lacking the light chain). In some embodiments, the antibody derivative is an ScFv-Fc. In some embodiments, the antibody is an ScFv-$C_H3$.

Other antibodies and derivatives are known, a number of non-limiting examples of which are disclosed in Deyev and Lebedenko (2008, BioEssays 30:904-918).

Many antibodies have a $K_D$ value in the low micromolar to nanomolar range, with high affinity antibodies having low nanomolar $K_D$ values and very high affinity antibodies having picomolar $K_D$ values. In some embodiments, the antibody or antibody derivative binds the cell surface epitope with a $K_D$ of less than 500 nM, less than 400 nM, less than 300 nM, less than 200 nM, less than 100 nM, less than 50 nM, less than 10 nM, less than 5 nM, or less than 1 nM. In some embodiments, the antibody may bind the binding substrate with a picomolar $K_D$ ($10^{-10}$ M to $10^{-12}$ M). The above binding affinities are obtainable using known display technologies, such as mRNA display, phage display, ribosome display, and yeast display, to screen libraries by selecting for specific and high-affinity for the desired target, and in some cases affinity maturation methods, i.e. generating a secondary library of variants of the selected clone using error-prone PCR or DNA shuffling, etc., followed an affinity selection with reduced amounts of target or off-rate selection.

In some embodiments, the covalent conjugate comprises: 18V4F, 4R34.1.19, A-803, Abagovomab, Abciximab, Abituzumab, Abrezekimab, Abrilumab, Adalimumab, ADCPF-06688992, Adecatumumab, Ado-trastuzumab, Afelimomab, Afutuzumab, AGS16F, Alacizumab, Alemtuzumab, Alirocumab, ALKS4230, Altumomab, Amatuximab, AMG191, AMG531, Anatumomab, Andecaliximab, Anetumab, Anifrolumab, Anti-HM1.24, Apolizumab, Aprutumab, Arcitumomab, ARD5, Aselizumab, ASG-15ME, Atezolizumab, Atinumab, AUTO2, Avelumab, Azintuxizumab, B-701, Basiliximab, Bavituximab, BAY1179470, Bectumomab, Begelomab, Belantamab, Belimumab, Bemarituzumab, Benralizumab, Bersanlimab, Bertilimumab, Bevacizumab, BI-505, Biciromab, BIIB023, Bimagrumab, Bimekizumab, BION-1301, Bivatuzumab, Bleselumab, Blinatumomab, Blontuvetmab, Blosozumab, BMS-986148, BMS-986156, BMS-986179, Brentuximab, Brodalumab, Brolucizumab, Brontictuzumab, BTH1704, Burosumab, C7-FcDT, Cabiralizumab, Camidanlumab, Camrelizumab, CAN04, Canakinumab, Cantuzumab, CAP-100, Caplacizumab, capromab, Carotuximab, Catumaxomab, CC-90002, CD133KDEL, CD147-CART, CD96-S32F, CDX-1401, Cedelizumab, Cemiplimab, Cergutuzumab, Cetrelimab, Cetuximab, Cibisatamab, Citatuzumab, Cixutumumab, Claudiximab, Clenoliximab, Clivatuzumab, Codrituzumab, Cofetuzumab, Coltuximab, COM701, COM902, Conatumumab, Crizanlizumab, Crotedumab, CSL324, Cusatuzumab, Dacetuzumab, Daclizumab, Dalotuzumab, Dapirolizumab, Daratumumab, Darleukin, DCR2, Dectrekumab, Demcizumab, Denintuzumab, Denosumab, Depatuxizumab, Derlotuximab, Detumomab, Dinutuximab, Dorlimomab, Drozitumab, Duligotuzumab, Dupilumab, Durvalumab, Duvortuxizumab, Ecromeximab, Eculizumab, Edrecolomab, Efalizumab, EGFR806, EJ212_007-C12-5, ELB01101, Elgemtumab, Elotuzumab, Elsilimomab, Emactuzumab, Emapalumab, EMD525797, Emibetuzumab, Enapotamab, Enavatuzumab, Enfortumab, Enoblituzumab, Enoticumab, EOL4G8, Epratuzumab, Ertumaxomab, Etaracizumab, Evolocumab, Fanolesomab, Faralimomab, Farletuzumab, Fezakinumab, Fibatuzumab, Ficlatuzumab, Flanvotumab, Flotetuzumab, FLYSYN, Foralumab, Galiximab, Gancotamab, Ganitumab, Gatipotuzumab, Gavilimomab, GD2Bi-aATC, Gemtuzumab, GI-270384, Gilvetmab, Girentuximab, Glembatumumab, Golimumab, Gomiliximab, GSK2849330, Guselkumab, HB-n1, HFE7A, HLX20, HS-110, Hu3ST93, Ibalizumab, Ibritumomab, Icrucumab, Ifabotuzumab, Igovomab, Imalumab, Imaprelimab, IMC-CS4, Imgatuzumab, Inclacumab, Indatuximab, Indusatumab, Inebilizumab, Infliximab, Inotuzumab, Intetumumab, Iomab-B, iPH5401, Ipilimumab, Iratumumab, Isatuximab, Iscalimab, Istiratumab, Itolizumab, Ixekizumab, Keliximab, KH7B9, KTN0182A, KU42.33C, Labetuzumab, Ladiratuzumab, Lanadelumab, Lanalumab, Laprituximab, Lemalesomab, Leronlimab, Letolizumab, Lexatumumab, Lifastuzumab, Lilotomab, Lintuzumab, Lirilumab, Lokivetmab, Loncastuximab, Lorvotuzumab, Losatuxizumab, Lucatumumab, Lulizumab, Lumretuzumab, Lupartumab, Lutikizumab, LY3321367, LY3435151, M290, Mapatumumab, Margetuximab, Maslimomab, Matuzumab, Mavrilimumab, MBG453, MCLA-117, MEDI3617, MEDI3622, MEN1112, Mepolizumab, Milatuzumab, Minretumomab, Mirvetuximab, Mitumomab, MLS102, MM-111, MMP9, MNRP1685A, Modotuximab, Mogamulizumab, Monalizumab, Moxetumomab, MOXR0916, Muromonab, MVT-5873, Nacolomab, Naptumomab, Naratuximab, Narnatumab, Natalizumab, Navicixizumab, Necitumumab, Nerelimomab, Nesvacumab, Netakimab, NI-0101, Nimotuzumab, Nivolumab, NNC0151-00000000, Nofetumomab, Obinutuzumab, Ocaratuzumab, Ocrelizumab, Odulimomab, Ofatumumab, Olaratumab, Oleclumab, olokizumab, Omalizumab, Onartuzumab, Ontuxizumab, Onvatilimab, Opicinumab, Oportuzumab, Oregovomab, Otelixizumab, Otlertuzumab, Oxelumab, Pamrevlumab, Panitumumab, Pankomab, Parsatuzumab, Pasotuxizumab, Patritumab, PD-0360324, PDR001, Pembrolizumab, Pemtumomab, Pertuzumab, PF-00547659, PF-03446962, PF-04518600, PF-06650808, Pidilizumab, Pinatuzumab, Pintumomab, Plozalizumab, Polatuzumab, Prezalumab, Priliximab, Pritumumab, PTK7-ADC, Quilizumab, Radretumab, Ramucirumab, Ranibizumab, Ravagalimab, Refanezumab, REGN2176, Relatlimab, Reslizumab, RG7287, Rilotumumab, Rinucumab, Risankizumab, Rituximab, RO-001, R06958688, Robatumumab, Romilkimab, Romosozumab, Rovalpituzumabtesirine, Rovelizumab, Rozanolixizumab, Ruplizumab, Sacituzumab, Samalizumab, Samrotamab, SAR252067, SAR408701, Sarilumab, Satralizumab, Satumomab, Secukinumab, Selicrelumab, Seribantumab, Setrusumab, SGN-15, SGN-CD123A, SGN-CD228A, SGN-CD352A, SGN-CD47M, SGN-CD48A, SGN-CD70A, SGN-LIV1A, SHP647, Siamab.com, Sibrotuzumab, Siltuximab, Simtuzumab, Sirtratumab, SL-279252, Sofituzumab, Solitomab, Sonepcizumab, Sontuzumab, Spartalizumab, Sphingomab, SS1 (dsFv) PE38 (CAT-5001), Sulesomab, TAB004, Tabalumab, Tacatuzumab, Tadocizumab, Talacotuzumab, Tamtuvetmab, Taplitumomab, Tarextumab, Telimomab, Telisotuzumab, Tenatumomab, Teneliximab, Teplizumab, Tepoditamab, Teprotumumab, Theralizumab, Tigatuzumab, Tildrakizumab, Timigutuzumab, Timolumab, Tiragotumab, Tislelizumab, Tisotumab, TKH2, Tocilizumab, Tomuzotuximab, Tositumomab, Trastuzumab, Tregalizumab, Tremelimumab, TSR-022, TTX-030, Tucotuzumab, Ublituximab, Ulocuplumab, Urelumab, Ustekinumab, Ustekinumab, Vadastuximab, Vanalimab, Vapaliximab, Varlilumab, Vatelizumab, Vedolizumab, Vepalimomab, Vesencumab, Visilizumab, Vobarilizumab, Vofatamab, Volociximab, Vonlerolizumab, Vopratelimab, Vorsetuzumab, Votumumab, Vunakizumab, VX15/2503, Y-443, Zalutumumab, Zanolimumab, Zenocutuzumab, Ziralimumab, or Zolbetuximab.

In some embodiments, the antibody or the antibody derivative specifically binds to a human cell surface protein (comprising the epitope) selected from: HER2, folate receptor, EGFR, CD20, FGFR3, Napi2b, CD33A, CEACAM5, EPCAM, CD3e, CD30, or PSMA. In some embodiments, the antibody or antibody derivative is or comprises an anti-HER2 antibody or derivative thereof, an anti-folate receptor antibody or derivative thereof, an anti-EGFR antibody or derivative thereof, an anti-CD20 antibody or derivative thereof, an anti-FGFR3 antibody or derivative thereof, an anti-Napi2b antibody or derivative thereof, an anti-CD33 antibody or derivative thereof, an anti-CEACAM5 antibody or derivative thereof, an anti-EPCAM antibody or derivative thereof, an anti-CD3e antibody or derivative thereof, an anti-CD30 antibody or derivative thereof, or an anti-PSMA antibody or derivative thereof. In some embodiments, the antibody is or comprises: Trastuzumab, Mirvetuximab, Panitumumab, Lifastuzumab, Labetuzumab, Citatuzumab, Rituximab, Ofatumumab, Vadastuximab, Vofatamab, Foralumab, Brentuximab, or hj591.

In some embodiments, the LL37-derived domains are spaced apart in the covalent conjugate to favour intermolecular non-covalent association between the LL37-derived polypeptides (i.e. multimerization) over intramolecular association. For example, but without limitation, in some embodiments two LL37-derived polypeptides may be disposed on opposite sides of the antibody or antibody derivative. In some embodiments, the LL37-derived polypeptides (e.g. the first and second LL37-derived polypeptides) may be spaced apart from each other by at least a distance equal to the length of the LL37-derived polypeptide plus any linker that may be between the LL37-derived polypeptide and the antibody or antibody derivative, the distance apart measured from where the LL37-derived polypeptide (or the linker if present) attaches to the antibody or to the antibody derivative. In alternative embodiments, the LL37-derived polypeptides may be spaced at least 100, at least 105, at least 110, at least 115, at least 120, at least 125, at least 130, at least 135, at least 140, at least 145, at least 150, at least 155, at least 160, at least 165, at least 170, at least 175, at least 180, at least 185, at least 190, at least 195, at least 200, at least 205, at least 210, at least 215, at least 220, at least 225, at least 230, at least 235, at least 240, at least 245, at least 250, at least 255, at least 260, at least 265, at least 270, at least 275, at least 280, at least 285, at least 290, at least 295, at least 300, at least 305, at least 310, at least 315, at least 320, at least 325, at least 330, at least 335, at least 340, at least 345, or at least 350 Å apart, measured from where the LL37-derived polypeptide (or the linker if present) attaches to the antibody or to the antibody derivative. In some embodiments, the at least two amphipathic polypeptides are symmetrically disposed in the covalent conjugate.

Without limitation, in some embodiments, an LL37-derived polypeptide may be attached directly or indirectly to the C-terminus of an antibody heavy chain (or heavy chain fragment) or the C-terminus of an antibody light chain, optionally with a linker separating the LL37-derived polypeptide from the antibody or antibody derivative. Without limitation, the site of attachment or the linker may include: a peptide bond; a disulfide linkage; an isopeptide bond; or a 1,2,3-triazole linkage. In some embodiments, the LL37-derived polypeptide is attached, with or without an intervening linker, to the C-terminus of the antibody light chain. In some embodiments, the LL37-derived polypeptide is attached, with or without an intervening linker, to the C-terminus of the antibody heavy chain. In some embodiments, the LL37-derived polypeptides are attached, with or without an intervening linker, to the C-termini of the heavy chain and the light chain. In some embodiments, the antibody or the antibody derivative comprises a first heavy chain constant region and a second heavy chain constant region, wherein the first LL37-derived polypeptide is coupled directly or indirectly to a C-terminus of the first heavy chain constant region and the second LL37-derived polypeptide is coupled directly or indirectly to a C-terminus of the second heavy chain constant region. In some embodiments, the antibody or the antibody derivative comprises a first light chain constant region and a second light chain constant region, wherein the first LL37-derived polypeptide is coupled directly or indirectly to a C-terminus of the first light chain constant region and the second LL37-derived polypeptide is coupled directly or indirectly to a C-terminus of the second light chain constant region.

Since antibody monomers are dimeric, they may be symmetrical. As used herein in the context of antibodies, the term "antibody monomer" refers to the dimeric disulfide-bonded complex of two heavy chains and two light chains, or just two heavy chains for heavy chain only antibodies. As used herein in the context of antibody derivatives, the term "antibody monomer" refers to the dimeric disulfide-bonded complex of two heavy chains or two heavy chain fragments and, when present, two light chains. Due to this symmetry, the LL37-derived polypeptides may be symmetrically coupled to the same location on both heavy chains, and/or on both light chains. Accordingly, in some embodiments the antibody or the antibody derivative comprises a first heavy chain constant region and a second heavy chain constant region, wherein the first LL37-derived polypeptide is coupled directly or indirectly to the first heavy chain constant region and the second LL37-derived polypeptide is coupled directly or indirectly to the same amino acid residue in the second heavy chain constant region. In some embodiments, the antibody or the antibody derivative comprises a first light chain constant region and a second light chain constant region, wherein the first LL37-derived polypeptide is coupled directly or indirectly to the first light chain constant region and the second LL37-derived polypeptide is coupled directly or indirectly to the same amino acid residue in the second light chain constant region.

In some embodiments, the ratio of LL37-derived polypeptides per antibody monomer in the covalent conjugate is exactly 2:1. In some embodiments, the ratio of LL37-derived polypeptides per antibody monomer in the covalent conjugate is exactly 4:1. In some embodiments, the ratio of LL37-derived polypeptides per antibody monomer in the covalent conjugate is exactly 6:1. In some embodiments, the ratio of LL37-derived polypeptides per antibody monomer in the covalent conjugate is exactly 8:1. In some embodiments, the ratio of LL37-derived polypeptides per antibody monomer is a multiple of 2.

In some embodiments, the antibody/derivative and the LL37-derived polypeptides may be separated by linkers (e.g. peptide linkers, or PEG-containing linker, and the like). For example, the linker may be flexible or rigid. Non-limiting examples of rigid and flexible linkers are provided in Chen et al. (Adv Drug Deliv Rev. 2013; 65(10):1357-1369). In some embodiments, the linker is a PEG-containing linker (e.g. PEG4-maleimide, and the like). In some embodiments, the linker is a peptide linker of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50 or more than 50 amino acid residues. In some embodiments, the linker is a peptide linker of 1-25 residues or 1-10 residues. In some embodiments, the linker is a peptide linker of $X_{1-10}$, wherein each X is independently Gly, Ser, Glu, Gln, Ala, Leu, Iso, Lys, Arg, Pro, or another amino acid. In some embodiments, the peptide linker is at least 4 residues long. In some embodiments, the linker is a peptide linker of $X_{4-10}$, wherein each X is independently Gly, Ser, Glu, Gln, Ala, Leu, Iso, Lys, Arg, Pro, or another amino acid. In some embodiments, each X (in $X_{1-10}$ or $X_{4-10}$) is independently Gly, Ala or Ser. In some embodiments, the first LL37-derived polypeptide is coupled to the antibody or to the antibody derivative through a first peptide linker and the second LL37-derived polypeptide is coupled to the antibody or to the antibody derivative through a second peptide linker. In some embodiments, the first peptide linker and the second peptide linker are the same. In some embodiments, the first peptide linker and the second peptide linker are different.

In embodiments where the linker is absent or is a peptide linker, attachment of a LL37-derived polypeptide to a C-terminus of an antibody/derivative chain (heavy chain, heavy chain fragment, or light chain) may be genetically encoded so that cell surface binding conjugate can be expressed as a recombinant fusion protein. In embodiments where the LL37-derived polypeptide is coupled to the antibody/derivative as a recombinantly expressed fusion protein, a linker may be present but is not required.

In other embodiments, but without limitation, a LL37-derived polypeptide may be joined post-translationally using an enzymatic reaction. For example, a sortase enzyme (e.g. sortase A, B, C, D and the like) may be used to catalyze the covalent linkage of the LL37-derived polypeptide to the cell surface binding portion. Using *Staphylococcus aureus* Sortase A (SrtA) as a non-limiting example, the recognition sequence (LPXTG) is added to the C-terminus of the first protein to be ligated (e.g. an antibody heavy chain) while an oligo-glycine sequence is added to the N-terminus of the second protein to be ligated (e.g. an LL37-derived polypeptide). Using these two proteins as substrates, Sortase A will cleave the C-terminal Gly of the first protein and ligate the cleaved C-terminal end to the N-terminus of the second protein. Additional residues may be added after the recognition sequence, e.g. SEQ ID NO:22 is recognized by SrtA). Any known sortase enzyme and its cognate recognition sequence may be used (see, e.g., Mao et al., 2004, *J. Am. Chem. Soc.*, 126: 2670; Swee et al., 2013, *Proc. Nat. Acad. Sci. U.S.A.* 110:1428-1433). Sortase enzymes have been used to catalyze the ligation of polypeptides as well as the conjugation of oligoglycine-modified non-protein molecules to proteins, including the production of antibody and antibody fragments labeled with small molecules or protein moieties and antibody-drug conjugates (see, e.g. Beerli et al., 2015, *PLOS ONE* 10(7):e0131177). The coding sequences of sortases, including sortase A, are well known in the art and are publicly available in biological sequence databases and elsewhere (e.g. U.S. Pat. No. 7,238,489). The sortase recognition sequences for various sortase enzymes are known, e.g. *Staphylococcus aureus* sortase A (LPXTG) (SEQ ID NO: 23), *Streptococcus pyogenes* sortase A (LPXT (A/G)) (SEQ ID NO: 24), *Clostridium difficile* sortase ((S/P) PXTG)) (SEQ ID NO: 25), *S. pyogenes* SrtC (QVPTG) (SEQ ID NO: 26), engineered sortase enzymes (e.g. see Dorr et al., 2014, *Proc Natl Acad Sci USA* 111: 13343-13348, which discloses a sortase that recognizes LAXTG of SEQ ID NO: 27 and a sortase that recognizes LPXSG of SEQ ID NO: 28), wherein "X" denotes any amino acid residue.

Covalent linkages may alternatively be formed between two specific residues in the antibody/derivative and LL37-derived polypeptides using, for example: 1) the intein-mediated in-vivo ligation of proteins or peptides (see, e.g., Shah and Muir, 2014, *Chem. Sci.* 5: 446; Carvajal-Vallejos et al., 2012, *J. Biol. Chem.* 287: 28686); 2) iso-peptide bond formation between the side chains of lysine and aspartate/asparagine/glutamine/glutamate of a specific sequence tag in proteins or polypeptides (see, e.g., Zakeri and Howarth, 2010, *J. Am. Chem. Soc.* 132: 4526; Fierer et al., 2014, *Proc. Natl. Acad. Sci. U.S.A.* 111: E1176; Veggiani et al., 2014, *Trends Biotechnol.* 32: 506; Rashidian et al., 2013, *Biocon-jug. Chem.* 24: 1277); 3) disulfide bond formation between terminally-attached peptide-recognition domains (see, e.g., Rossi et al., 2012, *Trends Pharmacol. Sci.* 33: 474); and click chemistry to couple azides and terminal alkynes, resulting in 1,2,3-triazole formation (See Example 6, which shows modifying antibody glycan groups to have an azide and then reacting the azide with an alkyne-containing LL37-linked compound, namely DBCO-PEG4-maleimide-LL37). Many other methods are known, e.g. ligation using lipoic acid ligase, ligation using formylglycine-generating enzyme, and the like.

The covalent conjugate may comprise a single payload or a plurality of payloads. The payload(s) may be present in a ratio (i.e. payload-to-antibody ratio) of 1, 2, 3, 4, 5, 6, 7, 8, 9, 10, 11, 12, 13, 14, 15, 16, 17, 18, 19, 20 or more than 20 relative to antibody monomer. The payload-to-antibody ratio is calculated using the average number of payload moieties conjugated to the antibody, so the ratio may be a fraction of the foregoing (e.g. 0.5, 1.5, and the like). For the same reason, a ratio given as an integer value includes decimal values that would round up or down to the given integer value. Similarly, a ratio given as a tenths place decimal would include any hundredths place decimals that round up or down to the given tenths place decimal. In some embodiments, the payload(s) is present in a ratio of 1, 2, 2.45, 2.5, 3, 4 or 8. The term "drug-to-antibody ratio" or "DAR", a term of art used for ADCs, is an example of a payload-to-antibody ratio. High payload-to-antibody ratios can be achieved by chaining a plurality of payloads together, e.g. using a Fleximer polymer (see Yurkovetskiy et al., Cancer Res; 75(16), 2015).

In some embodiments, the payload(s) are small molecule drugs that are toxic to human cells. As used herein, the term "small molecule drug" means any compound that is less than 3 kDa (e.g. 0.5 kDa, 1 kDa, 1.5 kDa, 2.0 kDa, 2.5 kDa, 2.99 kDa, and the like). The use of "Dalton" or "Da" in this context means g/mol, and the use of "kilodalton" or "kDa" in this context means kg/mol. The expression "toxic to human cells" means that the conjugated compound directly or indirectly, alone or in concert with another agent(s), arrests the growth of, or kills, human cells (e.g. a human cancer cell, a pathogen-infected human cell, or an immune cell), and further includes pro-drugs which only have cyto-toxic activity once released or activated following internal-ization into the target human cell. Non-limiting (and non-mutually exclusive) examples of a small molecule drug payload include a V-ATPase inhibitor, a HSP90 inhibitor, an IAP inhibitor, an mTor inhibitor, a microtubule stabilizer, a microtubule destabilizer, a dolastatin, a MetAP (methionine aminopeptidase), an inhibitor of nuclear export of proteins (e.g. a CRM1 inhibitor), a DPPIV inhibitor, an inhibitor of phosphoryl transfer reactions in mitochondria, a protein synthesis inhibitor, a kinase inhibitor, a CDK2 inhibitor, a CDK9 inhibitor, a proteasome inhibitor, a kinesin inhibitor, an HDAC inhibitor, a DNA damaging agent, a DNA alky-lating agent, a DNA intercalator, a DNA minor groove binder or a DHFR inhibitor, a radionuclide (e.g. a β-emitting radionuclide, $^{90}$Y, $^{131}$I, and the like)-containing compound, a chemotherapeutic moiety, an anti-cancer drug, an antimi-totic compound, an inhibitor of protein synthesis (e.g. an RNA polymerase II inhibitor), cyclophosphamide, vincris-tine, prednisolone, cyclophosphamide, methotrexate, 5-fluo-rouracil, a DNA-alkylating and/or intercalating molecules (e.g. doxorubicin, centanamycin, and the like), a DNA cleaving compound (e.g. calicheamicins, N-acetyl-γ-cali-cheamicin, and the like), SN-38, irinotecan, camptothecin, D6.5, a duocarmycin (e.g. duocarmycin, CC1065, MED-2460, and the like), an auristatin (e.g. MMAE, MMAF, and the like), a maytansine derivative, a maytansinoid (e.g. DM1, DM2, DM3, DM4, and the like), an amatoxin (e.g. anti-PSMA-α-amanitin and the like), durcomycin, pyrrol-benzodiazepines (e.g. PBD dimers, SGD-1882, and the like), an anthracycline, paclitaxel, mycotoxin, fungal toxin, as well as derivatives, analogues and prodrugs thereof. Tubulysins are highly cytotoxic peptides with antimitotic activity that disrupts cell microtubules, inhibits tubulin polymerization, and causes cell cycle arrest and triggersa-poptosis. Vinblastine causes M-phase specific cell cycle arrest, and it binds tubulin to inhibit the assembly of microtubules, mitotic spindle, and kinetochore, which are all essential for chromosomes separations during anaphase of mitosis. Mertansine, also called DM1 (and in some of its forms emtansine), is a tubulin inhibitor, and it can inhibit the assembly of microtubules by binding to tubulin (at the rhizoxin binding site). Doxorubicin is in the anthracycline and antitumor antibiotic family of medications. Doxorubicin interacts with DNA by intercalation and inhibition of mac-romolecular biosynthesis leading to cell death. Paclitaxel (or Taxol) is one of several cytoskeletal drugs that target tubu-lin. Taxol interferes in mitotic spindle assembly, chromo-some segregation, and cell division, blocking the progres-sion of mitosis and leading to apoptosis. Duocarmycin binds to the minor groove of DNA and alkylate the nucleobase adenine, and the irreversible alkylation of DNA disrupts the nucleic acid architecture, which eventually leads to cell death. SN38 in a topoisomerase I inhibitor, and SN38 stabilizes the complex between topoisomerase-I and DNA which collide with moving DNA replication forks, eventu-ally leading to double stranded DNA damage and cell death. In some embodiments, the payload(s) is a cytotoxic agent or drug selected from those listed above. In some embodi-ments, the payload is an auristatin. In some embodiments, the payload is a maytansinoid. In some embodiments, the payload is an anthracycline. In some embodiments, the payload is a duocarmycin. In some embodiments, the pay-load is a microtubule destabilizer (e.g. Taxol). In some embodiments, the payload is a topoisomerase I inhibitor. In some embodiment, the payload is MMAE, MMAF, DM1, DM2, DM3, DM4, pyrrolbenzodiazepine (PBD), doxorubi-cin, tubulysin, chalicheamicin, anthracycline, paclitaxel, duocarmycin, SN38, vinblastine, alpha-amantin, or any combination thereof. In some embodiments, the small mol-ecule drug is less than 3.0 kDa. In some embodiments, the small molecule drug is less than 2.5 kDa. In some embodi-ments, the small molecule drug is less than 2.0 kDa. In some embodiments, the small molecule drug is less than 1.8 kDa. In some embodiments, the cytotoxic small molecule drug has an $IC_{50}$ of less than 100 nM on human cells.

In some embodiments, the payload(s) are peptides and/or proteins other than LL37-derived polypeptides. In alternative embodiments, each of the proteins is less than 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, or 20 kDa. The term "protein" in this context includes a polypeptide chain as well as a multi-chain protein. in some embodiments, the peptide or protein payload is a therapeutic agent (e.g. an anticancer agent). In some embodiments, the peptide or protein payload is a cytotoxic agent (i.e. toxic to human cells, e.g. a cytotoxic agent such as a bacterial toxin, a viral toxin, and the like). In some embodiments, the peptide or protein payload is a diagnostic agent (e.g. a fluorescent or colorimetric marker, radio-labelled peptide/protein, a peptide/protein tag, or any other reporter domain), or a regulatory peptide/protein. In some embodiments, the payload is an apoptosis-inducing protein. In some embodiments, payload is a protease. In some embodiments, the payload is an RNAse. In some embodiments, the payload is a DNAse. In some embodiments, the payload is a transcription factor (e.g. a human transcription factor). The foregoing payloads are not limiting.

In some embodiments, the payload(s) is a proteolysis targeting chimera (PROTAC). In a nonlimiting example, the PROTAC may be heterofunctional small molecule(s) and/or polypeptide(s) comprised of at least two active domains and a linker, which together are capable of removing specific proteins inside cells by one domain binding to E2 or E3 ubiquitin ligase and the second domain binding to a protein targeted for destruction. In some embodiments, the PROTAC is comprised of heterofunctional small molecules. In some embodiments, the PROTAC is comprised of heterofunctional peptides and/or polypeptides. In some embodiments, the PROTAC is comprised of a combination of small molecule(s) and peptide(s)/polypeptide(s).

In some embodiments, the plurality of payloads comprises a combination of small molecule drugs (toxic to human cells) and peptides and/or proteins.

In some embodiments, the covalent conjugate comprises an antibody drug conjugate. As used herein, "antibody drug conjugate", "antibody-drug conjugate" and "ADC" interchangeably refer to conjugates of antibodies that are linked to a cytotoxic payload. In some embodiments the cytotoxic payload is any one or more of the payloads listed above that are cytotoxic (or toxic to human cells). In some embodiments, the cytotoxic payload is an auristatin. In some embodiments, the cytotoxic payload a maytansinoid. In some embodiments, the cytotoxic agent is an anthracycline. In some embodiments, the cytotoxic payload is a duocarmycin. In some embodiments, the cytotoxic payload is a microtubule destabilizer (e.g. Taxol). In some embodiments, the cytotoxic payload is a topoisomerase I inhibitor. In some embodiments, the cytotoxic payload is MMAE, DM1, Doxorubicin, Paclitaxel, Taxol, Duocarmycin, SN38, or any combination thereof. The cytotoxic payload may be present in any ratio relative to the antibody. For example, but without limitation, in some embodiments the cytotoxic payload is present in a Drug to Antibody Ratio (DAR) of 1, 2, 3, 4, 5, 6, 7, 8, 9, 10, 11, 12, 13, 14, 15, 16, 17, 18, 19, 20 or more than 20. The DAR is calculated using the average number of drug moieties conjugated to the antibody, so the ratio may be a fraction of the foregoing (e.g. 0.5, 1.5, 2.45, 2.5 and the like). For the same reason, a ratio given as an integer value includes decimal values that would round up or down to the given integer value. Similarly, a ratio given as a tenths place decimal would include any hundredths place decimals that round up or down to the given tenths place decimal. In some embodiments, DAR is 1, 2, 2.45, 2.5, 3, 4 or 8. High DARs can be achieved by chaining a plurality of small molecule payloads together, e.g. using a Fleximer polymer (see Yurkovetskiy et al., Cancer Res; 75(16), 2015).

In some embodiments, an increase in internalization of a covalent conjugate into the target cells would result in increased internalization of the linked payload(s) (see, Harper et al., (2013) *Methods Mol. Biol.,* 1045, 41; Kim and Kim (2015) *Biomol. Ther. (Seoul),* 23, 493; Vezina et al., (2017) *J. Clin. Pharmacol.,* 57, S11), increasing the efficacy of payload(s) which rely on internalization for their intended effect.

Various covalent linkers are known for connecting a payload to an antibody In some embodiments, the linker is cleavable. In some embodiments, the linker is non-cleavable. Non-limiting examples of cleavable linkers include chemically-labile linkers (e.g. hydrazones, disulfides, and the like, i.e. those which cleave upon exposure to a particular chemical environment in the cell such as the lysosome etc) and enzyme-cleavable linkers such as protease-labile linkers (e.g. valine-citrulline (vc) dipeptide linkers, self-immolative p-aminobenzylcarbamate dipeptide-based linkers, PEGylated and non-PEGylated β-glucuronide linkers, and the like). Non-limiting examples of non-cleavable linkers include thioether linkers, maleimidocaproyl (mc) linkers, and the like. A review of antibody-drug conjugates with a discussion of payloads and linkers is provided in Kim and Kim, 2015, *Biomol Ther (Seoul)* 23: 493-509. Methods for attaching a linker to an antibody are known in the art. In some embodiments, the linker comprises a cathepsin cleavage site, a furin cleavage site, or a secretory signal peptidase cleavage site.

In various embodiments, the payload(s) (e.g. a cytotoxic agent(s) or other payload(s)), optionally with a linker, may be covalently attached to the antibody or to the antibody derivative by forming a disulfide bond with a thiol group of a cysteine residue in the cell surface binding portion, and in some embodiments multiple payloads, optionally with linkers, may be attached in this way. In various embodiments, the payloads, optionally with a linker, may be covalently attached to the antibody or to the antibody derivative using click chemistry.

In various embodiments, the LL37-derived polypeptides may be used as anchors for loading a payload(s) (e.g. a cytotoxic agent(s), small molecule drug, peptide, or protein). This has the advantage of not needing to disrupt the disulfide bonds in the native structure of the cell surface binding portion (e.g. when a LL37-derived polypeptide is attached as a recombinant fusion peptide, or post-translationally by using a sortase reaction or other enzymatic reaction, click chemistry, and the like). For example, a cysteine residue may be added to the sequence of a LL37-derived polypeptide (e.g. using peptide synthesis). Without limitation, the cysteine residue may be added C-terminal (or alternatively N-terminal) relative to the core residues of the LL37-derived polypeptide. Without limitation, the cysteine residue may be added to the C-terminus (or alternatively the N-terminus) of the LL37-derived polypeptide. For example, but without limitation, SEQ ID NO: 35 comprises LL37 and a free C-terminal cysteine. The free terminal cysteine of an LL37-derived peptide may then be used to attach a payload that also has a free thiol (e.g. VcMMAE and the like). For example, but without limitation, VcMMAE (or another ve-cytotoxin or vc-payload) may be conjugated to the free C-terminal thiol of an LL37-derived polypeptide, LL37 (Cys) (e.g. SEQ ID NO:35 and the like). In the example of a covalent conjugate comprising an antibody, each of the LL37(Cys)-conjugated antibodies may have 2 or more free cysteine thiols available for conjugation to Vc-MMAE (or the other vc-cytotoxin or vc-payload). Depending on the reaction order, antibody-LL37(Cys-payload) is produced by first ligating the antibody to the LL37(Cys) polypeptide, and followed by chemical conjugation to vc-payload. In some embodiments, LL37(Cys) polypeptide is first conjugated to vc-payload to form LL37(Cys-payload), and then LL37 (Cys-payload) is ligated to the antibody to produce antibody-[LL37(Cys-payload)]. In either reaction order, the interchain disulfide bonds between heavy and light chains remain intact. The LL37(Cys) may comprise full-length LL37 or any other LL37-derived polypeptide defined herein. The foregoing example also applies to antibody derivatives.

Peptide or protein payloads may alternatively be coupled using the same methods described herein for coupling the LL37-derived polypeptides.

Without wishing to be bound by theory, conjugation of LL37-derived polypeptides to antibodies, ADCs or derivatives thereof at a ratio of at least two LL37-derived polypeptides per antibody monomer may result in covalent conjugates that can form multimers through intermolecular non-covalent association between the LL37-derived polypeptide domains. This may at least in part be the result of an increased concentration of LL37-derived polypeptides at the cell surface due to the binding of the covalent conjugates to the cell surface antigen. In addition, LL37 has been reported to bind outer leaflet phosphatidylserine through its positively charged and hydrophobic side chains, and to oligomerize on the cell surface (see, Sancho-Vaello et al., 2017, Sci. Rep. 7, 15371). Phosphatidylserine (PS) is normally exclusively found in the intracellular leaflet in the plasma membrane of most mammalian cells, but this asymmetric distribution of phosphatidylserine is lost in many diseased or stressed/unhealthy cells (e.g., see De et al., 2018, Mol. Ther. Nucleic Acids., 10, 9). As a result, phosphatidylserine is found in the outer leaflet of various cell types that are targets for therapeutic agents, e.g. cancer cells, infected cells, and autoimmune cells involved in autoimmune conditions/diseases. Accordingly, but without wishing to be bound by theory, the presence of phosphatidylserine in the outer leaflet of the target cell may encourage multimerization of covalent conjugates linked with at least two LL37-derived polypeptides per antibody monomer. The notion that the covalent conjugates are multimerizing at the target cell surface is well supported by the Examples in this disclosure, which show that conjugation with LL37 allows antibodies to dramatically surpass the saturation limit for antibody-binding without LL37-conjugation (see Examples 2 and 11). Importantly, this is not an effect shared by PS-binding domains in general as the Examples in this disclosure show that ADC conjugates with symmetrically linked PS-binding proteins (i.e., Annexin V, Evectin2, Synaptotagamin C2A, Apolipoprotein H V-domains covalently linked to both C-termini of light chains in an antibody) did not provide any significant ADC efficacy enhancement over ADC without PS-binding proteins (see FIG. 39 Panel B). This is in contrast to what was observed in the Examples of this disclosure for conjugating LL37 to antibodies/ADCs, which was shown to significantly enhance the delivery of antibody and greatly improve drug efficacy over ADC without LL37 conjugation. The Examples therefore support a mechanism of action in which the covalent conjugates in this disclosure are multimerizing on the target cell surface, enabling oversaturation of antigen-binding and a dramatic increase in both antibody delivery and ADC drug efficacy. The Examples also show that LL37-linked antibodies exhibit little or no toxicity to cancer cells based on the numerous delivery assays shown herein using high concentrations of LL37-linked antibodies on different cancer cell lines (see FIGS. 3, 4, 5, 6, 7, 8, 9, 24, 28, 29, 30, and 40). The covalent conjugates disclosed herein are therefore ideally suited to improve therapeutic efficacy of existing ADCs.

In some embodiments, the human cell is a cancer cell. In some embodiments, the human cell is a pathogen-infected human cell. In some embodiments, the human cell is an immune cell involved in an autoimmune condition or disease. In some embodiments, the human cell is a human cell line. In some embodiments, the human cell is a human cancer cell line. In some embodiments, the human cell has an outer leaflet that comprises phosphatidylserine. In some embodiments, the human cell has a detectable level of cell surface phosphatidylserine. In some embodiments, the human cell has a low level of cell surface phosphatidylserine. In some embodiments, the human cell has a medium level of cell surface phosphatidylserine. In some embodiments, the human cell has a high level of cell surface phosphatidylserine. In some embodiments, the outer leaflet of the human cell is a diseased or unhealthy cell that comprises more phosphatidylserine than found in the same cell type when healthy, e.g. at least 10%, at least 20%, at least 30%, at least 40%, at least 50%, at least 60%, at least 70%, at least 80%, at least 90%, at least 100%, at least 150%, or at least 200% more than a healthy reference cell of the same type.

In some embodiments, the cell surface epitope is part of a cell surface protein of the human cell, or is part of a protein-containing cell surface antigen (e.g. a glycoprotein or a lipoprotein). As used herein, the term "cell surface protein" includes cell surface glycoproteins, cell surface lipoproteins and protein-containing cell surface antigens. The actual epitope bound by the cell surface binding portion may or may not comprise amino acid residues. The cell surface protein may comprise part of a tumor-specific antigen (e.g. a summary of various antigens are described in Kim and Kim, 2015, *Biomol Ther (Seoul)* 23: 493-509). The cell surface protein may be a cell surface receptor, which are specialized integral membrane proteins that take part in communication between the cell and the cellular environment. Without wishing to be bound by theory, in certain embodiments of the covalent conjugate that target cell surface receptors (i.e. the antibody in the conjugate specifically binds a surface-exposed portion of the cell surface receptor), increased internalization of the conjugate-bound receptor complex may proceed by receptor-mediated endocytosis (e.g. Austin et al., (2004), *Mol. Biol. Cell,* 15, 5268; Tarcic and Tarden (2013), Vesicle Trafficking in Cancer (Springer publishing, ISBN 978-1-4614-6528-7), 361).

Non-limiting examples of cell surface proteins include HER2, alternatively spliced extra domains A and B of fibronectin, CD3e, CD19, CD20, CD22, CD30, CD33, CD33A, CD37, CD56, CD66e, CD70, CD74, CD79b, CD98, CD138, GPNMB, PSMA, TROP-2, SC-16, EGFR (HER1), CAIX, ETBR, TF, NaPi2b, STEAP1, FRα, LIV-1, Nectin-4, SLITRK6, CA6, ENPP3, GCC, Mesotherin, 5T4, folate receptor, CEACAM5, EpCAM, FGFR3, and the like. In some embodiments, the cell surface protein comprises part of human epidermal growth factor receptor 2 (HER2). In some embodiments, the cell surface protein comprises part of CD20. In some embodiments, the cell surface protein comprises folate receptor. In some embodiments, the cell surface protein comprises folate receptor and the target cell is a folate-expressing cell (e.g. SKOV3, OVCAR3, ovarian cancer cell, ovary epithelial adenocarcinoma, and the like). The cell surface protein may comprise part of a cell surface receptor. In some embodiments, the cell surface protein is HER2 and the target cell is a HER2-expressing cell (e.g. OVCAR3, RT4V6, BT474, T47D, RT112, U87MG, AGS, SKOV3, a breast cancer cell, a breast ductal carcinoma cell, a mammary gland ductal carcinoma cell, an ovarian cancer cell, an ovary epithelial adenocarcinoma cell, a stomach cancer cell, a stomach gastric adenocarcinoma cell, a uterine cancer cell, salivary gland tumor cell, NSCLC cell, a glioblastoma cell, and the like). In certain embodiments, the HER2-expressing cell is a high-HER2 expressing cell. In other embodiments, the HER2-expressing cell is a medium-HER2 expressing cell. In other embodiments, the HER2-expressing cell is a low-HER2 expressing cell. For example, overexpression of HER2 contributes to the pathogenesis and progression of certain aggressive forms of breast cancer (e.g., Mitri et al. (2012), Chemother. Res. Pract., 2012, 743193). Overexpression of HER2 is also known to occur in ovarian (e.g., Teplinsky and Muggia (2014), Gynecol. Oncol., 135, 364), stomach (e.g., Boku N. (2014), Gastric Cancer, 17, 1) and aggressive forms of uterine cancer, such as uterine serous endometrial carcinoma (e.g., Buza et al. (2014), Arch. Pathol. Lab. Med., 138, 343). In addition, increased HER2 levels have been related to salivary gland tumors and non-small cell lung cancer (NSCLC) (e.g., Carden et al. (2009), Clin. Pharmacol. Ther., 85, 131). HER2 proteins form clusters in cell membranes that play role in tumor genesis (e.g., Kaufmann et al. (2011), J. Microsc., 242, 46). HER2 is therefore associated with increased disease recurrence and a poor prognosis and has also become an important biomarker and target of therapy for the disease.

In some embodiments, the cell surface protein or antigen (either of which contains the cell surface epitope) comprises: 5AC (Mucin 5AC), 5T4, activin receptor-like kinase 1, ACVR2B, adenocarcinoma antigen, alpha-fetoprotein, AOC3, AXL, c-Met, C242 antigen (CanAg) novel glycoform of MUC1, CA-125, *Canis lupus familiaris* IL31, tumor-associated glycoprotein 72 antigen, Addressin, Angiopoietin-2, C5, CA19-9, Carbonic anhydrase 9 (CA-IX), CCL11, CD3, CD1a, CD1b, CD1c, CD1d, CD1e, CD2, CD3d, CD3e, CD3g, CD4, CD5, CD6, CD7, CD8a, CD8b, CD9, CD10, CD11a, CD11b, CD11c, CD11d, CD13, CD14, CD15s, CD15su, CD15u, CD16a, CD16b, CD17, CD18, CD19, CD20, CD21, CD22, CD23, CD24, CD25, CD26, CD27, CD28, CD29, CD30, CD31, CD32A, CD32B, CD32C, CD33, CD34, CD35, CD36, CD37, CD38, CD39, CD40, CD41, CD42a, CD42b, CD42c, CD42d, CD43, CD44, CD44v6, CD45, CD46, CD47, CD48, CD49a, CD49b, CD49c, CD49d, CD49e, CD49f, CD50, CD51, CD52, CD53, CD54, CD55, CD56, CD57, CD58, CD59, CD60a, CD60b, CD60c, CD61, CD62E, CD62L, CD62P, CD63, CD64a, CD65, CD65s, CD66a, CD66b, CD66c, CD66d, CD66e, CD66f, CD68, CD69, CD70, CD71, CD72, CD73, CD74, CD75, CD75s, CD77, CD79A, CD79B, CD80, CD81, CD82, CD83, CD84, CD85A, CD85B, CD85C, CD85D, CD85F, CD85G, CD85H, CD85I, CD85J, CD85K, CD85M, CD86, CD87, CD88, CD89, CD90, CD91, CD92, CD93, CD94, CD95, CD96, CD97, CD97B, CD98, CD99, CD99R, CD100, CD101, CD102, CD103, CD104, CD105, CD106, CD107a, CD107b, CD108, CD109, CD110, CD111, CD112, CD112R, CD113, CD114, CD115, CD116, CD117, CD118, CD119, CD120a, CD120b, CD121a, CD121b, CD122, CD123, CD124, CD125, CD126, CD127, CD129, CD130, CD131, CD132, CD133, CD134, CD135, CD136, CD137, CD138, CD140A, CD140B, CD141, CD142, CD143, CD144, CD146, CD147, CD148, CD150, CD151, CD152, CD153, CD154, CD155, CD156a, CD156b, CD156c, CD157, CD158a, CD158B1, CD158B2, CD158C, CD158D, CD158E1, CD158E2, CD158F1, CD158F2, CD158G, CD158H, CD158I, CD158J, CD158K, CD159a, CD159c, CD160, CD161, CD162, CD163, CD164, CD165, CD166, CD167a, CD167b, CD168, CD169, CD170, CD171, CD172a, CD172b, CD172g, CD173, CD174, CD175, CD175s, CD176, CD177, CD178, CD179a, CD179b, CD180, CD181, CD182, CD183, CD184, CD185, CD186, CD191, CD192, CD193, CD194, CD195, CD196, CD197, CD198w, CD199, CD200, CD201, CD202b, CD203c, CD204, CD205, CD206, CD207, CD208, CD209, CD210, CD212, CD213a1, CD213a2, CD215, CD217, CD218a, CD218b, CD220, CD221, CD222, CD223, CD224, CD225, CD226, CD227, CD228, CD229, CD230, CD231, CD232, CD233, CD234, CD235a, CD235b, CD236, CD236R, CD238, CD239, CD240CE, CD240D, CD241, CD242, CD243, CD244, CD246, CD247, CD248, CD249, CD252, CD253, CD254, CD256, CD257, CD258, CD261, CD262, CD263, CD264, CD265, CD266, CD267, CD268, CD269, CD270, CD271, CD272, CD273, CD274, CD275, CD276, CD277, CD278, CD279, CD280, CD281, CD282, CD283, CD284, CD286, CD288, CD289, CD290, CD292, CD293w, CD294, CD295, CD296, CD297, CD298, CD299, CD300A, CD300C, CD300E, CD300F, CD301, CD302, CD303, CD304, CD305, CD306, CD307a, CD307b, CD307c, CD307d, CD307e, CD309, CD312, CD314, CD315, CD316, CD317, CD318, CD319, CD320, CD321, CD322, CD324, CD325, CD326, CD327, CD328, CD329, CD331, CD332, CD333, CD334, CD335, CD336, CD337, CD338, CD339, CD340, CD344, CD349, CD350, CD351, CD352, CD353, CD354, CD355, CD357, CD358, CD360, CD361, CD362, CD363, CD364, CD365, CD366, CD367, CD368, CD369, CD370, CD371, CD66, CTGF, Cytokeratin, DLL1, DLL3, DLL4, EGFL7, EGFR, EPHA3, FAP, FcRn, FGF23, Fibrin, Fibronectin, FRalpha, Ganglioside D2, gp75, GPC3, Guanylate cyclase 2C, Hematopoietin 1, Hepatocyte growth factor, Her3, Histone H1, HLA-DR, IgE, IL-13, IL-17, IL-18, IL-2, IL-22, IL-31, IL-5, IL-6, IL1RAP, IL23, INFA1, Integrin beta-7, Interferon receptor, IL-1, Interleukin 23, KLKB1, LEC, Leucine-rich repeat-containing protein 15, LINGO-1, LIV1A, Lysyl oxidase homolog 2, Mesothelin, MIF, MMP9, Myelin-associated glycoprotein, Nectin-4, NOTCH1, NOTCH2, Notch3, PCSK9, PS, PSMA (GCPII), PTK7, Reticulon 4 (NOGO), Sclerostin, SLITRK6, Sodium-dependent phosphate transport protein 2B (NaPi2b), Sphin-gosine-1-phosphate (SIP), STEAP1, TcRa, Tenascin C (TN-C), TIGIT, TROP-2, Tumor necrosis factor, TWEAK, VEGFA, VEGFR1, VEGFR2, VEGRF1, Vimentin, VISTA, or von Willebrand factor.

This disclosure also provides nucleic acids encoding certain embodiments of the aforementioned covalent conjugates (e.g. recombinant proteins). For example, this disclosure provides one or more nucleic acids encoding the covalent conjugate or a precursor (e.g.: an LL37-derived polypeptide linked antibody/derivative or payload-antibody/derivative conjugate).

For covalent conjugate precursors that can be expressed as a single polypeptide (e.g. a fusion protein comprising an antibody heavy chain, an optional peptide linker, and the LL37-derived polypeptide), a single nucleic acid molecule may be used. The nucleic acid may be incorporated into a vector (e.g. a plasmid). In some embodiments, the nucleic acid is incorporated into the expression cassette of a plasmid or a chromosome. The nucleic acid may therefore be operatively linked to a promoter and terminator for expression in a cell (e.g. a prokaryotic or eukaryotic cell, such as a mammalian cell or mammalian cell line or the like). The nucleic acid may be codon-optimized for expression in the cell. The plasmid may further comprise an origin of replication for replication in the cell. The plasmid may further comprise a selection marker (e.g. an antibiotic resistance gene in an expression cassette).

Antibodies and some antibody derivatives are multi-chain proteins post-translationally linked by disulfide bonds. Accordingly, a polycistronic nucleic acid and/or a plurality of nucleic acids may be used to encode the antibody/derivative, the covalent conjugate or a precursor, e.g. an LL37-derived polypeptide linked antibody/derivative or payload-antibody/derivative conjugate. The polycistronic nucleic acid may be incorporated into a vector (e.g. a plasmid). The polycistronic nucleic acid may be incorporated into an expression cassette of a plasmid or a chromosome. Accordingly, in some embodiments the polycistronic nucleic acid may be operatively linked to a promoter and terminator for expression in a cell (e.g. a prokaryotic or eukaryotic cell, such as a mammalian cell or mammalian cell line or the like). Alternatively, the plurality of nucleic acids may be incorporated into a vector (e.g. a plasmid) or a plurality of vectors (e.g. a plurality of plasmids) and/or chromosomes. In some embodiments, each of the plurality of nucleic acids may be incorporated into a separate expression cassette, either on separate vectors and/or chromosomes or on the same vector/chromosome. Accordingly, each of the plurality of nucleic acids may be operatively linked to separate promoters and terminators for expression of the plurality of subunits (nucleic acid and/or protein) in a cell. For example, without limitation a first nucleic acid encoding the heavy chain (or fragment thereof) of an antibody/derivative fused to the LL37-derived polypeptide (optionally with a peptide linker therebetween) may be operatively linked to a first promoter and terminator, and a second nucleic acid encoding the light chain of the antibody/derivative may be operatively linked to a second promoter and terminator. The nucleic acid(s) may be codon-optimized for expression in the expression host cell. The plasmid may further comprise an origin of replication for replication in the expression host cell. The plasmid may further comprise a selection marker (e.g. an antibiotic resistance gene in an expression cassette). Suitable expression systems (including suitable plasmids and expression host cells) for prokaryotic and eukaryotic (including mammalian) cells are known and commercially available.

III. Pharmaceutical Compositions

There is also disclosed a pharmaceutical composition comprising the covalent conjugate as defined herein (e.g. any embodiment as described in Section II). The pharmaceutical compositions of this disclosure may be administered to a subject using any convenient means capable of resulting in the desired therapeutic effect or diagnostic effect. Thus, the cell surface binding conjugates may be formulated into a pharmaceutical composition by combination with appropriate, pharmaceutically acceptable carriers, pharmaceutically acceptable diluents, or other pharmaceutically acceptable excipients and may be formulated into preparations in solid, semi-solid, liquid or gaseous forms, such as tablets, capsules, powders, granules, ointments, solutions, suppositories, injections, inhalants and aerosols. In some embodiments, the pharmaceutical composition comprises the cell surface binding conjugate of this disclosure and one or more pharmaceutically acceptable carriers, excipients and/or stabilizers. Such pharmaceutically acceptable carriers, excipients and/or stabilizers are nontoxic to recipients at the dosages and concentrations used, and include, without limitation, buffers (e.g. phosphate, citrate, and other organic acids), antioxidants (e.g. ascorbic acid, glutathione, cysteine, methionine and citric acid); preservatives (e.g. ethanol, benzyl alcohol, phenol, m-cresol, p-chlor-m-cresol, methyl or propyl parabens, benzalkonium chloride, or combinations thereof), amino acids (e.g. arginine, glycine, ornithine, lysine, histidine, glutamic acid, aspartic acid, isoleucine, leucine, alanine, phenylalanine, tyrosine, tryptophan, methionine, serine, proline and combinations thereof), monosaccharides, disaccharides or other carbohydrates, low molecular weight (e.g. less than about 10 residues) polypeptides, proteins (e.g. gelatin, serum albumin or the like), chelating agents (e.g. EDTA), sugars (e.g. trehalose, sucrose, lactose, glucose, mannose, maltose, galactose, fructose, sorbose, raffinose, glucosamine, N-methylglucosamine, galactosamine, and neuraminic acid), non-ionic surfactants (e.g. Tween™, Brij™, Pluronics™, Triton-X™, polyethylene glycol (PEG), and the like) or combinations thereof.

The pharmaceutical compositions may comprise the covalent conjugate in the form of a pharmaceutically acceptable salt, or may be used alone or in appropriate association, as well as in combination, with other pharmaceutically active compounds.

Actual methods of preparing pharmaceutical compositions in forms suitable for the various routes of administration (e.g. oral, pulmonary, intravenous, subcutaneous, intramuscular and the like) are known, or will be apparent, to those skilled in the art (e.g., Remington's Pharmaceutical Sciences, Mack Publishing Company, Easton, Pennsylvania, 17th edition, 1985). The pharmaceutical composition will in any event comprise a quantity of the covalent conjugate sufficient to achieve the treatment of the condition or disease in the subject (i.e. an effective amount). Non-limiting exemplary concentrations of a covalent conjugate in the pharmaceutical compositions of this disclosure may range from about 1 mg/mL to about 200 mg/mL or from about 50 mg/mL to about 200 mg/mL, or from about 150 mg/mL to about 200 mg/mL.

IV. Uses & Methods

The covalent conjugates defined herein (e.g. as described in Section II) or the pharmaceutical compositions defined herein (e.g. as described in Section III) have various uses. For example, the above have uses as research tools or as therapeutic agents.

The terms "treat", "treatment" or "treating" as used herein includes achieving a therapeutic benefit. A therapeutic benefit includes eradication or amelioration of the underlying disorder or condition being treated (e.g. partial or complete halting of the progression of the particular disorder, or partial or complete reversal of the particular disorder) and further includes the eradication or amelioration of one or more of the physiological symptoms associated with the underlying condition such that an improvement is observed in the subject, notwithstanding the fact that the subject may still be affected by the condition.

Certain embodiments of the covalent conjugate defined herein (e.g. as described in Section II and including without limitation any embodiment defined in Section II) may be used for delivering, or for increasing delivery of, the antibody, antibody derivative, or the payload(s) conjugated to the antibody or the antibody derivative to a human cell (e.g. a cancer cell or other human cell) that expresses the cell surface epitope that the antibody/derivative specifically binds. Certain embodiments of the covalent conjugate may be used for intracellular delivery, or for increasing intracellular delivery of, the antibody, the antibody derivative, or the payload(s) conjugated to the antibody or the antibody derivative to the human cell. In certain embodiments, the covalent conjugate may be used for delivering, or for increasing delivery of, the payload(s) to the human cell. As such, this disclosure provides a method for increasing delivery of the antibody or antibody derivative (or the payload(s)) to a human cell, comprising contacting the human cell with the covalent conjugate, wherein the human cell expresses the cell surface epitope that the antibody or the antibody derivative specifically binds. In some of these embodiments, the human cell is a cancer cell, and some other embodiments the human cell is an immune cell. In some embodiments, the method/use may further comprise conjugating the LL37-derived polypeptide to the antibody, the antibody derivative to form the covalent conjugate comprising the LL37-derived polypeptide. In some embodiments, the method/use may further comprise conjugating the LL37-derived polypeptide to an antibody-payload conjugate or an antibody derivative-payload conjugate to form the covalent conjugate comprising the LL37-derived polypeptide. In some embodiments, the method/use may further comprise conjugating the payload(s) to a covalent conjugate comprising the LL37-derived polypeptide and the antibody or the antibody derivative to form a covalent conjugate comprising the antibody or antibody derivative, the LL37-derived polypeptides, and the payloads. In some embodiments, the method/use may further comprise conjugating the LL37-derived polypeptides to a covalent conjugate comprising the antibody or the antibody derivative and the payload(s) (e.g. an ADC and the like) to form a covalent conjugate comprising the antibody or antibody derivative, the LL37-derived polypeptides, and the payload(s). The use and the method may be an in vitro or ex vivo use and method, respectively, or may be an in vivo use and method, respectively. As described in Section II, the increase in delivery includes increased delivery to the cell surface and, in certain embodiments may include increased intracellular delivery. As described in Section II, in alternative embodiments, delivery may be increased by at least 2-fold, at least 3-fold, at least 4-fold, at least 5-fold, at least 6-fold, at least 7-fold, at least 8-fold, at least 9-fold, at least 10-fold, at least 11-fold, at least 12-fold, at least 13-fold, at least 14-fold, at least 15-fold, at least 16-fold, at least 17-fold, at least 18-fold, at least 19-fold or at least 20-fold, e.g. when delivery is measured in vitro (as described in the Examples herein) at a concentration of 100 nM conjugate or cell surface binding portion.

In certain embodiments where the payload(s) (as defined herein, e.g. as described in Section II) comprise a detectable marker (e.g. a fluorescent marker, a colorimetric marker, a primary marker that is visualizable using a detectable secondary marker that binds the primary marker, or any other marker), the covalent conjugate may be used in research assays or in in vitro diagnostic tests to identify the presence, level, localization or morphology (depending on the application) of cells (e.g. in a cell line, or in a cell or tissue obtained from a subject) that are positive for the cell surface epitope that is specifically bound by the antibody or the antibody derivative. Accordingly, there is provided a method comprising contacting the cells with the covalent conjugate and detecting the bound or internalized conjugate or payload(s).

Furthermore, for embodiments where the covalent conjugate (as defined herein, e.g. as described in Section II and including without limitation any embodiments defined in Section II) comprises a payload(s), and the payload(s) comprise an imaging agent (e.g. a radiocontrast agent or a magnetic resonance imaging contrast agent), the covalent conjugate may be used in diagnostic tests to identify the presence, level, localization or morphology (depending on the application) of cells or tissues of a subject that are positive for the cell surface epitope that is specifically bound by the cell antibody. Accordingly, there is provided a method comprising contacting the cells with the covalent conjugate (ex vivo or by administration to a subject) and detecting the bound or internalized conjugate or payload(s), e.g. by imaging a subject or imaging a sample obtained from a subject.

In some embodiments, there is the use of the covalent conjugate for detecting or imaging a condition or disease selected from Table 1, wherein the covalent conjugate comprises: an antibody selected from Table 1 which corresponds to the condition or disease to be detected; a detectable payload(s); and the first LL37-derived peptide and the second LL37-derived peptide as defined herein (e.g. as described in Section II). The conjugate may be for ex vivo use or for in vivo use. In some embodiments, there is a method of detecting a condition or disease selected from Table 1 (below) in a subject. The method comprises: (i) administering to the subject a covalent conjugate comprising: an antibody or a derivative thereof selected from Table 1 corresponding to the condition or disease to be detected; a detectable payload(s); and a first LL37-derived peptide and a second LL37-derived peptide as defined herein (e.g. as described in Section II); and (ii) detecting or imaging the conjugate or payload(s) in tissue of the subject. The method may be an ex vivo method. The method may be an in vivo method.

TABLE 1

List of antibodies and their associated condition(s) or disease(s) to be detected or imaged (i.e. diagnostic indication)

| Tradename | Antibody or Derivative | Target | Type | Condition or Disease to be Detected/ Imaged |
|---|---|---|---|---|
| NeutroSpec ™ | Fanolesomab | CD15 | Murine MAb | Equivocal appendicitis |
| NeutroSpec ™ | Fanolesomab | CD15 | Murine | Equivocal appendicitis |
| Humaspect ™ | Votumumab | Cyto-keratin-tumor-associated antigen | MAb | Carcinoma of the colon or rectum |
| ProstaScint ™ | Capromab | Tumor surface antigen PSMA | Murine MAb | Prostate adenocarcinoma |
| OncoScin ™ | Satumomab | TAG-72 | Murine MAb | Colorectal and ovarian cancers |

In some embodiments, there is a method of treating a cancer in a human subject comprising administering to the subject a covalent conjugate as defined herein (e.g. as described in Section II and including any such embodiment defined in Section II), wherein the antibody or the antibody derivative of the covalent conjugate selectively binds tumor cells of the cancer, and wherein the payload of the covalent conjugate is toxic to human cells. In some embodiments, there is a use of a covalent conjugate as defined herein (e.g.

as described in Section II and including any such embodiment defined in Section II) in manufacture of a medicament for treating a cancer, wherein the antibody or the antibody derivative of the covalent conjugate selectively binds tumor cells of the cancer, and wherein the payload of the covalent conjugate is toxic to human cells. In some embodiments of the method and use, respectively, the payload has an $IC_{50}$ of less than 100 nM on human cells. In some embodiments of the method and use, respectively, the covalent conjugate comprises: 18V4F, 4R34.1.19, A-803, Abagovomab, Abciximab, Abituzumab, Abrezekimab, Abrilumab, Adalimumab, ADCPF-06688992, Adecatumumab, Ado-trastuzumab, Afelimomab, Afutuzumab, AGS16F, Alacizumab, Alemtuzumab, Alirocumab, ALKS4230, Altumomab, Amatuximab, AMG191, AMG531, Anatumomab, Andecaliximab, Anetumab, Anifrolumab, Anti-HM1.24, Apolizumab, Aprutumab, Arcitumomab, ARD5, Aselizumab, ASG-15ME, Atezolizumab, Atinumab, AUTO2, Avelumab, Azintuxizumab, B-701, Basiliximab, Bavituximab, BAY1179470, Bectumomab, Begelomab, Belantamab, Belimumab, Bemarituzumab, Benralizumab, Bersanlimab, Bertilimumab, Bevacizumab, BI-505, Biciromab, B11B023, Bimagrumab, Bimekizumab, BION-1301, Bivatuzumab, Bleselumab, Blinatumomab, Blontuvetmab, Blosozumab, BMS-986148, BMS-986156, BMS-986179, Brentuximab, Brodalumab, Brolucizumab, Brontictuzumab, BTH1704, Burosumab, C7-FcDT, Cabiralizumab, Camidanlumab, Camrelizumab, CAN04, Canakinumab, Cantuzumab, CAP-100, Caplacizumab, capromab, Carotuximab, Catumaxomab, CC-90002, CD133KDEL, CD147-CART, CD96-S32F, CDX-1401, Cedelizumab, Cemiplimab, Cergutuzumab, Cetrelimab, Cetuximab, Cibisatamab, Citatuzumab, Cixutumumab, Claudiximab, Clenoliximab, Clivatuzumab, Codrituzumab, Cofetuzumab, Coltuximab, COM701, COM902, Conatumumab, Crizanlizumab, Crotedumab, CSL324, Cusatuzumab, Dacetuzumab, Daclizumab, Dalotuzumab, Dapirolizumab, Daratumumab, Darleukin, DCR2, Dectrekumab, Demcizumab, Denintuzumab, Denosumab, Depatuxizumab, Derlotuximab, Detumomab, Dinutuximab, Dorlimomab, Drozitumab, Duligotuzumab, Dupilumab, Durvalumab, Duvortuxizumab, Ecromeximab, Eculizumab, Edrecolomab, Efalizumab, EGFR806, EJ212_007-C12-5, ELB01101, Elgemtumab, Elotuzumab, Elsilimomab, Emactuzumab, Emapalumab, EMD525797, Emibetuzumab, Enapotamab, Enavatuzumab, Enfortumab, Enoblituzumab, Enoticumab, EOL4G8, Epratuzumab, Ertumaxomab, Etaracizumab, Evolocumab, Fanolesomab, Faralimomab, Farletuzumab, Fezakinumab, Fibatuzumab, Ficlatuzumab, Flanvotumab, Flotetuzumab, FLYSYN, Foralumab, Galiximab, Gancotamab, Ganitumab, Gatipotuzumab, Gavilimomab, GD2Bi-aATC, Gemtuzumab, GI-270384, Gilvetmab, Girentuximab, Glembatumumab, Golimumab, Gomiliximab, GSK2849330, Guselkumab, HB-n1, HFE7A, HLX20, HS-110, Hu3S193, Ibalizumab, Ibritumomab, Icrucumab, Ifabotuzumab, Igovomab, Imalumab, Imaprelimab, IMC-CS4, Imgatuzumab, Inclacumab, Indatuximab, Indusatumab, Inebilizumab, Infliximab, Inotuzumab, Intetumumab, Iomab-B, iPH5401, Ipilimumab, Iratumumab, Isatuximab, Iscalimab, Istiratumab, Itolizumab, Ixekizumab, Keliximab, KH7B9, KTN0182A, KU42.33C, Labetuzumab, Ladiratuzumab, Lanadelumab, Lanalumab, Laprituximab, Lemalesomab, Leronlimab, Letolizumab, Lexatumumab, Lifastuzumab, Lilotomab, Lintuzumab, Lirilumab, Lokivetmab, Loncastuximab, Lorvotuzumab, Losatuxizumab, Lucatumumab, Lulizumab, Lumretuzumab, Lupartumab, Lutikizumab, LY3321367, LY3435151, M290, Mapatumumab, Margetuximab, Maslimomab, Matuzumab, Mavrilimumab, MBG453, MCLA-117, MED13617, MED13622, MEN1112, Mepolizumab, Milatuzumab, Minretumomab, Mirvetuximab, Mitumomab, MLS102, MM-111, MMP9, MNRP1685A, Modotuximab, Mogamulizumab, Monalizumab, Moxetumomab, MOXR0916, Muromonab, MVT-5873, Nacolomab, Naptumomab, Naratuximab, Namatumab, Natalizumab, Navicixizumab, Necitumumab, Nerelimomab, Nesvacumab, Netakimab, NI-0101, Nimotuzumab, Nivolumab, NNC0151-00000000, Nofetumomab, Obinutuzumab, Ocaratuzumab, Ocrelizumab, Odulimomab, Ofatumumab, Olaratumab, Oleclumab, olokizumab, Omalizumab, Onartuzumab, Ontuxizumab, Onvatilimab, Opicinumab, Oportuzumab, Oregovomab, Otelixizumab, Otlertuzumab, Oxelumab, Pamrevlumab, Panitumumab, Pankomab, Parsatuzumab, Pasotuxizumab, Patritumab, PD-0360324, PDR001, Pembrolizumab, Pemtumomab, Pertuzumab, PF-00547659, PF-03446962, PF-04518600, PF-06650808, Pidilizumab, Pinatuzumab, Pintumomab, Plozalizumab, Polatuzumab, Prezalumab, Priliximab, Pritumumab, PTK7-ADC, Quilizumab, Radretumab, Ramucirumab, Ranibizumab, Ravagalimab, Refanezumab, REGN2176, Relatlimab, Reslizumab, RG7287, Rilotumumab, Rinucumab, Risankizumab, Rituximab, RO-001, R06958688, Robatumumab, Romilkimab, Romosozumab, Rovalpituzumabtesirine, Rovelizumab, Rozanolixizumab, Ruplizumab, Sacituzumab, Samalizumab, Samrotamab, SAR252067, SAR408701, Sarilumab, Satralizumab, Satumomab, Secukinumab, Selicrelumab, Seribantumab, Setrusumab, SGN-15, SGN-CD123A, SGN-CD228A, SGN-CD352A, SGN-CD47M, SGN-CD48A, SGN-CD70A, SGN-LIV1A, SHP647, Siamab.com, Sibrotuzumab, Siltuximab, Simtuzumab, Sirtratumab, SL-279252, Sofituzumab, Solitomab, Sonepcizumab, Sontuzumab, Spartalizumab, Sphingomab, SS1 (dsFv) PE38 (CAT-5001), Sulesomab, TAB004, Tabalumab, Tacatuzumab, Tadocizumab, Talacotuzumab, Tamtuvetmab, Taplitumomab, Tarextumab, Telimomab, Telisotuzumab, Tenatumomab, Teneliximab, Teplizumab, Tepoditamab, Teprotumumab, Theralizumab, Tigatuzumab, Tildrakizumab, Timigutuzumab, Timolumab, Tiragotumab, Tislelizumab, Tisotumab, TKH2, Tocilizumab, Tomuzotuximab, Tositumomab, Trastuzumab, Tregalizumab, Tremelimumab, TSR-022, TTX-030, Tucotuzumab, Ublituximab, Ulocuplumab, Urelumab, Ustekinumab, Ustekinumab, Vadastuximab, Vanalimab, Vapaliximab, Varlilumab, Vatelizumab, Vedolizumab, Vepalimomab, Vesencumab, Visilizumab, Vobarilizumab, Vofatamab, Volociximab, Vonlerolizumab, Vopratelimab, Vorsetuzumab, Votumumab, Vunakizumab, VX15/2503, Y-443, Zalutumumab, Zanolimumab, Zenocutuzumab, Ziralimumab, or Zolbetuximab. In some embodiments of the method and use, respectively, the antibody, the antibody derivative or the antibody-drug conjugate comprises: an anti-HER2 antibody, an anti-folate receptor antibody, an anti-EGFR antibody, an anti-CD20 antibody, an anti-FGFR3 antibody, an anti-Napi2b antibody, an anti-CEACAM5 antibody, an anti-EPCAM antibody, or an anti-PSMA antibody. In some embodiments of the method and use, respectively, the covalent conjugate comprises: Trastuzumab, Mirvetuximab, Panitumumab, Lifastuzumab, Labetuzumab, Citatuzumab, Rituximab, Vadastuximab, Vofatamab, Ofatumumab, Foralumab, Brentuximab, or hj591. In some embodiments of the method and use, respectively, the covalent conjugate comprises Trastuzumab. In some embodiments of the method or use, respectively, the covalent conjugate comprises an antibody, an antibody derivative, or an antibody-drug conjugate (ADC) selected from Table 2 or Table 3 and the and the cancer is a cancer indicated in Table 2 or 3 as being treated by the antibody or ADC selected from Table 2 or 3. In some embodiments, the cancer comprises a solid tumor, and the covalent conjugate comprises: 5B1(MVT-5873), Abagovomab, Abituzumab, Abrezekimab, ADCPF-06688992, Adecatumumab, AGS16F, Alacizumab, ALKS4230, Altumomab, Amatuximab, AMG191, Anatumomab, Andecaliximab, Anetumab, Anti-HM1.24, Aprutumab, Arcitumomab, ASG-15ME, Atezolizumab, Atinumab, Avelumab, B-701, Bavituximab, BAY1179470, Bemarituzumab, Bersanlimab, Bevacizumab, BI-505, Bivatuzumab, Bleselumab, BMS-986148SS1, BMS-986156, BMS-986179, Brolucizumab, Brontictuzumab, BTH1704Pemtumomab, Cabiralizumab, Camrelizumab, CAN04, Cantuzumab, Carotuximab, Catumaxomab, CC-90002, CD133KDEL, CD147-CART, CDX-1401, Cemiplimab, Cergutuzumab, Cetrelimab, Cetuximab, Cibisatamab, Citatuzumab, Cixutumumab, Claudiximab, Clivatuzumab, Codrituzumab, Cofetuzumab, COM701, Com902, Conatumumab, Crizanlizumab, Crotedumab, Cusatuzumab, Dacetuzumab, Dalotuzumab, Dectrekumab, Demcizumab, Depatuxizumab, Derlotuximab, dinutuximab, Drozitumab, Duligotuzumab, Durvalumab, Ecromeximab, Edrecolomab, EGFR806, Elgemtumab, Emactuzumab, EMD525797, Emibetuzumab, Enapotamab, Enavatuzumab, Enfortumab, Enoblituzumab, Enoticumab, EOL4G8, Ertumaxomab, Etaracizumab, Fanolesomab, Farletuzumab, Fibatuzumab, Ficlatuzumab, Flanvotumab, Gancotamab, Ganitumab, Gatipotuzumab, Gavilimomab, GD2Bi-aATC, GI-270384, Gilvetmab, Girentuximab, Glembatumumab, GSK2849330, HLX20, HS-110, Hu3S193, Icrucumab, Ifabotuzumab, Igovomab, Imalumab, Imaprelimab, IMC-CS4, Imgatuzumab, Inclacumab, Indatuximab, Indusatumab, Intetumumab, iPH5401, Ipilimumab, Iscalimab, Istiratumab, KH7B9, KTN0182A, KU42.33C, Labetuzumab, Ladiratuzumab, Laprituximab, Leronlimab, Lexatumumab, Lifastuzumab, Lirilumab, Lorvotuzumab, Losatuxizumab, Lucatumumab, Lulizumab, Lumretuzumab, Lupartumab, Lutikizumab, LY3321367, LY3435151, Mapatumumab, Margetuximab, C7-FcDT, Matuzumab, MBG453, MEDI3617, MEDI3622, Milatuzumab, Minretumomab, Mirvetuximab, Mitumomab, MLS102, MM-111, MMP9, MNRP1685A, Modotuximab, Monalizumab, MOXR0916, Nacolomab, Naptumomab, Narnatumab, Navicixizumab, Necitumumab, Nesvacumab, Nimotuzumab, Nivolumab, NNC0151-00000000, Nofetumomab, Olaratumab, Oleclumab, Onartuzumab, Ontuxizumab, Onvatilimab, Oportuzumab, Oregovomab, Oxelumab, Pamrevlumab, Panitumumab, Pankomab, Parsatuzumab, Pasotuxizumab, Patritumab, PD-0360324, PDR001, PE38 (CAT-5001), Pembrolizumab, Pertuzumab, PF-03446962, PF-04518600, PF-06650808, Pidilizumab, Pintumomab, Pritumumab, PTK7-ADC, Ramucirumab, Ranibizumab, Ravagalimab, Relatlimab, RG7287, Rilotumumab, RO-001, R06958688, Robatumumab, Romilkimab, Rovalpituzumab, Sacituzumab, Samrotamab, SAR408701, Sarilumab, Satralizumab, Satumomab, Selicrelumab, Seribantumab, SGN-15, SGN-CD228A, SGN-CD47M, SGN-CD70A, SGN-LIV1A, Sibrotuzumab, Sirtratumab, SL-279252, Sofituzumab, Solitomab, Sonepcizumab, Sontuzumab, Spartalizumab, Sphingomab, TAB004, Tacatuzumab, Tarextumab, Telisotuzumab, Tenatumomab, Teneliximab, Teprotumumab, Theralizumab, Tigatuzumab, Timigutuzumab, Timolumab, Tiragotumab, Tislelizumab, Tisotumab, TKH2HB-n1, Tocilizumab, Tomuzotuximab, Trastuzumab, Tremelimumab, TSR-022, TTX-030, Tucotuzumab, Urelumab, Vanalimab, Vapaliximab, Varlilumab, Vatelizumab, Vepalimomab, Vesencumab, Vobarilizumab, Vofatamab, Volociximab, Volociximab, Vonlerolizumab, Vopratelimab, Vorsetuzumab, Votumumab, VX15/2503, Y-443, Zalutumumab, Zenocutuzumab, Ziralimumab, or Zolbetuximab. In some embodiments, the cancer comprises a liquid tumor and the covalent conjugate comprises: A-803, ADCPF-06688992, Afutuzumab, Alemtuzumab, AMG191, AMG531, Anti-HM1.24, Apolizumab, Atezolizumab, AUTO2, Avelumab, Azintuxizumab, Basiliximab, Bectumomab, Belantamab, Bersanlimab, BI-505, BION-1301, Bleselumab, Blinatumomab, Blontuvetmab, Brentuximab, Cabiralizumab, Camidanlumab, Camrelizumab, CAN04, CAP-100, CC-90002, CD133KDEL, CD96-S32F, CDX-1401, Cedelizumab, Cemiplimab, Cetrelimab, Cixutumumab, Clenoliximab, Codrituzumab, Coltuximab, Com902, Conatumumab, Crotedumab, Cusatuzumab, Dacetuzumab, Daclizumab, Dalotuzumab, Dapirolizumab, Daratumumab, Darleukin, DCR2, Dectrekumab, Denintuzumab, Detumomab, Drozitumab, Durvalumab, Duvortuxizumab, Efalizumab, EJ212_007-C12-5, ELB01101, Elotuzumab, Elsilimomab, Emactuzumab, Emibetuzumab, Enapotamab, Epratuzumab, Fanolesomab, Fibatuzumab, Ficlatuzumab, Flotetuzumab, FLYSYN, Foralumab, Galiximab, Ganitumab, Gemtuzumab, GI-270384, Gilvetmab, Gomiliximab, HFE7A, Hu3S193, Ibalizumab, Ibritumomab, Ifabotuzumab, IMC-CS4, Inebilizumab, Inotuzumab, Iomab-B, Ipilimumab, Iratumumab, Isatuximab, Iscalimab, Istiratumab, Itolizumab, Keliximab, KTN0182A, Leronlimab, Letolizumab, Lexatumumab, Lilotomab, Lintuzumab, Lirilumab, Loncastuximab, Lucatumumab, Lulizumab, Lutikizumab, Maslimomab, MCLA-117, MEN1112, Milatuzumab, Mitumomab, Mogamulizumab, Monalizumab, Moxetumomab, Muromonab, Nacolomab, Naratuximab, Natalizumab, NI-0101, Nivolumab, Nofetumomab, Obinutuzumab, Ocaratuzumab, Ocrelizumab, Odulimomab, Ofatumumab, Olokizumab, Onartuzumab, Otelixizumab, Otlertuzumab, Oxelumab, PD-0360324, PDR001, Pembrolizumab, Pidilizumab, Pinatuzumab, Polatuzumab, Priliximab, Radretumab, Ravagalimab, REGN2176, Relatlimab, Rilotumumab, Rinucumab, Rituximab, RO-001, Robatumumab, Romilkimab, Rovelizumab, Ruplizumab, Samalizumab, Sarilumab, Satralizumab, Selicrelumab, SGN-15, SGN-CD123A, SGN-CD352A, SGN-CD47M, SGN-CD48A, SGN-CD70A, Siltuximab, SL-279252, Sontuzumab, Spartalizumab, Tabalumab, Talacotuzumab, Tamtuvetmab, Taplitumomab, Telimomab, Telisotuzumab, Teneliximab, Teplizumab, Tepoditamab, Teprotumumab, Theralizumab, Tigatuzumab, Tiragotumab, Tislelizumab, Tocilizumab, Tositumomab, Tregalizumab, Tremelimumab, TTX-030, Ublituximab, Ulocuplumab, Vadastuximab, Vanalimab, Varlilumab, Visilizumab, Vobarilizumab, Vorsetuzumab, or Zanolimumab. In some embodiments, the cancer is treatable by checkpoint inhibitor therapy and the covalent conjugate comprises: ALKS4230, Atezolizumab, Avelumab, Bleselumab, Cabiralizumab, Camrelizumab, CDX-1401, Cemiplimab, Cetrelimab, COM701, Com902, Dacetuzumab, Durvalumab, EGFR806, Elsilimomab, Emactuzumab, Enoblituzumab, Gilvetmab, HLX20, HS-110, Imalumab, IMC-CS4, Ipilimumab, Iscalimab, Lucatumumab, Lulizumab, MEDI3622, Monalizumab, MOXR0916, Nivolumab, Olokizumab, Oxelumab, PD-0360324, PDR001, Pembrolizumab, PF-04518600, Pidilizumab, Ravagalimab, Relatlimab, Samalizumab, Selicrelumab, Siltuximab, SL-279252, Spartalizumab, TAB004, Teneliximab, Theralizumab, Tiragotumab, Tislelizumab, Tremelimumab, Urelumab, Vanalimab, Varlilumab, Vonlerolizumab, or Vopratelimab.

TABLE 2

List of antibodies/derivatives and antibody-drug conjugates (ADCs),
target antigens and condition(s) or disease(s) to be treated

| Antibody, Antibody Derivative or ADC | Target | Condition/Disease |
|---|---|---|
| 3F8 | GD2 ganglioside | neuroblastoma |
| Abagovomab | CA-125 (imitation) | ovarian cancer |
| Abituzumab | CD51 | cancer |
| Adecatumumab | EpCAM | prostate and breast cancer |
| Afutuzumab | CD20 | lymphoma |
| Alacizumab pegol | VEGFR2 | cancer |
| Altumomab pentetate | CEA | colorectal cancer |
| Amatuximab | mesothelin | cancer |
| Anatumomab mafenatox | TAG-72 | non-small cell lung carcinoma |
| Anetumab ravtansine | MSLN | cancer |
| Apolizumab | HLA-DRbeta | hematological cancers |
| Aprutumab ixadotin | FGFR2 | solid tumors known to express fibroblast growth factor receptor 2 (FGFR2) |
| Arcitumomab | CEA | gastrointestinal cancers (diagnosis) |
| Ascrinvacumab | activin receptor-like kinase 1 | cancer |
| Atezolizumab | PD-L1 | cancer |
| Avelumab | PD-L1 | cancer |
| Azintuximab vedotin | CD319 | cancer |
| Bavituximab | phosphatidylserine | cancer |
| BCD-100 | PD1 | melanoma |
| Bectumomab | CD22 | non-Hodgkin's lymphoma (detection) |
| Belantamab mafodotin | BCMA | cancer |
| Bemarituzumab | FGFR2 | cancer |
| Besilesomab | CEA-related antigen | inflammatory lesions and metastases (detection) |
| Biciromab | fibrin II, fibrin II beta chain | thromboembolism (diagnosis) |
| Bimagrumab | ACVR2B | inhibitor |
| Bivatuzumab mertansine | CD44 v6 | squamous cell carcinoma |
| Blinatumomab | CD19 | pre-B ALL (CD19+); leukemia |
| Brentuximab vedotin | CD30 (TNFRSF8) | Hodgkin lymphoma; Anaplastic large-cell lymphoma |
| Brontictuzumab | Notch 1 | cancer |
| Cabiralizumab | CSF1R | metastatic pancreatic cancer |
| Camidanlumab tesirine | CD25 | non-Hodgkin lymphoma, acute lymphoblastic leukemia, acute myeloid leukemia |
| Camrelizumab | programmed cell death 1 | hepatocellular carcinoma |
| Cantuzumab mertansine | mucin CanAg | colorectal cancer etc. |
| Cantuzumab ravtansine | MUC1 | cancers |
| Capromab pendetide | PSMA | prostate cancer (detection) |
| Carotuximab | endoglin | angiosarcoma |
| Catumaxomab | EpCAM, CD3 | ovarian cancer, malignant ascites, gastric cancer |
| CBR96-doxorubicin immunoconjugate | Lewis-Y antigen | cancer |
| Cemiplimab | PCDC1 | cancer |
| Cetrelimab | programmed cell death 1 | cancer |
| Cetuximab | EGFR | metastatic colorectal cancer and head and neck cancer |
| Cibisatamab | CEACAM5 | cancer |
| Citatuzumab bogatox | EpCAM | ovarian cancer and other solid tumors |
| Cixutumumab | IGF-1 receptor (CD221) | solid tumors |
| Clivatuzumab tetraxetan | MUC1 | pancreatic cancer |
| Codrituzumab | glypican 3 | cancer |
| Cofetuzumab pelidotin | PTK7 | cancer |
| Coltuximab ravtansine | CD19 | cancer |
| Conatumumab | TRAIL-R2 | cancer |
| Cusatuzumab | CD70 | cancer |
| Dacetuzumab | CD40 | hematologic cancers |
| Dalotuzumab | IGF-1 receptor (CD221) | cancer etc. |
| Daratumumab | CD38 | Multiple myeloma |
| Denintuzumab mafodotin | CD19 | cancer |
| Depatuxizumab mafodotin | EGFR | glioblastoma |
| Derlotuximab biotin | histone complex | recurrent glioblastoma multiforme |
| Detumomab | B-lymphoma cell | lymphoma |
| Dinutuximab | GD2 ganglioside | neuroblastoma |

TABLE 2-continued

List of antibodies/derivatives and antibody-drug conjugates (ADCs),
target antigens and condition(s) or disease(s) to be treated

| Antibody, Antibody Derivative or ADC | Target | Condition/Disease |
|---|---|---|
| Drozitumab | DR5 | cancer |
| DS-8201 | HER2 | gastric or gastroesophageal junction adenocarcinoma |
| Duligotuzumab | ERBB3 (HER3) | testicular cancer |
| Durvalumab | PD-L1 | cancer |
| Duvortuxizumab | CD19, CD3E | cancer |
| Ecromeximab | GD3 ganglioside | malignant melanoma |
| Edrecolomab | EpCAM | colorectal carcinoma |
| Elgemtumab | ERBB3 (HER3) | cancer |
| Elotuzumab | SLAMF7 | multiple myeloma |
| Emactuzumab | CSF1R | cancer |
| Emibetuzumab | HGFR | cancer |
| Enapotamab vedotin | AXL | cancer |
| Enavatuzumab | TWEAK receptor | cancer |
| Enfortumab vedotin | nectin-4 | urothelial cancer |
| Enoblituzumab | CD276 | cancer |
| Ensituximab | 5AC | cancer |
| Epratuzumab | CD22 | cancer, SLE |
| Ertumaxomab | HER2/neu, CD3 | breast cancer |
| Etaracizumab | integrin $\alpha_{v}\beta_{3}$ | melanoma, prostate cancer, ovarian cancer etc. |
| Farletuzumab | folate receptor 1 | ovarian cancer |
| FBTA05 | CD20 | chronic lymphocytic leukemia |
| Figitumumab | IGF-1 receptor (CD221) | adrenocortical carcinoma, non-small cell lung carcinoma etc. |
| Flanvotumab | TYRP1 (glycoprotein 75) | melanoma |
| Flotetuzumab | IL 3 receptor | hematological malignancies |
| Futuximab | EGFR | cancer |
| Galiximab | CD80 | B-cell lymphoma |
| Gancotamab | IGF-1 | cancer |
| Ganitumab | IGF-1 receptor (CD221) | cancer |
| Gatipotuzumab | MUC1 | cancer |
| Gemtuzumab ozogamicin | CD33 | acute myelogenous leukemia |
| Girentuximab | carbonic anhydrase 9 (CA-IX) | clear cell renal cell carcinoma |
| Glembatumumab vedotin | GPNMB | melanoma, breast cancer |
| IBI308 | PD1 | squamous cell non-small cell lung cancer |
| Ibritumomab tiuxetan | CD20 | non-Hodgkin's lymphoma |
| Icrucumab | VEGFR-1 | cancer |
| Ifabotuzumab | EPHA3 | cancer |
| Igovomab | CA-125 | ovarian cancer (diagnosis) |
| Iladatuzumab vedotin | CD97B | cancer |
| IMAB362 | CLDN18.2 | gastrointestinal adenocarcinomas and pancreatic tumor |
| Imgatuzumab | EGFR | cancer |
| Inclacumab | selectin P | cardiovascular disease |
| Indatuximab ravtansine | SDC1 | cancer |
| Indusatumab vedotin | GUCY2C | cancer |
| Inebilizumab | CD19 | cancer |
| Intetumumab | CD51 | solid tumors (prostate cancer, melanoma) |
| Inotuzumab ozogamicin | CD22 | ALL |
| Ipilimumab | CD152 | melanoma |
| Iomab-B | CD45 | leukemia, lymphoma |
| Iratumumab | CD30 (TNFRSF8) | Hodgkin's lymphoma |
| Isatuximab | CD38 | multiple myeloma |
| Iscalimab | CD40 | Head and neck cancer |
| Istiratumab | IGF1R, CD221 | advanced solid tumors |
| Labetuzumab | CEA | colorectal cancer |
| Ladiratuzumab vedotin | LIV-1 | cancer |
| Laprituximab emtansine | EGFR | Solid tumors |
| Lemalesomab | NCA-90 | Granulocyte cancer |
| Lexatumumab | TRAIL-R2 | cancer |
| Lifastuzumab vedotin | phosphate-sodium co-transporter | cancer |
| Loncastuximab tesirine | CD19 | cancer |
| Losatuxizumab vedotin | EGRF, ERBB1 HER1 | cancer |
| Lilotomab satetraxetan | CD37 | cancer |
| Lintuzumab | CD33 | cancer |

TABLE 2-continued

List of antibodies/derivatives and antibody-drug conjugates (ADCs),
target antigens and condition(s) or disease(s) to be treated

| Antibody, Antibody Derivative or ADC | Target | Condition/Disease |
|---|---|---|
| Lirilumab | KIR2DL1 | solid and hematological cancers |
| Lorvotuzumab mertansine | CD56 | cancer |
| Lucatumumab | CD40 | multiple myeloma, non-Hodgkin's lymphoma, Hodgkin's lymphoma |
| Lumiliximab | CD23 | chronic lymphocytic leukemia |
| Lumretuzumab | ERBB3 (HER3) | cancer |
| MABpl | IL1A | colorectal cancer |
| Mapatumumab | TRAIL-R1 | cancer |
| Margetuximab | HER2 | breast cancer |
| Matuzumab | EGFR | colorectal, lung and stomach cancer |
| Milatuzumab | CD74 | multiple myeloma and other hematological malignancies |
| Minretumomab | TAG-72 | tumor detection (and therapy) |
| Mirvetuximab soravtansine | folate receptor alpha | ovarian cancer |
| Mitumomab | GD3 ganglioside | small cell lung carcinoma |
| Modotuximab | EGFR extracellular domain III | cancer |
| Mogamulizumab | CCR4 | adult T-cell leukemia/lymphoma |
| Monalizumab | NKG2A | rheumatoid arthritis, gynecologic malignancies, and other cancers |
| Mosunetuzumab | CD3E, MS4A1, CD20 | cancer |
| Moxetumomab pasudotox | CD22 | hairy cell leukemia |
| Nacolomab tafenatox | C242 antigen | colorectal cancer |
| Naptumomab estafenatox | 5T4 | non-small cell lung carcinoma, renal cell carcinoma |
| Naratuximab emtansine | CD37 | non-Hodgkin's lymphoma, chronic lymphocytic leukemia, B-Cell Lymphomas |
| Narnatumab | RON | cancer |
| Navicixizumab | DLL4 | cancer |
| Naxitamab | c-Met | high-risk neuroblastoma and refractory osteomedullary disease |
| Necitumumab | EGFR | non-small cell lung carcinoma |
| Nimotuzumab | EGFR | squamous cell carcinoma, head and neck cancer, nasopharyngeal cancer, glioma |
| Nivolumab | PD-1 | cancer |
| Obinutuzumab | CD20 | Chronic lymphatic leukemia |
| Ocaratuzumab | CD20 | cancer |
| Ofatumumab | CD20 | chronic lymphocytic leukemia |
| Olaratumab | PDGF-R α | cancer |
| Oleclumab | 5'-nucleotidase | pancreatic and colorectal cancer |
| Onartuzumab | human scatter factor receptor kinase | cancer |
| Ontuxizumab | TEM1 | cancer |
| Oportuzumab monatox | EpCAM | bladder cancer |
| Oregovomab | CA-125 | ovarian cancer |
| Otlertuzumab | CD37 | cancer |
| Pamrevlumab | CTGF | idiopathic pulmonary fibrosis (IPF), pancreatic cancer |
| Panitumumab | EGFR | colorectal cancer |
| Pankomab | tumor specific glycosylation of MUC1 | ovarian cancer |
| Parsatuzumab | EGFL7 | cancer |
| Pasotuxizumab | folate hydrolase | cancer |
| Patritumab | ERBB3 (HER3) | cancer |
| PDR001 | PD1 | melanoma |
| Pembrolizumab | PD-1 | melanoma and other cancers |
| Pemtumomab | MUC1 | cancer |
| Pertuzumab | HER2/neu | cancer |
| Pidilizumab | PD-1 | cancer |
| Pinatuzumab vedotin | CD22 | cancer |
| Pintumomab | adenocarcinoma antigen | adenocarcinoma |
| Polatuzumab vedotin | CD79B | diffuse large B-cell lymphoma |
| Pritumumab | vimentin | brain cancer |
| Racotumomab | NGNA ganglioside | non-small cell lung cancer |
| Radretumab | fibronectin extra domain-B | cancer |
| Ramucirumab | VEGFR2 | solid tumors |
| Rituximab | CD20 | lymphomas, leukemias, some autoimmune disorders |

TABLE 2-continued

List of antibodies/derivatives and antibody-drug conjugates (ADCs),
target antigens and condition(s) or disease(s) to be treated

| Antibody, Antibody Derivative or ADC | Target | Condition/Disease |
|---|---|---|
| Robatumumab | IGF-1 receptor (CD221) | cancer |
| Rosmantuzumab | root plate-specific spondin 3 | cancer |
| Rovalpituzumab tesirine | DLL3 | small cell lung cancer |
| Sacituzumab govitecan | TROP-2 | triple-negative breast cancer |
| Samalizumab | CD200 | cancer |
| Samrotamab vedotin | LRRC15 | cancer |
| Satumomab pendetide | TAG-72 | cancer (diagnosis) |
| Seribantumab | ERBB3 (HER3) | cancer |
| Sibrotuzumab | FAP | cancer |
| SGN-CD19A | CD19 | acute lymphoblastic leukemia and B-cell non-Hodgkin lymphoma |
| Sirtratumab vedotin | SLITRK6 | cancer |
| Sofituzumab vedotin | CA-125 | ovarian cancer |
| Solitomab | EpCAM | gastrointestinal, lung, and other cancers |
| Sonepcizumab | sphingosine-1-phosphate | choroidal and retinal neovascularization |
| Spartalizumab | PDCD1, CD279 | cancer |
| Tacatuzumab tetraxetan | alpha-fetoprotein | cancer |
| Taplitumomab paptox | CD19 | cancer |
| Tarextumab | Notch receptor | cancer |
| Tavolimab | CD134 | cancer |
| Telisotuzumab vedotin | HGFR | cancer |
| Tenatumomab | tenascin C | cancer |
| Tepoditamab | dendritic cell-associated lectin 2 | cancer |
| Tetulomab | CD37 | cancer |
| TGN1412 | CD28 | chronic lymphocytic leukemia |
| Tigatuzumab | TRAIL-R2 | cancer |
| Timigutuzumab | HER2 | cancer |
| Tiragotumab | TIGIT | cancer |
| Tislelizumab | PCDC1, CD279 | non-small cell lung cancer |
| Tisotumab vedotin | coagulation factor III | relapsed or refractory cervical cancer |
| Tomuzotuximab | EGFR, HER1 | cancer |
| Tositumomab | CD20 | follicular lymphoma |
| Tovetumab | CD140a | cancer |
| Trastuzumab | HER2/neu | breast cancer |
| Trastuzumab emtansine | HER2/neu | breast cancer |
| TRBS07 | GD2 ganglioside | melanoma |
| Tremelimumab | CTLA-4 | non-small cell lung, head & neck, urothelial cancer |
| Tucotuzumab celmoleukin | EpCAM | cancer |
| Tuvirumab | hepatitis B virus | chronic hepatitis B |
| Ublituximab | MS4A1 | chronic lymphocytic leukemia |
| Ulocuplumab | CXCR4 (CD184) | Mutated CXCR4 Waldenstrom Macroglobulinemia |
| Urelumab | 4-1BB (CD137) | cancer etc. |
| Utomilumab | 4-1BB (CD137) | diffuse large B-cell lymphoma |
| Vadastuximab talirine | CD33 | Acute myeloid leukemia |
| Vandortuzumab vedotin | STEAP1 | cancer |
| Vantictumab | Frizzled receptor | cancer |
| Varlilumab | CD27 | solid tumors |
| Veltuzumab | CD20 | non-Hodgkin's lymphoma |
| Vepalimomab | AOC3 (VAP-1) | inflammation |
| Vesencumab | NRP1 | solid malignancies |
| Volociximab | integrin α5β1 | solid tumors |
| Vonlerolizumab | CD134 | cancer |
| Vorsetuzumab mafodotin | CD70 | cancer |
| Votumumab | tumor antigen CTAA16.88 | colorectal tumors |
| XMAB-5574 | CD19 | diffuse large B-cell lymphoma |
| Zalutumumab | EGFR | squamous cell carcinoma of the head and neck |
| Zanolimumab | CD4 | T-cell lymphoma |
| Zatuximab | HER1 | cancer |
| Zenocutuzumab | ERBB3, HER3 | cancer |
| Zolbetuximab | CLDN18 | cancer |

TABLE 3

List of antibodies derivatives thereof or antibody-drug conjugates (ADCs) and
their associated condition(s) or disease(s) to be treated

| Tradename | Antibody, Antibody Derivative, or ADC | Target | Type | Condition/Disease |
|---|---|---|---|---|
| Bavencio ™ | Avelumab | PD-L1 | Human IgG1/κ | Metastatic Merkel cell carcinoma |
| Imfinzi ™ | Durvalumab | PD-L1 | Human IgG1/κ | Metastatic urothelial carcinoma |
| Lartruvo ™ | Olaratumab | PDGFR-α | Human IgG1 | Sarcoma |
| Darzalex ™ | Daratumumab | CD38 | Human IgG1/κ | Multiple myeloma |
| Empliciti ™ | Elotuzumab | SLAMF7 | Human IgG1 | Multiple myeloma |
| Portrazza ™ | Necitumumab | EGFR | Human IgG1 | Carcinoma, non-small-cell lung |
| Tecentriq ™ | Atezolizumab | PD-L1 | Human IgG1 | Metastatic non-small cell lung cancer |
| Opdivo ™ | Nivolumab | PD-1 | Human IgG4 | Carcinoma; non-small-cell lung carcinoma; renal cell Hodgkin disease melanoma |
| Unituxin ™ | Dinutuximab | GD2 | Human IgG1/κ | Neuroblastoma |
| Keytruda ™ | Pembrolizumab | PD-1 | Human IgG4 | Melanoma |
| Cyramza ™ | Ramucirumab | VEGF | Human IgG1 | Stomach neoplasms |
| Kadcyla ™ | Trastuzumab emtansine | HER2 | Humanized IgG1 as ADC | Breast cancer |
| Perjeta ™ | Pertuzumab | HER2 | Humanized IgG1 | Breast cancer |
| Gazyvaro ™ | Obinutuzumab | CD20 | Humanized IgG1 | CLL |
| Adcetris ™ | Brentuximab | CD30 (conjugate of Mab and MMAE) | Chemeric IgG1 as ADC (antibody drug conjugate) | Hodgkin lymphoma (HL), systemic anaplastic large cell lymphoma (ALCL) |
| Vervoy ™ | Ipilimumab | CTLA-4 | Human IgG1 | Melanoma |
| Arzerra ™ | Ofatumumab | CD20 | Human IgG1 | Chronic lymphocytic leukemia |
| RoActemra ™ | Tocilizumab | IL6R receptor | Humanized IgG1 | Rheumatoid arthritis |
| Removab ™ | Catumaxomab | EpCAM and CD3 | Trifunctional MAb IgG2a/IgG2b | Malignant ascites in patients with EpCAM-positive carcinomas |
| Vectibix ™ | Panitumumab | EGFR | Human IgG2 | Metastatic colorectal carcinoma |
| Proxinium ™ | Catumaxomab | EpCAM | Humanized MAb | Head and neck cancer |
| Erbitux ™ | Cetuximab | EGFR | Chimeric IgG1 | Head and neck cancer; colorectal cancer |
| Zevalin ™ | Ibritumomab tiuxetan | CD20 | Murine IgG1 | Non-Hodgkin's lymphoma |
| Bexxar ™ | Tositumomab and iodine 131 tositumomab | CD20 | Murine IgG2a | Non-Hodgkin's lymphoma |
| Campath ™ | Alemtuzumab | CD52 | Humanized IgG1 | B-cell chronic lymphocytic leukemia |
| Herceptin ™ | Trastuzumab | HER-2 | Humanized IgG1 | Breast cancer; metastatic gastric or gastroesophageal junction adenocarcinoma |
| Mylotarg ™ | Gemtuzumab ozogamicin | CD33 | Humanized IgG4/toxin conjugate | Acute myeloic leucemia (AML) |
| Rituxan ™ MabThera ™ | Rituximab | CD20 | Chimeric IgG1 | Non-Hodgkin's lymphoma; chronic lymphocytic leukemia; rheumatoid arthritis |

In some embodiments, there is a method of treating an autoimmune disease or condition in a human subject comprising administering to the subject a covalent conjugate as defined herein (e.g. as described in Section II and including any such embodiment defined in Section II), wherein the antibody or the antibody derivative of the covalent conjugate selectively binds immune cells causing the autoimmune disease or condition, and wherein the payload of the covalent conjugate is toxic to human cells. In some embodiments, there is a use of a covalent conjugate as defined herein (e.g. as described in Section II and including any such embodiment defined in Section II) in manufacture of a medicament for treating an autoimmune disease or condition, wherein the antibody or the antibody derivative of the covalent conjugate selectively binds immune cells causing the autoimmune disease or condition, and wherein the payload of the covalent conjugate is toxic to human cells. In some embodiments of the method and use, respectively, the payload has an $IC_{50}$ of less than 100 nM on human cells. In some embodiments of the method and use, respectively, the covalent conjugate comprises: 18V4F, 4R34.1.19, Abciximab, Abrilumab, Adalimumab, ADF-06688992, Afelimomab, Alirocumab, Andecaliximab, Anifrolumab, Aselizumab, Basiliximab, Begelomab, Belimumab, Benralizumab, Bersanlimab, Bertilimumab, BI-505, BIIB023, Bimagrumab, Bimekizumab, Bleselumab, Blosozumab, Brodalumab, Burosumab, Camidanlumab, Canakinumab, CD147-CART, Cedelizumab, Clenoliximab, Crotedumab, Dacetuzumab, Daclizumab, Dapirolizumab, Daratumumab, Dectrekumab, Denosumab, Dorlimomab, Dupilumab, Efalizumab, Emapalumab, Etaracizumab, Evolocumab, Fezakinumab, Flotetuzumab, Gavilimomab, GI-270384, Glembatumumab, Golimumab, Guselkumab, HFE7A, Hu3S193, Ibalizumab, Infliximab, iPH5401, Isatuximab, Iscalimab, Ixekizumab, Keliximab, Lanalumab, Lemalesomab, Letolizumab, Lokivetmab, Lucatumumab, Lutikizumab, LY3321367, M290, Mavrilimumab, MBG453, Mepolizumab, Milatuzumab, Mitumomab, MMP9, Natalizumab, Nerelimomab, Netakimab, NI-0101, NNC0151-00000000, Odulimomab, Omalizumab, Opicinumab, Oxelumab, Pamrevlumab, PF-00547659, Plozalizumab, Prezalumab, Priliximab, Quilizumab, Ravagalimab, REGN2176, Reslizumab, Rinucumab, Risankizumab, RO-001, Romilkimab, Romosozumab, Rozanolixizumab, Ruplizumab, SAR252067, Sarilumab, Satralizumab, Secukinumab, Selicrelumab, Setrusumab, SGN-15, SGN- CD123A, SHP647, Simtuzumab, SL-279252, Sonepcizumab, Sulesomab, Tabalumab, Tadocizumab, Talacotuzumab, Tamtuvetmab, Telimomab, Tenatumomab, Teneliximab, Tildrakizumab, Timolumab, Tisotumab, Tocilizumab, Tregalizumab, TSR-022, Ustekinumab, Ustekinumab, Vanalimab, Vapaliximab, Vatelizumab, Vedolizumab, Vepalimomab, Vobarilizumab, Vunakizumab, VX15/2503, Zanolimumab, or Ziralimumab.

LL37 is a cathelicidin peptide of human origin, suggesting that cathelicidin peptides from other species may also be able to enhance antibody delivery to target cells.

IV. Sequences

Table 4 lists various sequences referenced in this application.

TABLE 4

| SEQ ID NO | Sequence (amino acid or DNA 5' to 3') | Other identifying information |
|---|---|---|
| 1 | LLGDFFRKSKEKIGKEFKRIVQRIKDFLRNLVPRTES | full length LL37 (*homo sapiens*) |
| 2 | GGLLGDFFRKSKEKIGKEFKRIVQRIKDFLRNLVPRTES | GG-LL37 (artificial) |
| 3 | MDWTWRILFLVAAATGAHSEVQLVESGGGLVQPGGSLRLSCAASGF NIKDTYIHWVRQAPGKGLEWVARIYPTNGYTRYADSVKGRFTISAD TSKNTAYLQMNSLRAEDTAVYYCSRWGGDGFYAMDYWGQGTLVTVS SASTKGPSVFPLAPSSKSTSGGTAALGCLVKDYFPEPVTVSWNSGA LTSGVHTFPAVLQSSGLYSLSSVVTVPSSSLGTQTYICNVNHKPSN TKVDKKVEPKSCDKTHTCPPCPAPELLGGPSVFLFPPKPKDTLMIS RTPEVTCVVVDVSHEDPEVKFNWYVDGVEVHNAKTKPREEQYNSTY RVVSVLTVLHQDWLNGKEYKCKVSNKALPAPIEKTISKAKGQPREP QVYTLPPSRDELTKNQVSLTCLVKGFYPSDIAVEWESNGQPENNYK TTPPVLDSDGSFFLYSKLTVDKSRWQQGNVFSCSVMHEALHNHYTQ KSLSLSPGK | Anti-HER2 mAb (Trastuzumab) heavy chain (artificial); Secretory signal peptide at 1-19 |
| 4 | MLPSQLIGFLLLWVPASRGDIQMTQSPSSLSASVGDRVTITCRASQ DVNTAVAWYQQKPGKAPKLLIYSASFLYSGVPSRFSGSRSGTDFTL TISSLQPEDFATYYCQQHYTTPPTFGQGTKLEIKRTVAAPSVFIFP PSDEQLKSGTASVVCLLNNFYPREAKVQWKVDNALQSGNSQESVTE QDSKDSTYSLSSTLTLSKADYEKHKVYACEVTHQGLSSPVTKSFNR GECGGGGSLPMTGGHG | Anti-HER2 mAb (Trastuzumab) light chain (artificial); Secretory signal peptide at 1-19 |
| 5 | CTGGGTCACCGTGGTAGCGGCTCTTGACTCGAGCACCACCAC- CACCA CACTGAG | forward PCR primer (artificial) |
| 6 | AGAGCCGCTACCACGGTGACCCAGTTTTGACGGCAGAT- CACAGTAGC GGCAACCGC | reverse PCR primer (artificial) |
| 7 | ATGGGCAGCAGCCATCACCACCATCATCACCATCACAGCGGCAGCG ATTACAAGGATGACGACGACAAGGCTGGCAGCCATATGGCTAGCGT GGACAACAAATTCAACAAAGAACAACAAAACGCGTTCTATGAGATC TTACATTTACCTAACTTAAACGAAGAACAACGAAACGCCTTCATCC AAAGTTTAAAAGATGACCCAAGCCAAAGCGCTAACCTTTTAGCAGA AGCTAAAAAGCTAAACGACGCTCAGGCGCCGAAAGGTACCGGATCC GAATTCATGGTTAGCGAACTGATTAAGGAAAATATGCACATGAAAC TGTATATGGAAGGCACCGTCAACAATCATCACTTTAAATGCACGAG TGAAGGTGAAGGCAAGCCGTATGAAGGCACCCAGACGATGCGTATT AAAGCAGTGGAAGGCGGTCCGCTGCCGTTTGCATTCGATATTCTGG CCACCAGTTTTATGTACGGTTCCAAAACCTTCATTAACCATACGCA GGGCATCCCGGATTTCTTTAAACAAAGTTTTCCGGAAGGTTTCACC TGGGAACGTGTGACCACGTATGAAGACGGCGGTGTTCTGACCGCCA CGCAGGATACGTCCCTGCAAGACGGCTGTCTGATTTACAATGTTAA AATCCGCGGTGTCAACTTCCCGAGCAATGGCCCGGTTATGCAGAAA AAGACCCTGGGTTGGGAAGCATCTACCGAAACGCTGTATCCGGCTG ATGGTGGTCTGGAAGGTCGTCGAGACATGGCTCTGAAACTGGTGGG CGGTGGCCATCTGATTTGCAACCTGAAGACCACGTACCGTTCTAAA AAGCCGGCGAAAAATCTGAAGATGCCGGGTGTCTATTACGTGGATC GTCGCCTGGAACGCATCAAAGAAGCCGACAAGGAAACCTATGTTGA | structural gene sequence of Z-RFP (artificial) |

TABLE 4-continued

| Sequences | | |
|---|---|---|
| SEQ ID NO | Sequence (amino acid or DNA 5' to 3') | Other identifying information |
| | ACAGCATGAAGTGGCGGTTGCCCGCTACTGTGATCTGCCGTCAAAA CTGGGTCACCGTGGTAGCGGCTCT | |
| 8 | ATGGATTGGACATGGAGGATTCTGTTCCTGGTGGCTGCAGCTACTG GAGCTCATTCTGAGGTGCAGCTGGTGGAATCAGGAGGAGGACTGGT GCAGCCAGGAGGATCTCTGAGACTGTCTTGCGCCGCCAGCGGCTTC AACATCAAGGACACCTACATCCATTGGGTCCGGCAGGCTCCAGGAA AAGGACTGGAATGGGTGGCTAGGATCTACCCCACCAACGGCTACAC CCGATACGCAGACAGCGTGAAGGGCAGGTTCACCATCAGCGCCGAT ACCAGCAAGAACACCGCCTACCTGCAGATGAACAGCCTGAGAGCCG AGGACACCGCCGTGTACTATTGTAGCCGGTGGGGAGGAGACGGCTT CTACGCTATGGATTATTGGGGCCAGGGAACACTGGTGACAGTGTCT AGCGCTAGCACCAAGGGACCTAGCGTGTTTCCTCTGGCCCCTTCTA GCAAGAGCACAAGCGGAGGAACAGCCGCTCTGGGCTGTCTGGTGAA AGACTACTTCCCCGAGCCAGTGACCGTGTCTTGGAACTCAGGAGCC CTGACAAGCGGAGTGCACACATTTCCAGCCGTGCTGCAGAGCAGCG GACTGTACTCTCTGAGCAGCGTGGTGACCGTGCCTTCTTCTTCTCT GGGCACCCAGACCTACATCTGCAACGTGAACCACAAGCCCAGCAAC ACCAAGGTGGACAAGAAGGTGGAGCCCAAGTCTTGCGACAAAACAC ATACTTGCCCTCCATGTCCAGCTCCAGAACTGCTGGGAGGACCAAG CGTGTTCCTGTTCCCTCCTAAGCCCAAGGACACCCTGATGATCAGC CGGACCCCAGAAGTGACTTGCGTGGTGGTGGACGTGTCCCACGAAG ACCCCGAGGTCAAGTTCAATTGGTACGTGGACGGAGTGGAGGTGCA CAACGCTAAGACCAAGCCCAGGGAGGAGCAGTACAACAGCACCTAC AGGGTGGTGTCCGTGCTGACAGTGCTGCACCAGGATTGGCTGAACG GCAAGGAGTACAAGTGCAAGGTGTCCAACAAGGCCCTGCCAGCTCC CATCGAGAAGACCATCAGCAAGGCCAAGGGACAGCCTAGAGAGCCT CAGGTGTACACCCTGCCTCCTTCTAGGGACGAGCTGACCAAGAACC AGGTGTCCCTGACTTGCCTCGTGAAGGGCTTCTACCCCAGCGACAT CGCAGTGGAGTGGGAAAGCAACGGTCAGCCAGAGAACAACTACAAG ACCACCCCCCCAGTGCTGGACAGCGACGGCAGCTTCTTCCTGTACA GCAAGCTGACCGTGGACAAAAGCCGCTGGCAGCAGGGCAACGTGTT CTCTTGCAGCGTGATGCACGAGGCCCTGCACAACCACTACACCCAG AAGAGCCTGAGCCTGAGCCCAGGAAAG | cDNA of heavy chain for anti-HER2 mAb (Trastuzumab, artificial); 1-57 encodes the N-terminal secretory signal peptide |
| 9 | ATGCTGCCCAGCCAGCTGATCGGCTTTCTGCTGCTGTGGGTGCCTG CCTCCAGAGGCGACATCCAGATGACCCAGAGCCCCATCCAGCCTGTC TGCCTCCGTGGGCGACAGAGTGACCATCACATGCCGCGCTTCTCAG GATGTGAACACAGCCGTGGCTTGGTACCAGCAGAAGCCTGGCAAGG CCCCCAAAGCTGCTGATCTACTCCGCCTCTTTCCTGTATTCCGGCGT GCCAAGCAGGTTTTCCGGCAGCCGGTCTGGAACCGACTTCACCCTG ACAATCTCTTCCCTGCAGCCCGAGGATTTTGCCACATACTATTGCC AGCAGCACTATACCACACCCCCTACCTTCGGCCAGGGCACAAAGCT GGAGATCAAGAGGACCGTGGCCGCTCCTAGCGTGTTCATCTTTCCA CCCTCTGACGAGCAGCTGAAGTCTGGCACAGCTTCCGTGGTGTGCC TGCTGAACAACTTCTACCCACGGGAGGCCAAGGTGCAGTGGAAGGT GGATAACGCTCTGCAGTCCGGCAATAGCCAGGAGTCTGTGACCGAG CAGGACTCCAAGGATAGCACATATTCTCTGAGCTCTACCCTGACAC TGTCCAAGGCCGATTACGAGAAGCACAAGGTGTATGCTTGCGAGGT GACCCATCAGGGCCTGTCCAGCCCCGTGACAAAGTCTTTCAATAGG GGAGAGTGTGGAGGAGGAGGCTCCCTGCCTATGACCGGCGGCCATG GC | cDNA of light chain for anti-HER2 mAb (Trastuzumab, artificial); 1-57 encodes the N-terminal secretory signal peptide |
| 10 | ACTGACGAATTCATGGTGAGCAAGGGCGAGGAGCTGTTCACC | forward-direction PCR primer (artificial) |
| 11 | ACTGACCTCGAGTTACTTGTACAGCTCGTCCATGCCGAGAGTG | reverse-direction PCR primer (artificial) |
| 12 | ATGGGCAGCAGCCATCACCACCATCATCACCATCACAGCGGCAGCG ATTACAAGGATGACGACGACAAGGCTGGCAGCCATATGGCTAGCGT GGACAACAAATTCAACAAAGAACAACAAAACGCGTTCTATGAGATC TTACATTTACCTAACTTAAACGAAGAACAACGAAACGCCTTCATCC AAAGTTTAAAAGATGACCCAAGCCAAAGCGCTAACCTTTTAGCAGA AGCTAAAAAGCTAAACGACGCTCAGGCGCCGAAAGGTACCGGATCC GAATTCATGGTGAGCAAGGGCGAGGAGCTGTTCACCGGGGTGGTGC CCATCCTGGTCGAGCTGGACGGCGACGTAAACGGCCACAAGTTCAG CGTGTCCGGCGAGGGCGAGGGCGATGCCACCTACGGCAAGCTGACC CTGAAGTTCATCTGCACCACCGGCAAGCTGCCCGTGCCCTGGCCCA CCCTCGTGACCACCCTGACCTACGGCGTGCAGTGCTTCAGCCGCTA CCCCGACCACATGAAGCAGCACGACTTCTTCAAGTCCGCCATGCCC GAAGGCTACGTCCAGGAGCGCACCATCTTCTTCAAGGACGACGGCA ACTACAAGACCCGCGCCGAGGTGAAGTTCGAGGGCGACACCCTGGT | structural gene sequence of Z-GFP (artificial) |

TABLE 4-continued

| | Sequences | |
|---|---|---|
| SEQ ID NO | Sequence (amino acid or DNA 5' to 3') | Other identifying information |
| | GAACCGCATCGAGCTGAAGGGCATCGACTTCAAGGAGGACGGCAAC ATCCTGGGGCACAAGCTGGAGTACAACTACAACAGCCACAACGTCT ATATCATGGCCGACAAGCAGAAGAACGGCATCAAGGTGAACTTCAA GATCCGCCACAACATCGAGGACGGCAGCGTGCAGCTCGCCGACCAC TACCAGCAGAACACCCCCATCGGCGACGGCCCCGTGCTGCTGCCCG ACAACCACTACCTGAGCACCCAGTCCGCCCTGAGCAAAGACCCCAA CGAGAAGCGCGATCACATGGTCCTGCTGGAGTTCGTGACCGCCGCC GGGATCACTCTCGGCATGGACGAGCTGTACAAG | |
| 13 | LLGDFFRKSKEKIGKEFKRIVQRIK | PEP#35 fragment of LL37 (homo sapiens) |
| 14 | IGKEFKRIVQRIKDFLRNLVPRTES | PEP#36 fragment of LL37 (homo sapiens) |
| 15 | LLGDFFRKSKEKIGKEFKR | PEP#37 fragment of LL37 (homo sapiens) |
| 16 | IVQRIKDFLRNLVPRTES | PEP#38 fragment of LL37 (homo sapiens) |
| 17 | LLGDFFRKSKEKI | PEP#39 fragment of LL37 (homo sapiens) |
| 18 | IGKEFKRIVQRI | PEP#40 fragment of LL37 (homo sapiens) |
| 19 | KDFLRNLVPRTES | PEP#41 fragment of LL37 (homo sapiens) |
| 20 | KSKEKIGKEFKRIVQ | PEP#42 fragment of LL37 (homo sapiens) |
| 21 | RIKDFLRNLVPRTES | PEP#43 fragment of LL37 (homo sapiens) |
| 22 | LPMTGGHG | Sortase recognition sequence (artificial) |
| 23 | LPXTG | SrtA recognition sequence (artificial, derived from Staphylococcus aureus) |
| 24 | LPXT(A/G) | srt A recognition sequence (artificial, derived from Streptococcus pyogenes) |
| 25 | (S/P)PXTG | sortase recognition sequence (artificial, derived from Clostridium difficile) |
| 26 | QVPTG | SrtC recognition sequence (Streptococcus pyogenes) |
| 27 | LAXTG | Engineered sortase recognition sequence (artificial) |

TABLE 4-continued

| Sequences | | |
|---|---|---|
| SEQ ID NO | Sequence (amino acid or DNA 5' to 3') | Other identifying information |
| 28 | LPXSG | Engineered sortase recognition sequence (artificial) |
| 29 | MGSTAILALLLAVLQGVCSQVQLLQSGAELKKPGESLKISCKGSGY SFTSYWIAWVRQMPGKGLEYMGLIYPGDSDTKYSPSFQGQVTISVD KSVSTAYLQWSSLKPSDSAVYFCARHDVGYCTDRTCAKWPEWLDNW GQGTLVTVSSGGGGSGGGGSGGGGSQSVLTQPPSVSAAPGQKVTIS CSGSSSNIGNNYVSWYQQLPGTAPKLLIYGHTNRPAGVPDRFSGSK SGTSASLAISGFRSEDEADYYCASWDYTLSGWVFGGGTKLTVLGGS EPKSCDKTHTCPPCPAPELLGGPSVFLFPPKPKDTLMISRTPEVTC VVVDVSHEDPEVKFNWYVDGVEVHNAKTKPREEQYNSTYRVVSVLT VLHQDWLNGKEYKCKVSNKALPAPIEKTISKAKGQPREPQVYTLPP SRDELTKNQVSLTCLVKGFYPSDIAVEWESNGQPENNYKTTPPVLD SDGSFFLYSKLTVDKSRWQQGNVFSCSVMHEALHNHYTQKSLSLSP GK | Anti-HER2 (scFv)-Fc (artificial); Secretory signal peptide at 1-19 |
| 30 | ATGGGCTCTACAGCCATCCTGGCACTGCTGCTGGCCGTGCTGCAGG GGGTGTGCTCTCAGGTGCAGCTGCTGCAGAGCGGAGCCGAGCTGAA GAAGCCCGGCGAGAGCCTGAAGATCAGCTGCAAGGGCAGCGGCTAC AGCTTCACCAGCTACTGGATCGCCTGGGTCCGGCAGATGCCTGGCA AGGGCCTGGAATACATGGGCCTGATCTACCCCGGCGATAGCGACAC CAAGTACAGCCCCAGCTTCCAGGGCCAGGTCACCATCAGCGTGGAC AAGAGCGTGTCCACCGCCTACCTGCAGTGGAGCAGCCTGAAGCCCA GCGACAGCGCCGTGTACTTCTGCGCCAGACACGACGTGGGCTACTG CACCGACAGAACCTGCGCCAAGTGGCCCGAGTGGCTGGATAATTGG GGCCAGGGCACCCTGGTCACAGTGTCCTCTGGCGGCGGAGGAAGTG GAGGGGGAGGAAGCGGAGGAGGGGGCAGCCAGTCTGTCCTGACCCA GCCCCCTTCTGTGTCTGCCGCCCCTGGCCAGAAAGTGACCATCAGC TGCTCCGGCTCCAGCAGCAACATCGGCAACAACTACGTGTCCTGGT ATCAGCAGCTGCCCGGCACAGCCCCCAAGCTGCTGATCTACGGCCA CACCAACAGACCTGCCGGCGTGCCCGATAGATTCAGCGGCAGCAAG AGCGGCACCAGCGCCAGCCTGGCCATCAGCGGCTTCAGAAGCGAGG ACGAGGCCGACTACTACTGCGCCAGCTGGGACTACACACTGAGCGG CTGGGTGTTCGGCGGAGGGACCAAGCTGACCGTCCTGGGCGGATCC GAACCCAAGAGCTGCGACAAGACCCACACCTGCCCCCCTTGTCCTG CTCCGGAGCTGCTGGGCGGACCCAGCGTGTTCCTGTTCCCCCCCAA GCCCAAGGACACCCTGATGATCAGCCGGACCCCCGAAGTGACCTGC GTGGTGGTGGACGTGTCCCACGAGGACCCTGAAGTGAAGTTCAATT GGTACGTGGACGGCGTGGAGGTGCACAACGCCAAGACCAAGCCCCG GGAGGAACAGTACAACAGCACCTACCGGGTGGTGTCCGTGCTGACA GTGCTGCACCAGGACTGGCTGAACGGCAAAGAATACAAGTGCAAGG TGTCCAACAAGGCCCTGCCTGCACCCATCGAGAAAACCATCAGCAA GGCCAAGGGCCAGCCCAGAGAACCCCAGGTGTACACCCTGCCACCC AGCAGAGATGAGCTGACCAAGAACCAGGTGTCACTGACCTGCCTCG TGAAGGGCTTCTACCCCAGCGATATCGCCGTGGAGTGGGAGAGCAA CGGCCAGCCTGAGAACAACTACAAGACCACCCCCCCTGTGCTGGAC AGCGACGGCAGCTTCTTCCTGTACAGCAAGCTGACAGTGGACAAGT CCCGGTGGCAGCAGGGCAACGTGTTCTCTTGCTCCGTGATGCACGA GGCCCTGCACAACCACTACACCCAGAAGTCCCTAAGCTTGAGCCCC GGCAAG | cDNA of Anti-HER2 (scFv)-Fc (artificial); nucleotides 1-57 encode the N-terminal secretory signal peptide |
| 31 | MDWTWRILFLVAAATGAHSEVQLVESGGGLVQPGGSLRLSCAASGF NIKDTYIHWVRQAPGKGLEWVARIYPTNGYTRY-ADSVKGRFTI SAD TSKNTAYLQMNSLRAEDTAVYYCSRWGGDGFYAMDYWGQGTLVTVS SASTKGPSVFPLAPSSKSTSGGTAALGCLVKDYFPEPVTVSWNSGA LTSGVHTFPAVLQSSGLYS-LSSVVTVPSSSLGTQTYI CNVNHKPSN TKVDKKVEPKSCDKTHTCPPCPAPELLGGPSVFLFPPKPKDTLMIS RTPEVTCVVVDVSHEDPEVKFNWYVDGVEVHNAKTKPREEQYNSTY RVVSVLTVLHQDWLNGKEYKCKVSNKALPAPIEKTISKAKGQPREP QVYTLPPSRDELTKNQVSLTCLVKGFYPSDIAVEWESNGQPENNYK TTPPVLDSDGSFFLYSKLTVDKSRWQQGNVFSCSVMHEALHNHYTQ KSLSLSPGKGGGGSLLGDFFRKSKEKIGKEFKRIVQRIKDFLRNLV PRTES | Anti-HER2 mAb heavy chain-LL37 fusion (artificial); secretory signal peptide at 1-19 |
| 32 | ATGGATTGGACATGGAGGATTCTGTTCCTGGTGGCTGCAGCTACTG GAGCTCATTCTGAGGTGCAGCTGGTGGAATCAGGAGGAGGACTGGT GCAGCCAGGAGGATCTCTGAGACTGTCTTGCGCCGCCAGCGGCTTC AACATCAAGGACACCTACATCCATTGGGTCCGGCAGGCTCCAGGAA AAGGACTGGAATGGGTGGCTAGGATCTACCCCACCAACGGCTACAC CCGATACGCAGACAGCGTGAAGGGCAGGTTCACCATCAGCGCCGAT ACCAGCAAGAACACCGCCTACCTGCAGATGAACAGCCTGAGAGCCG | cDNA of Anti-HER2 mAb heavy chain-LL37 fusion (artificial); nucleotides 1-57 encode the N-terminal secretory |

TABLE 4-continued

| | Sequences | |
|---|---|---|
| SEQ ID NO | Sequence (amino acid or DNA 5' to 3') | Other identifying information |
| | AGGACACCGCCGTGTACTATTGTAGCCGGTGGGGAGGAGACGGCTT CTACGCTATGGATTATTGGGGCCAGGGAACACTGGTGACAGTGTCT AGCGCTAGCACCAAGGGACCTAGCGTGTTTCCTCTGGCCCCTTCTA GCAAGAGCACAAGCGGAGGAACAGCCGCTCTGGGCTGTCTGGTGAA AGACTACTTCCCCGAGCCAGTGACCGTGTCTTGGAACTCAGGAGCC CTGACAAGCGGAGTGCACACATTTCCAGCCGTGCTGCAGAGCAGCG GACTGTACTCTCTGAGCAGCGTGGTGACCGTGCCTTCTTCTTCTCT GGGCACCCAGACCTACATCTGCAACGTGAACCACAAGCCCAGCAAC ACCAAGGTGGACAAGAAGGTGGAGCCCAAGTCTTGCGACAAAACAC ATACTTGCCCTCCATGTCCAGCTCCAGAACTGCTGGGAGGACCAAG CGTGTTCCTGTTCCCTCCTAAGCCCAAGGACACCCTGATGATCAGC CGGACCCCAGAAGTGACTTGCGTGGTGGTGGACGTGTCCCACGAAG ACCCCGAGGTCAAGTTCAATTGGTACGTGGACGGAGTGGAGGTGCA CAACGCTAAGACCAAGCCCAGGGAGGAGCAGTACAACAGCACCTAC AGGGTGGTGTCCGTGCTGACAGTGCTGCACCAGGATTGGCTGAACG GCAAGGAGTACAAGTGCAAGGTGTCCAACAAGGCCCTGCCAGCTCC CATCGAGAAGACCATCAGCAAGGCCAAGGGACAGCCTAGAGAGCCT CAGGTGTACACCCTGCCTCCTTCTAGGGACGAGCTGACCAAGAACC AGGTGTCCCTGACTTGCCTCGTGAAGGGCTTCTACCCCAGCGACAT CGCAGTGGAGTGGGAAAGCAACGGTCAGCCAGAGAACAACTACAAG ACCACCCCCCCAGTGCTGGACAGCGACGGCAGCTTCTTCCTGTACA GCAAGCTGACCGTGGACAAAAGCCGCTGGCAGCAGGGCAACGTGTT CTCTTGCAGCGTGATGCACGAGGCCCTGCACAACCACTACACCCAG AAGAGCCTGAGCCTGAGCCCAGGAAAGGGAGGAGGAGGCTCCCTGC TCGGCGACTTCTTCCGGAAGTCCAAGGAGAAGATTGGCAAGGAGTT CAAGCGCATCGTGCAGAGAATCAAGGACTTCCTGCGGAATCTGGTG CCTAGAACCGAAAGC | signal peptide |
| 33 | MLPSQLIGFLLLWVPASRGDIQMTQSPSSLSASVGDRVTITCRASQ DVNTAVAWYQQKPGKAPKLLIYSASFLYSGVPSRFSGSRSGTDFTL TISSLQPEDFA- TYYCQQHYTTPPTFGQGTKLEI KRTVAAPSVFIFP PSDEQLKSGTASVVCLLNNFYPREAKVQWKVDNALQSGNSQESVTE QDSKDSTYSLSSTLTLSKADYEKHKVYACEVTHQGLSSPVTKSFNR GECGGGGSLLGDFFRKSKEKIGKEFKRIVQRIKDFLRNLVPRTES | Anti-HER2 mAb Light chain-LL37 fusion (artificial); secretory signal peptide at 1-19 |
| 34 | ATGCTGCCCAGCCAGCTGATCGGCTTTCTGCTGCTGTGGGTGCCTG CCTCCAGAGGCGACATCCAGATGACCCAGAGCCCATCCAGCCTGTC TGCCTCCGTGGGCGACAGAGTGACCATCACATGCCGCGCTTCTCAG GATGTGAACACAGCCGTGGCTTGGTACCAGCAGAAGCCTGGCAAGG CCCCAAAGCTGCTGATCTACTCCGCCTCTTTCCTGTATTCCGGCGT GCCAAGCAGGTTTTCCGGCAGCCGGTCTGGAACCGACTTCACCCTG ACAATCTCTTCCCTGCAGCCCGAGGATTTTGCCACATACTATTGCC AGCAGCACTATACCACACCCCCTACCTTCGGCCAGGGCACAAAGCT GGAGATCAAGAGGACCGTGGCCGCTCCTAGCGTGTTCATCTTTCCA CCCTCTGACGAGCAGCTGAAGTCTGGCACAGCTTCCGTGGTGTGCC TGCTGAACAACTTCTACCCACGGGAGGCCAAGGTGCAGTGGAAGGT GGATAACGCTCTGCAGTCCGGCAATAGCCAGGAGTCTGTGACCGAG CAGGACTCCAAGGATAGCACATATTCTCTGAGCTCTACCCTGACAC TGTCCAAGGCCGATTACGAGAAGCACAAGGTGTATGCTTGCGAGGT GACCCATCAGGGCCTGTCCAGCCCCGTGACAAAGTCTTTCAATAGG GGAGAGTGTGGAGGAGGAGGCTCCCTGCTCGGCGACTTCTTCCGGA AGTCCAAGGAGAAGATTGGCAAGGAGTTCAAGCGCATCGTGCAGAG AATCAAGGACTTCCTGCGGAATCTGGTGCCTAGAACCGAAAGC | cDNA of Anti-HER2 mAb Light chain-LL37 fusion (artificial); nucleotides 1-57 encode the N-terminal secretory signal peptide |
| 35 | LLGDFFRKSKEKIGKEFKRIVQRIKDFLRNLVPRTESC | PEP#94 LL37 derived peptide (artificial) |
| 36 | QVQLVQSGAEVVKPGASVKISCKASGYTFTGYFMNWVKQSPGQSLE WIGRIHPYDGDTFYNQKFQGKATLTVDKSSNTAHMELLSLTSEDFA VYYCTRYDGSRAMDYWGQGTTVTVSSASTKGPSVFPLAPSSKSTSG GTAALGCLVKDYFPEPVTVSWNSGALTSGVHTFPAVLQSSGLYSLS SVVTVPSSSLGTQTYICNVNHKPSNTKVDKKVEPKSCDKTHTCPPC PAPELLGGPSVFLFPPKPKDTLMISRTPEVTCVVVDVSHEDPEVKF NWYVDGVEVHNAKTKPREEQYNSTYRVVSVLTVLHQDWLNGKEYKC KVSNKALPAPIEKTISKAKGQPREPQVYTLPPSRDELTKNQVSLTC LVKGFYPSDIAVEWESNGQPENNYKTTPPVLDSDGSFFLYSKLTVD KSRWQQGNVFSCSVMHEALHNHYTQKSLSLSPGK | Anti-Folate receptor mAb heavy chain (artificial); secretory signal peptide is removed from N-terminus |

TABLE 4-continued

| | Sequences | |
|---|---|---|
| SEQ ID NO | Sequence (amino acid or DNA 5' to 3') | Other identifying information |
| 37 | DIVLTQSPLSLAVSLGQPAIISCKASQSVSFAGTSLMHWYHQKPGQ QPRLLIYRASNLEAGVPDRFSGSGSKTDFTLTISPVEAEDAATYYC QQSREYPYTFGGGTKLEIKRTVAAPSVFIFPPSDEQLKSGTASVVC LLNNFYPREAKVQWKVDNALQSGNSQESVTEQDSKDSTYSLSSTLT LSKADYEKHKVYACEVTHQGLSSPVTKSFNRGECGGGGSLPETGGH G | Anti-Folate receptor mAb light chain (artificial); secretory signal peptide is removed from N-terminus |
| 38 | MPLLLLLPLLWAGALAQVQLQESGPGLVKPSETLSLTCTVSGGSVS SGDYYWTWIRQSPGKGLEWIGHIYYSGNTNYNPSLKSRLTISIDTS KTQFSLKLSSVTAADTAIYYCVRDRVTGAFDIWGQGTMVTVSSAST KGPSVFPLAPSSKSTSGGTAALGCLVKDYFPEPVTVSWNSGALTSG VHTFPAVLQSSGLYSLSSVVTVPSSSLGTQTYICNVNHKPSNTKVD KRVEPKSCDKTHTCPPCPAPELLGGPSVFLFPPKPKDTLMISRTPE VTCVVVDVSHEDPEVKFNWYVDGVEVHNAKTKPREEQYNSTYRVVS VLTVLHQDWLNGKEYKCKVSNKALPAPIEKTISKAKGQPREPQVYT LPPSREEMTKNQVSLTCLVKGFYPSDIAVEWESNGQPENNYKTTPP VLDSDGSFFLYSKLTVDKSRWQQGNVFSCSVMHEALHNHYTQKSLS LSPGK | Anti-EGFR mAb (Panitumumab) heavy chain (artificial); secretory signal peptide at 1-16 |
| 39 | MRLPAQLLGLLMLWVSGSSGDIQMTQSPSSLSASVGDRVTITCQAS QDISNYLNWYQQKPGKAPKLLIYDASNLETGVPSRFSGSGSGTDFT FTISSLQPEDIATYFCQHFDHLPLAFGGGTKVEIKRTVAAPSVFIF PPSDEQLKSGTASVVCLLNNFYPREAKVQWKVDNALQSGNSQESVT EQDSKDSTYSLSSTLTLSKADYEKHKVYACEVTHQGLSSPVTKSFN RGECGGGGSLPMTGGHG | Anti-EGFR mAb (Panitumumab) light chain (artificial); secretory signal peptide at 1-20 |
| 40 | MPLLLLLPLLWAGALAEVQLVESGGGLVQPGRSLRLSCAASGFTFN DYAMHWVRQAPGKGLEWVSTISWNSGSIGYADSVKGRFTISRDNAK KSLYLQMNSLRAEDTALYYCAKDIQYGNYYYGMDVWGQGTTVTVSS ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKRVEPKSCDKTHTCPPCPAPELLGGPSVFLFPPKPKDTLMISR TPEVTCVVVDVSHEDPEVKFNWYVDGVEVHNAKTKPREEQYNSTYR VVSVLTVLHQDWLNGKEYKCKVSNKALPAPIEKTISKAKGQPREPQ VYTLPPSREEMTKNQVSLTCLVKGFYPSDIAVEWESNGQPENNYKT TPPVLDSDGSFFLYSKLTVDKSRWQQGNVFSCSVMHEALHNHYTQK SLSLSPGK | Anti-CD20 mAb (Ofatumumab) heavy chain (artificial); secretory signal peptide at 1-16 |
| 41 | MRLPAQLLGLLMLWVSGSSGEIVLTQSPATLSLSPGERATLSCRAS QSVSSYLAWYQQKPGQAPRLLIYDASNRATGIPARFSGSGSGTDFT LTISSLEPEDFAVYYCQQRSNWPITFGQGTKVEIKRTVAAPSVFIF PPSDEQLKSGTASVVCLLNNFYPREAKVQWKVDNALQSGNSQESVT EQDSKDSTYSLSSTLTLSKADYEKHKVYACEVTHQGLSSPVTKSFN RGECGGGGSLPMTGGHG | Anti-CD20 mAb (Ofatumumab) light chain (artificial); secretory signal peptide at 1-20 |
| 42 | MPLLLLLPLLWAGALAEVQLVESGGGLVQPGGSLRLSCAASGFSFS DFAMSWVRQAPGKGLEWVATIGRVAFHTYYPDSMKGRFTISRDNSK NTLYLQMNSLRAEDTAVYYCARHRGFDVGHFDFWGQGTLVTVSSAS TKGPSVFPLAPSSKSTSGGTAALGCLVKDYFPEPVTVSWNSGALTS GVHTFPAVLQSSGLYSLSSVVTVPSSSLGTQTYICNVNHKPSNTKV DKRVEPKSCDKTHTCPPCPAPELLGGPSVFLFPPKPKDTLMISRTP EVTCVVVDVSHEDPEVKFNWYVDGVEVHNAKTKPREEQYNSTYRVV SVLTVLHQDWLNGKEYKCKVSNKALPAPIEKTISKAKGQPREPQVY TLPPSREEMTKNQVSLTCLVKGFYPSDIAVEWESNGQPENNYKTTP PVLDSDGSFFLYSKLTVDKSRWQQGNVFSCSVMHEALHNHYTQKSL SLSPGK | Anti-Napi2b mAb (Lifastuzumab) heavy chain (artificial); secretory signal peptide at 1-16 |
| 43 | MRLPAQLLGLLMLWVSGSSGDIQMTQSPSSLSASVGDRVTITCRSS ETLVHSSGNTYLEWYQQKPGKAPKLLIYRVSNRFSGVPSRFSGSGS GTDFTLTISSLQPEDFATYYCFQGSFNPLTFGQGTKVEIKRTVAAP SVFIFPPSDEQLKSGTASVVCLLNNFYPREAKVQWKVDNALQSGNS QESVTEQDSKDSTYSLSSTLTLSKADYEKHKVYACEVTHQGLSSPV TKSFNRGECGGGGSLPMTGGHG | Anti-Napi2b mAb (Lifastuzumab) light chain; Secretory signal peptide at 1-20 |
| 44-45 | (purposefully left blank) | |
| 46 | MPLLLLLPLLWAGALAQVQLVQSGAEVKKPGASVKVSCKASGYTFT NYDINWVRQAPGQGLEWIGWIYPGDGSTKYNEKFKAKATLTADTST STAYMELRSLRSDDTAVYYCASGYEDAMDYWGQGTTVTVSSASTKG PSVFPLAPSSKSTSGGTAALGCLVKDYFPEPVTVSWNSGALTSGVH TFPAVLQSSGLYSLSSVVTVPSSSLGTQTYICNVNHKPSNTKVDKR VEPKSCDKTHTCPPCPAPELLGGPSVFLFPPKPKDTLMISRTPEVT CVVVDVSHEDPEVKFNWYVDGVEVHNAKTKPREEQYNSTYRVVSVL TVLHQDWLNGKEYKCKVSNKALPAPIEKTISKAKGQPREPQVYTLP | Anti-CD33A mAb (Vadastuximab) heavy chain (artificial); secretory signal peptide at 1-16 |

TABLE 4-continued

Sequences

| SEQ ID NO | Sequence (amino acid or DNA 5' to 3') | Other identifying information |
|---|---|---|
|  | PSREEMTKNQVSLTCLVKGFYPSDIAVEWESNGQPENNYKTTPPVL DSDGSFFLYSKLTVDKSRWQQGNVFSCSVMHEALHNHYTQKSLSLS PGK |  |
| 47 | MRLPAQLLGLLMLWVSGSSGDIQMTQSPSSLSASVGDRVTINCKAS QDINSYLSWFQQKPGKAPKTLIYRANRLVDGVPSRFSGSGSGQDYT LTISSLQPEDFATYYCLQYDEFPLTFGGGTKVEIKRTVAAPSVFIF PPSDEQLKSGTASVVCLLNNFYPREAKVQWKVDNALQSGNSQESVT EQDSKDSTYSLSSTLTLSKADYEKHKVYACEVTHQGLSSPVTKSFN RGECGGGGSLPMTGGHG | Anti-CD33A mAb (Vadastuximab) light chain (artificial); secretory signal peptide at 1-20 |
| 48 | MPLLLLLPLLWAGALAEVQLVESGGGVVQPGRSLRLSCSASGFDFT TYWMSWVRQAPGKGLEWIGEIHPDSSTINYAPSLKDRFTISRDNAK NTLFLQMDSLRPEDTGVYFCASLYFGFPWFAYWGQGTPVTVSSAST KGPSVFPLAPSSKSTSGGTAALGCLVKDYFPEPVTVSWNSGALTSG VHTFPAVLQSSGLYSLSSVVTVPSSSLGTQTYICNVNHKPSNTKVD KRVEPKSCDKTHTCPPCPAPELLGGPSVFLFPPKPKDTLMISRTPE VTCVVVDVSHEDPEVKFNWYVDGVEVHNAKTKPREEQYNSTYRVVS VLTVLHQDWLNGKEYKCKVSNKALPAPIEKTISKAKGQPREPQVYT LPPSREEMTKNQVSLTCLVKGFYPSDIAVEWESNGQPENNYKTTPP VLDSDGSFFLYSKLTVDKSRWQQGNVFSCSVMHEALHNHYTQKSLS LSPGK | Anti-CEACAM5 mAb (Labetuzumab) heavy chain (artificial); secretory signal peptide at 1-16 |
| 49 | MRLPAQLLGLLMLWVSGSSGDIQLTQSPSSLSASVGDRVTITCKAS QDVGTSVAWYQQKPGKAPKLLIYWTSTRHTGVPSRFSGSGSGTDFT FTISSLQPEDIATYYCQQYSLYRSFGQGTKVEIKRTVAAPSVFIFP PSDEQLKSGTASVVCLLNNFYPREAKVQWKVDNALQSGNSQESVTE QDSKDSTYSLSSTLTLSKADYEKHKVYACEVTHQGLSSPVTKSFNR GECGGGGSLPMTGGHG | Anti-CEACAM5 mAb (Labetuzumab) light chain (artificial); secretory signal peptide at 1-20 |
| 50 | MPLLLLLPLLWAGALAEVQLVQSGPGLVQPGGSVRISCAASGYTFT NYGMNWVKQAPGKGLEWMGWINTYTGESTYADSFKGRFTFSLDTSA SAAYLQINSLRAEDTAVYYCARFAIKGDYWGQGTLLTVSSASTKGP SVFPLAPSSKSTSGGTAALGCLVKDYFPEPVTVSWNSGALTSGVHT FPAVLQSSGLYSLSSVVTVPSSSLGTQTYICNVNHKPSNTKVDKRV EPKSCDKTHTCPPCPAPELLGGPSVFLFPPKPKDTLMISRTPEVTC VVVDVSHEDPEVKFNWYVDGVEVHNAKTKPREEQYNSTYRVVSVLT VLHQDWLNGKEYKCKVSNKALPAPIEKTISKAKGQPREPQVYTLPP SREEMTKNQVSLTCLVKGFYPSDIAVEWESNGQPENNYKTTPPVLD SDGSFFLYSKLTVDKSRWQQGNVFSCSVMHEALHNHYTQKSLSLSP GK | Anti-EpCAM mAb (Citatuzumab); heavy chain (artificial); secretory peptide at 1-16 |
| 51 | MRLPAQLLGLLMLWVSGSSGDIQMTQSPSSLSASVGDRVTITCRST KSLLHSNGITYLYWYQQKPGKAPKLLIYQMSNLASGVPSRFSSSGS GTDFTLTISSLQPEDFATYYCAQNLEIPRTFGQGTKVEIKRTVAAP SVFIFPPSDEQLKSGTASVVCLLNNFYPREAKVQWKVDNALQSGNS QESVTEQDSKDSTYSLSSTLTLSKADYEKHKVYACEVTHQGLSSPV TKSFNRGECGGGGSLPMTGGHG | Anti-EpCAM mAb (Citatuzumab) light chain (artificial); secretory peptide at 1-20 |
| 52-61 | (purposefully left blank) |  |
| 62 | MDWTWRILFLVAAATGAHSEVQLVESGGGLVQPGGSLRLSCAASGF TFTSTGISWVRQAPGKGLEWVGRIYPTNGSTNYADSVGRFTISADT SKNTAYLQMNSLRAEDTAVYYCARTYGIYDLYVDYTEYVMDYWGQG TLVTVSSASTKGPSVFPLAPSSKSTSGGTAALGCLVKDYFPEPVTV SWNSGALTSGVHTFPAVLQSSGLYSLSSVVTVPSSSLGTQTYICNV NHKPSNTKVDKKVEPKSCDKTHTCPPCPAPELLGGPSVFLFPPKPK DTLMISRTPEVTCVVVDVSHEDPEVKFNWYVDGVEVHNAKTKPREE QYNSTYRVVSVLTVLHQDWLNGKEYKCKVSNKALPAPIEKTISKAK GQPREPQVYTLPPSRDELTKNQVSLTCLVKGFYPSDIAVEWESNGQ PENNYKTTPPVLDSDGSFFLYSKLTVDKSRWQQGNVFSCSVMHEAL HNHYTQKSLSLSPGK | Anti-FGFR3 mAb (Vofatamab) heavy chain (artificial); secretory peptide at 1-19 |
| 63 | ATGGATTGGACATGGAGGATTCTGTTCCTGGTGGCTGCAGCTACTG GAGCTCATTCTGAGGTGCAGCTGGTGGAATCAGGAGGAGGACTGGT GCAGCCAGGAGGATCTCTGAGACTGTCTTGCGCCGCCAGCGGCTTC ACCTTTACCTCTACCGGCATCTCTTGGGTGAGACAGGCCCCTGGCA AGGGCCTGGAGTGGGTGGGCAGAATCTACCCTACAAACGGATCTAC CAACTACGCCGATTCTGTGGGCAGATTCACAATCTCTGCCGATACA TCTAAGAACACAGCTTACCTGCAGATGAACTCTCTGAGAGCTGAGG ATACAGCTGTGTACTATTGTGCTAGAACATACGGCATCTACGATCT GTACGTGGATTATACAGAGTACGTGATGGATTATTGGGGCCAGGGA ACACTGGTGACAGTGTCTAGCGCTAGCACCAAGGGACCTAGCGTGT TTCCTCTGGCCCCTTCTAGCAAGAGCACAAGCGGAGGAACAGCCGC | cDNA of Anti-FGFR3 mAb (Vofatamab) heavy chain (artificial); secretory signal peptide sequence (nucleotides 1-57) included at 5' end |

TABLE 4-continued

| | Sequences | |
|---|---|---|
| SEQ ID NO | Sequence (amino acid or DNA 5' to 3') | Other identifying information |

TCTGGGCTGTCTGGTGAAAGACTACTTCCCCGAGCCAGTGACCGTG
TCTTGGAACTCAGGAGCCCTGACAAGCGGAGTGCACACATTTCCAG
CCGTGCTGCAGAGCAGCGGACTGTACTCTCTGAGCAGCGTGGTGAC
CGTGCCTTCTTCTTCTCTGGGCACCCAGACCTACACTCTGCAACGTG
AACCACAAGCCCAGCAACACCAAGGTGGACAAGAAGGTGGAGCCCA
AGTCTTGCGACAAAACACATACTTGCCCTCCATGTCCAGCTCCAGA
ACTGCTGGGAGGACCAAGCGTGTTCCTGTTCCCTCCTAAGCCCAAG
GACACCCTGATGATCAGCCGGACCCCAGAAGTGACTTGCGTGGTGG
TGGACGTGTCCCACGAAGACCCCGAGGTCAAGTTCAATTGGTACGT
GGACGGAGTGGAGGTGCACAACGCTAAGACCAAGCCCAGGGAGGAG
CAGTACAACAGCACCTACAGGGTGGTGTCCGTGCTGACAGTGCTGC
ACCAGGATTGGCTGAACGGCAAGGAGTACAAGTGCAAGGTGTCCAA
CAAGGCCCTGCCAGCTCCCATCGAGAAGACCATCAGCAAGGCCAAG
GGACAGCCTAGAGAGCCTCAGGTGTACACCCTGCCTCCTTCTAGGG
ACGAGCTGACCAAGAACCAGGTGTCCCTGACTTGCCTCGTGAAGGG
CTTCTACCCCAGCGACATCGCAGTGGAGTGGGAAAGCAACGGCTCAG
CCAGAGAACAACTACAAGACCACCCCCCCCAGTGCTGGACAGCGACG
GCAGCTTCTTCCTGTACAGCAAGCTGACCGTGGACAAAAGCCGCTG
GCAGCAGGGCAACGTGTTCTCTTGCAGCGTGATGCACGAGGCCCTG
CACAACCACTACACCCAGAAGAGCCTGAGCCTGAGCCCAGGAAAG

| 64 | MLPSQLIGFLLLWVPASRGDIQMTQSPSSLSASVGDRVTITCRASQ DVSTAVAWYQQKPGKAPKLLIYSASFLYSGVPSRFSGSGSGTDFTL TISSLQPEDFATYYCQQSYTTPPTFGQGTKVEIKRTVAAPSVFIFP PSDEQLKSGTASVVCLLNNFYPREAKVQWKVDNALQSGNSQESVTE QDSKDSTYSLSSTLTLSKADYEKHKVYACEVTHQGLSSPVTKSFNR GECGGGGSLPMTGGHG | Anti-FGFR3 mAb (Vofatamab) light chain (artificial); secretory signal peptide at 1-19 |
| 65 | ATGCTGCCCAGCCAGCTGATCGGCTTTCTGCTGCTGTGGGTGCCTG CCTCCAGAGGCGACATCCAGATGACCCAGAGCCCATCCAGCCTGTC TGCCTCCGTGGGCGACAGAGTGACCATCACATGCCGCGCTTCTCAG GATGTGTCCACAGCTGTGGCCTGGTACCAGCAGAAGCCTGGCAAGG CCCCTAAGCTGCTGATCTACTCTGCTTCTTTTCTGTATTCTGGCGT GCCTTCTAGATTTTCTGGCTCTGGCAGCGGCACAGATTTTACACTG ACAATCTCTTCTCTGCAGCCTGAGGATTTTGCTACATATTACTGTC AGCAGTCTTACACAACACCTCCTACATTTGGCCAGGGCACAAAGGT GGAGATCAAGAGGACCGTGGCCGCTCCTAGCGTGTTCATCTTTCCA CCCTCTGACGAGCAGCTGAAGTCTGGCACAGCTTCCGTGGTGTGCC TGCTGAACAACTTCTACCCACGGGAGGCCAAGGTGCAGTGGAAGGT GGATAACGCTCTGCAGTCCGGCAATAGCCAGGAGTCTGTGACCGAG CAGGACTCCAAGGATAGCACATATTCTCTGAGCTCTACCCTGACAC TGTCCAAGGCCGATTACGAGAAGCACAAGGTGTATGCTTGCGAGGT GACCCATCAGGGCCTGTCCAGCCCCGTGACAAAGTCTTTCAATAGG GGAGAGTGTGGAGGAGGAGGCTCCCTGCCTATGACCGGCGGCCATG GC | cDNA of Anti-FGFR3 mAb (Vofatamab) light chain (artificial); secretory signal peptide sequence (nucleotide# 1-57) included at 5' end |
| 66 | MDWTWRILFLVAAATGAHSEVQLVQSGPEVKKPGATVKISCKTSGY TFTEYTIHWVKQAPGKGLEWIGNINPNNGGTTYNQKFEDKATLTVD KSTDTAYMELSSLRSEDTAVYYCAAGWNFDYWGQGTLLTVSSASTK GPSVFPLAPSSKSTSGGTAALGCLVKDYFPEPVTVSWNSGALTSGV HTFPAVLQSSGLYSLSSVVTVPSSSLGTQTYICNVNHKPSNTKVDK KVEPKSCDKTHTCPPCPAPELLGGPSVFLFPPKPKDTLMISRTPEV TCVVVDVSHEDPEVKFNWYVDGVEVHNAKTKPREEQYNSTYRVVSV LTVLHQDWLNGKEYKCKVSNKALPAPIEKTISKAKGQPREPQVYTL PPSRDELTKNQVSLTCLVKGFYPSDIAVEWESNGQPENNYKTTPPV LDSDGSFFLYSKLTVDKSRWQQGNVFSCSVMHEALHNHYTQKSLSL SPG | Anti-PSMA mAb, hj591 heavy chain (artificial); secretory signal peptide at 1-19 |
| 67 | ATGGATTGGACATGGAGGATTCTGTTCCTGGTGGCTGCAGCTACTG GAGCTCATTCTGAGGTGCAGCTGGTGCAGTCTGGACCTGAGGTGAA GAAGCCTGGCGCCACTGTGAAGATTTCTTGTAAGACATCTGGATAT ACTTTCACTGAATACACTATTCATTGGGTGAAGCAGGCCCCTGGCA AGGGCCTGGAGTGGATCGGTAACATTAATCCTAACAACGGCGGCAC TACATATAATCAGAAGTTTGAGGATAAGGCTACACTGACAGTGGAT AAAAGCACAGATACAGCTTACATGGAGCTGTCTTCTCTGAGATCTG AAGATACCGCTGTGTATTATTGTGCCGCCGGATGGAATTTTGACTA CTGGGGTCAGGGCACTTTACTGACTGTGTCCTCCGCAAGCACTAAG GGACCTTCTGTGTTTCCTCTGGCTCCTAGCTCTAAGTCCACATCTG GCGGAACCGCTGCTCTGGGATGTCTGGTGAAAGATTATTTCCCTGA GCCTGTGACAGTGAGTTGGAACTCTGGCGCCCTGACTAGCGGCGTG CATACCTTTCCTGCCGTGCTGCAGTCTTCTGGCCTGTATTCTCTGT CTTCTGTGGTGACCGTGCCATCTAGCTCTCTGGGAACACAGACATA CATCTGTAATGTTAATCATAAGCCTTCTAATACAAAGGTTGATAAG AAAGTGGAGCCTAAGAGCTGTGATAAGACTCACACCTGCCCTCCTT GTCCTGCCCCTGAACTGCTGGGAGGCCCTAGTGTGTTCCTGTTTCC | cDNA of Anti-PSMA mAb, hj591 heavy chain (artificial); secretory signal peptide sequence (nucleotide# 1-57) included at 5' end |

TABLE 4-continued

| Sequences | | |
|---|---|---|
| SEQ ID NO | Sequence (amino acid or DNA 5' to 3') | Other identifying information |
| | TCCAAAGCCAAAGGATACACTGATGATCTCTAGAACCCCTGAGGTG ACATGTGTGGTGGTGGATGTGTCACATGAAGATCCTGAGGTGAAGT TTAATTGGTATGTGGATGGAGTGGAAGTGCATAATGCTAAGACCAA GCCTAGAGAGGAGCAGTATAATTCTACCTATAGAGTGGTGTCTGTG CTGACAGTGCTGCACCAGGATTGGCTGAATGGAAAGGAATACAAGT GTAAAGTGAGTAATAAGGCCCTGCCTGCTCCTATTGAGAAAACAAT TTCTAAGGCTAAGGGACAGCCTAGAGAGCCACAGGTGTACACACTG CCTCCTAGTAGAGATGAACTGACAAAGAACCAGGTGTCTCTGACAT GTCTGGTGAAGGGCTTTTATCCATCTGATATTGCCGTGGAGTGGGA GTCTAATGGGCAGCCTGAAAACAATTATAAAACTACACCTCCTGTG CTGGATAGTGATGGCTCTTTCTTTCTGTACTCTAAGCTGACTGTGG ATAAGTCTAGGTGGCAGCAGGGCAACGTGTTTAGCTGTAGCGTGAT GCATGAGGCCCTCCATAACCACTATACGCAGAAGTCACTGAGCCTG AGCCCAGGA | |
| 68 | MLPSQLIGFLLLWVPASRGDIQMTQSPSSLSTSVGDRVTLTCKASQ DVGTAVDWYQQKPGPSPKLLIYWASTRHTGIPSRFSGSGSGTDFTL TISSLQPEDFADYYCQQYNSYPLTFGPGTKVDIKRTVAAPSVFIFP PSDEQLKSGTASVVCLLNNFYPREAKVQWKVDNALQSGNSQESVTE QDSKDSTYSLSSTLTLSKADYEKHKVYACEVTHQGLSSPVTKSFNR GECGGGGSLPMTGGHG | Anti-PSMA mAb, hj591 light chain (artificial); secretory signal peptide at 1-19 |
| 69 | ATGCTGCCCAGCCAGCTGATCGGCTTTCTGCTGCTGTGGGTGCCTG CCTCCAGAGGCGATATCCAGATGACACAGTCTCCTAGCTCTCTGAG CACCTCTGTGGGAGATAGAGTGACCCTGACATGTAAGGCCTCTCAG GATGTGGGCACTGCCGTGGATTGGTATCAGCAGAAGCCTGGCCCTT CTCCTAAGCTGCTGATCTATTGGGCTTCTACTAGACATACAGGCAT CCCTTCTAGGTTCAGCGGCTCTGGCTCTGGAACTGATTTTACACTG ACCATCTCTTCTCTGCAGCCTGAGGATTTTGCTGATTACTACTGTC AGCAGTATAATAGCTACCCTCTGACCTTCGGCCCTGGCACAAAGGT GGACATCAAGAGGACCGTGGCCGCTCCTAGCGTGTTCATCTTTCCA CCCTCTGACGAGCAGCTGAAGTCTGGCACAGCTTCCGTGGTGTGCC TGCTGAACAACTTCTACCCACGGGAGGCCAAGGTGCAGTGGAAGGT GGATAACGCTCTGCAGTCCGGCAATAGCCAGGAGTCTGTGACCGAG CAGGACTCCAAGGATAGCACATATTCTCTGAGCTCTACCCTGACAC TGTCCAAGGCCGATTACGAGAAGCACAAGGTGTATGCTTGCGAGGT GACCCATCAGGGCCTGTCCAGCCCCGTGACAAAGTCTTTCAATAGG GGAGAGTGTGGAGGAGGAGGCTCCCTGCCTATGACCGGCGGCCATG GC | cDNA of Anti-PSMA mAb, hj591 light chain (artificial); secretory signal peptide sequence (nucleotides 1-57) included at 5' end |
| 70-73 | (purposefully left blank) | |
| 74 | FRKSKEKIGKFFKRIVQRIFDFLRNLVMMWLL | PEP#48 LL37 derived peptide (artificial) |
| 75 | LLGDFFRQSKEKIGKEFQQIVQQIKDFLQNLVPQTES | PEP#49 LL37 derived peptide (artificial) |
| 76 | LLGDFFRASKEKIGKEFAAIVQAIKDFLANLVPATES | PEP#50 LL37 derived peptide (artificial) |
| 77 | KEFKRIVQRIKDFLRGGGGSRLFDKIRQVIRKFEKG | PEP#55 LL37 derived peptide (artificial) |
| 78 | GGSVFQFLGRIIHHVGNFVHGFSHVF | PEP#86, Clavanin B, an alpha-helical antimicrobial peptide (Styela clava) |
| 79 | SYS MEHFR WGKPV | PEP#98, an antimicrobial anti-inflammatory peptide alpha-melanocyte-stimulating hormone (MSH) |

TABLE 4-continued

| SEQ ID NO | Sequence (amino acid or DNA 5' to 3') | Other identifying information |
|---|---|---|
| 80 | RAIGGGLSSVGGGSSTIKY | PEP#99, Keratin-derived antimicrobial peptide (KDAMP) (*homo sapiens*) |
| 81 | (Purposefully left blank) | |
| 82 | DHYNCVSSGGQCLYSACPIFKIQGTCYRGKAKCCK | PEP#102, human beta-defensin 1, hBD1 (*homo sapiens*) |
| 83 | (Purposefully left blank) | |
| 84 | VCSCRLVFCRRTELRVGNCLIGGVSFTYCCTRV | PEP#104, human neutrophil peptide 4 (HNP4) , an alpha defensin (*homo sapiens*) |
| 85-93 | (Purposefully left blank) | |
| 94 | QVQLQQPGAELVKPGASVKMSCKASGYTFTSYNMHWVKQTPGRGLE WIGAIYPGNGDTSYNQKFKGKATLTADKSSSTAYMQLSSLTSEDSA VYYCARSTYYGGDWYFNVWGAGTTVTVSAASTKGPSVFPLAPSSKS TSGGTAALGCLVKDYFPEPVTVSWNSGALTSGVHTFPAVLQSSGLY SLSSVVTVPSSSLGTQTYICNVNHKPSNTKVDKKAEPKSCDKTHTC PPCPAPELLGGPSVFLFPPKPKDTLMISRTPEVTCVVVDVSHEDPE VKFNWYVDGVEVHNAKTKPREEQYNSTYRVVSVLTVLHQDWLNGKE YKCKVSNKALPAPIEKTISKAKGQPREPQVYTLPPSRDELTKNQVS LTCLVKGFYPSDIAVEWESNGQPENNYKTTPPVLDSDGSFFLYSKL TVDKSRWQQGNVFSCSVMHEALHNHYTQKSLSLSPGK | Anti-CD20 mAb (Rituximab) heavy chain (artificial); secretory signal peptide is removed from N-terminus |
| 95 | QIVLSQSPAILSASPGEKVTMTCRASSSVSYIHWFQQKPGSSPKPW IYATSNLASGVPVRFSGSGSGTSYSLTISRVEAEDAATYYCQQWTS NPPTFGGGTKLEIKRTVAAPSVFIFPPSDEQLKSGTASVVCLLNNF YPREAKVQWKVDNALQSGNSQESVTEQDSKDSTYSLSSTLTLSKAD YEKHKVYACEVTHQGLSSPVTKSFNRGECGGGGSLPMTGGHG | Anti-CD20 mAb (Rituximab) light chain (artificial); secretory signal peptide is removed from N-terminus |
| 96 | MMWLL | PEP#47 (artificial) |
| 97 | KEFKRIVQRIKDFLR | PEP#51 fragment of LL37 (*homo sapiens*) |
| 98-102 | (purposefully left blank) | |
| 103 | VQRIK | PEP#58 fragment of LL37 (*homo sapiens*) |
| 104 | IVQRIKD | PEP#59 fragment of LL37 (*homo sapiens*) |
| 105 | KRIVQRIKDFL | PEP#60 fragment of LL37 (*homo sapiens*) |
| 106 | EFKRIVQRIK | PEP#61 fragment of LL37 (*homo sapiens*) |
| 107 | VQRIKDFLRN | PEP#62 fragment of LL37 (*homo sapiens*) |
| 108 | EKIGKEFKRIVQRIKDFLRN | PEP#63 fragment of LL37 (*homo sapiens*) |

TABLE 4-continued

| SEQ ID NO | Sequence (amino acid or DNA 5' to 3') | Other identifying information |
|---|---|---|
| 109 | EFKRIVQRIKDFLRNLVPRT | PEP#64 fragment of LL37 (*homo sapiens*) |
| 110 | GSIGKEFKRIVQRIKDFLR | PEP#66 LL37 derived peptide (artificial) |
| 111 | SETRPVLNRLFDKIRQVIRKFEKGI | Reverse sequence of residues 13-37 of LL37 (artificial) |
| 112 | (purposefully left blank) | |
| 113 | AAGGACCACCGCATCTCTACA | Forward qRT-PCR primer (5' to 3') for survivin (artificial) |
| 114 | CCAAGTCTGGCTCGTTCTCAGT | Reverse qRT-PCR primer (5' to 3') for surviving (artificial) |
| 115 | GAAGGTGAAGGTCGGAGTC | Forward qRT-PCR primer (5' to 3') for GAPDH (artificial) |
| 116 | GAAGATGGTGATGGGATTTC | Reverse qRT-PCR primer (5' to 3') for GAPDH (artificial) |
| 117 | ATGGATTGGACATGGAGGATTCTGTTCCTGGTGGCTGCAGCTACTG GAGCTCATTCTGAGGTGCAGCTGGTGGAATCAGGAGGAGGACTGGT GCAGCCAGGAGGATCTCTGAGACTGTCTTGCGCCGCCAGCGGCTTC AACATCAAGGACACCTACATCCATTGGGTCCGGCAGGCTCCAGGAA AAGGACTGGAATGGGTGGCTAGGATCTACCCCACCAACGGCTACAC CCGATACGCAGACAGCGTGAAGGGCAGGTTCACCATCAGCGCCGAT ACCAGCAAGAACACCGCCTACCTGCAGATGAACAGCCTGAGAGCCG AGGACACCGCCGTGTACTATTGTAGCCGGTGGGGAGGAGACGGCTT CTACGCTATGGATTATTGGGGCCAGGGAACACTGGTGACAGTGTCT AGCGCTAGCACCAAGGGACCTAGCGTGTTTCCTCTGGCCCCTTCTA GCAAGAGCACAAGCGGAGGAACAGCCGCTCTGGGCTGTCTGGTGAA AGACTACTTCCCCGAGCCAGTGACCGTGTCTTGGAACTCAGGAGCC CTGACAAGCGGAGTGCACACATTTCCAGCCGTGCTGCAGAGCAGCG GACTGTACTCTCTGAGCAGCGTGGTGACCGTGCCTTCTTCTTCTCT GGGCACCCAGACCTACATCTGCAACGTGAACCACAAGCCCAGCAAC ACCAAGGTGGACAAGAAGGTGGAGCCCAAGTCTTGCGACAAAACAC ATACTTGCCCTCCATGTCCAGCTCCAGAACTGCTGGGAGGACCAAG CGTGTTCCTGTTCCCTCCTAAGCCCAAGGACACCCTGATGATCAGC CGGACCCCAGAAGTGACTTGCGTGGTGGTGGACGTGTCCCACGAAG ACCCCGAGGTCAAGTTCAATTGGTACGTGGACGGAGTGGAGGTGCA CAACGCTAAGACCAAGCCCAGGGAGGAGCAGTACAACAGCACCTAC AGGGTGGTGTCCGTGCTGACAGTGCTGCACCAGGATTGGCTGAACG GCAAGGAGTACAAGTGCAAGGTGTCCAACAAGGCCCTGCCAGCTCC CATCGAGAAGACCATCAGCAAGGCCAAGGGACAGCCTAGAGAGCCT CAGGTGTACACCCTGCCTCCTTCTAGGGACGAGCTGACCAAGAACC AGGTGTCCCTGACTTGCCTCGTGAAGGGCTTCTACCCCAGCGACAT CGCAGTGGAGTGGGAAAGCAACGGTCAGCCAGAGAACAACTACAAG ACCACCCCCCCAGTGCTGGACAGCGACGGCAGCTTCTTCCTGTACA GCAAGCTGACCGTGGACAAAAGCCGCTGGCAGCAGGGCAACGTGTT CTCTTGCAGCGTGATGCACGAGGCCCTGCACAACCACTACACCCAG AAGAGCCTGAGCCTGAGCCCCAGGAGGAGGAGGAGGCTCCGGCGGCG GCGGAAGCCTGCCTATGACCGGAGGCCATCACCACCATCATCAC | cDNA of heavy chain for anti-HER2 mAb (Trastuzumab, artificial)-(G4S)2- LPMTGGHHHHH H; 1-57 encodes the N-terminal secretory signal peptide |
| 118 | actgacGAATTCGGCCGGCCGCCACCATGGATTGGACATGGAGGAT TCTGTTCCTG | Forward PCR primer (5' to 3'), EcoRI site at position 7-12 |
| 119 | actgacGGATCCCTCGAGTCAGTGATGATGGTGGTGATGGCCTCCG GTcataggCAGgcttccgccgccgccggagcctcctcctccTCCTG GGCTCAGGCTCAGGCTCTTCTGGGTGTAG | Reverse PCR primer (5' to 3'), BamHI site at position 7-12 |

TABLE 4-continued

Sequences

| SEQ ID NO | Sequence (amino acid or DNA 5' to 3') | Other identifying information |
|---|---|---|
| 120 | ATGCTGCCCAGCCAGCTGATCGGCTTTCTGCTGCTGTGGGTGCCTG CCTCCAGAGGCGACATCCAGATGACCCAGAGCCCATCCAGCCTGTC TGCCTCCGTGGGCGACAGAGTGACCATCACATGCCGCGCTTCTCAG GATGTGAACACAGCCGTGGCTTGGTACCAGCAGAAGCCTGGCAAGG CCCCAAAGCTGCTGATCTACTCCGCCTCTTTCCTGTATTCCGGCGT GCCAAGCAGGTTTTCCGGCAGCCGGTCTGGAACCGACTTCACCCTG ACAATCTCTTCCCTGCAGCCCGAGGATTTTGCCACATACTATTGCC AGCAGCACTATACCACACCCCCTACCTTCGGCCAGGGCACAAAGCT GGGAGATCAAGAGGACCGTGGCCGCTCCTAGCGTGTTCATCTTTCCA CCCTCTGACGAGCAGCTGAAGTCTGGCACAGCTTCCGTGGTGTGCC TGCTGAACAACTTCTACCCACGGGAGGCCAAGGTGCAGTGGAAGGT GGATAACGCTCTGCAGTCCGGCAATAGCCAGGAGTCTGTGACCGAG CAGGACTCCAAGGATAGCACATATTCTCTGAGCTCTACCCTGACAC TGTCCAAGGCCGATTACGAGAAGCACAAGGTGTATGCTTGCGAGGT GACCCATCAGGGCCTGTCCAGCCCCGTGACAAAGTCTTTCAATAGG GGAGAGTGTGGAGGAGGAGGCTCCGGCGGCGGCGGAAGCCTGGCCG AGACCGGAGGCCATCACCACCATCATCAC | cDNA of light chain for anti-HER2 mAb (Trastuzumab, artificial)-(G4S)2-LAETGGHHHHH H; 1-57 encodes the N-terminal secretory signal peptide |
| 121 | actgacGAATTCGGCCGGCCGCCACCATGCTGCCCAGCCAGCTGAT CGGCTTTCTG | Forward PCR primer (5' to 3'), EcoRI site at position 7-12 |
| 122 | actgacGGATCCCTCGAGTCAGTGATGATGGTGGTGATGGCCTCCG GTCTCGGCCAGgcttccgccgccgccGGAGCCTCCTCCTCCACACT CTCCCCTATTG | Reverse PCR primer (5' to 3'), BamHI site at position 7-12 |
| 123 | MDWTWRILFLVAAATGAHSEVQLVESGGGLVQPGGSLRLSCAASGF NIKDTYIHWVRQAPGKGLEWVARIYPTNGYTRYADSVKGRFTISAD TSKNTAYLQMNSLRAEDTAVYYCSRWGGDGFYAMDYWGQGTLVTVS SASTKGPSVFPLAPSSKSTSGGTAALGCLVKDYFPEPVTVSWNSGA LTSGVHTFPAVLQSSGLYSLSSVVTVPSSSLGTQTYICNVNHKPSN TKVDKKVEPKSCDKTHTCPPCPAPELLGGPSVFLFPPKPKDTLMIS RTPEVTCVVVDVSHEDPEVKFNWYVDGVEVHNAKTKPREEQYNSTY RVVSVLTVLHQDWLNGKEYKCKVSNKALPAPIEKTISKAKGQPREP QVYTLPPSRDELTKNQVSLTCLVKGFYPSDIAVEWESNGQPENNYK TTPPVLDSDGSFFLYSKLTVDKSRWQQGNVFSCSVMHEALHNHYTQ KSLSLSPGGGGGSGGGGSLPMTGGHHHHHH | Anti-HER2 mAb heavy chain-(G4S)2-LPMTGGHHHHHH H fusion (artificial); secretory signal peptide at 1-19 |
| 124 | MLPSQLIGFLLLWVPASRGDIQMTQSPSSLSASVGDRVTITCRASQ DVNTAVAWYQQKPGKAPKLLIYSASFLYSGVPSRFSGSRSGTDFTL TISSLQPEDFA- TYYCQQHYTTPPTFGQGTKLEI KRTVAAPSVFIFP PSDEQLKSGTASVVCLLNNFYPREAKVQWKVDNALQSGNSQESVTE QDSKDSTYSLSSTLTLSKADYEKHKVYACEVTHQGLSSPVTKSFNR GECGGGGSGGGGSLAETGGHHHHHH | Anti-HER2 mAb Light chain-(G4S)2-LAETGGHHHHH H fusion (artificial); secretory signal peptide at 1-19 |
| 125 | ATGGGCAGCAGCCATCACCACCATCATCACCATCACAGCGGCAGCG ATTACAAGGATGACGACGACAAGGCTGGCAGCCATATGGCTAGCGT GGACAACAAATTCAACAAAGAACAACAAAACGCGTTCTATGAGATC TTACATTTACCTAACTTAAACGAAGAACAACGAAACGCCTTCATCC AAAGTTTAAAAGATGACCCAAGCCAAAGCGCTAACCTTTTAGCAGA AGCTAAAAAGCTAAACGACGCTCAGGCGCCGAAAGGTACCGGATCC GAATTCATGGTTAGCGAACTGATTAAGGAAAATATGCACATGAAAC TGTATATGGAAGGCACCGTCAACAATCATCACTTTAAATGCACGAG TGAAGGTGAAGGCAAGCCGTATGAAGGCACCCAGACGATGCGTATT AAAGCAGTGGAAGGCGGTCCGCTGCCGTTTGCATTCGATATTCTGG CCACCAGTTTTATGTACGGTTCCAAAACCTTCATTAACCATACGCA GGGCATCCCGGATTTCTTTAAACAAAGTTTTCCGGAAGGTTTCACC TGGGAACGTGTGACCACGTATGAAGACGGCGGTGTTCTGACCGCCA CGCAGGATACGTCCCTGCAAGACGGCTGTCTGATTTACAATGTTAA AATCCGCGGTGTCAACTTCCCGAGCAATGGCCCGGTTATGCAGAAA AAGACCCTGGGTTGGGAAGCATCTACCGAAACGCTGTATCCGGCTG ATGGTGGTCTGGAAGGTCGTGCAGACATGGCTCTGAAACTGGTGGG CGGTGGCCATCTGATTTGCAACCTGAAGACCACGTACCGTTCTAAA AAGCCGGCGAAAAATCTGAAGATGCCGGGTGTGTATTACGTGGATC GTCGCCTGGAACGCATCAAAGAAGCCGACAAGGAAACCTATGTTGA ACAGCATGAAGTGGCGGTTGCCCGCTACTGTGATCTGCCGTCAAAA CTGGGTCACCGTGCGGCCGCAGGCAGCCTGCTGGGCGACTTCTTCC GCAAAAGCAAAGAGAAGATTGGCAAAGAATTTAAGCGCATTGTGCA GCGTATTAAGGATTTCCTGCGCAATCTGGTGCCGCGTACCGAAAGC GGTAGCGGCTCTTGA | Structural gene sequence of Z-RFP-LL37 (5' to 3'), (artificial) |

TABLE 4-continued

| | Sequences | |
| --- | --- | --- |
| SEQ ID NO | Sequence (amino acid or DNA 5' to 3') | Other identifying information |
| 126 | GGCAAAGAATTTAAGCGCATTGTGCAGCGTATTAAGGATTTCCTGC GCAATCTGGTGCCGCGTACCGAAAGCGGTAGCGGCTCTTGACTCGA GC | forward-direction PCR primer (5' to 3'), (artificial) |
| 127 | GCTTAAATTCTTTGCCAATCTTCTCTTTGCTTTTGCGGAAGAAGTC GCCCAGCAGGCTGCCTGCGGCCGCACGGTGACCCAGTTTTGACGGC | reverse-direction PCR primer (5' to 3'), (artificial) |
| 128 | ATGGAGCTGGCGGCCTTGTGCCGCTGGGGGCTCCTCCTCGCCCTCT TGCCCCCCGGAGCCGCGAGCACCCAAGTGTGCACCGGCACAGACAT GAAGCTGCGGCTCCCTGCCAGTCCCGAGACCCACCTGGACATGCTC CGCCACCTCTACCAGGGCTGCCAGGTGGTGCAGGGAAACCTGGAAC TCACCTACCTGCCCACCAATGCCAGCCTGTCCTTCCTGCAGGATAT CCAGGAGGTGCAGGGCTACGTGCTCATCGCTCACAACCAAGTGAGG CAGGTCCCACTGCAGAGGCTGCGGATTGTGCGAGGCACCCAGCTCT TTGAGGACAACTATGCCCTGGCCGTGCTAGACAATGGAGACCCGCT GAACAATACCACCCCTGTCACAGGGGCCTCCCCAGGAGGCCTGCGG GAGCTGCAGCTTCGAAGCCTCACAGAGATCTTGAAAGGAGGGGTCT TGATCCAGCGGAACCCCCAGCTCTGCTACCAGGACACGATTTTGTG GAAGGACATCTTCCACAAGAACAACCAGCTGGCTCTCACACTGATA GACACCAACCGCTCTCGGGCCTGCCACCCCTGTTCTCCGATGTGTA AGGGCTCCCGCTGCTGGGGAGAGAGTTCTGAGGATTGTCAGAGCCT GACGCGCACTGTCTGTGCCGGTGGCTGTGCCCGCTGCAAGGGGCCA CTGCCCACTGACTGCTGCCATGAGCAGTGTGCTGCCGGCTGCACGG GCCCCAAGCACTCTGACTGCCTGGCCTGCCTCCACTTCAACCACAG TGGCATCTGTGAGCTGCACTGCCCAGCCCTGGTCACCTACAACACA GACACGTTTGAGTCCATGCCCAATCCCGAGGGCCGGTATACATTCG GCGCCAGCTGTGTGACTGCCTGTCCCTACAACTACCTTTCTACGGA CGTGGGATCCTGCACCCTCGTCTGCCCCCTGCACAACCAAGAGGTG ACAGCAGAGGATGGAACACAGCGGTGTGAGAAGTGCAGCAAGCCCT GTGCCCGAGTGTGCTATGGTCTGGGCATGGAGCACTTGCGAGAGGT GAGGGCAGTTACCAGTGCCAATATCCAGGAGTTTGCTGGCTGCAAG AAGATCTTTGGGAGCCTGGCATTTCTGCCGGAGAGCTTTGATGGGG ACCCAGCCTCCAACACTGCCCCGCTCCAGCCAGAGCAGCTCCAAGT GTTTGAGACTCTGGAAGAGATCACAGGTTACCTATACATCTCAGCA TGGCCGGACAGCCTGCCTGACCTCAGCGTCTTCCAGAACCTGCAAG TAATCCGGGGACGAATTCTGCACAATGGCGCCTACTCGCTGACCCT GCAAGGGCTGGGCATCAGCTGGCTGGGGCTGCGCTCACTGAGGGAA CTGGGCAGTGGACTGGCCCTCATCCACCATAACACCCACCTCTGCT TCGTGCACACGGTGCCCTGGGACCAGCTCTTTCGGAACCCGCACCA AGCTCTGCTCCACACTGCCAACCGGCCAGAGGACGAGTGTGTGGGC GAGGGCCTGGCCTGCCACCAGCTGTGCGCCCGAGGGCACTGCTGGG GTCCAGGGCCCACCCAGTGTGTCAACTGCAGCCAGTTCCTTCGGGG CCAGGAGTGCGTGGAGGAATGCCGAGTACTGCAGGGGCTCCCCAGG GAGTATGTGAATGCCAGGCACTGTTTGCCGTGCCACCCTGAGTGTC AGCCCCAGAATGGCTCAGTGACCTGTTTTGGACCGGAGGCTGACCA GTGTGTGGCCTGTGCCCACTATAAGGACCCTCCCTTCTGCGTGGCC CGCTGCCCCAGCGGTGTGAAACCTGACCTCTCCTACATGCCCATCT GGAAGTTTCCAGATGAGGAGGGCGCATGCCAGCCTTGCCCCATCAA CTGCACCCACTCCTGTGTGGACCTGGATGACAAGGGCTGCCCCGCC GAGCAGAGAGCCAGCCCTCTGACGACGCGTGCTGTGGGCCAGGACA CGCAGGAGGTCATCGTGGTGCCACACTCCTTGCCCTTTAAGGTGGT GGTGATCTCAGCCATCCTGGCCCTGGTGGTGCTCACCATCATCTCC CTTATCATCCTCATCATGCTTTGGCAGAAGAAGCCACGTTAG | Structural gene sequence of human HER2 extracellular domain (5' to 3'); 1-66 encodes the N-terminal secretory signal peptide. |
| 129 | MPLLLLLLPLLWAGALAQVQLVESGGGVVQPGRSLRLSCAASGFKFS GYGMHWVRQAPGKGLEWVAVIWYDGSKKYYVDSVKGRFTISRDNSK NTLYLQMNSLRAEDTAVYYCARQMGYWHFDLWGRGTLVTVSSASTK GPSVFPLAPSSKSTSGGTAALGCLVKDYFPEPVTVSWNSGALTSGV HTFPAVLQSSGLYSLSSVVTVPSSSLGTQTYICNVNHKPSNTKVDK RVEPKSCDKTHTCPPCPAPELLGGPSVFLFPPKPKDTLMISRTPEV TCVVVDVSHEDPEVKFNWYVDGVEVHNAKTKPREEQYNSTYRVVSV LTVLHQDWLNGKEYKCKVSNKALPAPIEKTISKAKGQPREPQVYTL PPSREEMTKNQVSLTCLVKGFYPSDIAVEWESNGQPENNYKTTPPV LDSDGSFFLYSKLTVDKSRWQQGNVFSCSVMHEALHNHYTQKSLSL SPGK | Anti-CD3e mAb (Foralumab) heavy chain (artificial); secretory signal peptide at 1-16 |

TABLE 4-continued

Sequences

| SEQ ID NO | Sequence (amino acid or DNA 5' to 3') | Other identifying information |
|---|---|---|
| 130 | MRLPAQLLGLLMLWVSGSSGEIVLTQSPATLSLSPGERATLSCRAS QSVSSYLAWYQQKPGQAPRLLIYDASNRATGIPARFSGSGSGTDFT LTISSLEPEDFAVYYCQQRSNWPPLTFGGGTKVEIKRTVAAPSVFI FPPSDEQLKSGTASVVCLLNNFYPREAKVQWKVDNALQSGNSQESV TEQDSKDSTYSLSSTLTLSKADYEKHKVYACEVTHQGLSSPVTKSF NRGECGGGGSLPMTGGHG | Anti-CD3e mAb (Foralumab) light chain (artificial); secretory signal peptide at 1-20 |
| 131 | MPLLLLLPLLWAGALAEVQLVQSGAEVKKPGASVKVSCKASGYRFT NYWIHWVRQAPGQGLEWIGGINPGNNYATYRRKFQGRVTMTADTST STVYMELSSLRSEDTAVYYCTREGYGNYGAWFAYWGQGTLVTVSSA STKGPSVFPLAPSSKSTSGGTAALGCLVKDYFPEPVTVSWNSGALT SGVHTFPAVLQSSGLYSLSSVVTVPSSSLGTQTYICNVNHKPSNTK VDKRVEPKSCDKTHTCPPCPAPELLGGPSVFLFPPKPKDTLMISRT PEVTCVVVDVSHEDPEVKFNWYVDGVEVHNAKTKPREEQYNSTYRV VSVLTVLHQDWLNGKEYKCKVSNKALPAPIEKTISKAKGQPREPQV YTLPPSREEMTKNQVSLTCLVKGFYPSDIAVEWESNGQPENNYKTT PPVLDSDGSFFLYSKLTVDKSRWQQGNVFSCSVMHEALHNHYTQKS LSLSPGK | Anti-CD22 mAb (Inotuzumab) heavy chain (artificial); secretory signal peptide at 1-16 |
| 132 | MRLPAQLLGLLMLWVSGSSGDVQVTQSPSSLSASVGDRVTITCRSS QSLANSYGNTFLSWYLHKPGKAPQLLIYGISNRFSGVPDRFSGSGS GTDFTLTISSLQPEDFATYYCLQGTHQPYTFGQGTKVEIKRTVAAP SVFIFPPSDEQLKSGTASVVCLLNNFYPREAKVQWKVDNALQSGNS QESVTEQDSKDSTYSLSSTLTLSKADYEKHKVYACEVTHQGLSSPV TKSFNRGECGGGGSLPMTGGHG | Anti-CD22 mAb (Inotuzumab) light chain (artificial); secretory signal peptide at 1-20 |
| 133 | MAQVLRGTVTDFPGFDERADAETLRKAMKGLGTDEESILTLLTSRS NAQRQEISAAFKTLFGRDLLDDLKSELTGKFEKLIVALMKPSRLYD AYELKHALKGAGTNEKVLTEIIASRTPEELRAIKQVYEEEYGSSLE DDVVGDTSGYYQRMLVVLLQANRDPDAGIDEAQVEQDAQALFQAGE LKWGTDEEKFITIFGTRSVSHLRKVFDKYMTISGFQIEETIDRETS GNLEQLLLAVVKSIRSIPAYLAETLYYAMKGAGTDDHTLIRVMVSR SEIDLFNIRKEFRKNFATSLYSMIKGDTSGDYKKALLLLCGEDD | Annexin V (Homo Sapiens) |
| 134 | MAFVKSGWLLRQSTILKRWKKNWFDLWSDGHLIYYDDQTRQNIEDK VHMPMDCINIRTGQECRDTQPPDGKSKDCMLQIVCRDGKTISLCAE STDDCLAWKFTLQDSRTN | Evectin 2 (Homo Sapiens) |

The present invention is further illustrated by the following examples.

V. Examples

Among other things, the following examples show that conjugating various LL37-derived peptides to antibodies enhances the delivery and effectiveness of existing antibody drugs, which improves the effectiveness of existing drugs for their approved indications and lowers the dosage required for therapeutic effect.

The following examples also show that conjugation with an LL37-derived peptide may transform drugs which were not effective (due to low availability of particular cell surface targets) into effective drugs without increasing toxicity to the subject (because selectivity of the delivery is substantially retained). This includes not only expanding the therapeutic use of existing drugs to new indications, but also expands the landscape of potential therapeutic/diagnostic agents because antibodies and other protein or nucleic acid binding scaffolds which were not particularly effective for therapeutic or diagnostic use (due to the low availability of particular cell surface targets) may be transformed into effective therapeutic and diagnostic agents by conjugation with the LL37-derived peptides disclosed herein. Certain embodiments of the cell surface binding conjugates of the present disclosure may therefore enhance the potency, efficacy, and safety of antibody-based therapeutics.

Figure 1:
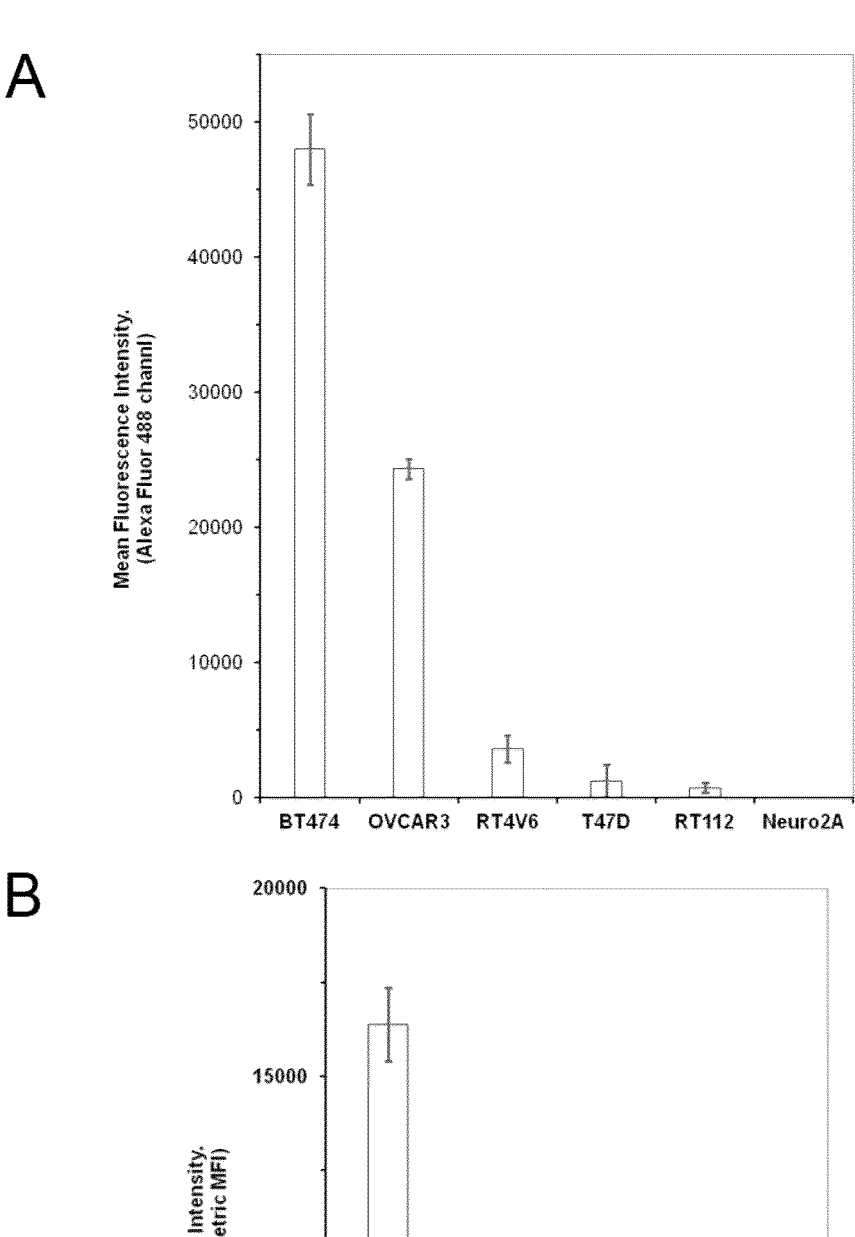
FIG. 1 shows five graphs comparing the relative level of HER2 present on various cell types (high, medium or low HER2-expressing cell lines or non-HER2 expressing, e.g. Neuro2A), measured using an immune-fluorescent label in a Fluorescence-activated cell sorting (FACS) instrument. For Panel A, the immune-fluorescent label is anti-HER2(scFv)-Fc-Fluorescein. For Panel B, the immune-fluorescent label is anti-HER2(scFv)-Fc-Alexafluor405. For Panels C and D and E, the immune-fluorescent label is anti-HER2 mAb-Alexafluor647.
Figure 1:
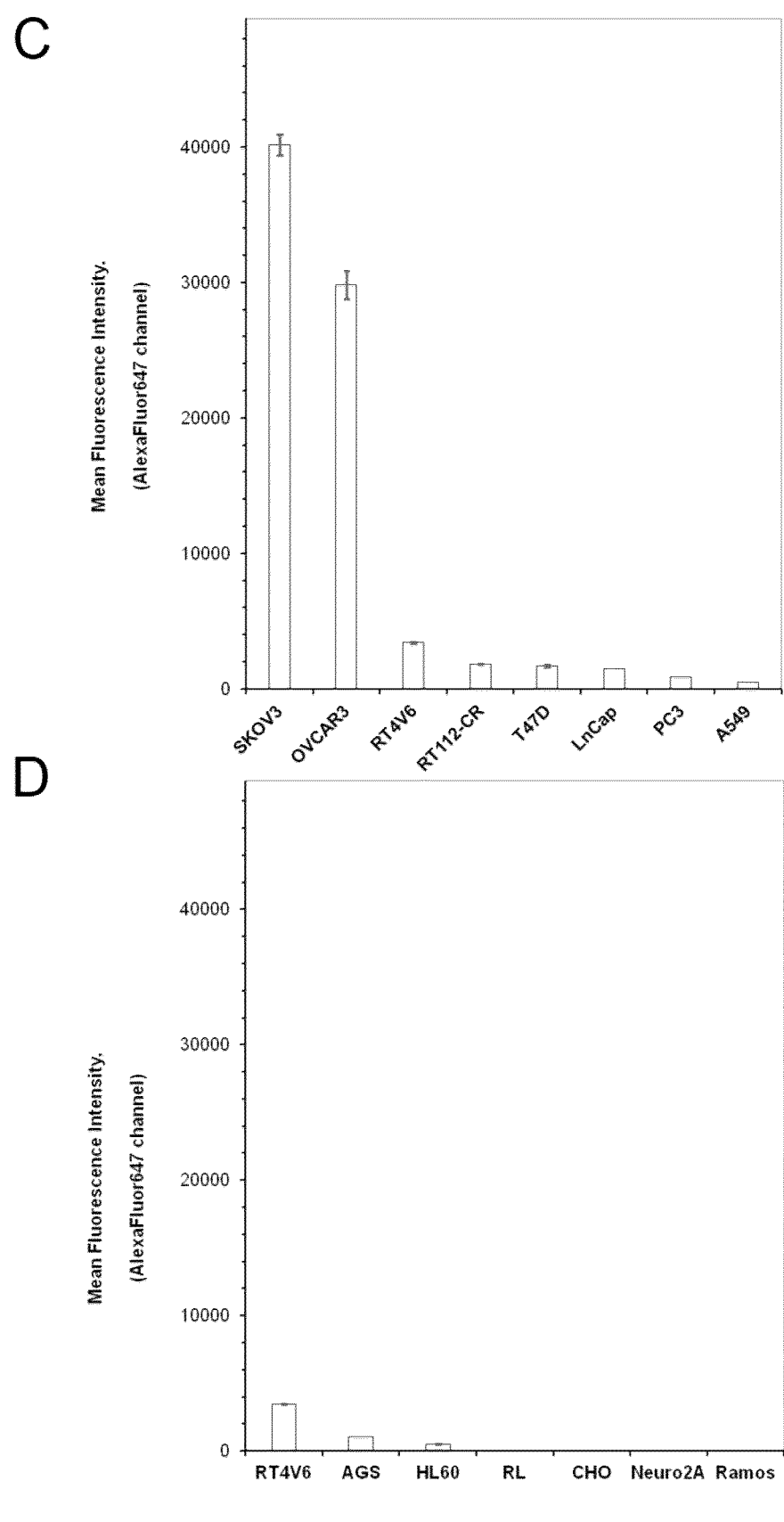
Figure 1:
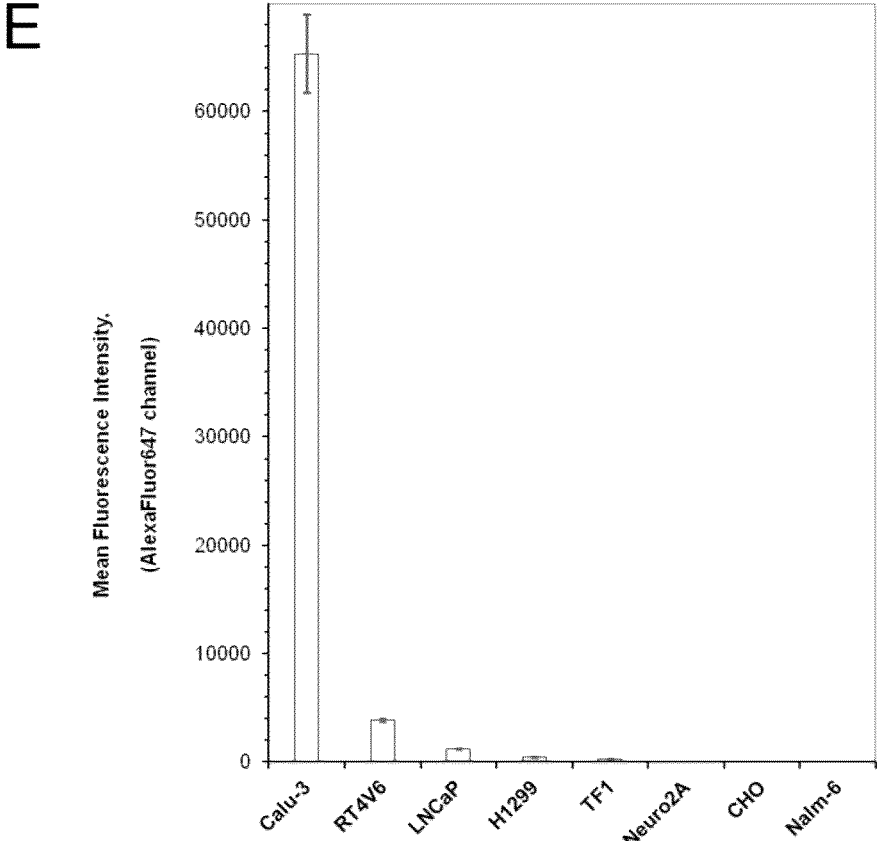

Example 1. A Covalent Conjugate Comprising LL37 Enhances Delivery of Receptor-Specific Antibody to the Target Cells FIG. 1 shows that the relative level of HER2 (a cancer biomarker) of different cell types can be accurately quantified with a Fluorescein-labelled HER2-specific antibody (i.e., scFv and mAb) in a Fluorescence-activated cell sorting (FACS) instrument. For Panel A, the immune-fluorescent label is anti-HER2(scFv)-Fc-Fluorescein. For Panel B, the immune-fluorescent label is anti-HER2(scFv)-Fc-Alexafluor405. For Panels C and D and E, the immune-fluorescent label is anti-HER2 mAb-Alexafluor647. BT474 is a human breast ductal carcinoma cell line with high level of HER2 on the cell surface. OVCAR3 is a human ovary epithelial adenocarcinoma cell line with medium-to-high level of HER2 on the cell surface. RT4V6 is a human bladder carcinoma cell line with low-to-medium level of HER2 on the cell surface. T47D is a human mammary gland ductal carcinoma cell line with low level of HER2. RT112 is a human bladder carcinoma cell line with low level of HER2. U87MG is a human glioblastoma cell line that express low level of HER2. Neuro2A is a mouse neuroblastoma cell line that does not express HER2. SKOV3 is a human ovarian cancer cell line with medium-to-high level of HER2 on the cell surface. LnCap is an androgen-sensitive human prostate adenocarcinoma cell line with low level of HER2. PC3 is a human prostate cancer cell line with low level of HER2. A549 is a human adenocarcinomic alverolar basal epithelial cell line with low level of HER2. AGS is a human stomach gastric adenocarcinoma cell line with low level of HER2. HL60 is a human leukemia cell line with low level of HER2. CHO is a Chinese hamster ovary epithelial cell line that does not express HER2. Ramos is a human lymphoblast cancer cell line that does not express HER2. Calu-3 is a human lung cancer cell line with high level of HER2 on the cell surface. H1299 is a human non-small cell lung carcinoma cell line with low level of HER2. TF1 is a human bone marrow erythroleukemia cell line with low level of HER2. Nalm-6 is a human peripheral blood B cell precursor leukemia cell line that does not express HER2. The level of HER2 present on cells were quantified by measuring the geometric mean fluorescence intensity. (i.e.: for Panel A, the Alexa Fluor 488 color channel in the FACS detector emitted from Fluorescein-linked anti-HER2(scFv)-Fc, which targets HER2, was used; for Panel B, the Pacific Blue color channel was used; for Panels C and D and E, the AlexaFluor647 color channel was used).

Delivery of monoclonal antibody (mAb) to target cells was compared to delivery of the same mAb conjugated to the full-length LL37 peptide. To quantify delivery of the mAb, a fluorescent Fc-binding protein (Z-RFP) was constructing by linking the Z-domain (e.g., Nilsson et al. (1987), Protein Eng., 1, 107) of a high affinity antibody-binding Protein A to a red fluorescent protein (RFP) as a fluorescent marker. The formation of a complex between Z-RFP and a mAb therefore permits the presence of the mAb to be quantified in a flow cytometry instrument.

Figure 2:
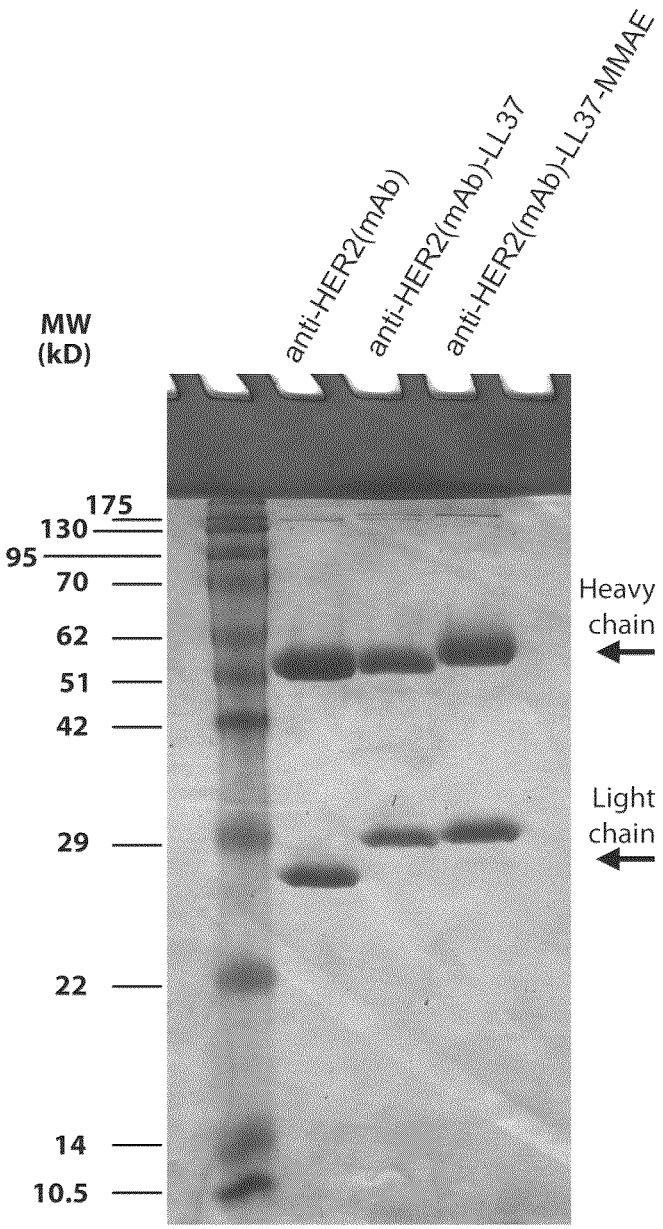
FIG. 2 shows the quantity of LL37-linked anti-HER2 mAb-MMAE drug conjugate on SDS-PAGE (i.e. under reducing conditions).

FIG. 2 shows (1) that LL37 can be specifically and fully conjugated to the C-terminus of the light chain in an anti-HER2 mAb forming a stable LL37-linked antibody, and (2) that LL37 conjugation is compatible with downstream chemical modification procedures involved in cytotoxin-linking to form an LL37-linked antibody drug conjugate (ADC). The predicted molecular weights derived from the amino acid sequence of heavy chain and light chain in anti-HER2 mAb are 49.3 kDa and 24.5 kDa, respectively. During protein synthesis, glycosylation of the heavy chain Fc region resulted in a final heavy chain size of ~55 kDa. Sortase catalyzed the ligation of LL37 peptide (molecular weight of 4.5 kDa) to the C-terminus of light chain producing the LL37-linked light chain of 29 kDa. After conjugating the VcMMAE (molecular weight of 1.3 kDa) to the 8 reduced cysteine side chains in an LL37-linked anti-HER2 mAb (6 in the heavy chains and 2 in the light chains in a mAb), the molecular weight of heavy chains and light chains were increased to 59 kDa and 30 kDa, respectively, in the anti-HER2 mAb-LL37-MMAE.

Figure 3:
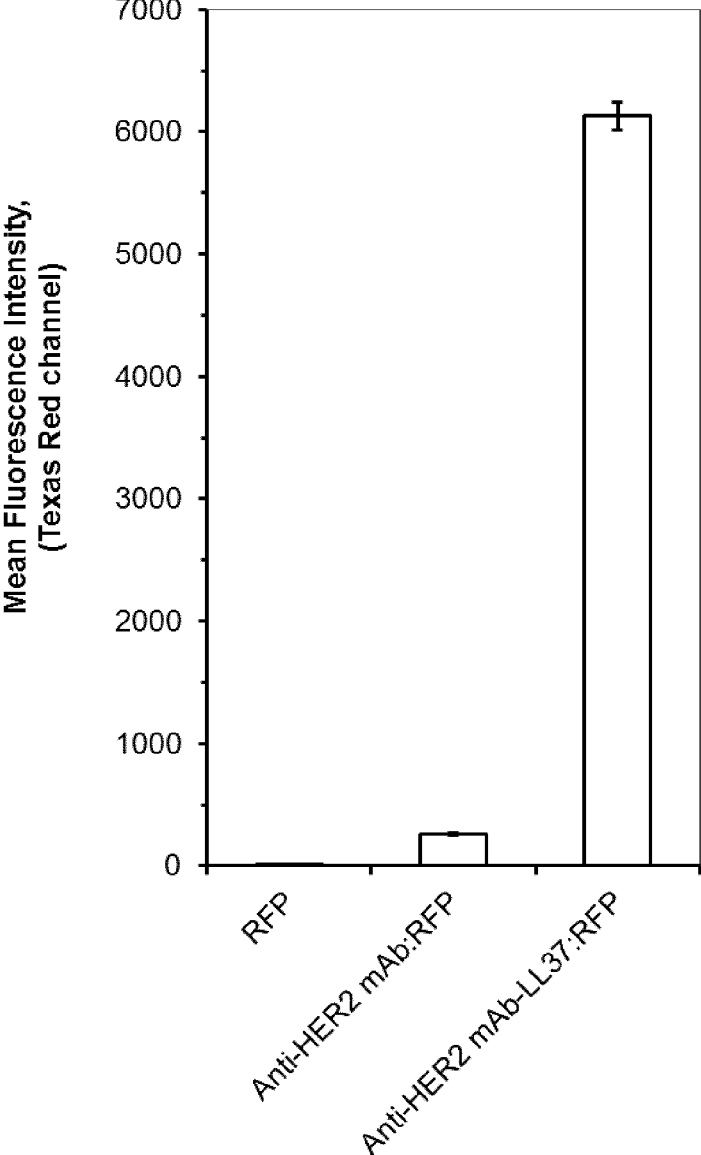
FIG. 3 shows a graph comparing the fluorescence of OVCAR3 cells (HER2+ human cancer cell line) treated with Z-RFP, Z-RFP-bound anti-HER2 mAb, or Z-RFP-bound anti-HER2 mAb conjugated with LL37.

FIG. 3 shows a graph comparing the fluorescence of OVCAR3 cells (medium-to-high HER2+ human cancer cell line) treated with Z-RFP, Z-RFP-bound anti-HER2 mAb, or Z-RFP-bound anti-HER2 mAb conjugated with LL37. This result shows that conjugation with LL37 enhances delivery of anti-HER2 mAb to HER2+ cells. Anti-HER2 mAb alone was delivered to OVCAR3 cells, but conjugation to LL37 increased the delivery of anti-HER2 mAb by more than 20-fold. This result therefore shows that conjugation with LL37 substantially enhances delivery of anti-HER2 mAb to medium-to-high HER2+ cells.

Figure 4:
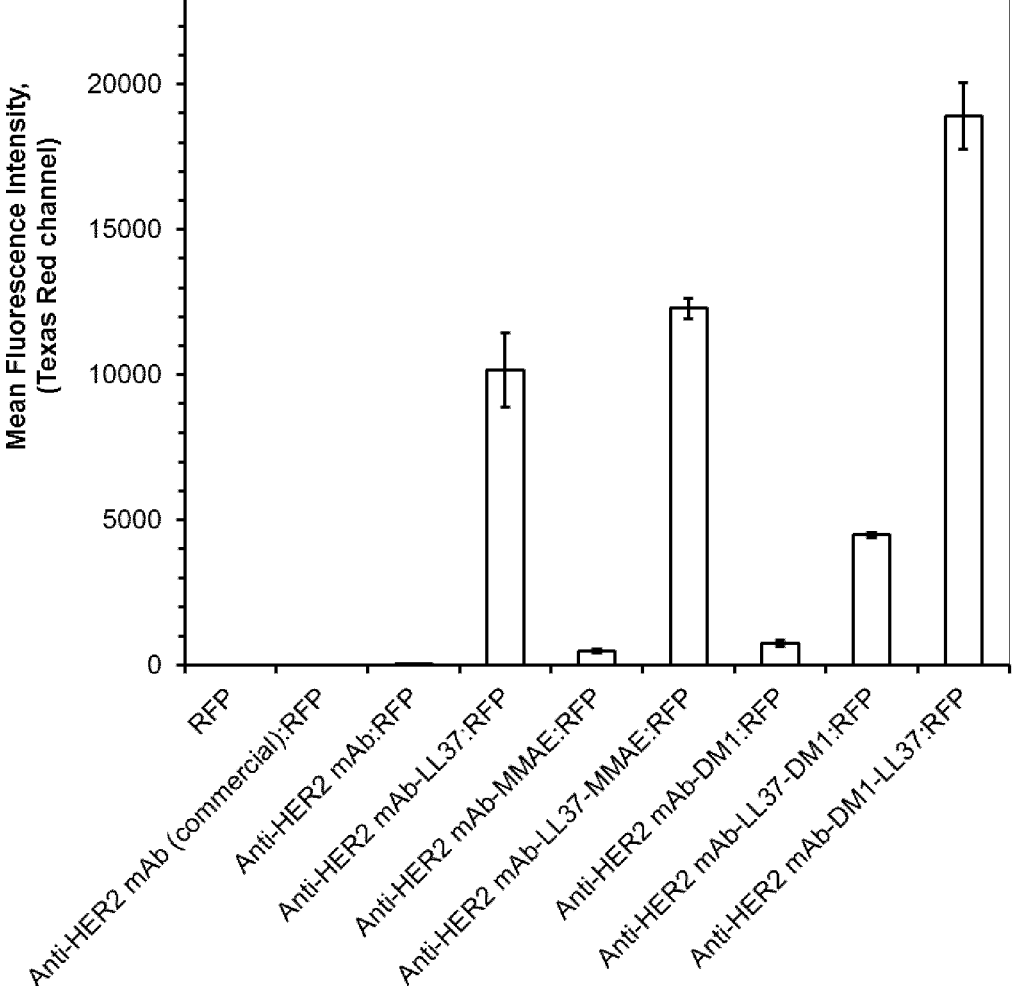
FIG. 4 shows a graph comparing the fluorescence of RT4V6 cells (HER2+ human bladder cancer cell line) treated with Z-RFP, Z-RFP-bound anti-HER2 mAb, Z-RFP-bound anti-HER2 mAb conjugated with LL37, Z-RFP-bound anti-HER2 ADC (MMAE), Z-RFP-bound anti-HER2 ADC (MMAE) conjugated with LL37, Z-RFP-bound anti-HER2 ADC (DM1), or Z-RFP-bound anti-HER2 ADC (DM1) conjugated with LL37.

The above experiment was repeated with an antibody-drug conjugate (ADC) and a low-to-medium HER2+ bladder cancer cell line (RT4V6). FIG. 4 shows a graph comparing the fluorescence of RT4V6 cells treated with Z-RFP, Z-RFP-bound anti-HER2 mAb, Z-RFP-bound anti-HER2 mAb conjugated with LL37, Z-RFP-bound anti-HER2 ADC (MMAE), Z-RFP-bound anti-HER2 ADC (MMAE) conjugated with LL37, Z-RFP-bound anti-HER2 ADC (DM1), Z-RFP-bound anti-HER2 ADC (DM1) conjugated with LL37. Notably, anti-HER2 mAb alone was poorly delivered to the low-to-medium HER2+RT4V6 cells, but when conjugated to LL37 the delivery was increased by more than 20-fold. This result shows that conjugation with LL37 enhances delivery of anti-HER2 mAb and ADC to low-to-medium HER2+ cells.

Figure 5:
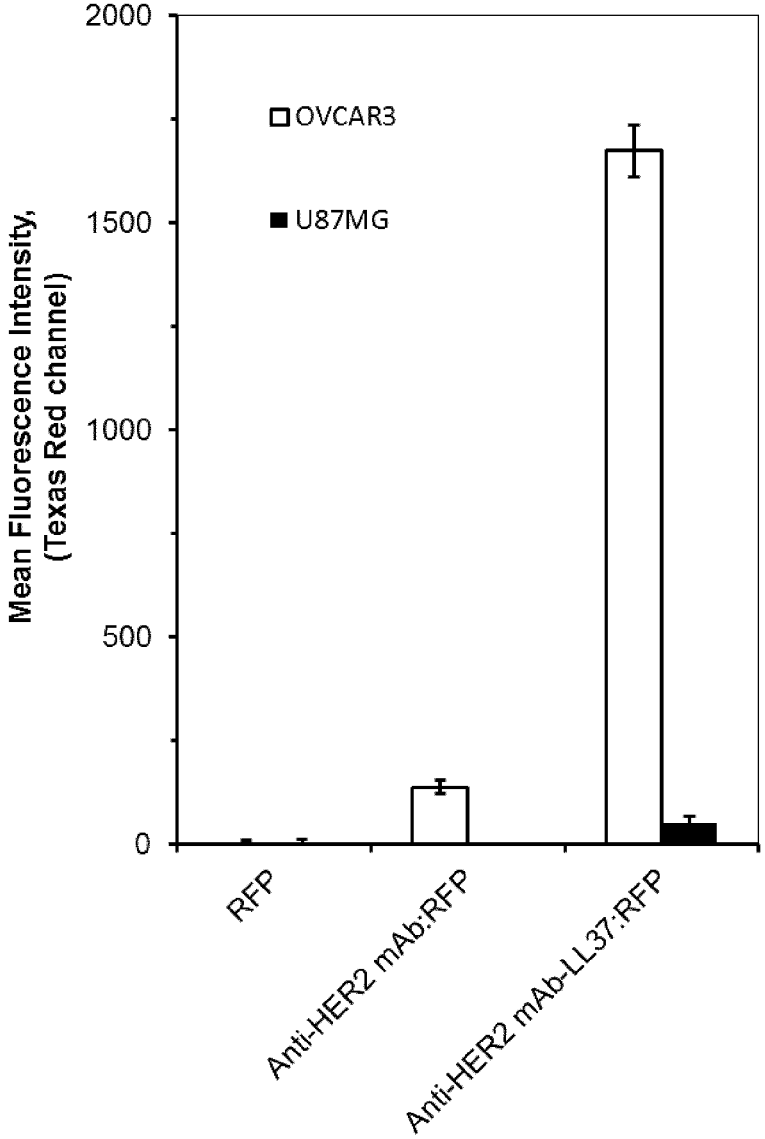
FIG. 5 shows a graph comparing the fluorescence of two different cell lines, namely OVCAR3 (HER2+ human cancer cell line) and U87MG (a low HER2+ human glioblastoma cell line), treated with Z-RFP, Z-RFP-bound anti-HER2 mAb, or Z-RFP-bound anti-HER2 mAb conjugated with LL37.
Figure 6:
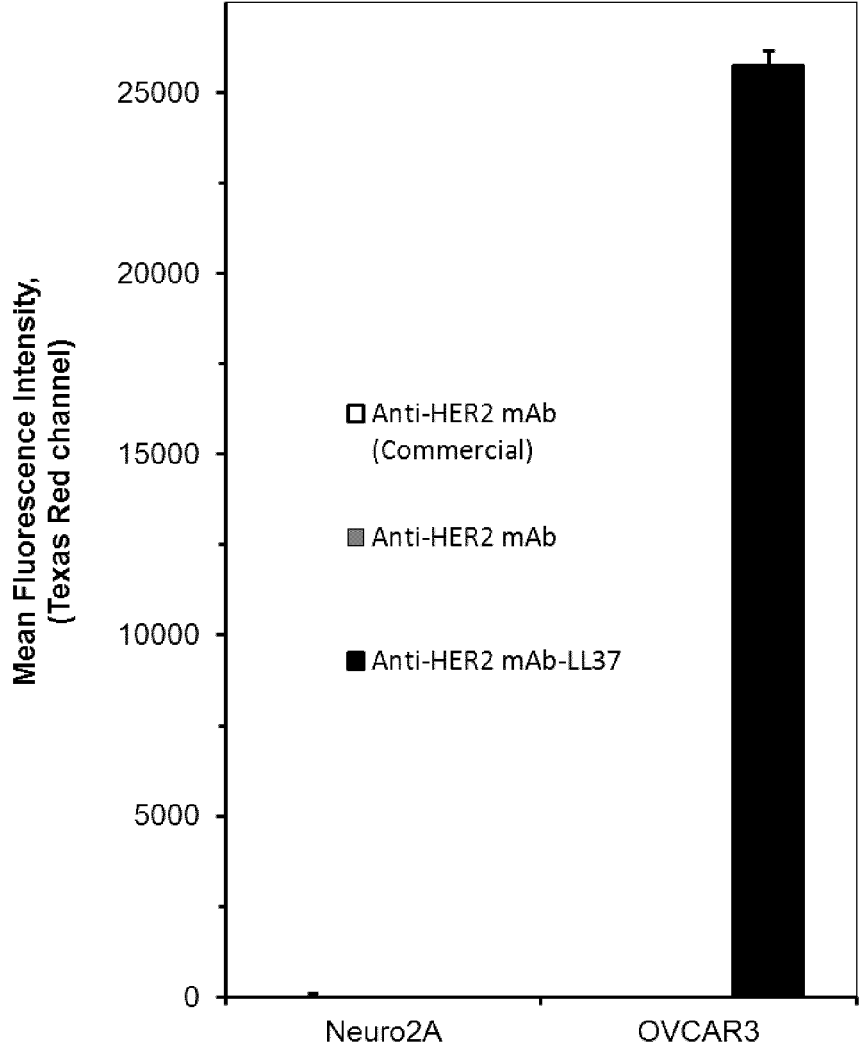
FIG. 6 shows a graph comparing the fluorescence of two difference cell lines, namely OVCAR3 (HER2+ human cancer cell line) and Neuro2A (HER2− mouse brain cell line), treated with Z-RFP-bound anti-HER2 mAb, or Z-RFP-bound anti-HER2 mAb conjugated with LL37.

FIGS. 5 and 6 show that LL37-conjugation enhanced the selective delivery of anti-HER2 mAb to OVCAR3 cells (a medium-to-high HER2+ cell line). FIG. 5 shows a graph comparing the fluorescence of two different cell lines, namely OVCAR3 and U87MG (a low HER2+ human glioblastoma cell line), treated with Z-RFP, Z-RFP-bound anti-HER2 mAb, or Z-RFP-bound anti-HER2 mAb conjugated with LL37. Similarly, FIG. 6 shows a graph comparing the fluorescence of OVCAR3 and Neuro2A (HER2− mouse brain cell line), treated with Z-RFP-bound anti-HER2 mAb, or Z-RFP-bound anti-HER2 mAb conjugated with LL37. The LL37-conjugated anti-HER2 mAb increased the mAb delivery to OVCAR3 by at least 20-fold, but did not increase delivery to the HER2− cell lines (Neuro2A in FIG. 6). This result therefore shows that conjugation with LL37 selectively increases mAb delivery for cells that express the specific cell surface binding moiety of the target cell (i.e. HER2, in the present case).

Figure 7:
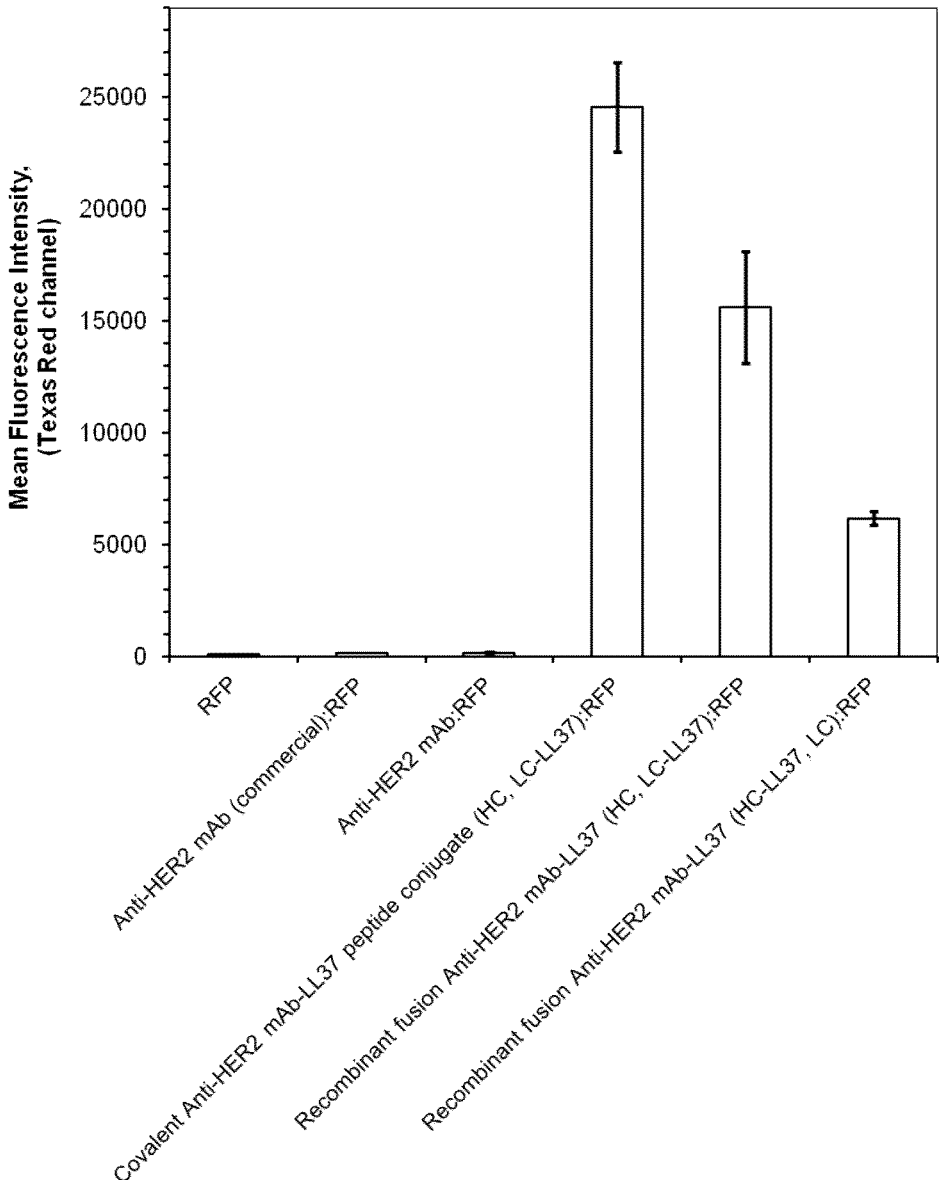
FIG. 7 shows a graph comparing various covalently linked mAb-LL37 protein-peptide conjugate to mAb-LL37 recombinant fusion proteins.

LL37 can be linked to the heavy chain of an antibody, and produces strong delivery enhancement. FIG. 7 shows that LL37 linked to the C-terminus of the heavy chain in an anti-HER2 mAb amplifies the delivery of anti-HER2 mAb to HER2+ cells (namely, OVCAR3, a human ovary epithelial adenocarcinoma cell line with medium-to-high level of HER2 on the cell surface) comparable to when LL37 is linked to the light chain of the anti-HER2 mAb. FIG. 7 also shows that the LL37 sequence can be added to the antibody structural genes and be produced (i.e, expressed and purified) as a recombinant fusion protein, and the recombinant fusion versions of anti-HER2 mAb with either an LL37-linked light chain or an LL37-linked heavy chain have comparable level of target cell delivery enhancements.

Now referring to FIG. 7 in further detail, anti-HER2 mAb alone (i.e., purchased from commercial source, or produced in-house) at 100 nM recognizes the HER2 receptor on OVCAR3, but the delivery efficiency is low. LL37 can be linked to an anti-HER2 mAb using different methods (e.g., enzyme-mediated conjugation or recombinant fusion) and in different configurations (e.g., linked to the heavy chain or the light chain). For all of the different linking methods and configurations tested, LL37 attachment enabled and amplified the delivery of anti-HER2 mAbs to OVCAR3. This includes the covalently linked anti-HER2 mAb-LL37 peptide conjugate (HC, LC-LL37), in which the LL37 peptide is covalently linked to the C-terminus of light chain (LC). A similar recombinant fusion of anti-HER2 mAb-LL37 (HC, LC-LL37), in which the LL37 cDNA sequence is fused to the C-terminus of light chain (LC) in the expression plasmid and produced as a recombinant protein, also is shown to provide a high level of delivery efficiency comparable to the covalent conjugate of Anti-HER2 mAb-LL37 peptide (HC, LC-LL37). The recombinant fusion of anti-HER2 mAb-LL37 (HC-LL37, LC), in which the LL37 nucleotide sequence is fused to the C-terminus of the heavy chain (HC) in the expression plasmid and produced as a recombinant protein, also showed a high level of delivery efficiency to OVCAR3 cells in this comparison. The delivery of anti-HER2 antibodies was quantitated by measuring the red fluorescence intensity (i.e., PE-Texas Red color channel in the FACS detector) emitted from Z-RFP bound to anti-HER2 mAb (or to the LL37-linked anti-HER2 mAbs). The Z-domain (i.e. the "Z" in Z-RFP) is a stable 6.6 kD protein fragment derived from the B domain of Protein A, and retains high specificity and affinity for the human IgG1 Fc domain (see, Nilsson et al. (1987), Protein Eng., 1, 107). As shown in FIG. 7, the non-specific binding of Z-RFP to OVCAR3 (i.e., RFP alone, without antibody) is negligible.

Experimental Procedures for Examples in FIG. 1

The recombinant anti-HER2(scFv)-Fc protein (of SEQ ID No: 29) was produced in HEK293 cell using the Polyethylene imine (PEI) transient transfection method, and the expression plasmid used contains the anti-HER2(scFv)-Fc structural gene (of SEQ ID No: 30) in pcDNA3.1(+). The structural gene encodes a secretory signal peptide at the N-terminus to facilitate protein secretion and production in serum-free media (HyClone SFM4HEK293 media from GE Lifesciences). The expressed anti-HER2(scFv)-Fc was purified from the serum-free media using the Protein A affinity chromatographic method.

Anti-HER2(scFv)-Fc-Fluorescein, used in FIG. 1 (panel A), was produced by reacting the purified anti-HER2(scFv)-Fc to the Fluorescein isocyanate (FITC), and purified using the Fluorescein-EX Protein Labeling kit from Molecular Probes (Catalog number: F10240). Briefly, 1 mg of anti-HER2(scFv)-Fc in PBS buffer was adjusted to pH 8.0 with bicarbonate, and was added to 100 μg of Fluorescein isocyanate in a microcentrifuge tube to initiate the reaction. After 1 hour of incubation on a rocking incubator at room temperature, the clear supernatant was purified on G25 Sephadex size-exclusion chromatography (i.e., PD-10 desalting column). Elution fractions containing the Fluorescein-labeled anti-HER2(scFv)-Fc were combined and concentrated in a 30 kD MWCO centrifugal concentrator. Using the same reaction scheme and purification method, the anti-HER2(scFv)-Fc-AlexaFluor405, used in FIG. 1 (panel B), was produced from the purified anti-HER2(scFv)-Fc and the AlexaFluor405-NHS Ester (succinimidyl ester) (Thermo Fisher Catalog number A30000).

Anti-HER2 mAb cloning, expression, and purification. The structural gene encoding the anti-HER2 mAb heavy chain (SEQ ID NO: 8) and anti-HER2 mAb light chain (SEQ ID NO: 9) were produced by gene synthesis, and sub-cloned separately into the EcoRI-BamHI sites in the pTT5 mammalian expression vectors. The sequences of the anti-HER2 mAb heavy (SEQ ID NO: 8) and light chains (SEQ ID NO: 9) in separate pTT5 plasmids were confirmed by sequencing analysis of the entire open reading frames.

Expression of anti-HER2 mAb (SEQ ID NOs: 3 and 4) was done by transient transfection co-delivering both the heavy and light chains (SEQ ID NOs: 8 and 9) in pTT5 plasmids (mixed in an optimized ratio) into the CHO-BRI-rc-TA-55E1 cells. Following DNA transfection, cells were induced with cumate for 16 days to select a stable pool of highly protein expressing cells. Following the selection, these cells were isolated for protein expression in a fed-batch method (i.e., fresh media continuously added during cell growth) over the 11 day period. At the end of cell growth, the culture media was harvested, and the secreted anti-HER2 mAb was purified from the clear supernatant of the culture media by Protein A binding chromatography to produce anti-HER2 mAb, in phosphate buffered saline (PBS), having a purity of >99%. The functional assembly of the anti-HER2 mAb was verified using gel filtration and SDS-PAGE.

Anti-HER2 mAb-AlexaFluor647, used in FIG. 1 (panel C and D and E), was produced by reacting the purified anti-HER2 mAb to the AlexaFluor 647-NHS Ester (succinimidyl ester) using the AlexaFluor 647 Antibody Labeling Kit from Thermo Fisher (Catalog number: A20186). Briefly, 1 mg of anti-HER2 mAb in PBS buffer was adjusted to pH 8.0 with bicarbonate, and was added to 100 μg of AlexaFluor647 in a microcentrifuge tube to initiate the reaction. After 1 hour of incubation on a rocking incubator at room temperature, the clear supernatant was purified on G25 Sephadex size-exclusion chromatography (i.e., PD-10 desalting column). Elution fractions containing the AlexaFluor647-labeled anti-HER2 mAb were combined and concentrated in a 30 kD MWCO centrifugal concentrator.

Delivery assay: For the comparison shown in FIG. 1 (panel A), the adherent cells were washed with PBS and detached from culturing plate into suspension with trypsin treatment, and then neutralized in 10% FBS containing media. The assay was done in triplicate for each cell line. In microcentrifuge tubes, cells and 100 nM of Fluorescein-labeled anti-HER2(scFv)-Fc were incubated for 30 minutes on ice to facilitate binding. The cells were then isolated (i.e, centrifugation), washed with cold PBS twice, and resuspended in FACS buffer (2% v/v FBS, 2 mM EDTA, 0.05% w/v sodium azide in PBS) in FACS tubes on ice. The level of HER2 in cell is measured by the delivered Fluorescein-labeled anti-HER2(scFv)-Fc, and the sample FACS tubes were stored on ice until flow cytometry analysis on a LSRII-561 machine. For the comparison shown in FIG. 1 (panel B), the cells were also prepared (i.e., PBS wash, detachment with trypsin, neutralization with 10% FBS containing media) using the same procedures. The cells were incubated with 100 nM of anti-HER2(scFv)-Fc-AlexaFluor405 for 1 hour on ice, and then processed (i.e., two rounds of PBS wash, followed by resuspension in FACS buffer) for flow cytometry analysis (excitation wavelength of 405 nm, emission wavelength of 450 nm). For the comparison shown in FIG. 1 (panels C and D and E), the cells were incubated with 10 μg/ml of anti-HER2 mAb-AlexaFluor647 for 30 minutes at 4 degree Celsius, and then washed with 1×PBS, followed by resuspension in FACS buffer for flow cytometry analysis. The delivery of anti-HER2 mAb-AlexaFluor647 was quantitated in FACS with laser compatible with excitation wavelength of 650 nm and emission wavelength of 665 nm.

Experimental Procedures for Examples in FIG. 3

Cloning, expression and purification of Z-RFP: The expression plasmid for Z-RFP was made from the pET-28a+ bacterial expression plasmid containing the structural gene of Z-RFP. Using the forward and reverse oligonucleotide primers (SEQ ID NOs: 5 and 6, respectively) in a Quick-Change site-directed mutagenesis procedure, the expression plasmid encoding the Z-RFP was created. The sequence was confirmed by sequencing analysis of the entire Z-RFP structural gene (SEQ ID NO: 7).

Z-RFP is highly expressed in *Escherichia coli* Rosetta II (DE3) in LB media following induction with IPTG and overnight incubation at room temperature (18° C.).

The bright red fluorescent *E. coli* cells containing the expressed Z-RFP were harvested, and lysed by sonication (50% duty cycle per pulse, 30-second sonication pulse for 10 times, cooling the sonicator probe on ice between pulses).

The lysate was clarified by centrifugation (15,000×g, 60 minutes, 4° C.) to remove insoluble cell debris. The clear supernatant containing the expressed Z-RFP was isolated on a Nickel-NTA chromatography resin, and was purified using an imidazole elution gradient. Sample fractions containing the majority of Z-RFP were combined and dialyzed in 20 mM Tris-HCl (pH 8.0) and 160 mM NaCl overnight. The buffer-exchanged Z-RFP was concentrated in a centrifugal diafiltration device to finalize the purification. High purity Z-RFP (>95% purity as judged from SDS-PAGE with Coomassie Blue staining) was obtained using this method.

Anti-HER2 mAb cloning, expression, and purification. The structural gene encoding the anti-HER2 mAb heavy chain (SEQ ID NO: 8) and anti-HER2 mAb light chain (SEQ ID NO: 9) were produced by gene synthesis, and sub-cloned separately into the EcoRI-BamHI sites in the pTT5 mammalian expression vectors. The sequences of the anti-HER2 mAb heavy (SEQ ID NO: 8) and light chains (SEQ ID NO: 9) in separate pTT5 plasmids were confirmed by sequencing analysis of the entire open reading frames.

Expression of anti-HER2 mAb (SEQ ID NOs: 3 and 4) was done by transient transfection co-delivering both the heavy and light chains (SEQ ID NOs: 8 and 9) in pTT5 plasmids (mixed in an optimized ratio) into the CHO-BRI-rc-TA-55E1 cells. Following DNA transfection, cells were induced with cumate for 16 days to select a stable pool of highly protein expressing cells. Following the selection, these cells were isolated for protein expression in a fed-batch method (i.e., fresh media continuously added during cell growth) over the 11 day period. At the end of cell growth, the culture media was harvested, and the secreted anti-HER2 mAb was purified from the clear supernatant of the culture media by Protein A binding chromatography to produce anti-HER2 mAb, in phosphate buffered saline (PBS), having a purity of >99%. The functional assembly of the anti-HER2 mAb was verified using gel filtration and SDS-PAGE.

Anti-HER2 mAb-LL37 production: A 4.6 kDa LL37 peptide (GG-LL37) was synthesized with two additional N-terminal Gly residues (SEQ ID NO: 2). GG-LL37 was dissolved at 10.6 mg/ml (i.e., 2.3 mM) in PBS at room temperature, sterile-filtered, and stored at −20° C. The GG-LL37 peptide was linked to a sortase (SrtA) recognition sequence (namely, LPMTGGHG; SEQ ID NO: 22) added to the C-terminus of the light chain of an anti-HER2 mAb (encoded by SEQ ID NO: 9). The heavy chain of the anti-HER2 mAb is encoded by SEQ ID NO: 8. The reaction contained 400 μM of GG-LL37 peptide, 40 μM equivalent of sortase recognition sequence in the form of 20 μM of Anti-HER2 mAb, 1 μM sortase, 1 mM TCEP, and 5 mM CaCl₂, in a buffered solution (20 mM Tris-HCl, pH 7.5, 150 mM NaCl). The reaction was incubated inside a 37° C. incubator for 16 hours, and then EDTA (pH 7.5) was added to 10 mM in the reaction mixture to chelate calcium and stop the reaction. A sample aliquot of reaction mixture was analyzed on SDS-PAGE to verify the LL37-linked anti-HER2 mAb (i.e., an up-shift of the light chain molecular weight from ~25 kD to ~30 kD), and greater than 95% of antibody light chain carries the covalently linked LL37. The LL37-linked anti-HER2 mAb was then purified by Protein A affinity chromatography, and buffer-exchanged to phosphate buffer saline. The purity of LL37-linked anti-HER2 mAb was greater than 95% as verified on SDS-PAGE. Following the sortase reaction, the light chain of the anti-HER2 mAb is covalently linked to LL37 through a 11-amino acid peptide linker corresponding to residues 234 to 244 of SEQ ID NO:4 (residues 243-246 of SEQ ID NO:4 are cleaved and replaced with the N-terminal diglycine of GG-LL37).

Delivery assay: 100 nM of anti-HER2 mAb (or the LL37-linked anti-HER2 mAb, also represented as anti-HER2 mAb-LL37) and 100 nM of Z-RFP was added to OVCAR3 cells sub-cultured to 80% confluency level in 48-well plate, and incubated at 37° C. incubator for 4 hours. The plate was then removed from the incubator, and the culturing media was removed from the adherent OVCAR3. First, the adherent OVCAR3 was washed gently with an equal volume of ice-cold PBS. Second, the PBS wash was replaced with an equal volume of a pre-chilled acidic buffer (200 mM glycine, pH 2.5, 500 mM NaCl), and the plate was incubated on ice for 5-10 minutes. Lastly, the acidic wash was removed by aspiration, and the adherent OVCAR3 was gently washed with equal volume of ice-cold PBS. For FACS analysis, the adherent OVCAR3 was treated with trypsin at 37° C. for 1-2 minutes, neutralized in FACS buffer (2% v/v FBS, 2 mM EDTA, 0.05% w/v sodium azide in PBS), and transferred to FACS tubes on ice. The FACS samples were stored on ice until flow cytometry analysis on a LSRII-561 machine. The delivery of anti-HER2 mAb was quantitated by measuring the red fluorescence intensity (i.e., PE-Texas Red color channel in the FACS detector) emitted from Z-RFP bound to anti-HER2 mAb.

Experimental Procedures for Examples in FIG. 4

Z-RFP, anti-HER2 mAb, and the LL37-linked antibody were produced using the same procedure as described above.

MMAE conjugation to mAb. The MMAE-linked antibodies were produced by reacting the Maleimidocaproyl-valine-citrulline-p-aminobenzoyloxycarbonyl-monomethyl auristatin (also known as Vc-MMAE, CAS no. 646502-53-6, M.W. 1316.6 g/mol) dissolved in DMSO to the TCEP-reduced antibodies. Briefly, following the conjugation method described in Doronina et al. (2003) Nat. Biotechnol., 21, 778., 8 molecules of Vc-MMAE were chemically linked to the 8 SH groups generated from the TCEP reduction, and produced the conjugates with 8 MMAE per anti-HER2 mAb. The MMAE-linked antibodies were purified through Sephadex G25 size exclusion chromatography (PD10 column) in PBS buffer.

DM1 conjugation to mAb. The DM1-linked antibodies were produced by reacting the SMCC-DM1 (CAS no. 1228105-51-8, M.W. 1072.6 g/mol) dissolved in DMSO to the antibodies. Briefly, using a molar ratio of 6 SMCC-DM1 per mAb in the reaction, we chemically linked and produced the conjugates with about 3-4 DM1 per anti-HER2 mAb. The DM1-linked antibodies were purified through Sephadex G25 size exclusion chromatography (PD10 column) in PBS buffer.

Delivery assay. 100 nM of anti-HER2 mAb (or the LL37-linked antibody, or the LL37-linked anti-HER2 mAb-MMAE or anti-HER2 mAb-DM1 conjugates) and 100 nM of Z-RFP was added to the RT4V6 cells grown to 80% confluency level in 48-well plate, and incubated at 37° C. incubator for 4 hours. The plate was then removed from the incubator, and the culturing media was removed from the adherent RT4V6. First, the adherent RT4V6 was washed gently with an equal volume of PBS. For FACS analysis, the adherent RT4V6 was treated with trypsin at 37 degree C. for 3-5 minutes, neutralized in FACS buffer (2% v/v FBS, 2 mM EDTA, 0.05% w/v sodium azide in PBS), and transferred to FACS tubes on ice. The sample FACS tubes were stored on ice until flow cytometry analysis on a LSRII-561 machine. The delivery of anti-HER2 mAb was quantitated by measuring the red fluorescence intensity (i.e., PE-Texas Red color channel in the FACS detector) emitted from Z-RFP bound to anti-HER2 mAb.

Experimental Procedures for Examples in FIGS. 5 and 6

Z-RFP, anti-HER2 mAb, and the LL37-linked antibody were produced using the same procedure as described above.

Delivery assay. 100 nM of anti-HER2 mAb (or the LL37-linked anti-HER2 mAb, also represented as anti-HER2 mAb-LL37) and 100 nM of Z-RFP was added to the cells grown to about 80% confluence level [i.e., OVCAR3 cells (HER2+), U87MG cells (low HER2+), Neuro2A cells (HER2−) grown to approximately 0.1 million cells/ml] in 48-well plates, and incubated at 37° C. incubator for 4 hours. The plate was then removed from the incubator, and the culturing media was removed from the adherent cells. First, the adherent cells were washed gently with an equal volume of ice-cold PBS. Second, the PBS wash was replaced with an equal volume of a pre-chilled acidic buffer (200 mM glycine, pH 2.5, 500 mM NaCl), and the plate was incubated on ice for 5-10 minutes. Lastly, the acidic wash was removed by aspiration, and the adherent cells were gently washed with equal volume of ice-cold PBS. For FACS analysis, the adherent cells were treated with trypsin at 37° C. for 5-10 minutes until cells dissociated from plate, neutralized in FACS buffer (2% v/v FBS, 2 mM EDTA, 0.05% w/v sodium azide in PBS), and transferred to FACS tubes on ice. The FACS samples were stored on ice until flow cytometry analysis on a LSRII-561 machine. The delivery of anti-HER2 mAb was quantitated by measuring the red fluorescence intensity (i.e., PE-Texas Red color channel in the FACS detector) emitted from Z-RFP bound to anti-HER2 mAb.

Experimental Procedures for Examples in FIG. 7

Anti-HER2 mAb-LL37 (i.e., HC, LC-LL37) was produced by following the same method as described (above)

Recombinant fusion anti-HER2 mAb (HC-LL37, LC) cloning, expression and purification: The coding sequences of LL37 is joined in frame to the C-terminus (3' end) of the anti-HER2 mAb heavy chain sequence (SEQ ID No: 31). For expression, CHO cell is co-transfected with the pTT5 plasmids that encode the anti-HER2 mAb heavy chain-LL37 fusion structural gene (SEQ ID No: 32) and another pTT5 plasmid that encodes anti-HER2 mAb light chain (SEQ ID No: 9). The protein (SEQ ID No: 31 and 4) was purified on Protein A affinity chromatography.

Recombinant fusion anti-HER2 mAb (HC, LC-LL37) cloning, expression and purification: The coding sequences of LL37 is joined in frame to the C-terminus (3' end) of the anti-HER2 mAb light chain sequence (SEQ ID No: 33). For expression, CHO cell is co-transfected with the pTT5 plasmids that encode the anti-HER2 mAb heavy chain (SEQ ID No: 8) and the light chain-LL37 fusion (SEQ ID No: 34). The protein (SEQ ID No: 3 and 33) was purified on Protein A affinity chromatography.

Delivery assay was carried out by co-incubating OVCAR3 cells with 100 nM antibody mAb and 100 nM Z-RFP for 4 hours at 37 degree C. The culturing media was removed from the adherent cells, and washed twice with equal volume of ice-cold PBS. For FACS analysis, the adherent cells were treated with trypsin at 37° C. for about 5 minutes until cells dissociated from plate, neutralized in FACS buffer (2% v/v FBS, 2 mM EDTA, 0.05% w/v sodium azide in PBS), and transferred to FACS tubes on ice. The FACS samples were stored on ice until flow cytometry analysis on a LSRII-561 machine. The delivery of anti-HER2 mAb was quantitated by measuring the red fluorescence intensity (i.e., PE-Texas Red color channel in the FACS detector) emitted from Z-RFP bound to anti-HER2 mAb.

Figure 8:
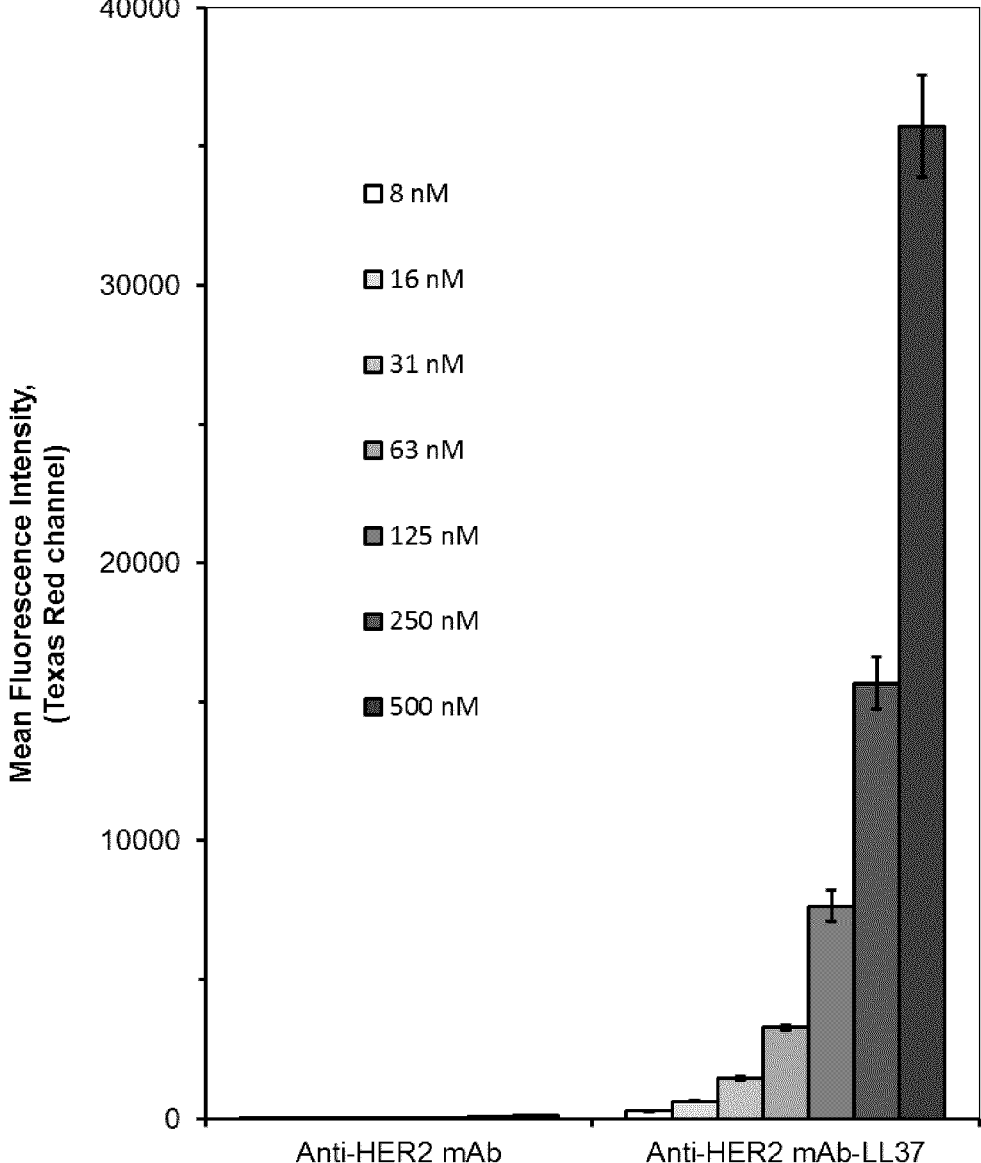
FIG. 8 shows a graph comparing fluorescence of OVCAR3 (HER2+ human cancer cell line) treated with various concentrations of Z-RFP-bound anti-HER2 mAb, or Z-RFP-bound anti-HER2 mAb conjugated with LL37.

Example 2. An Antibody-LL37 Covalent Conjugate Increases Delivery Beyond the Saturation Limit of the Cell Surface Target FIG. 8 compares the delivery of anti-HER2 mAb versus anti-HER2 mAb-LL37 to OVCAR3 cells (a medium-to-high HER2+ cell) at increasing antibody concentrations, visualized using Z-RFP fluorescence as described above. Anti-HER2 mAb readily saturates its cognate receptors on the target cell; i.e. adding more antibody does not increase the delivery efficiency (see plateau near the baseline). In contrast, delivery for the LL37-linked anti-HER2 mAb to OVCAR3 cells continued to increase as antibody concentration increased. For the highest antibody concentration tested (500 nM), LL37 conjugation nearly amplifies the total antibody delivery to the target cells by 350-fold. This result therefore shows that conjugation with LL37 enhances delivery of anti-HER2 mAb to HER2+ cells far beyond the saturation limit without LL37.

Figure 9:
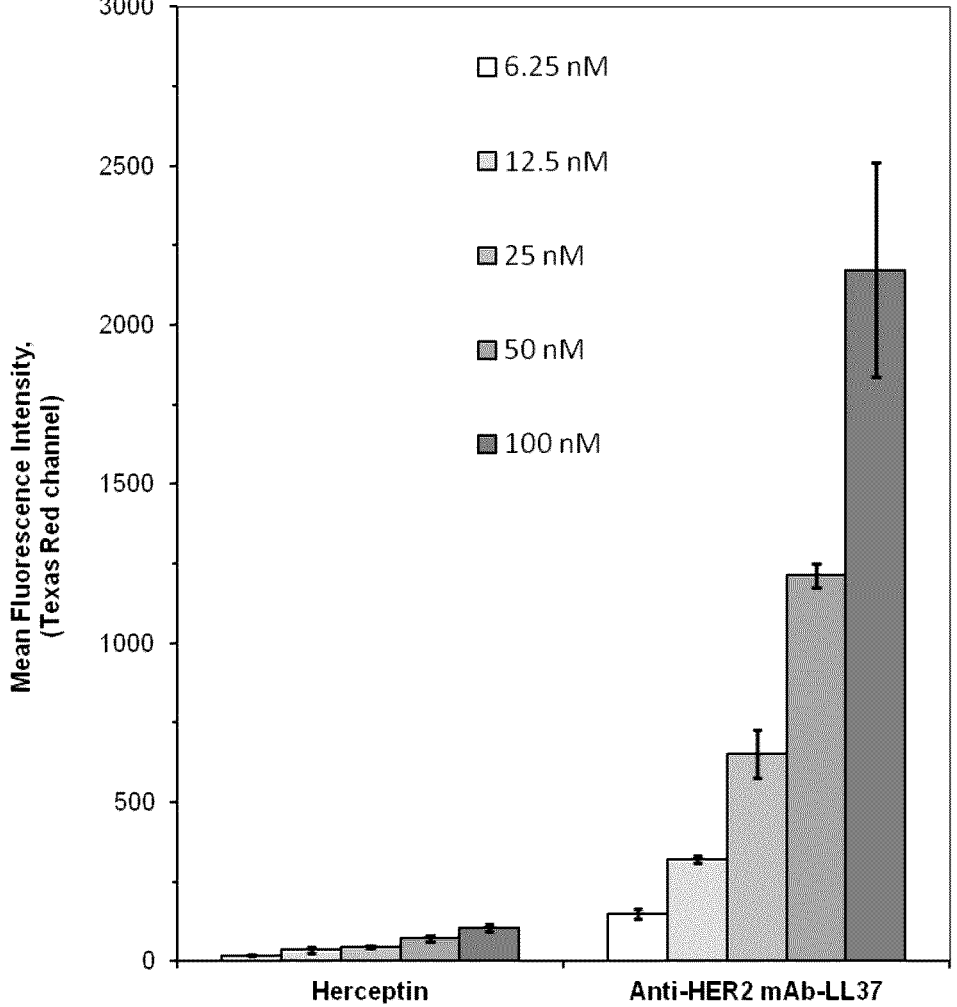
FIG. 9 shows a graph comparing fluorescence of BT474 (HER2+ human cancer cell line) treated with various concentrations of Z-RFP-bound anti-HER2 mAb, or Z-RFP-bound anti-HER2 mAb conjugated with LL37.

Similarly, FIG. 9 shows that LL37 also greatly amplifies the delivery of anti-HER2 mAb to BT474 cells (a high HER2 expressing cell) at increasing antibody concentrations.

Experimental Procedures for Examples in FIG. 8

Z-RFP, anti-HER2 mAb, and the LL37-linked antibody were produced using the same procedure as described above.

Delivery assay. anti-HER2 mAb (or the LL37-linked anti-HER2 mAb, also represented as anti-HER2 mAb-LL37) and equivalent molar amount of Z-RFP were added to OVCAR3 cells sub-cultured to 80% confluency level at indicated final concentrations (i.e., 500 nM, 250 nM, 125 nM, 62.5 nM, 31.25 nM, 15.625 nM, and 7.8125 nM) in 48-well plate, and incubated at 37 degree C. incubator for 3 hours. The plate was then removed from the incubator, and the culturing media was removed from the adherent OVCAR3. First, the adherent OVCAR3 were washed gently with an equal volume of PBS. For FACS analysis, the adherent OVCAR3 were treated with trypsin at 37 degree C. for 3-5 minutes, neutralized in FACS buffer (2% v/v FBS, 2 mM EDTA, 0.05% w/v sodium azide in PBS), and transferred to FACS tubes on ice. The sample FACS tubes were stored on ice until flow cytometry analysis on the LSRII-561 machine at UBC Life Sciences Center. The delivery of anti-HER2 mAb was quantitated by measuring the red fluorescence intensity (i.e., PE-Texas Red color channel in the FACS detector) emitted from Z-RFP bound to anti-HER2 mAb.

Experimental Procedures for Examples in FIG. 9

Z-RFP, anti-HER2 mAb, and the LL37-linked antibody were produced using the same procedure as described above. Delivery assay with BT474 cells was also carried out using the same procedure as described above.

Example 3. LL37 Enhances Antibody Drug Conjugate (ADC) Payload and Effectiveness Cytotoxic agents/drugs can be used to destroy cancer cells, e.g. by inhibiting cell division. While cytotoxic drugs affect all dividing cells, attachment to a cancer-specific antibody ensures targeted killing of cancer cells and elimination of cancer tumors.

Figure 10:
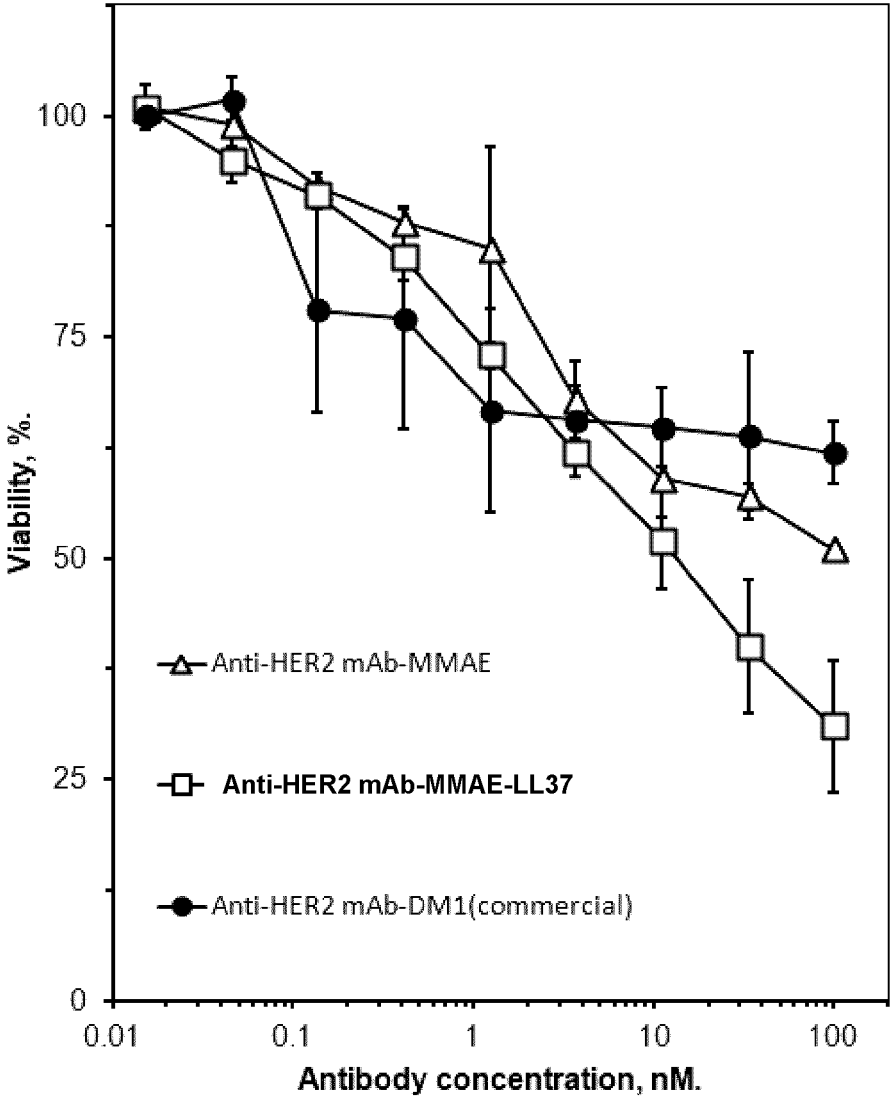
FIG. 10 shows a graph comparing the viability of OVCAR3 (HER2+ human cancer cell line) after 24 hrs treatment with anti-HER2 ADC (MMAE), anti-HER2 ADC (DM1), or anti-HER2 ADC (MMAE) conjugated with LL37.
Figure 11:
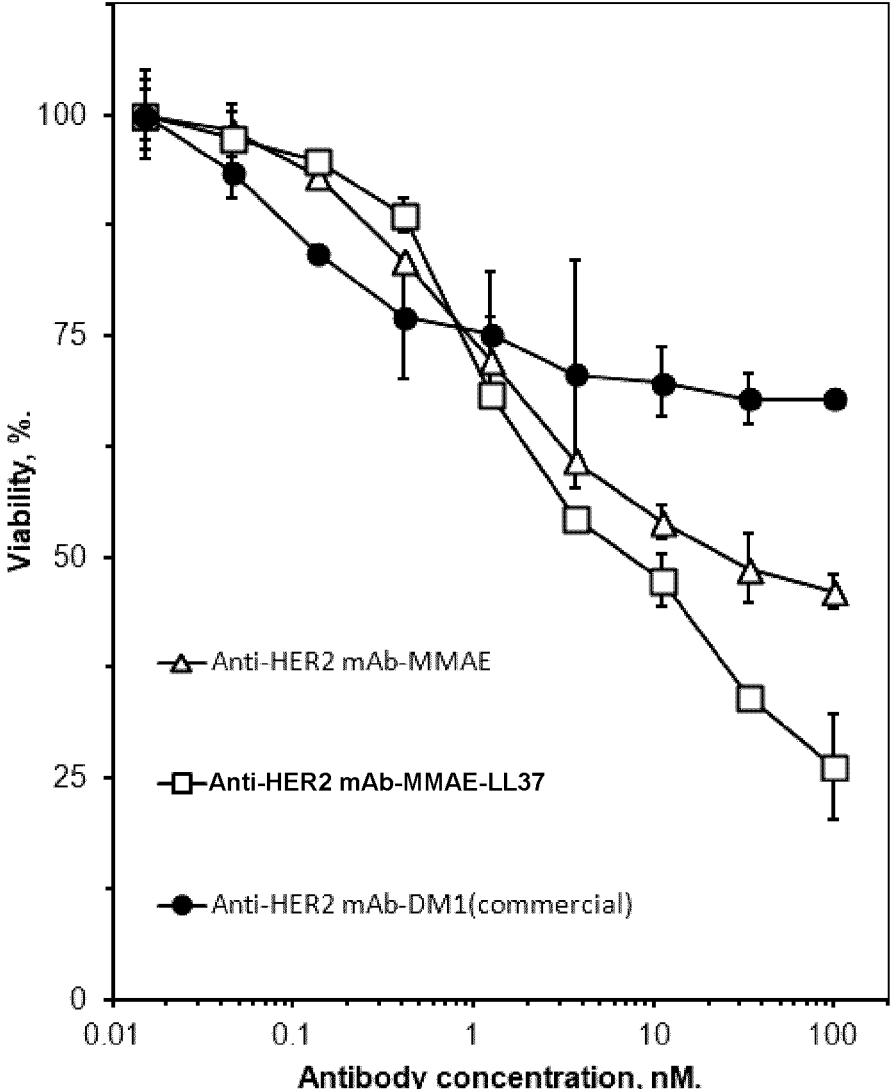
FIG. 11 shows a graph comparing the viability of OVCAR3 (HER2+ human cancer cell line) after 72 hrs treatment with anti-HER2 ADC (MMAE), anti-HER2 ADC (DM1), or anti-HER2 ADC (MMAE) conjugated with LL37.
Figure 12:
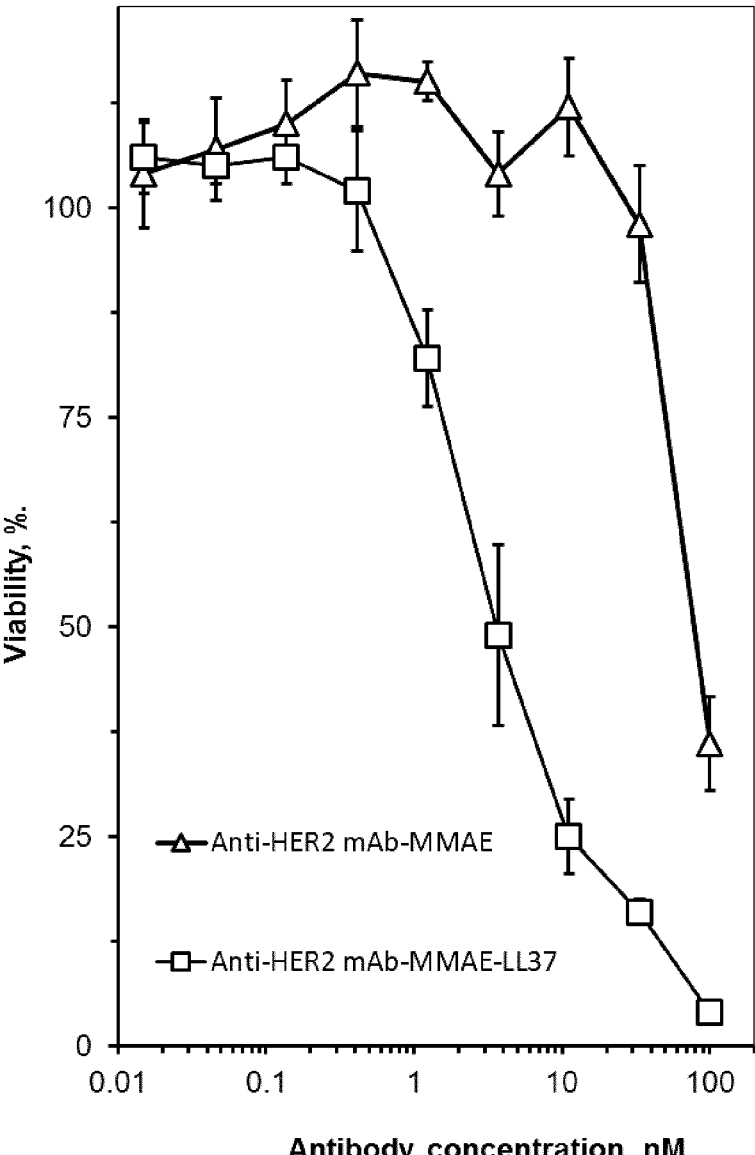
FIG. 12 shows a graph comparing the viability of RT4V6 cells (HER2+ human bladder cancer cell line) after 72 hrs treatment with anti-HER2 ADC (MMAE), or anti-HER2 ADC (MMAE) conjugated with LL37.
Figure 13:
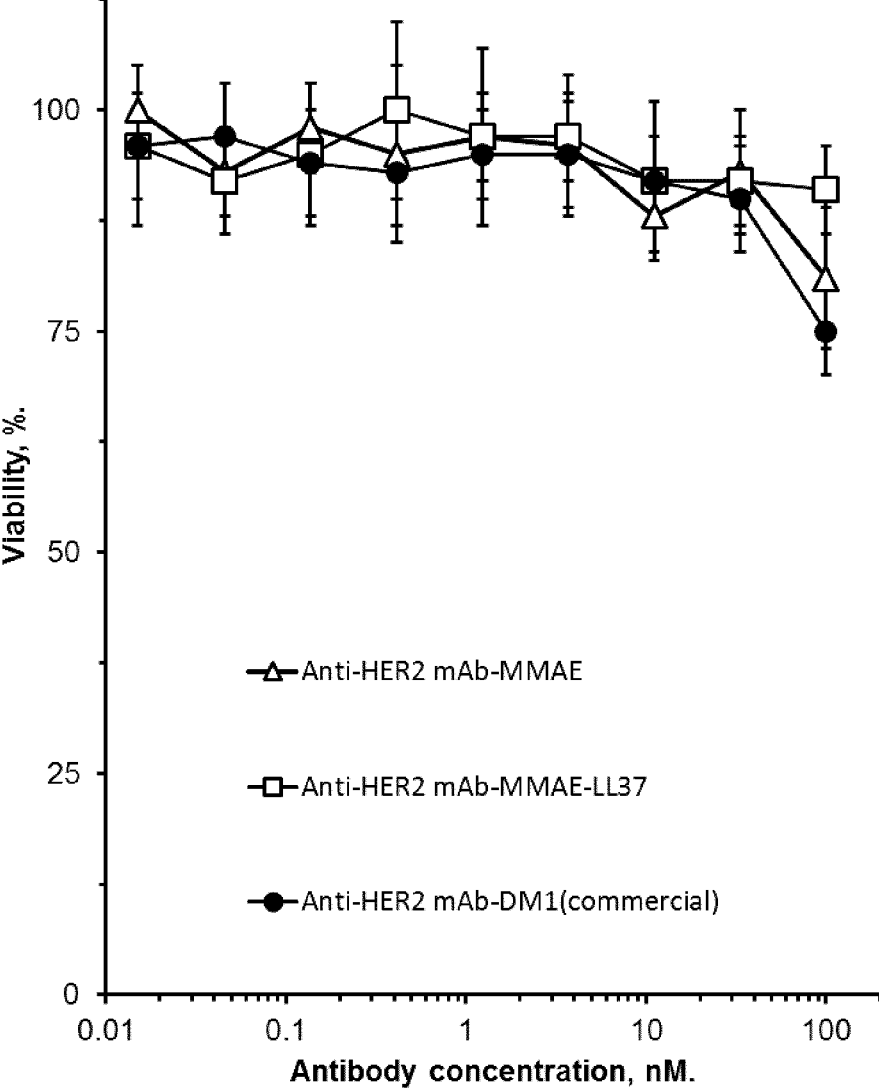
FIG. 13 shows a graph comparing the viability of Neuro2A (HER2– mouse brain cell line) after 72 hrs treatment with anti-HER2 ADC (MMAE), anti-HER2 ADC (DM1), or anti-HER2 ADC (MMAE) conjugated with LL37.

FIGS. 10 and 11 show that LL37-conjugated anti-HER2 ADC (MMAE) is more effective at killing the OVCAR3 (a medium-to-high HER2+ cell) than conventional antibody-drug conjugates in both 24 and 72 hours treatments, respectively. FIG. 12 shows that conjugation with LL37 enhances antibody killing of RT4V6 (a human bladder carcinoma cell line with low-to-medium level of HER2 on the cell surface) from an effective killing dose (ED50) of 70 nM with anti-HER2 ADC (MMAE) to 4 nM with anti-HER2 ADC (MMAE) conjugated with LL37. FIG. 13 shows that LL37-conjugated anti-HER2 ADC (MMAE) exhibits comparable level of background cytotoxicity as native anti-HER2 ADC (MMAE) when used to treat Neuro2A (a HER2– mouse neuroblastoma cell line).

Figure 14:
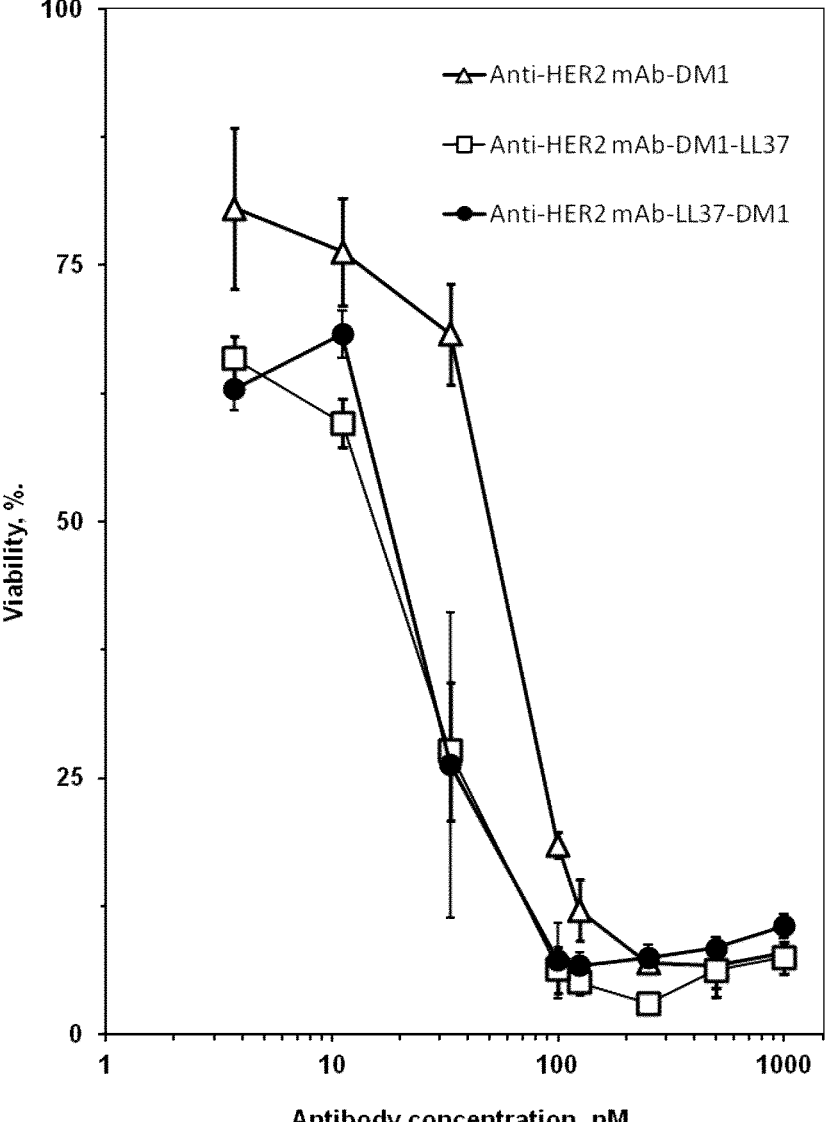
FIG. 14 shows a graph comparing the viability of RT4V6 cells (a low to medium HER2+ cell line) after 72 hrs treatment with anti-HER2 ADC (DM1), without LL37, or with anti-HER2 ADC (DM1) linked to LL37 in either of two configurations (i.e. anti-HER2 mAb-DM1-LL37 or anti-HER2 mAb-LL37-DM1).

FIG. 14 shows that conjugation with LL37 enhances killing of RT4V6 (a human bladder carcinoma cell line with low-to-medium level of HER2 on the cell surface) with anti-HER2 ADC (DM1), as seen by the lower viability at increasing concentrations of LL37-linked ADCs (i.e., anti-HER2 mAb-DM1-LL37, or anti-HER2 mAb-LL37-DM1) compared to anti-HER2 mAb-DM1 (no LL37). Cell viability was measured using the XTT assay after treating/incubating the cells with antibody drug conjugate for 72 hours in a 37 degree C. tissue culture incubator.

Figure 15:
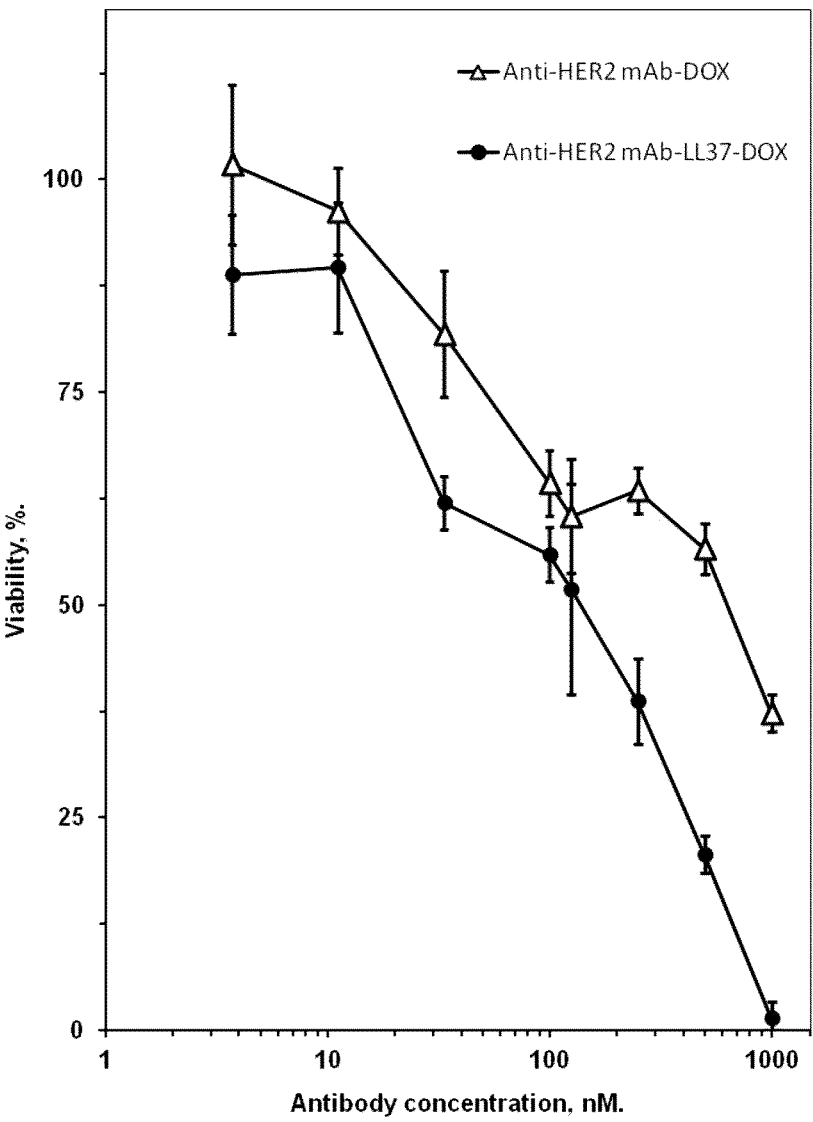
FIG. 15 shows a graph comparing the viability of RT4V6 cells (a low to medium HER2+ cell line) after 72 hrs treatment with anti-HER2 ADC (Doxorubicin) (i.e. anti-HER2 mAb-DOX), without LL37, or with anti-HER2 ADC (Doxorubicin) linked to LL37 (i.e. anti-HER2 mAb-LL37-DOX).

FIG. 15 shows that conjugation with LL37 enhances killing of RT4V6 (a human bladder carcinoma cell line with low-to-medium level of HER2 on the cell surface) with anti-HER2 ADC (Doxorubicin), as seen by the lower viability at increasing concentration of anti-HER2 mAb-DOX (no LL37) compared to LL37-linked ADC (doxorubicin) (i.e. anti-HER2 mAb-LL37-DOX). Cell viability was measured using the XTT assay after treating/incubating the cells with antibody-drug conjugate for 72 hours in a 37 degree C. tissue culture incubator.

Figure 16:
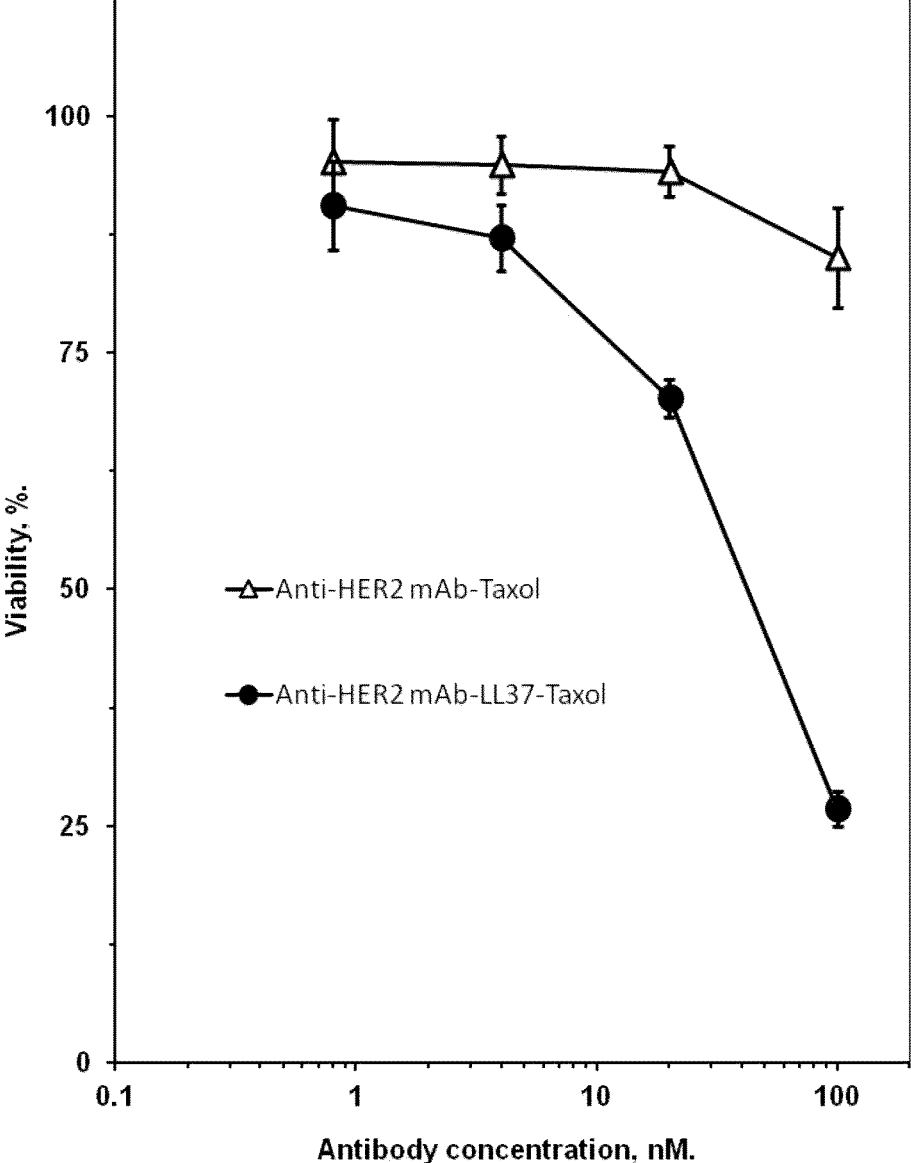
FIG. 16 shows a graph comparing the viability of OVCAR3 cells (a medium to high HER2+ cell line) after 3 hrs treatment with anti-HER2 ADC (Taxol) (i.e. anti-HER2 mAb-Taxol), without LL37, or with anti-HER2 ADC (Taxol) linked to LL37 (i.e. anti-HER2 mAb-LL37-Taxol).
Figure 17:
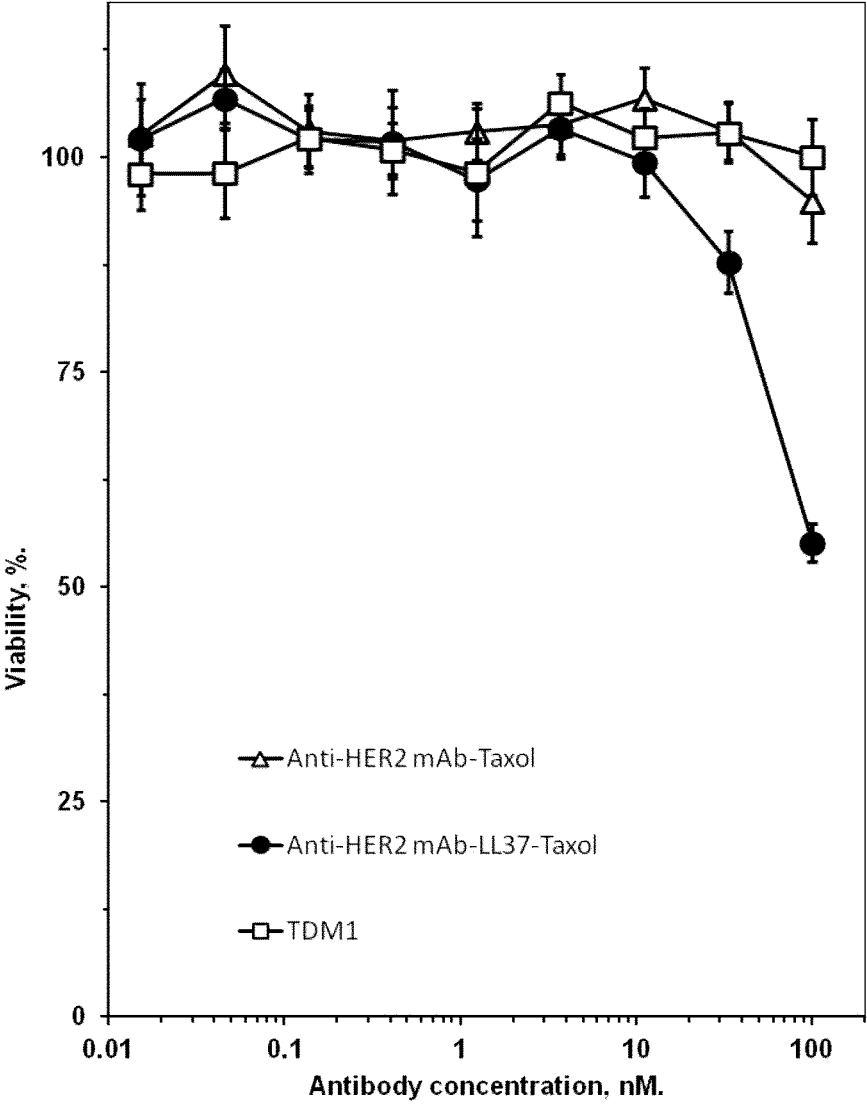
FIG. 17 shows a graph comparing the viability of T47D cells (a low HER2+ cell line) after 3 hrs treatment with anti-HER2 ADC (Taxol) (i.e. anti-HER2 mAb-Taxol), without LL37, or with anti-HER2 ADC (Taxol) linked to LL37 (i.e. anti-HER2 mAb-LL37-Taxol). The graph also shows cell viability after treatment with anti-HER2 ADC (DM1).

FIGS. 16 and 17 show that conjugation with LL37 enhances the killing of OVCAR3 (human ovary epithelial adenocarcinoma cell line with medium-to-high level of cell surface HER2), RT4V6 (human bladder carcinoma cell line with low-to-medium level of cell surface HER2), and T47D (human breast cancer cell line with low level of cell surface HER2) cells, respectively, with anti-HER2 ADC (Taxol), as shown by the lower cell viability at increasing concentration of anti-HER2 mAb-LL37-Taxol compared to anti-HER2 mAb-Taxol (no LL37). Killing efficiency of the anti-HER2 ADCs was analyzed by measuring the cell viability (i.e. XTT assay) after separately treating/incubating the cells with the ADCs for 3 hours in a 37 degree C. tissue culture incubator.

Figure 18:
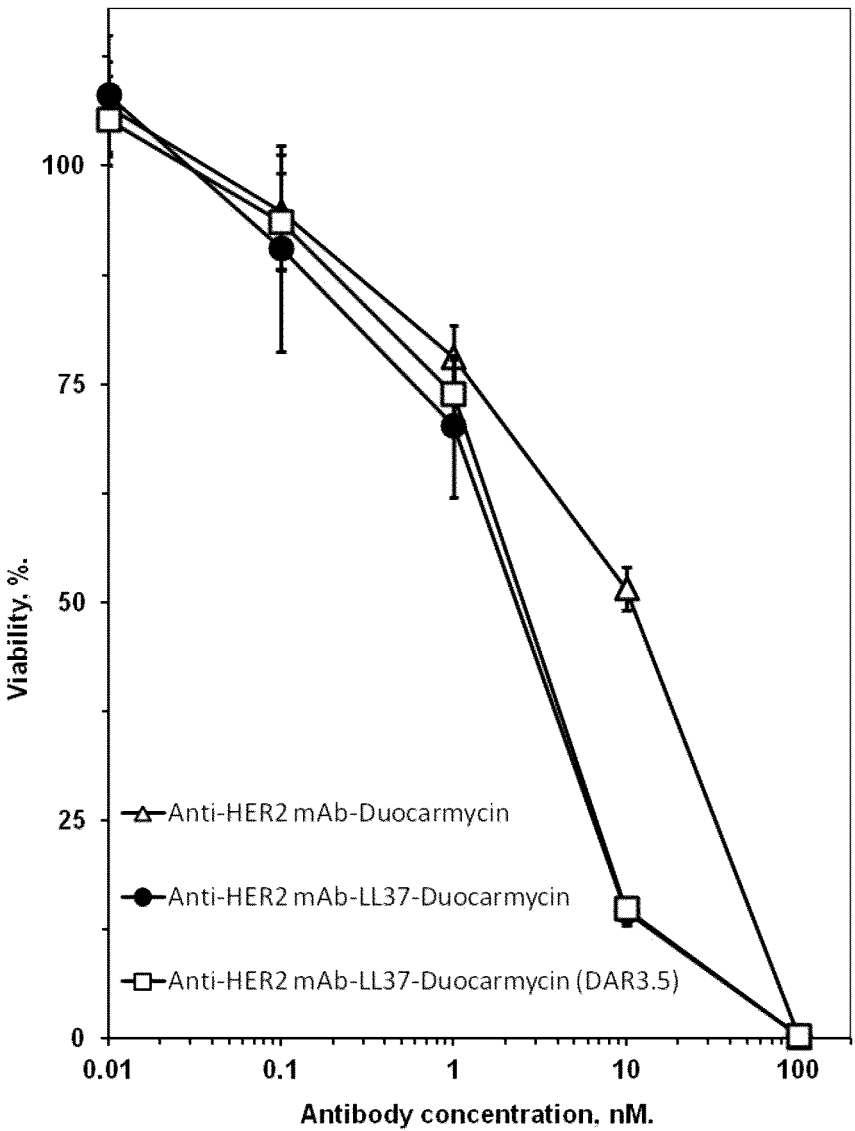
FIG. 18 shows a graph comparing the viability of RT4V6 cells (a low to medium HER2+ cell line) after 72 hrs treatment with anti-HER2 ADC (Duocarmycin) (i.e. anti-HER2 mAb-Duocarmycin), without LL37, or with anti-HER2 ADC (Duocarmycin) linked to LL37 (i.e. anti-HER2 mAb-LL37-Duocarmycin). Drug to Antibody Ratio (DAR) of duocarmycin is shown in parentheses for one of the LL37-conjugated ADCs.

FIG. 18 shows that conjugation with LL37 enhances the killing of RT4V6 (human bladder carcinoma cell line with low-to-medium level of cell surface HER2) with anti-HER2 ADC (Duocarmycin), as shown by the lower cell viability at increasing concentration of anti-HER2 mAb-LL37-Duocarmycin compared to anti-HER2 mAb-Doxorubicin. Cell viability was measured using the XTT assay after treating/incubating the cells with antibody-drug conjugate for 72 hours in a 37 degree C. tissue culture incubator.

In the examples shown so far, the cytotoxic agents have been conjugated covalently (and post-translationally) to the reduced cysteine thiol groups generated from the interchain-disulfide bonds of the antibody heavy and light chains. Another option is to use LL37 itself as an anchor for loading cytotoxic agents. Without disrupting the disulfide bonds in the native antibody structure, MMAE can be linked to the C-terminus of LL37-Cys peptide (SEQ ID No: 35), which has an extra cysteine residue added to the C-terminus of LL37 sequence from peptide synthesis. By maintaining the native arrangements of disulfide bonds in the antibody structure, each of the LL37-Cys conjugated antibodies has 2 free cysteine thiols available for conjugation to MMAE. Depending on the reaction order, anti-HER2 mAb-LL37 (Cys-MMAE) is produced by first ligating anti-HER2 mAb to the LL37(Cys) peptide, and followed by chemical conjugation to VcMMAE. Alternatively, LL37(Cys) peptide is first conjugated to VcMMAE to form LL37(Cys-MMAE), and then LL37(Cys-MMAE) is ligated to anti-HER2 mAb to produce anti-HER2 mAb-[LL37(Cys-MMAE)]. In both anti-HER2 mAb-LL37(Cys-MMAE) and anti-HER2 mAb-[LL37(Cys-MMAE)] the interchain disulfide bonds between heavy and light chains remain intact.

Figure 19:
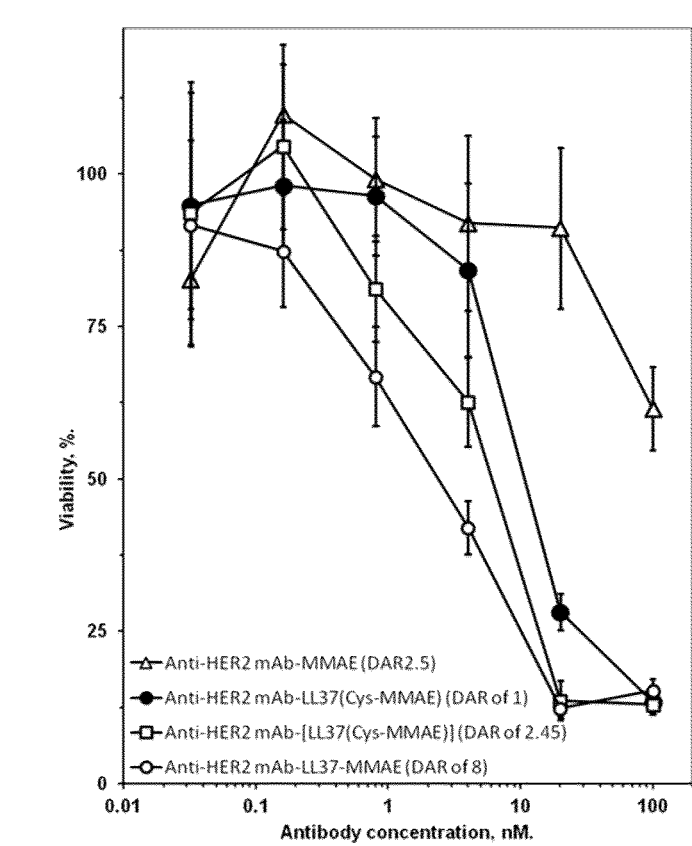
FIG. 19 shows two graphs comparing the viability of RT4V6 cells (a low to medium HER2+ cell line; Panel A) or OVCAR3 cells (a medium to high HER2+ cell line; Panel B) after 72 hours treatment with anti-HER2 ADC (MMAE) (i.e. anti-HER2 mAb-MMAE), without LL37, or with anti-HER2 mAb-LL37-MMAE (i.e. MMAE is linked to the reduced cysteines in the antibody heavy and light chains), or with anti-HER2 mAb-LL37(Cys-MMAE) or anti-HER2 mAb-[LL37(Cys-MMAE)](i.e. MMAE is linked to the LL37(Cys) in the C-terminus of light chain). Drug to Antibody Ratio (DAR) of MMAE is shown in parentheses.
Figure 19:
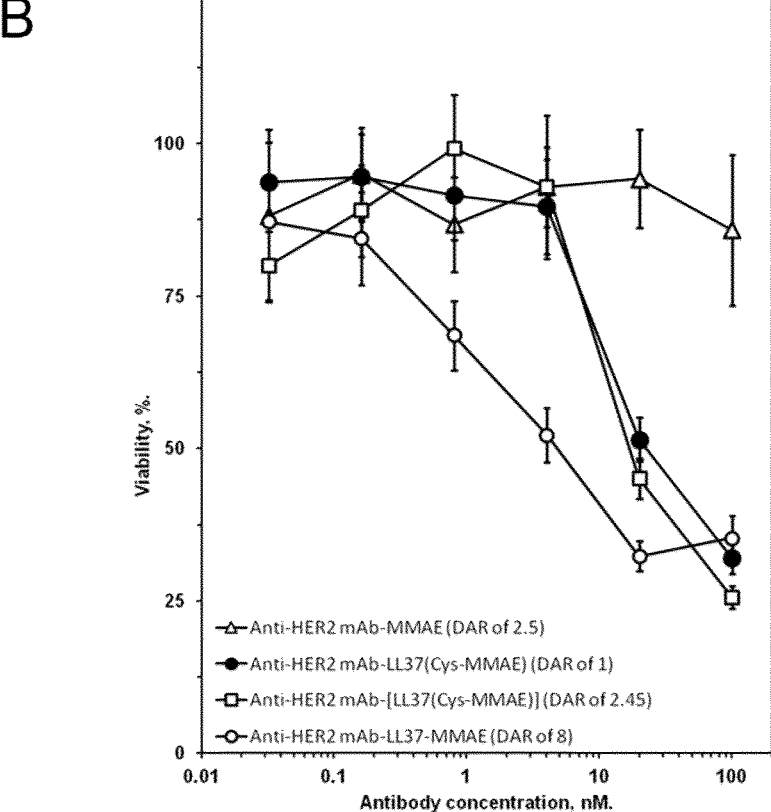

FIG. 19 shows that MMAE covalently linked to an LL37(Cys) moiety in the conjugates (i.e., anti-HER2 mAb-LL37(Cys-MMAE) and anti-HER2 mAb-[LL37(Cys-MMAE)]) have comparable cell killing efficacy to the MMAE that is linked to the heavy and light chain cysteines in the LL37-enhanced ADC (i.e, Anti-HER2 mAb-LL37-MMAE). This indicates that LL37 enhances the delivery of antibody, and can also serve as an anchor for carrying an additional payload. More specifically, FIG. 19 compares viability of two different cell types when treated with anti-HER2 ADC (MMAE) without LL37 or anti-HER2 ADC (MMAE) with different configurations of LL37 and MMAE. The target cell in Panel A is RT4V6 (human bladder carcinoma cell line with low-to-medium level of cell surface HER2), and the target cell in Panel B is OVCAR3 (human ovary epithelial adenocarcinoma cell line with medium-to-high level of cell surface HER2). As already shown in many of the examples above, anti-HER2 mAb-LL37-MMAE, is very effective at killing the HER2-expressing cancer cells, and the MMAEs are covalently conjugated to the thiol side chains of cysteine residues in the antibody heavy and light chains. The anti-HER2 mAb-[LL37(Cys-MMAE)] and anti-HER2 mAb-LL37(Cys-MMAE), which have MMAE linked to the LL37(Cys) in the C-terminus of light chain, produce comparable drug efficacies as anti-HER2 mAb-LL37-MMAE, which have MMAE linked to the reduced cysteines in the antibody heavy and light chains. The killing efficiency of the anti-HER2 mAb drug conjugates were analyzed by measuring the cell viability (i.e. XTT assay) after treating/incubating the cells with antibody-drug conjugate for 72 hours in a 37 degree C. tissue culture incubator.

Figure 20:
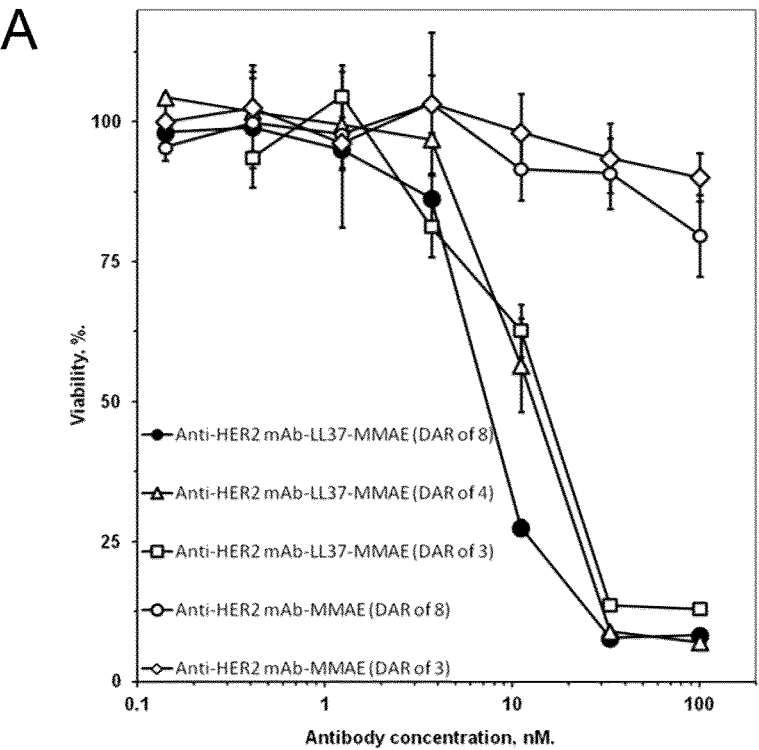
FIG. 20 shows two graphs comparing the viability of AGS cells (human stomach gastric adenocarcinoma cell line with low HER2+; Panel A) or RT4V6 cells (human bladder carcinoma cell line with low-to-medium HER2+; Panel B) after treatment (3 hours of treatment incubation for AGS cells in Panel A, and 3.5 hours of treatment incubation for RT4V6 cells in Panel B) with LL37-conjugated ADC (MMAE) and the same ADC without LL37, and with different Drug-to-Antibody Ratios (DARs).
Figure 20:
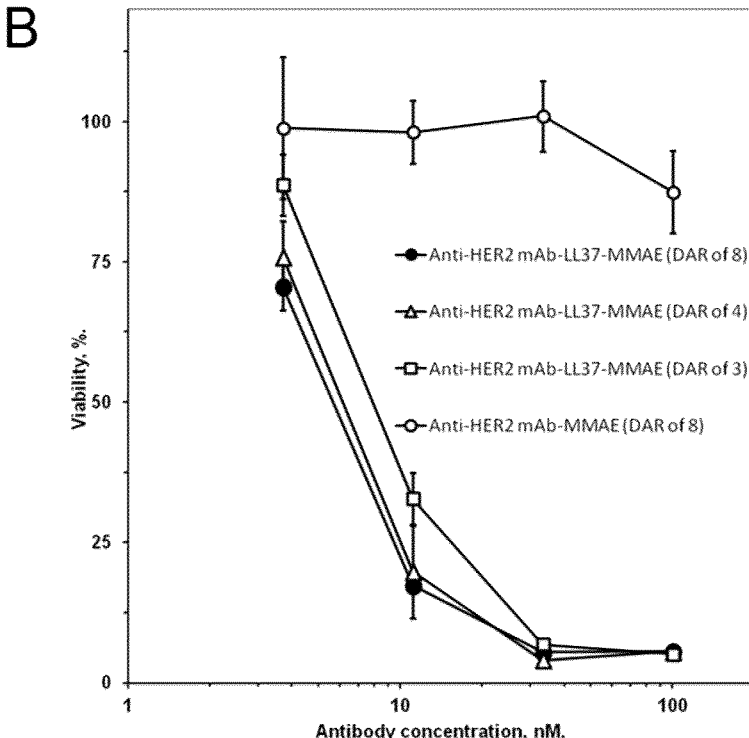

FIG. 20 shows that the Drug-to-Antibody Ratio (DAR) does not significantly affect the ADC delivery or ADC killing efficiency. FIG. 20 show that anti-HER2 mAb-MMAE (without LL37) having 3 covalently linked MMAE resulted in a comparable lack of reduction of cell viability as with an anti-HER2 mAb-MMAE (without LL37) having 8 covalently linked MMAEs. FIG. 20 also shows that anti-HER2 mAb-LL37-MMAE constructs with 3, 4, or 8 covalently linked MMAEs are all effective at killing cells, and are effective at comparable levels to each other (irrespective of DAR). The target cell in Panel A of FIG. 20 is AGS (human stomach gastric adenocarcinoma cell line expressing a low level of cell surface HER2), and the target cell in Panel B is RT4V6 (human bladder carcinoma cell line with low-to-medium level of cell surface HER2). In either panel, cell viability (i.e. XTT assay) was measured after treating/incubating the cells with antibody drug conjugate for 3 hrs in the 37 degree C. tissue culture incubator. The DAR of the ADCs in FIGS. 18 and 19 is also shown.

Referring to Panel A of FIG. 20, it is seen that without LL37 the two anti-HER2 mAb-MMAEs (i.e., one with a DAR of 8 and another with a DAR of 3) recognize the target AGS cells, but they are both ineffective at delivering the MMAE to the AGS cells (i.e., cells are still viable at high drug doses) regardless of the number of MMAE payloads they carry. In contrast, the three anti-HER2 mAb-LL37-MMAEs (i.e., DAR of 3, 4, and 8) are comparably effective at killing AGS cells regardless of the number of MMAE molecules they carry.

Referring to Panel B of FIG. 20, it is seen that without LL37 the anti-HER2 mAb-MMAEs (with a DAR of 8) recognizes the target RT4V6 cells, but is ineffective at delivering the MMAE to the RT4V6 cells (i.e., cells are still viable at high drug doses) regardless of the high number of MMAE payloads carried. In contrast, the three anti-HER2 mAb-LL37-MMAEs (i.e., DAR of 3, 4, and 8) are comparably effective at killing RT4V6 cells regardless of the number of MMAE molecules they carry.

While the foregoing has demonstrated that LL37 are effective at enhancing antibody delivery and targeted killing efficiency with anti-HER2 antibodies and ADCs, LL37 and its derivatives are also useful for enhanced delivery and targeted killing efficiency when conjugated to any antibody or ADC independent of its antigen-specificity. Indeed, LL37 conjugation is shown herein to enhance delivery for each of the following antibodies: anti-HER2 mAb (trastuzumab), anti-folate receptor mAb (mirvetuximab), anti-EGFR mAb (panitumumab), anti-Napi2b mAb (lifastuzumab), anti-CEACAM5 mAb (labeltuzumab), anti-EpCAM mAb (citatuzumab), anti-CD20 mAb (rituximab), anti-CD20 mAb (ofatumumab), anti-FGFR3 mAb (vofatamab), anti-PSMA mAb (hj591) and anti-CD33A mAb (Vadastuximab). Each of the foregoing antibodies are known to be tumor-specific and are used in current cancer therapies.

Figure 21:
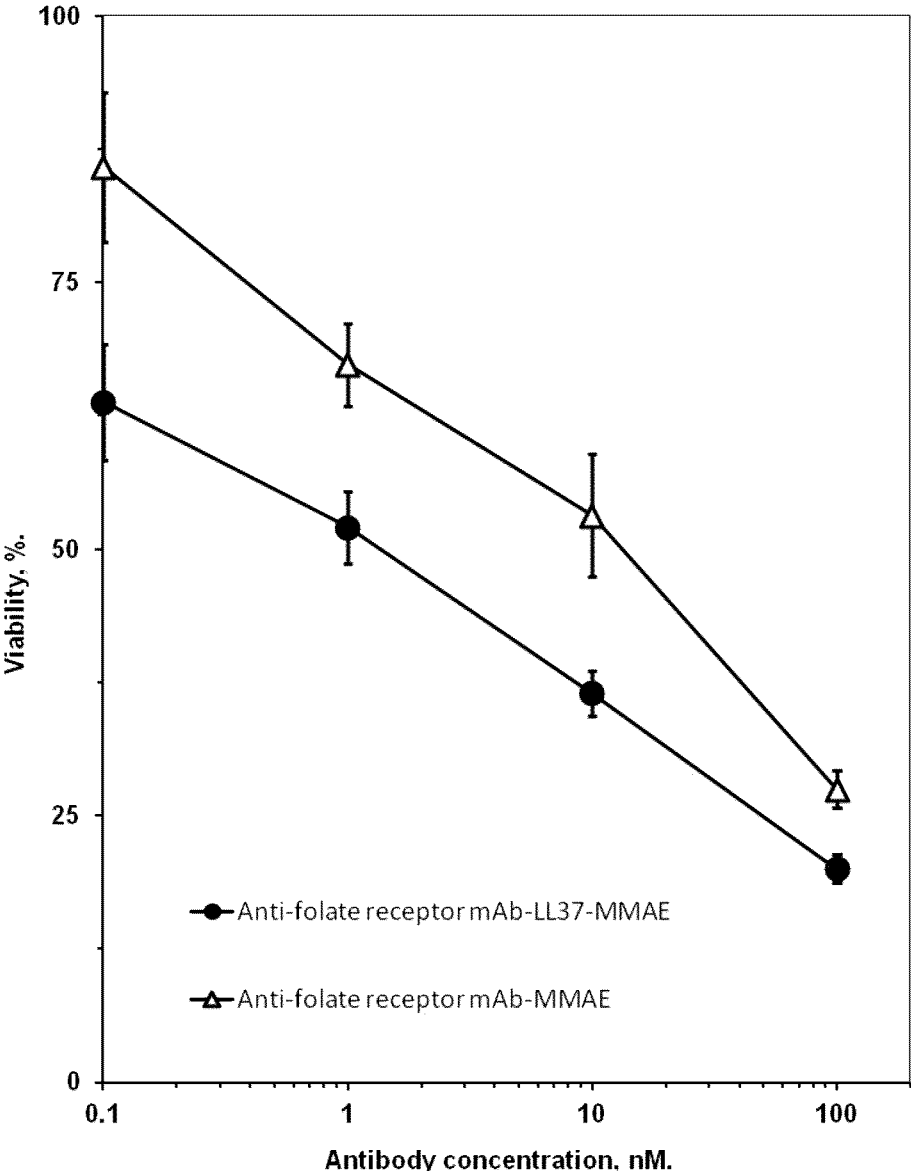
FIG. 21 shows a graph comparing the viability of SKOV3 cells (human ovarian cancer cell line with folate receptors on the cell surface) after 72 hrs treatment with anti-folate receptor ADC (MMAE) either linked to LL37 (i.e., anti-folate receptor mAb-LL37-MMAE) or without LL37 (i.e., anti-folate receptor mAb-MMAE).

FIG. 21 shows LL37 enhances the delivery of the cytotoxic agent MMAE, to kill SKOV3 through folate receptor. SKOV3 is a human ovarian cancer cell line with folate receptors on the cell surface. At increasing concentrations of antibody drug conjugate (ADC), the anti-folate receptor mAb-MMAE recognizes the folate receptor on SKOV3, and delivers MMAE to kill SKOV3 cells. In comparison, the LL37-linked ADCs (i.e., anti-folate receptor mAb-LL37-MMAE) are more effective at killing SKOV3 than anti-folate receptor mAb-MMAE. The killing efficiency of the anti-folate receptor mAb drug conjugates were analyzed by measuring the cell viability (i.e. XTT assay) after treating/incubating the cells with antibody-drug conjugate for 72 hours in a 37 degree C. tissue culture incubator.

Figure 22:
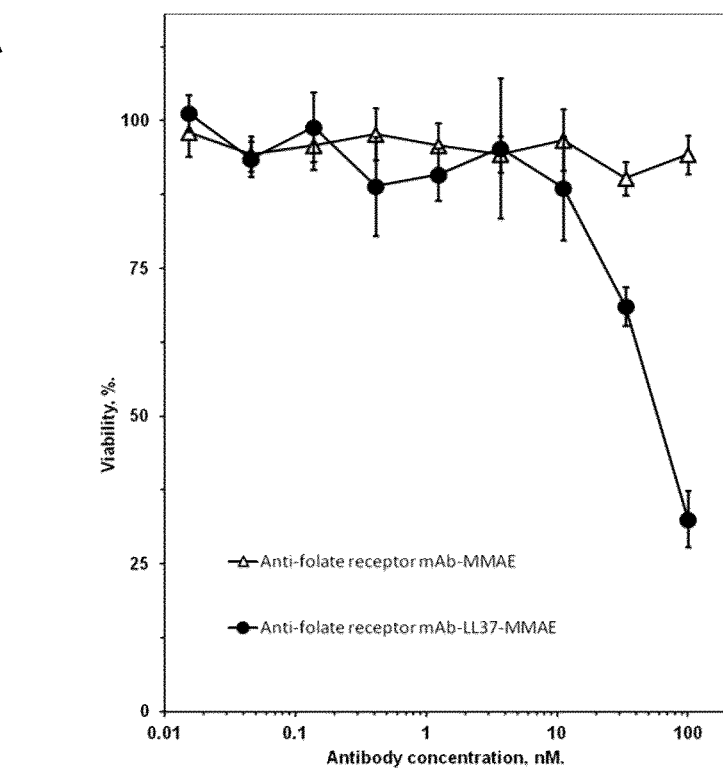
FIG. 22 shows two graphs comparing the viability of OVCAR3 cells (human ovary epithelial adenocarcinoma cell line with folate receptors on the cell surface) after 3 hrs (Panel A) or 72 hrs (Panel B) treatment with anti-folate receptor ADC (MMAE) either linked to LL37 (i.e., anti-folate receptor mAb-LL37-MMAE) or without LL37 (i.e., anti-folate receptor mAb-MMAE).
Figure 22:
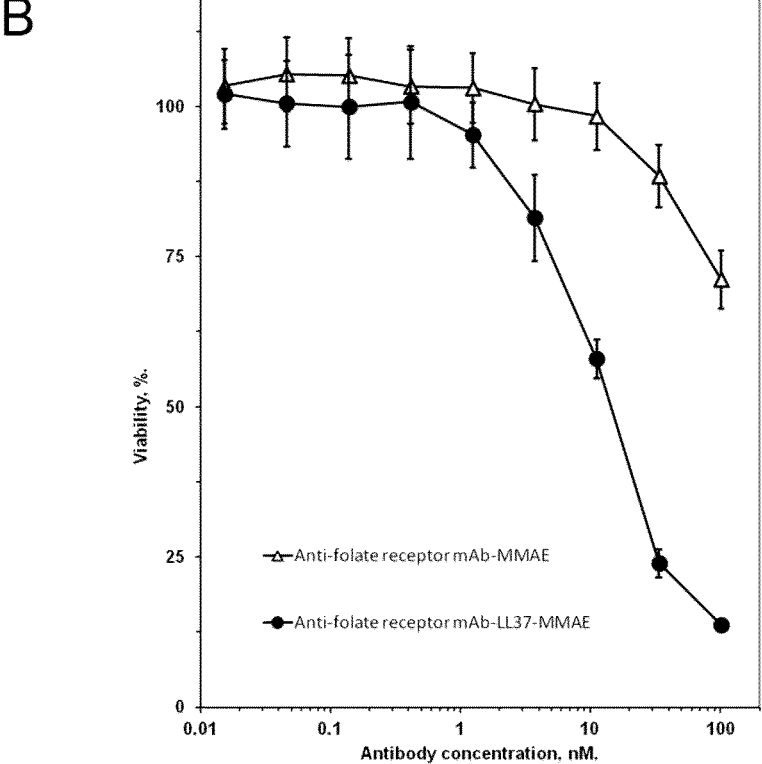

FIG. 22 shows LL37 enhances the delivery of the cytotoxic agent MMAE to kill OVCAR3 through folate receptor from two treatment/incubation time points, 3 hours for Panel A, and 72 hours for Panel B. OVCAR3 is a human ovary epithelial adenocarcinoma cell line with folate receptors on the cell surface. At increasing concentrations of antibody drug conjugate (ADC) the anti-folate receptor mAb recognizes the folate receptor on OVCAR3, and delivers MMAE to kill the OVCAR3 cells. In comparison, the LL37-linked ADCs (i.e., anti-folate receptor mAb-LL37-MMAE) are more effective at killing OVCAR3 than their corresponding ADCs without LL37 (i.e., anti-folate receptor mAb-MMAE). The killing efficiency of the anti-folate receptor mAb drug conjugates were analyzed by measuring the cell viability (i.e. XTT assay) after treating/incubating the cells with antibody drug conjugate for 3 hrs (Panel A) and 72 hours (Panel B) in the 37 degree C. tissue culture incubator.

The B-lymphocyte antigen CD20 is an activated-glycosylated phosphoprotein expressed and embedded on the surface of all B-cells during development and differentiation, and it is absent on terminally differentiated plasma cells. Overexpression of CD20 is correlated with leukemias. CD20 is recognized by many ani-CD20 mAbs, including rituximab and ofatumumab (and others). Ramos cells express and display CD20. As shown in Table 5, LL37-linked anti-CD20 rituximab is more effective than unconjugated rituximab in delivery to Ramos. Likewise, FIG. 23 (Panel A) shows LL37 enhances the delivery of the cytotoxic agent MMAE to kill Ramos cells through CD20. At increasing concentrations of antibody drug conjugate (ADC), the anti-CD20 mAb (ofatumumab)-MMAE recognizes the CD20 expressed on the surface of Ramos cells, and delivers the toxin MMAE to kill the Ramos cells. In comparison, the LL37-linked ADCs [i.e., anti-CD20 mAb (ofatumumab)-LL37-MMAE] are more effective at killing Ramos than anti-CD20 mAb-MMAE. The killing efficiency of the anti-CD20 mAb (ofatumumab) drug conjugates were analyzed by measuring the cell viability (i.e., XTT assay) after treating/incubating the cells with antibody drug conjugate for 72 hours in a 37 degree C. tissue culture incubator.

Figure 23:
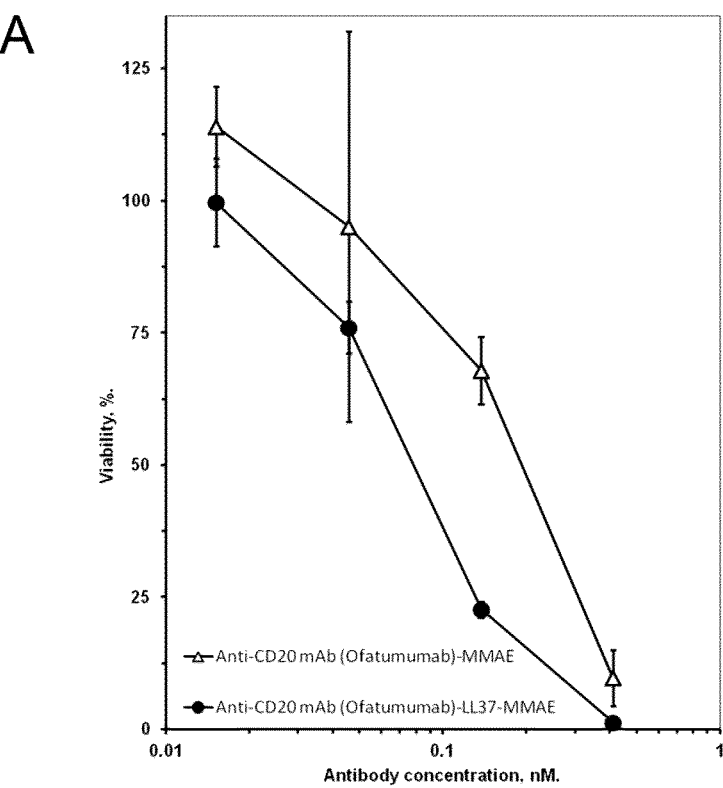
FIG. 23 (Panel A) shows a graph comparing the viability of Ramos cells (human B lymphocyte with CD20 on the cell surface) after 72 hrs treatment with anti-CD20 (Ofatumumab) ADC (MMAE) either linked to LL37 (i.e., anti-CD20 mAb-LL37-MMAE) or without LL37 (i.e., anti-CD20 mAb-MMAE).
Figure 23:
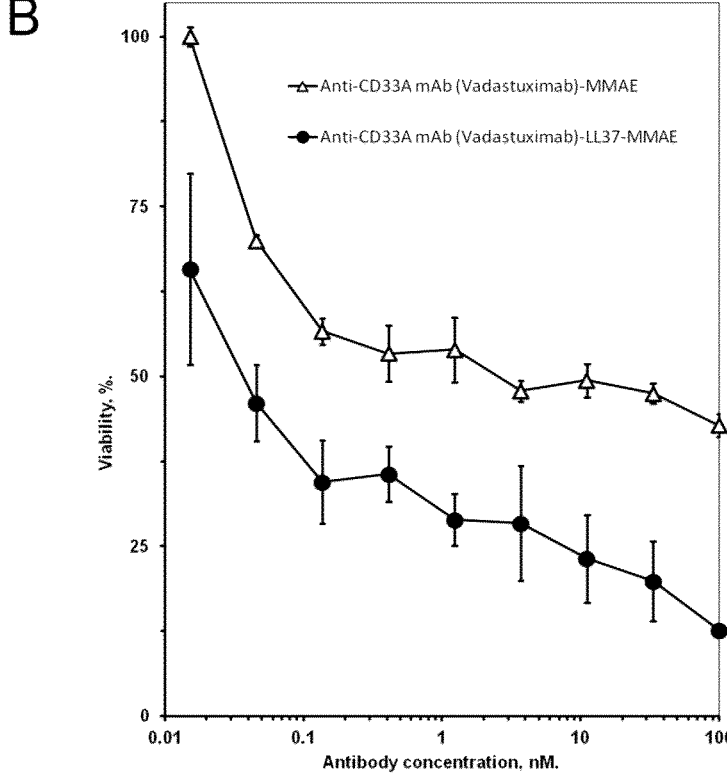

FIG. 23 (Panel B) shows LL37 enhances the delivery of the anti-cancer drug, MMAE, to kill HL60 cells through CD33A. HL60 is a human peripheral blood promyeloblast with CD33A on the cell surface. At increasing concentrations of antibody drug conjugate (ADC) the anti-CD33A mAb (Vadastuximab)-MMAE recognizes the CD33A on HL60 cells, and delivers the toxin MMAE to kill HL60 cells. In comparison, the LL37-linked ADCs (i.e., anti-CD33A mAb-LL37-MMAE) are more effective at killing HL60 cells than anti-CD33A mAb-MMAE. The killing efficiency of the anti-CD33A mAb drug conjugates were analyzed by measuring the cell viability (i.e., XTT assay) after treating/incubating the cells with antibody drug conjugate for 72 hours in a 37 degree C. tissue culture incubator.

Figure 24:
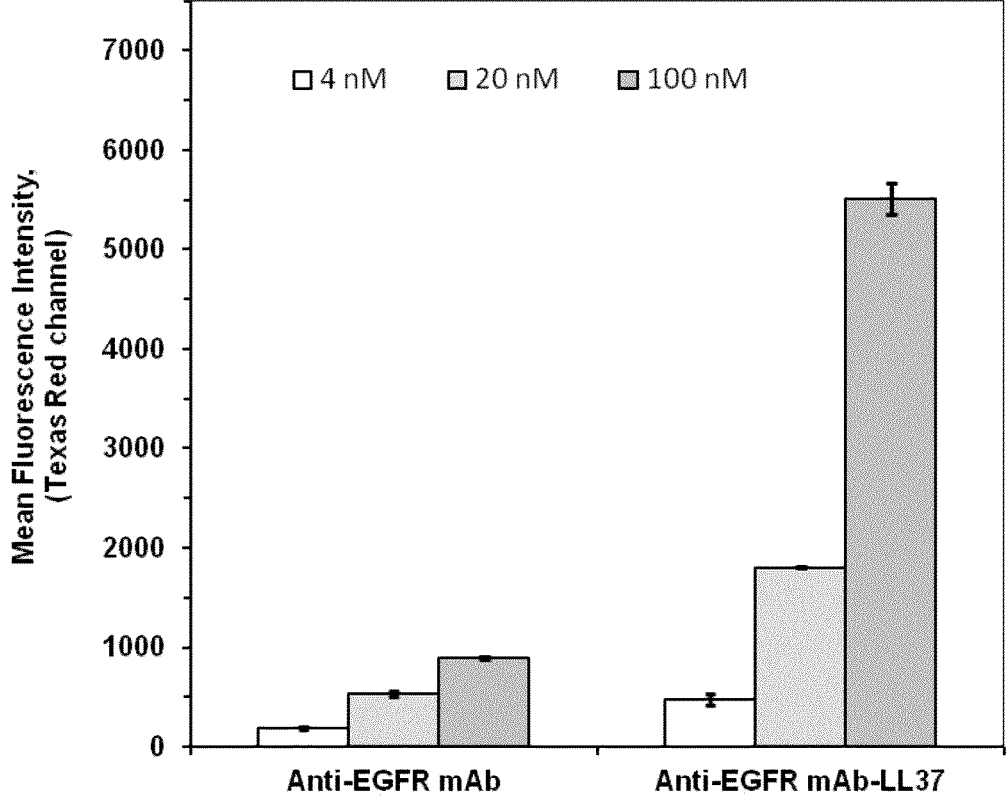
FIG. 24 shows a graph comparing fluorescence of MDA-MB-468 (human mammary gland cancer cell line expressing cell surface epidermal growth factor receptor (EGFR)) treated with various concentrations of Z-RFP-bound anti-EGFR mAb (panitumumab), or Z-RFP-bound anti-EGFR mAb (panitumumab) conjugated with LL37.

MDA-MB-468 is a cancer cell from human mammary gland tumor, and it expresses and displays epidermal growth factor receptor (EGFR) on the cell surface (see., Venugopal et al., 2018, PLoS One, 13, e0206109), which is recognized by the anti-EGFR mAb, panitumumab (see., Battaglin et al., 2017, Expert Opin. Biol. Ther., 17, 1297). FIG. 24 shows that LL37-conjugated panitumumab is much more efficient than panitumumab at delivery to MDA-MB-468 cells.

The sodium-dependent phosphate transport protein 2B (NaPi2b) is physiologically expressed in type II pneumocytes of lung and on the brush border membrane of small intestine, and increased expression of NaPi2b was recently correlated to development of ovary, thyroid, breast, or likely lung cancer (see., Levan et al., 2017, BMC Cancer, 17, 303). NaPi2b is recognized by anti-NaPi2b mAb, such as lifastuzumab (see., Banerjee et al., 2018, Ann. Oncol., 29, 917). The protein NaPi2b is expressed by OVCAR3, and Table 5 shows that LL37 conjugation significantly increases the delivery of lifastuzumab to the target OVCAR3 cells.

Fibroblast growth factor receptor 3 (FGFR3) is an integral membrane protein, and is expressed in tissues such as the cartilage, brain, intestine, and kidneys. FGFR3 interacts with fibroblast growth factors on the cell surface, and then initiates the tyrosine kinase signaling pathway to influence cell mitogenesis and differentiation. Overexpression of the FGFR3 mutant may be related to the development of bladder cancer (see., Gust et al., 2013, Mol. Cancer Ther. 12, 1245), and anti-FGFR3 mAb that inhibits FGFR3, such as vofatamab or B-701 (see., U.S. Pat. No. 8,410,250B2), has been developed as a treatment of bladder cancer. RT4v6 cells express and display FGFR3, and Table 5 shows that LL37 conjugation significantly increases the delivery of lifastuzumab to the target RT4v6 cells.

Carcinoembryonic antigen-related cell adhesion molecule 5 (CEACAM5) or CD66e is a GPI-anchored cell surface glycoprotein that regulates cell differentiation, apoptosis and cell polarity. Overexpression of CEACAM5 may promote tumor development. CEACAM5 has been used as a clinical biomarker for gastrointestinal or colorectal cancers (see., Chan and Stanners, 2007, Curr. Oncol., 14, 70). Anti-CEACAM5 mAb, such as labetuzumab, can selectively bind to CEAMCAM5, and its drug conjugates have been used for the treatment of colorectal cancer (see., Sharkey et al., 2018, Mol. Cancer Ther. 17, 196). LnCap cells expresses and display CEACAM5, and Table 5 shows that LL37 conjugation significantly increases the delivery of labetuzumab to LnCap.

Epithelial cell adhesion molecule (EpCAM) is a transmembrane glycoprotein mediating calcium-independent homotypic cell-cell adhesion in epithelia and epithelial-derived neoplasmas. EpCAM is involved in cell signaling, migration, proliferation, and differentiation. Overexpression of EpCAM has been correlated with cancer development, and EpCAM has been used as diagnostic marker for various cancers (see., Armstrong et al., 2003, Cancer Biol. Ther. 2, 320). Citatuzumab is an EpCAM-specific antibody, and its drug conjugates have been used in many anti-cancer therapies (see., Eyvazi et al., 2018, CuD. Cancer Drug Targets 18, 857). LnCap cells express EpCAM, and Table 5 shows that LL37-conjugated anti-EpCAM antibody citatuzumab is more effective than unconjugated citatuzumab for getting delivered to LnCap. 11002361 Prostate-specific membrane antigen (PSMA) is a transmembrane protein expressed in all forms of prostate tissue, and it is highly expressed in poorly differentiated, metastatic, and castration-resistant prostate cancer (see., von Eyben et al., 2018, Clin. Transl. Imaging 6, 145). Drug conjugates of anti-PSMA mAb have been developed to treat prostate cancers and PSMA-expressing tumors (see., Lutje et al., 2018, J. Nucl. Med. 59, 494). LnCap expresses PSMA, and Table 5 shows that LL37 conjugation greatly enhances the delivery of anti-PSMA antibody hj591 to LnCap compared to the unconjugated antibody.

TABLE 5

LL37 enhances delivery of cancer-specific antibodies to the target cell displaying cancer markers.

| mAb name | Target cell | Delivery efficiency ofmAb (i.e., mAb) | Delivery efficiency of the LL37-linked mAb (i.e., mAb-LL37) | Delivery enhance-ment |
|---|---|---|---|---|
| Anti-NaPi2b, Lifastuzumab | OVCAR3 | + | ++ | YES |
| Anti-CEACAM5, Labetuzumab | LnCap | + | ++ | YES |
| Anti-EpCAM, Citatuzumab | LnCap | ++ | +++ | YES |
| Anti-CD20, Rituximab | Ramos | ++ | +++ | YES |
| Anti-FGFR3, Vofatamab | RT4v6 | + | ++ | YES |

TABLE 5-continued

LL37 enhances delivery of cancer-specific antibodies to the target cell displaying cancer markers.

| mAb name | Target cell | Delivery efficiency ofmAb (i.e., mAb) | Delivery efficiency of the LL37-linked mAb (i.e., mAb-LL37) | Delivery enhance-ment |
|---|---|---|---|---|
| Anti-PSMA, hj591 | LnCap | ++ | +++ | YES |

+++ Strong Alexa Fluor 488 (cyan/green) fluorescent intensity
++ Medium level of Alexa Fluor 488 (cyan/green) fluorescent intensity
+ Weak, but noticeable Alexa Fluor 488 (cyan/green) fluorescent intensity}
− No signal

Experimental Procedures for Examples in FIGS. 10 and 11

Anti-HER2 mAb, the LL37-linked anti-HER2 mAb, the LL37-linked anti-HER2 mAb-MMAE conjugate, and the LL37-linked anti-HER2 mAb-DM1 conjugates were produced using the same procedures as described above.

Cell viability assay with XTT. On day 1, cells (OVCAR3) were seeded at about 0.02 to 0.025 million cells per ml concentration and incubated overnight in the 37 degree Celsius incubator. On day 2, the anti-HER2 mAb drug conjugates (i.e., anti-HER2 mAb-MMAE; anti-HER2 mAb-DM1), and the LL37-linked anti-HER2 mAb drug conjugates (i.e., anti-HER2 mAb-MMAE-LL37) were added to 100 nM final concentration in the culture media, and then incubated in the 37 degree Celsius incubator. One set was incubated for 24 hours, and another set for 72 hours. On day 3, the set with 24 hours, the treatment were removed, and replaced with fresh growth media, and continued incubation for the next 48 hours (for the total of 72 hours). On day 5, the set with both 24 hours and 72 hours treatments were analyzed. Briefly, the anti-HER2 mAb drug conjugate treatments were removed by replacing the old media with fresh complete growth media. XTT and PMS solutions were freshly prepared immediately before the assay, and were used right away. XTT/PMS were added to the treated cells to start the XTT reaction. The XTT reaction was incubated in the 37° C. tissue culture incubator until the 100% viability control (i.e., healthy growing cells without treatment) gave a spectral absorbance reading difference (i.e., OD475 minus OD660) of at least 1 (i.e., 3-4 hours for OVCAR3 cells). Spectral absorbance was measured at 475 nm (XTT) and 660 nm (background), and viability calculated from the spectral absorbance difference at 475 nm and 660 nm.

Experimental Procedures for Examples in FIGS. 12 and 13

Anti-HER2 mAb, the anti-HER2 mAb-MMAE conjugate, the LL37-linked anti-HER2 mAb, and the LL37-linked anti-HER2 mAb-MMAE conjugate were produced using the same procedures as described above. Anti-HER2 mAb-DM1 (commercial) is trastuzumab emtansine, Kadcyla™, and also known as TDM1.

Cell viability assay with XTT. On day 1, cells (RT4V6, Neuro2A) were seeded at about 0.02 to 0.025 million cells per ml concentration and incubated overnight in the 37° C. incubator. On day 2, the anti-HER2 mAb drug conjugates (i.e., anti-HER2 mAb-MMAE; anti-HER2 mAb-DM1), and the LL37-linked anti-HER2 mAb drug conjugates (i.e., anti-HER2 mAb-MMAE-LL37) were added to 100 nM final concentration in the culture media, and then incubated in the 37° C. incubator for 72 hours. On day 5, the anti-HER2 mAb drug conjugate treatments were removed by replacing the old media with fresh complete growth media. XTT and PMS solutions were freshly prepared immediately before the assay, and were used right away. XTT/PMS were added to the treated cells to start the XTT reaction. Incubate the XTT reaction in the 37° C. tissue culture incubator until the 100% viability control (i.e., healthy growing cells without treatment) gave a spectral absorbance reading difference (i.e., OD475 minus OD660) of at least 1 (i.e., 1 to 2 hours for Neuro2A cells, and 4+ hours for RT4V6 cells). Spectral absorbance was measured at 475 nm (XTT) and 660 nm (background), and viability calculated from the spectral absorbance difference at 475 nm and 660 nm.

Experimental Procedures for Examples in FIG. 14

DM1 conjugation to mAb. Same procedures as described above. Briefly, the DM1-linked antibodies were produced by reacting the SMCC-DM1 (Levena Biopharma CAT No. SET0101, CAS no. 1228105-51-8, M.W. 1072.6 g/mol) dissolved in DMSO to the antibody that was buffer-exchanged to PBS. Briefly, the chemical conjugation reaction, which is buffered to pH 8.0 with phosphate buffer, contains 40.7 µM of antibody (molecular weight of 147,500 g/mol) and 244 µM of SMCC-DM1 (6 SMCC-DM1 per mAb in the reaction), and the final DMSO concentration is kept just under 5% (v/v) of the final reaction volume. The reaction mixture was incubated at 25 degree Celsius for 1.5 hours, and the DM1-linked antibody was purified through Sephadex G25 size exclusion chromatography (PD10) equilibrated in PBS buffer. The final antibody drug conjugate (ADC) has a calculated drug-to-antibody ratio (DAR) of about 3-4.

Cell assay was done by treating/incubating the RT4V6 cells with antibody drug conjugates for 72 hours in the 37 degree C. tissue culture incubator. After treatment, cell viability was determined by XTT assay as described above.

Experimental Procedures for Examples in FIG. 15

Doxorubicin conjugation to mAb. The Doxorubicin-linked antibodies were produced by reacting the 6-maleimidocaproyl hydrazone-linked doxorubicin (CAS No. 1361644-26-9) to the TCEP-reduced antibodies. Briefly, following the method used for MMAE conjugation to mAb (see Experimental Procedure for Example 2), we chemically linked the doxorubicin to the TCEP-reduced mAb that has 8 reduced cysteine thiol side chains, and produced the conjugates with 6-7 doxorubicins per mAb. The Doxorubicin-linked antibodies were purified through Sephadex G25 size exclusion chromatography (PD10) in PBS buffer.

Cell assay was done by treating/incubating the RT4V6 cells with antibody drug conjugates for 72 hours in the 37 degree C. tissue culture incubator. After treatment, cell viability was determined by XTT assay as described above.

Experimental Procedures for Examples in FIG. 16

Taxol conjugation to mAb. The Taxol-linked antibodies were produced by reacting the maleimidocaproyl-Val-Cit-PAB-linked Paclitaxel (MedKoo Biosciences CAT No. 620102) to the TCEP-reduced antibodies in the presence of 20% (v/v) DMSO critical for the solubility of Taxol. Briefly, following the method used for MMAE conjugation to mAb (see Experimental Procedure for Example 2), the Taxol was chemically linked to TCEP-reduced mAb that has 8 reduced cysteine thiol side chains. The Taxol-linked antibodies were purified through Sephadex G25 size exclusion chromatography (PD10) in PBS buffer.

The cell assay was done by treating/incubating the OVCAR3 cells with antibody drug conjugates for 3 hours in the 37 degree C. tissue culture incubator. After treatment, cell viability was determined by XTT assay as described above.

Experimental Procedures for Examples in FIG. 17

The Taxol-linked antibodies were produced by following the same method as described above. TDM1 is the anti-HER2 mAb-DM1 (commercial), and is also known as trastuzumab emtansine, or Kadcyla™.

The cell assay was done by treating/incubating the T47D cells with antibody drug conjugates for 3 hours in the 37 degree C. tissue culture incubator. After treatment, cell viability was determined by XTT assay as described above.

Experimental Procedures for Examples in FIG. 18

Duocarmycin conjugation to mAb. The Duocarmycin-linked antibodies were produced by reacting the MA-PEG4-vc-PAB-DMEA-Duocarmycin SA (Levena Biopharma CAT No. SET0205) dissolved in DMSO to the TCEP-reduced antibodies. Briefly, following the method used for MMAE conjugation to mAb (see Experimental Procedures for Example 2), 8 molecules of Duocarmycin were chemically linked to the 8 SH groups generated from the TCEP reduction, and produced the conjugates with 8 Duocarmycin per mAb. The Duocarmycin-linked antibodies were purified through Sephadex G25 size exclusion chromatography (PD10) in PBS buffer.

For drug-to-antibody ratio (DAR) of 3.5, the chemical conjugation procedure involved the following modified procedure: 1) a partial reduction of mAb was carried out for 2 hours at 37 degree Celsius with 2.75 molar equivalents of TCEP to break 2 disulfide bonds releasing 4 reduced cysteine thiol side chains; 2) following the reduction reaction, DMSO was added to a final concentration of about 10% (v/v) to improve solubility of the maleimide-toxin to be added; 3) chemical conjugation to the toxin was carried out with 4.4 molar equivalents of MA-PEG4-vc-PAB-DMEA-Duocarmycin SA for 40 minutes at 22 degree Celsius, followed by quenching the unreacted maleimide-toxin with 8.8 molar equivalents of L-cysteine for 20 minutes at 4 degree Celsius; and 4) the Duocarmycin-linked antibodies were purified through Sephadex G25 size exclusion chromatography (PD10) in PBS buffer.

The cell assay was done by treating/incubating the RT4V6 cells with antibody drug conjugates for 72 hours in the 37 degree C. tissue culture incubator. After treatment, cell viability was determined by XTT assay as described above.

Experimental Procedures for Examples in FIG. 19

Anti-HER2 mAb-[LL37(Cys-MMAE)] production. In this method, MMAE was covalently linked to the cysteine thiol side chain at the C-terminus of LL37(Cys) peptide (SEQ ID No: 35). LL37(Cys)-MMAE was then conjugated to the C-terminus of the light chain in anti-HER2 mAb by sortase, forming the final product, i.e. anti-HER2 mAb-[LL37(Cys-MMAE)]. Briefly, the reaction mixture in PBS buffer (20 mM K/Na/HPO4, pH 7, 150 mM NaCl) contained 2.12 mM or 10 mg/ml of LL37(Cys) (SEQ ID NO:35) (molecular weight of 4,711 g/mol, stock of 20 mg/ml dissolved in PBS), 2.547 mM of VcMMAE (stock of 10 mM dissolved in DMSO), and 2% (w/v) of CHAPS [stock of 10% (w/v) dissolved in water]. The reaction mixture was incubated at room temperature (22 degree Celsius) for at least 18 hours (i.e., overnight reaction). It is noted that reaction mixture is cloudy at the start of the reaction, and gradually becomes clarified at the end. It is also noted that use of excess VcMMAE ensures that all the LL37(Cys) (SEQ ID No: 35) reacts with VcMMAE to form LL37(Cys-MMAE), and there is little to no free LL37(Cys) (SEQ ID No: 35) at the end of the reaction. The completed reaction mixture containing the LL37(Cys-MMAE) (2.12 mM) is used directly for conjugation to the anti-HER2 mAb. The following day, conjugation of LL37(Cys-MMAE) to anti-HER2 mAb was carried out at 37 degree C. for at least 15 hours (i.e., overnight reaction) in a reaction mixture that contained 100 μM of LL37(Cys-MMAE) [stock of 2.12 mM directly from the LL37(Cys)-to-VcMMAE reaction, 5 μM of Anti-HER2 mAb, 1 μM of sortase, 1 mM TCEP, 10% (v/v) of DMSO, 2% (w/v) of CHAPS, 5 mM Calcium chloride, 20 mM Tris-HCl (pH 7.5) and 150 mM NaCl. The anti-HER2 mAb-[LL37(Cys-MMAE)] was purified by Protein A affinity chromatography, and buffer exchanged to PBS. Using UV250 and UV280 absorbance, the purified anti-HER2 mAb-[LL37(Cys-MMAE)] mAb has an estimated drug-to-antibody ratio (DAR) of 2.45, indicating 2-3 MMAE per mAb.

Alternatively, LL37(Cys) (SEQ ID No: 35) was conjugated to the C-terminus of the light chain of anti-HER2 mAb by sortase, forming the intermediate, anti-HER2 mAb-LL37 (Cys). MMAE was covalently linked to the cysteine thiol side chain at the C-terminus of LL37(Cys), forming the final product, anti-HER2 mAb-LL37(Cys-MMAE). Briefly, the reaction mixture in 20 mM Tris-HCl (pH 7.5) and 150 mM NaCl buffer contained 360 μM of LL37(Cys) (SEQ ID NO: 35) (molecular weight of 4,711 g/mol, stock of 10 mg/ml dissolved in PBS), 20 μM of Anti-HER2 mAb, 1 μM of sortase, 1 mM TCEP, 5 mM Calcium chloride. The reaction mixture was incubated at 37 degree C. for 3 hours, and then is chilled to 4 degree Celsius. It is noted that lowering the temperature and adding a chelating agent (i.e., EDTA) is critical to prevent oxidation of the thiol side chain in the C-terminus of LL37(Cys). Hence, purification of anti-HER2 mAb-LL37(Cys) by Protein A affinity chromatography was carried out in the 4 degree Celsius refrigerator, and EDTA (pH 8.0) is added to 1 mM concentration in the column running buffer, elution buffer, neutralization buffer. Fractions that contain the purified anti-HER2 mAb-LL37(Cys) were pooled. The number of reactive free thiols was confirmed with Ellman's reagent [i.e., 5,5'-dithiobis-(2-nitrobenzoic acid) or DTNB] using the extinction coefficient of 14,150 M$^{-1}$ cm$^{-1}$ at 412 nm. DMSO was added to a final concentration of 10% (v/v), and VcMMAE was added in excess to the molar equivalents of free thiol side. The reaction was incubated at 4 degree Celsius for 40 minutes. Then, L-cysteine was added to 2 molar equivalents of VcMMAE used, and incubated at 4 degree Celsius for 20 minutes to inactivate excess (unreacted) VcMMAE. The reaction product, anti-HER2 mAb-LL37(Cys-MMAE), was purified on PD-10 size exclusion column, and then buffer-exchanged to PBS overnight. In the following day, using UV250 and UV280 absorbance, the purified LL37-MMAE linked anti-HER2 mAb has an estimated drug-to-antibody ratio of ~1, indicating ~1 MMAE per mAb.

The cell assays were done by treating/incubating the RT4V6 cells for Panel A, and OVCAR3 for Panel B, with antibody drug conjugates for 72 hours in the 37 degree C. tissue culture incubator. After treatment, cell viability was determined by XTT assay as described above.

Experimental Procedures for Examples in FIG. 20

MMAE conjugation to mAb for production of ADC with a DAR of 8. The antibody drug conjugates with a DAR of 8 were produced by following the same method as described in Example 1 above.

MMAE conjugation to mAb for production of ADC with a DAR less than or equal to 4. For drug-to-antibody ratio (DAR) of 4, the chemical conjugation procedure involves the following modified procedures: 1) A partial reduction of mAb was carried out for 2 hours at 37 degree Celsius with 2.75 molar equivalents of TCEP to break 2 disulfide bonds releasing 4 reduced cysteine thiol side chains; 2) after reduction reaction ended, DMSO was added to a final concentration of about 10% (v/v) to improve solubility of the maleimide-toxin to be added; 3) chemical conjugation to the toxin was carried out with 4.4 molar equivalents of Vc-MMAE for 40 minutes at 22 degree Celsius, followed by quenching the unreacted maleimide-toxin with 8.8 molar equivalents of L-cysteine for 20 minutes at 4 degree Celsius; 4) the MMAE-linked antibodies were purified through Sephadex G25 size exclusion chromatography (PD10) in PBS buffer.

The cell assays were done by treating/incubating the AGS cells for 3 hours (Panel A), and RT4V6 cells for 3.5 hours (Panel B), with antibody drug conjugates in the 37 degree C. tissue culture incubator. After treatment, cell viability was determined by XTT assay as described above.

Experimental Procedures for Examples in FIG. 21

Anti-folate receptor mAb cloning, expression, and purification. The final protein sequences for the anti-folate receptor mAb heavy chain (SEQ ID No: 36) and anti-folate receptor mAb light chain (SEQ ID No: 37) were reverse-translated and codon-optimized for gene synthesis, and sub-cloned separately into the EcoRI-BamHI sites in the pTT5 mammalian expression vectors. Expression and purification of anti-folate receptor mAb was done using the same production methods for anti-HER2 mAb as described in Example 1 above. Briefly, it involved transient transfection co-delivering both the heavy and light chains in pTT5 plasmids (mixed in an optimized ratio) into the CHO-BRI-rc-TA-55E1 cells. Following DNA transfection, cells were induced with cumate for 16 days to select a stable pool of highly protein-expressing cells. Following the selection, these cells were isolated for protein expression in a fed-batch method (i.e., fresh media continuously added during cell growth) over the 11 day period. At the end of cell growth, the culture media was harvested, and the secreted antibodies were purified from the clear supernatant of the culture media by Protein A binding chromatography. The produced anti-folate receptor mAb is in Dulbecco's Phosphate Buffered Saline (DPBS), and had a purity of >99%. The functional assembly of the anti-folate receptor mAb was verified on gel filtration and SDS-PAGE.

Anti-folate receptor mAb-LL37 production. The LL37-linked antibodies were produced by following the same method as described in Example 1 (above).

MMAE conjugation to mAb. The MMAE-linked antibodies were produced by following the same method as described in Example 1 (above).

Cell viability assay was carried out with XTT as described above.

Experimental Procedures for Examples in FIG. 22

Anti-folate receptor mAb, the LL37-linked antibody, and their conjugations to MMAE were produced using the same procedure as described above. Cell viability assay was carried out with XTT as described above.

Experimental Procedures for Examples in FIG. 23
(Panel A)

Anti-CD20 mAb (Ofatumumab) production. The final amino acid sequences for the anti-CD20 mAb (Ofatumumab) heavy chain (SEQ ID NO: 40) and anti-CD20 mAb (Ofatumumab) light chain (SEQ ID NO: 41) were reverse-translated and codon-optimized for gene synthesis, and sub-cloned separately into the EcoRI-BamHI sites in the pTT5 mammalian expression vectors. Expression and purification of anti-CD20 mAb (Ofatumumab) was done using the same production methods for anti-HER2 mAb as described in Example 1 (above). Briefly, transient transfection was used to co-deliver both the heavy and light chains in pTT5 plasmids (mixed in an optimized ratio) into the CHO-BRI-rc-TA-55E1 cells. Following DNA transfection, cells were induced with cumate for 16 days to select a stable pool of highly protein-expressing cells. Following the selection, these cells were isolated for protein expression in a fed-batch method (i.e., fresh media continuously added during cell growth) over the 11 day period. At the end of cell growth, the culture media was harvested, and the secreted antibodies were purified from the clear supernatant of the culture media by Protein A binding chromatography method. The produced anti-CD20 mAb (Ofatumumab) in Dulbecco's Phosphate Buffered Saline (DPBS) had a purity of >99%. The functional assembly of the anti-CD20 mAb (Ofatumumab) was verified on gel filtration and SDS-PAGE.

Anti-CD20 mAb (Ofatumumab)-LL37 production. The LL37-linked antibodies were produced from sortase-catalyzed ligation of the purified anti-CD20 mAb and the GG-LL37 peptide (SEQ ID NO: 2) by following the same method as described in Example 1 (above).

MMAE conjugation to mAb. The MMAE-linked antibodies were produced by following the same method as described in Example 1 (above).

Cell viability assay with XTT. The killing efficiency of the anti-CD20 mAb (Ofatumumab) drug conjugate was analyzed by measuring the cell viability (i.e. XTT) after treating/incubating the target cell, Ramos, with antibody drug conjugate for 72 hours in the 37 degree C. tissue culture incubator. The target cells, Ramos (ATCC Catalog No. ATCC CRL-1596, lot #70016960), was grown in suspension culture (i.e., in contrast to adherent cells), and at the end of 72 hours treatment with antibody drug conjugates, XTT/PMS reagent was added directly to the culture to start the XTT reaction, which was incubated in the 37° C. tissue culture incubator until the 100% viability control (i.e., healthy growing cells without treatment) gave a spectral absorbance reading difference (i.e., OD475 minus OD660) of at least 1. Spectral absorbance was measured at 475 nm (XTT) and 660 nm (background), and viability calculated from the spectral absorbance difference at 475 nm and 660 nm. The set with 72 hours treatment were analyzed.

Experimental Procedures for Examples in FIG. 23
(Panel B)

Anti-CD33A mAb (Vadastuximab) production. The final protein sequences for the anti-CD33A mAb (Vadastuximab) heavy chain (SEQ ID NO: 46) and anti-CD33A mAb (Vadastuximab) light chain (SEQ ID NO: 47) were reverse-translated and codon-optimized for gene synthesis, and sub-cloned separately into the EcoRI-BamHI sites in the pTT5 mammalian expression vectors. Expression and purification of anti-CD33A mAb (Vadastuximab) was also done using the same production methods for anti-HER2 mAb as described in Example 1 (above). Briefly, transient transfection was used to co-deliver both the heavy and light chains in pTT5 plasmids (mixed in an optimized ratio) into the CHO-BRI-rc-TA-55E1 cells. Following DNA transfection, cells were induced with cumate for 16 days to select a stable pool of highly protein-expressing cells. Following the selection, these cells were isolated for protein expression in a fed-batch method (i.e., fresh media continuously added during cell growth) over the 11 day period. At the end of cell growth, the culture media was harvested, and the secreted antibodies were purified from the clear supernatant of the culture media by the Protein A binding chromatography method. The produced anti-CD33A mAb (Vadastuximab) was in Dulbecco's Phosphate Buffered Saline (DPBS), and had a purity of >99%. The functional assembly of the anti-CD33A mAb (Vadastuximab) is verified on gel filtration and SDS-PAGE.

Anti-CD33A mAb (Vadastuximab)-LL37 production. The LL37-linked antibodies were produced by following the same method as described in Example 1 (above).

MMAE conjugation to mAb. The MMAE-linked antibodies were produced by following the same method as described in Example 1 (above).

Cell viability assay with XTT. The killing efficiency of the anti-CD33A mAb (Vadastuximab) drug conjugate were analyzed by measuring the cell viability (i.e. XTT) after treating/incubating the target cells, HL60, with antibody drug conjugate for 72 hours in the 37 degree C. tissue culture incubator. The target cells, HL60 (ATCC Catalog No. ATCC CCL-240, lot #70009351) were grown in suspension culture (i.e., in contrast to adherent cells), and at the end of 72 hours treatment with antibody drug conjugates, XTT/PMS reagent was added directly to the culture to start the XTT reaction, which was incubated in the 37° C. tissue culture incubator until the 100% viability control (i.e., healthy growing cells without treatment) gave a spectral absorbance reading difference (i.e., OD475 minus OD660) of at least 1. Spectral absorbance was measured at 475 nm (XTT) and 660 nm (background), and viability calculated from the spectral absorbance difference at 475 nm and 660 nm. The set with 72 hours treatment were analyzed.

Experimental Procedures for Examples in FIG. 24
and Table 5

Productions of mAbs. The sequences of the antibodies (see Table 6A, below) were reversed-translated and codon-optimized for gene synthesis, and sub-cloned into the EcoRI-BamHI sites in the pTT5 mammalian expression vectors. Expression and purification of these antibodies were performed using the same production methods used for anti-HER2 mAb production as described in Example 1. The antibodies are in Dulbecco's Phosphate Buffered Saline (DPBS), and have purities >99%. The functional assembly of the antibody are verified on gel filtration and SDS-PAGE. The LL37-linked antibodies were produced by following the same method as described in Example 1. The MMAE-linked antibodies were produced by following the same method as described in Example 1.

TABLE 6A

List of antibodies

| Antibody Name | Heavy chain sequence (SEQ ID No:) | Light chain sequence (SEQ ID No:) |
|---|---|---|
| Anti-HER2, Trastuzumab | 3 | 4 |
| Anti-folate receptor, Mirvetuximab | 36 | 37 |
| Anti-EGFR, Panitumumab | 38 | 39 |
| Anti-CD20, Ofatumumab | 40 | 41 |
| Anti-NaPi2b, Lifastuzumab | 42 | 43 |
| Anti-CD33A, Vadastuximab | 46 | 47 |
| Anti-CEACAM5, Labetuzumab | 48 | 49 |
| Anti-EpCAM, Citatuzumab | 50 | 51 |
| Anti-CD20, Rituximab | 94 | 95 |

The expression plasmids for the following antibodies (see Table 6B, below) were created from their respective protein structural sequences (i.e., reversed-translated and codon-optimized for gene synthesis, and sub-cloned into the EcoRI-BamHI sites in the pTT5 mammalian expression vectors). Expression and purification of these antibodies were done using the same production method used for anti-HER2 mAb production as described in Example 1. Briefly, transient transfection was used to co-deliver both the heavy and light chains in pTT5 plasmids (mixed in an optimized ratio) into the CHO-BRI-rc-TA-55E1 cells obtained from NRC-BRI (Montreal, QC, Canada). Following DNA transfection, cells were grown in a fed-batch method (i.e., fresh media continuously added during cell growth) over an 11 day period. At the end of cell growth, the culture media was harvested, and the secreted antibodies were purified from the clear supernatant of the culture media by Protein A binding chromatography. The produced antibodies were stable in phosphate buffered saline (PBS), and had a purity of >99%. The functional assembly of the antibodies was verified by gel filtration and SDS-PAGE. The LL37-linked antibodies were produced by following the same method as described in Example 1. The MMAE-linked antibodies were produced by following the same method as described in Example 1.

TABLE 6B

List of antibodies

| Antibody Name | Heavy chain protein (SEQ ID No:) | Heavy chain cDNA (SEQ ID No:) | Light chain protein (SEQ ID No:) | Light chain CDNA (SEQ ID No:) |
|---|---|---|---|---|
| Anti-FGFR3 mAb, Vofatamab | 62 | 63 | 64 | 65 |
| Anti-PSMA mAb, hj591 | 66 | 67 | 68 | 69 |

Delivery assay. For results shown in FIG. 24, the LL37-enhanced delivery efficiency for Anti-EGFR mAb (Panitumumab) (SEQ ID No: 38 and 39) was tested on MDA-MB-468 cells (i.e., anti-EGFR mAb was tested against anti-EGFR mAb-LL37). 100 nM of antibodies and 100 nM of Z-RFP were added to MDA-MB-468 cells cultured at 75% confluency, and were incubated at 37 degree C. for 3 hours. The culturing media containing the unbound antibodies were removed, and the MDA-MB-468 cells were washed with PBS. The adherent cells were treated with trypsin at 37 degree C. for 1-2 minutes, neutralized in FACS buffer (2% v/v FBS, 2 mM EDTA, 0.05% w/v sodium azide in PBS), and transferred to FACS tubes on ice. The delivery of antibodies to cells was quantitated by measuring the red fluorescence intensity (i.e., PE-Texas Red color channel in the FACS detector) emitted from Z-RFP bound to antibody. For anti-FGFR3, anti-Napi2b, anti-CEACAM5, anti-EP-CAM, anti-PSMA mabs shown in Table 5, 100 nM of antibodies (i.e., mAb or mAb-LL37) were added to the target cells were grown to about 60-70% confluency level adherent to the bottom well surfaces in the 48-well culturing plates, and incubated at 37 degree Celsius tissue culture incubator for 3 hours. At the end of incubation, the adherent target cells were washed twice with ice-cold PBS, fixed with 2% (w/v) formaldehyde in PBS at room temperature for 15 minutes, and washed twice with PBS at room temperature. The fixed adherent target cells were then permeabilized with 0.05% (v/v) Tween-20 in PBS at room temperature for 15 minutes. The permeabilized cells were then incubated with 5% (v/v) FBS, 0.05% (v/v) Tween-20 in PBS at 37 degree Celsius incubator for 30 minutes. The secondary antibody, Goat anti-human IgG-AlexaFluor 488, was added to 5 µg/ml in 5% (v/v) FBS, 0.05% (v/v) Tween-20 in PBS, and incubated with the treated target cells at 37 degree Celsius incubator for 30 minutes. After incubation, the labelled cells were washed twice with PBS, and stored in storage buffer [5% (v/v) FBS in PBS] at 4 degree Celsius until fluorescence microscope imaging. The delivery of mAb and mAb-LL37 were determined qualitatively by estimating the green fluorescence intensity emitted from the AlexFluor488-labelled secondary antibody bound to mAb or mAb-LL37. For anti-CD20 shown in Table 5, the assays were done similarly using the same PBS wash solution, fixing solution [2% (w/v) formaldehyde], permeabilization solution [0.05% (w/v) Tween-20 in PBS], blocking solution [5% (v/v) FBS in permeabilization solution], and storage solution [5% (v/v) in PBS] for detection with the secondary antibody, Goat anti-human IgG-AlexaFluor488. However, Ramos (ATCC Catalog No. ATCC CRL-1596, lot #70016960) was grown in suspension culture (i.e., in contrast to adherent cells), and the modification to the methods involves simply harvesting cells from the shaking culture flask for incubation with antibodies (or LL37-linked antibodies), and frequently pelleting down the target cells in the V-bottom 96-well polypropylene plate for downstream processes of PBS washing, fixing, permeabilizing, blocking, and the secondary antibody labelling. The secondary anti-human IgG-AlexaFluor488 labelled target cells were washed and resuspended in PBS, and transferred to the clear polystyrene 48-well plates for fluorescence microscope imaging.

Example 4. Comparable Cell-Mediated Cytotoxicity with Leukocytes Against BT474 Cells FIG. 25 shows that compared to the unconjugated antibody (i.e., Anti-HER2 mAb), the LL37-conjugated antibody (i.e., Anti-HER2 mAb-LL37) produces comparable level of the antibody-dependent cell-mediated cytoxicity against BT474 cell (a human breast ductal carcinoma cell line with high level of HER2 on the cell surface).

Figure 25:
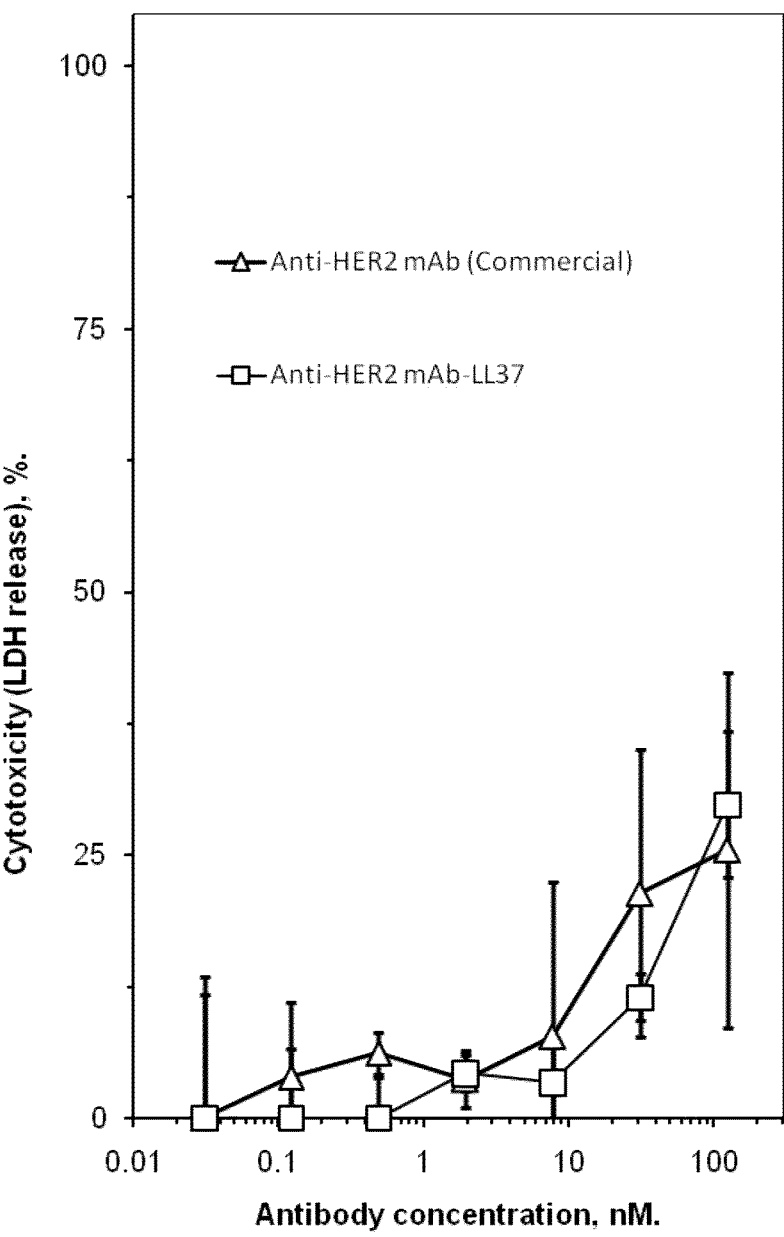
FIG. 25 shows a graph comparing leukocyte-mediated cytotoxicity of BT474 cells (high HER2+ breast cancer cells) treated with anti-HER2 mAb or anti-HER2 mAb conjugated with LL37, at various concentrations.

Experimental Procedures for Examples in FIG. 25

The LL37-linked anti-HER2 mAb were produced using the same procedures as described above.

LDH cytotoxicity assay. On day 1, BT474 cells were seeded at about 0.01 to 0.02 million cells per ml concentration in the 96-wells plate, and incubated overnight in the 37° C. incubator. On day 2, fresh leukocytes were isolated from a healthy blood donor, and were immediately combined with anti-HER2 mAb and anti-HER2 mAb-LL37 before adding to BT474 cells. Antibodies were added to final concentration as indicated in the figure. The leukocytes were added to BT474 using an effector-to-target ratio (E/T) of (6 to ~10):1 in the wells. The leukocyte-mediated antibody treatments were incubated for 24 hours in the 37° C. incubator. On day 3, the condition of BT474 was quantitatively determined by using the commercial LDH assay kit, CytoTox96 Non-Radioactive Cytotoxicity Assay from Promega.

Example 5. Effect of LL37 Deletions and or Substitutions on Delivery Efficiency When Conjugated to Anti-HER2 mAb To define the importance of certain residues within the full-length LL37 peptide, a series of LL37-derived peptides, including N- and C-terminal deletion constructs as well as variants comprising amino acid substitutions, were compared against full-length LL37 for their efficiency at delivering conjugated anti-HER2 mAb to T47D cells, a human mammary gland ductal carcinoma cell line with a low level of HER2 expression. The tested LL37-derived peptides and their anti-HER2 mAb delivery efficiencies (at 100 nM Ab) are shown in Table 7. For PEP #6, PEP #35-43 in Table 7 the delivery of anti-HER2 mAb was determined qualitatively by estimating the green fluorescence intensity emitted from Z-GFP bound to anti-HER2 mAb (or to the anti-HER2 mAb linked to the various LL37 deletion constructs and variants. The Z domain in Z-GFP is a stable 6.6 kD protein fragment derived from the B domain of Protein A, which retains high specificity and affinity for human IgG1 Fc domain (see, Nilsson et al. (1987), Protein Eng., 1, 107). The non-specific binding of Z-GFP to T47D (i.e., GFP alone) was negligible. For PEP #6, PEP #47-51, 55, 58-64, 66, and 94 in Table 7, the delivery of anti-HER2 mAb was determined qualitatively by estimating the green fluorescence intensity emitted from a secondary antibody, Goat anti-human IgG-AlexaFluor 488 in place of Z-GFP, for fluorescence detection of the cell-bound anti-HER2 mAb. The Goat anti-human IgG-AlexaFluor488 has high specificity and affinity for human IgG1 structure of anti-HER2 mAb.

As set out in Table 7 below, the various LL37-derived peptides tested show that a core sequence corresponding to residues 13-29 of SEQ ID NO:1 is sufficient to provide strong enhancement of antibody delivery (e.g. see PEP #66 in Table 7). From available structural information, residues 13-29 of SEQ ID NO: 1 correspond to a central alpha-helical core structure that is amphipathic, including high net positive charge and a hydrophobic patch. Table 7 further indicates that residues 20-37 of SEQ ID NO:1 is also sufficient to provide strong enhancement of delivery (see PEP #38 in Table 7).

Taken together, these two data indicate that N- and/or C-terminal deletions to a fragment of LL37 corresponding to residues 13-37 (i.e. PEP #36 in Table 7; SEQ ID NO: 14) can be made and still provide strong enhancement of antibody delivery. At the same time, Table 7 also shows that N- and C-terminal deletions are only tolerated up to a point (see PEP #62 in Table 7). However, Table 7 indicates that N- and/or C-terminal deletions can be made to PEP #36 (SEQ ID NO: 14) up to a total of 8 deleted amino acids while still retaining significant enhancement in the delivery of a cell surface binding conjugate. For example, PEP #66 includes a C-terminal truncation of 8 residues compared to PEP #36 and was observed to provide significant delivery enhancement (++). Furthermore, PEP #38 includes an N-terminal truncation of 7 residues compared to PEP #36 and was observed to provide significant delivery enhancement (++).

Notably, it was found that further deletions to PEP #36 (SEQ ID NO: 14) can be tolerated by linking together a plurality of LL37-derived peptides (compare PEP #55 to PEP #51 in Table 7). PEP #55 includes a pair of LL37-derived sequences that are palindromic: the N-terminally positioned LL37-derived sequence corresponds to residues 15-29 of LL37 (or PEP #36 with further truncations of 2 amino acids from the N-terminus plus 8 amino acids from the C-terminus—a total of 10 amino acids deleted), and the C-terminally positioned LL37-derived sequence corresponds to the inverse of the N-terminally positioned sequence. Importantly, the palindromic arrangement of these sequences is not considered a requirement for enhancing delivery, but instead evidences that shorter LL37-derived sequences (e.g. PEP #36 further truncated by up to 10 amino acids) enhance delivery when chained together and that the inverse of the LL37-derived sequences (e.g. SEQ ID NO: 111 and truncations thereof of up to 10 amino acids deleted from the N- and/or C-termini) are also useful for enhancing delivery of an antibody or antibody-payload conjugate.

Table 7 includes a column specifying the standard state surface area of hydrophobic residues ($sssA_H$; see Rose et al., 1995, Science, 229:834-838) calculated as the sum of the per residue standard state surface area for each hydrophobic residue within residues 13-37 of full length LL37 (i.e. calculated for PEP #36 residues; SEQ ID NO: 14 or its inverse, SEQ ID NO: 111). The calculated $sssA_H$ value for peptides that showed any level of delivery enhancement was observed to be as low as 837 Å$^2$ (see PEP #42 in Table 7), but the $sssA_H$ for peptides with strong delivery enhancement (i.e. "++" or "+++" in Table 7) was observed to be greater than 1400 Å$^2$ and the $sssA_H$ value was greater 1900 Å$^2$ for peptides with the same level of delivery enhancement as full length LL37. This data indicates that a minimum level of hydrophobic surface area is required for optimal delivery enhancement activity. Notably, not all peptides with greater than 1400 Å$^2$ or even 1900 Å$^2$ enhanced delivery at all, so a combination of sequence similarity (as defined in this application) and minimum $sssA_H$ is necessary for a functional LL37-derived peptide.

Table 7 also includes several LL37-derived peptides that include substitutions of LL37 residues (i.e. variants of LL37). PEP #48 (SEQ ID NO: 74) retains the highest delivery enhancement (+++), and includes an N-terminal deletion of 5 residues, retains central core residues 13-29 (of SEQ ID NO: 1) with a substitution of both a negatively charged core residue (Glu at position 16 of SEQ ID NO: 1) and a positively charged core residue (Lys at position 25 of SEQ ID NO: 1) to hydrophobic residues (Phe), and deletion/replacement of 5 C-terminal residues at positions 33-37 of SEQ ID NO: 1) to hydrophobic residues (namely to Met-Met-Trp-Leu-Leu or SEQ ID NO: 96). As a control, the C-terminal replacement residues grafted at the C-terminus of PEP #48 were tested as a peptide in isolation of LL37-derived residues (see PEP #47) and were confirmed to not enhance antibody delivery to target cells alone. This result shows that delivery enhancement is retained with at least two non-conservative mutations of the central core residues.

Substitution of 6 positively charged arginines and lysines to polar uncharged glutamines (at positions 8, 18, 19, 23, 29, and 34) as shown by PEP #49 (SEQ ID NO: 75) abolished the antibody delivery enhancement. In contrast, substitution of the same arginines and lysines (at position 8, 18, 19, 23, 29, and 34) to neutral and smaller alanines as shown by PEP #50 (SEQ ID NO: 76) resulted in a decrease in, but not abrogation of, delivery enhancement compared to full length LL37.

Figure 26A:
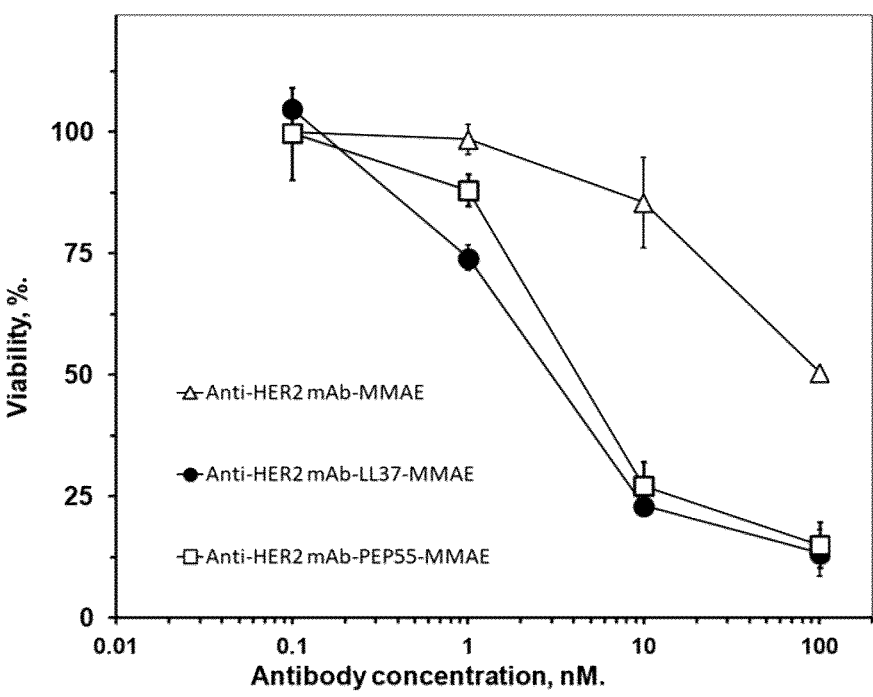
FIGS. 26A and 26B show two graphs comparing viability of RT4V6 cells (human bladder carcinoma cell line with low-to-medium level of HER2+.
Figure 26B:
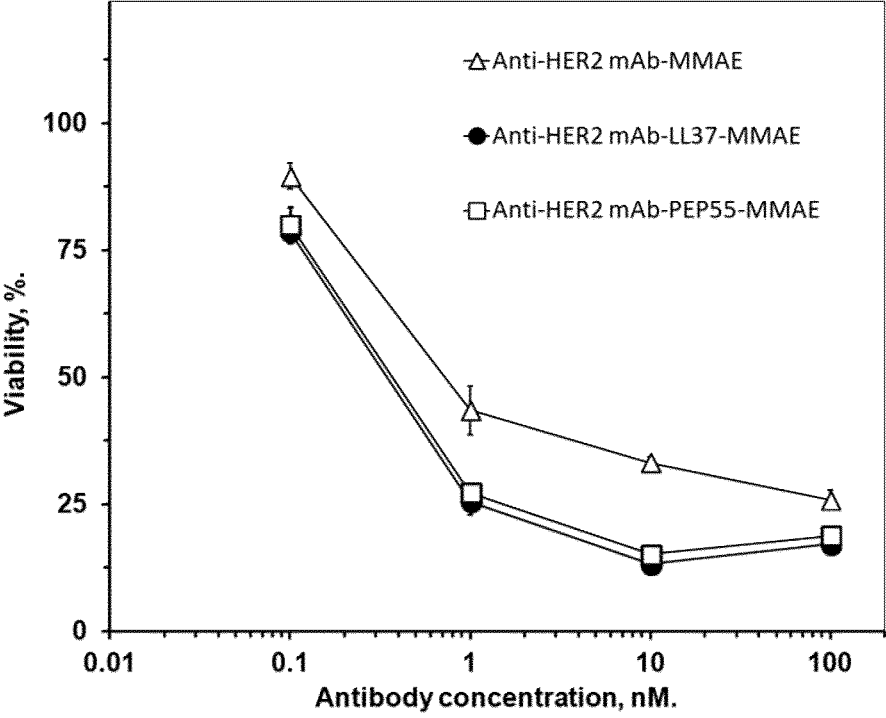
Figure 26C:
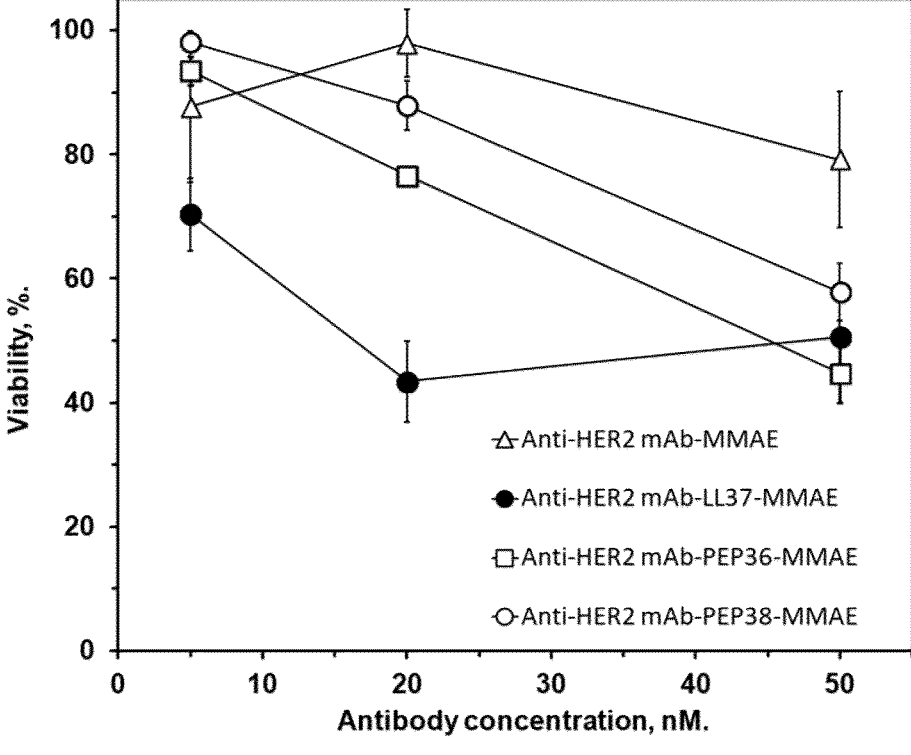
FIG. 26C shows a graph comparing viability of T47D cells (human breast cancer cell line with low level of HER2+) after treatment with anti-HER2 ADC (MMAE) (i.e. anti-HER2 mAb-MMAE), or anti-HER2 ADC (MMAE) conjugated to LL37 (i.e. anti-HER2 mAb-LL37-MMAE), LL37 derivative PEP36 (i.e. anti-HER2 mAb-PEP36-MMAE) or LL37 derivative PEP38 (i.e. anti-HER2 mAb-PEP38-MMAE).

As shown in FIGS. 26A to 26C, PEP #55 (SEQ ID NO: 77), PEP #36 (SEQ ID NO:14) and PEP #38 (SEQ ID NO:16) were further tested in the context of an antibody-drug conjugate (ADC). As shown in FIGS. 26A and 26B, PEP #55 was observed to strongly enhance ADC killing of RT4V6 cells (Panel A) and OVCAR3 cells (Panel B) cancer cells when conjugated to anti-HER2 ADC (MMAE) comparably to full length LL37. The killing efficiency of the anti-HER2 mAb drug conjugates were analyzed by measuring the cell viability (i.e. XTT assay) after treating/incubating the cells with antibody-drug conjugate for 72 hours in a 37 degree C. tissue culture incubator.

Similarly, FIG. 26C shows that both PEP #36 and PEP #38, each of which is shown in Table 7 to provide ++ level of delivery enhancement, enhanced the anti-HER2 mAb-MMAE drug conjugate to kill T47D cells (human breast cancer cell line with low level of HER2 on the cell surface). Accordingly, a ++ level of delivery enhancement is sufficient in the context of an ADC.

TABLE 7

| Anti-HER2 mAb delivery efficiency using LL37-derived peptide constructs | | | |
|---|---|---|---|
| Name | Sequence (N- to C- terminus) | Delivery efficiency | Total $sssA_{H}$, square Ångstrom |
| PEP#6 (LL37) | LLGDF FRKSK EKIGK EFKRI VQRIK DFLRN LVPRT ES | +++ | (1938.7) |
| PEP#35 | LLGDF FRKSK EKIGK EFKRI VQRIK | + | 1018.4 |
| PEP#36 | IGKEF KRIVQ RIKDF LRNLV PRTES | ++ | (1938.7) |
| PEP#37 | LLGDF FRKSK EKIGK EFKR | NI | (492) |
| PEP#38 | IVQRI KDFLR NLVPR TES | ++ | 1446.8 |
| PEP#39 | LLGDF FRKSK EKI | NI | (362) |
| PEP#40 | IGKEF KRIVQ RI | + | 1018.4 |
| PEP#41 | KDFLR NLVPR TES | NI | 920.3 |
| PEP#42 | KSKEK IGKEF KRIVQ | + | 837.4 |
| PEP#43 | RIKDF LRNLV PRTES | NI | 1096.3 |
| PEP#47 | MMWLL | NI | 1059.3 |
| PEP#48 | FRKSK EKIGK FFKRI VQRIF DFLRN LVMMW LL | +++ | 3162.1 |
| PEP#49 | LLGDF FRQSK EKIGK EFQQI VQQIK DFLQN LVPQT ES | NI | (1938.7) |
| PEP#50 | LLGDF FRASK EKIGK EFAAI VQAIK DFLAN LVPAT ES | + | (2592) |
| PEP#51 | KEFKR IVQRI KDFLR | NI | 1165 |
| PEP#55 | KEFKR IVQRI KDFLR GGGGS RLFDK IRQVI RKFEK G | +++ | 2330.4 |
| PEP#58 | VQRIK | NI | 345.5 |
| PEP#59 | IVQRI KD | NI | 691 |
| PEP#60 | KRIVQ RIKDF L | + | 942.4 |
| PEP#61 | EFKRI VQRIK | NI | 749.3 |
| PEP#62 | VQRIK DFLRN | NI | 761.4 |
| PEP#63 | EKIGK EFKRI VQRIK DFLRN | + | 1598.8 |
| PEP#64 | EFKRI VQRIK DFLRN LVPRT | + | 1669.6 |

TABLE 7-continued

Anti-HER2 mAb delivery efficiency using LL37-derived peptide constructs

| Name | Sequence (N- to C- terminus) | Delivery efficiency | Total sssA$_{H,}$ square Ångstrom |
|---|---|---|---|
| PEP#66 | GS IGKEF KRIVQ RIKDF LR | ++ | 1434.3 |
| PEP#94 | LLGDF FRKSK EKIGK EFKRI VQRIK DFLRN LVPRT ESC | +++ | (1938.7) |

+++ Same as LL37
++ Solid enhancement in delivery, but at lower efficiency than LL37
+ Small, but noticeable improvement over anti-HER2 mAb alone
NI No improvement over anti-HER2 mAb alone
Note#1:
All peptides listed in this table had two glycine residues added to the N-terminus for conjugation to the antibody.
Note#2:
Total sssAH (standard state surface area for hydrophobic residues) is the sum of the per residue sssA for each hydrophobic residue that is part of the central core hydrophobic patch (see., Rose et al., 1995, Science, 229:834).
Note#3:
For the calculated total sssAH values in bracket, only the amino acids beginning at residue #13 of LL37 (SEQ ID NO: 1) were included in the surface area calculation.

LL37 is reported to function as of an antimicrobial peptide. Antimicrobial peptides are active against bacteria, fungi and many enveloped and nonenveloped viruses. In humans, antimicrobial peptides are also called defensins (i.e., defensive peptides). Cells of the immune system contain these peptides to assist in killing phagocytosed bacteria, for example in neutrophil granulocytes and almost all epithelial cells. Most defensins function by binding to the microbial cell membrane, and, once embedded, forming pore-like membrane defects that allow efflux of essential ions and nutrients. Defensins or antimicrobial peptides are reported to act mainly by disrupting the structure of bacterial cell membranes and are found in many compartments of the body. Defensins are 18-45 amino acids in length, and includes six (in vertebrates) to eight conserved cysteine residues. In contrast, LL37 lacks cysteine residues, making LL37 the most usable defensin from a manufacturing and antibody manufacturing perspective.

LL37 does not share sequence similarity with other defensins. Nevertheless, given that LL37 shares defensing/antimicrobial function with other defensins, other peptide defensins were tested to determine if the surprising antibody delivery enhancement of LL37 is a common feature for defensins. Table 8 (below) shows no improvement in anti-HER2 mAb delivery to the target cell delivery for any antimicrobial peptide or defensin other than LL37, suggesting that strong/efficient target cell delivery of LL37 is unique (i.e., not generally applicable to all antimicrobial peptides), and is dependent to a certain extent on the structure of LL37 as indicated in Table 7 (above).

TABLE 8

Anti-HER2 mAb delivery efficiency using antimicrobial peptides

| Name | Sequence (N- to C- terminus) | Delivery efficiency |
|---|---|---|
| PEP#6 (LL37) | GG LLGDF FRKSK EKIGK EFKRI VQRIK DFLRN LVPRT ES | +++ |
| PEP#86 | GGS VFQFL GRIIH HVGNF VHGFS HVF | NI |
| PEP#98 | YSMEH FRWGK PV | NI |

TABLE 8-continued

Anti-HER2 mAb delivery efficiency using antimicrobial peptides

| Name | Sequence (N- to C- terminus) | Delivery efficiency |
|---|---|---|
| PEP#99 | RAIGG GLSSV GGGSS TIKY | NI |
| PEP#102 | DHYNC VSSGG QCLYS ACPIF KIQGT CYRGK AKCCK | NI |
| PEP#104 | VCSCR LVFCR RTELR VGNCL IGGVS FTYCC TRV | NI |

+++ Same as LL37
++ Solid enhancement in delivery, but at lower efficiency than LL37
+ Small, but noticeable improvement over anti-HER2 mAb alone
NI No improvement over anti-HER2 mAb alone
Note:
All peptides listed in this table had two glycine residues added to the N-terminus for conjugation to the antibody.

Experimental Procedures for Examples in Example 5 and Tables 7 and 8

Cloning, expression and purification of Z-GFP: The expression plasmid for Z-GFP was made from the bacterial expression plasmid encoding the structural gene of Z-RFP. Using the forward and reverse oligonucleotide primers (SEQ ID NOs: 10 and 11, respectively), the GFP structural gene was PCR amplified and sub-cloned. The expression plasmid encoding the Z-GFP was created. The sequence was confirmed by sequencing analysis of the entire Z-GFP structural gene (SEQ ID NO: 12). Z-GFP is highly expressed in E. coli Rosetta II (DE3) in LB media following induction with IPTG and overnight incubation at room temperature (18 degree Celsius). The bright green fluorescent E. coli cells containing the expressed Z-GFP was harvested, and lysed by sonication (50% duty cycle per pulse, do the 30-seconds sonication pulse for 10 times, and always cool the sonicator probe on ice between pulses). The lysate was clarified by centrifugation (15,000×g, 60 minutes, 4 degree Celsius) to remove insoluble cell debris. The clear supernatant containing the expressed Z-GFP was isolated on a Nickel-NTA chromatography resin, and was purified using an imidazole elution gradient. Sample fractions containing the majority of Z-GFP were combined and dialyzed in 20 mM Tris-HCl (pH 8.0) and 160 mM NaCl overnight. The buffer-exchanged Z-GFP was concentrated in a centrifugal diafiltration device to finalize the purification. High purity Z-GFP (>95% purity as judged from SDS-PAGE with Coomassie Blue staining) was obtained using this method.

Anti-HER2 mAb-Peptide production: Anti-HER2 mAb was produced using the same procedure as described above. LL37 and LL37-derived peptides were produced synthetically with two additional N-terminal glycine residues (e.g. as shown in SEQ ID NO:2 compared to SEQ ID NO:1) to enable the sortase reaction. The LL37-derived peptides (PEP #35 to #43, SEQ ID NOs: 13-21) were all dissolved at 10 mg/ml in phosphate buffer saline (PBS) at room temperature, sterile-filtered, and stored at −20° C. freezer. PEP #48 (SEQ ID: 74), PEP #49 (SEQ ID No: 75), and PEP #60 (SEQ ID NO: 105) were dissolved in 20% (v/v) acetonitrile in PBS. PEP #47 (SEQ ID NO: 96), PEP #86 (SEQ ID NO: 78), PEP #98 (SEQ ID NO: 79), PEP #99 (SEQ ID NO: 80), PEP #102 (SEQ ID NO: 82), and PEP #104 (SEQ ID NO: 84) were dissolved in DMSO. PEP #50 (SEQ ID No: 76), PEP #51 (SEQ ID No: 97), PEP #55 (SEQ ID No: 77), PEP #58 (SEQ ID No: 103), PEP #59 (SEQ ID No: 104), PEP #61 (SEQ ID No: 106), PEP #62 (SEQ ID No: 107), PEP #63 (SEQ ID No: 108), PEP #64 (SEQ ID No: 109), PEP #66 (SEQ ID No: 110), and PEP #94 (SEQ ID No: 35) were all dissolved in PBS. The LL37-derived peptides and antimicrobial peptides were each linked to the sortase (SrtA) recognition sequence (LPMTGGHG) added to the C-terminus of light chain in anti-HER2 mAb. The reaction contained 360 μM of LL37-derived peptide, 40 μM equivalent of sortase recognition sequence (i.e., 20 μM of anti-HER2 mAb), 1 μM sortase, 1 mM TCEP, and 5 mM CaCl₂, in a buffered solution (20 mM Tris-HCl, pH 7.5, 150 mM NaCl). The reaction was incubated inside a 37° C. incubator for 16 hours, and then EDTA (pH 7.5) was added to 10 mM in the reaction mixture to chelate calcium and stop the reaction. A sample aliquot of reaction mixture was analyzed on SDS-PAGE to verify the peptide-linked anti-HER2 mAb (i.e., an up-shift of the light chain molecular weight from −25 kD to ~27 kD-30 kD), and greater than 95% of antibody light chain carries the covalently linked LL37-derived peptide.

Delivery assay: The following delivery assay method was used on the anti-HER2 mAbs conjugated to the PEP #6, #35, #36, #37, #38, #39, #40, #41, #42, and #43 described in Table 7. 100 nM of anti-HER2 mAb (or the peptide-linked anti-HER2 mAb) and 100 nM of Z-GFP was added to T47D cells sub-cultured to 80% confluency level in 48-well plates, and incubated at 37 degree C. incubator for 4 hours. The plates were then removed from the incubator, and the culturing media was removed from the adherent cells. The adherent cells were washed gently with an equal volume of ice-cold PBS. Then, the PBS wash was replaced 250 μl of fresh PBS for fluorescence microscope imaging. The delivery of anti-HER2 mAb was determined qualitatively by estimating the green fluorescence intensity emitted from Z-GFP bound to anti-HER2 mAb.

The delivery assay for anti-HER2 mAb conjugated to peptides PEP #6, #47, #48, #49, #50, #51, #55, #58, #59, #60, #61, #62, #63, #64, #66, #94, shown in Table 7, were carried out similarly, but with a secondary antibody, Goat anti-human IgG-AlexaFluor 488 in place of Z-GFP, for fluorescence detection of the cell-bound anti-HER2 mAb. Briefly, 100 nM of anti-HER2 mAb (or anti-HER2 mAb-peptide conjugates) were added to the target cells grown to about 60-70% confluency level adherent to the bottom well surfaces in the 48-well culturing plates, and incubated at 37 degree Celsius tissue culture incubator for 3 hours. At the end of incubation, the adherent target cells were washed twice with ice-cold PBS, fixed with 2% (w/v) formaldehyde in PBS at room temperature for 15 minutes, and washed twice with PBS at room temperature. The fixed adherent target cells were then permeabilized with 0.05% (v/v) Tween-20 in PBS at room temperature for 15 minutes. The permeabilized cells were then incubated with 5% (v/v) FBS, 0.05% (v/v) Tween-20 in PBS at 37 degree Celsius incubator for 30 minutes. The secondary antibody, Goat anti-human IgG-AlexaFluor 488, was added to 5 μg/ml in 5% (v/v) FBS, 0.05% (v/v) Tween-20 in PBS, and incubated with the treated target cells at 37 degree Celsius incubator for 30 minutes. After incubation, the labelled cells were washed twice with PBS, and stored in storage buffer [5% (v/v) FBS in PBS] at 4 degree Celsius until fluorescence microscope imaging. The delivery of mAb and mAb-LL37-derived peptides were determined qualitatively by estimating the green fluorescence intensity emitted from the AlexFluor488-labelled secondary antibody bound to mAb or mAb-LL37-derived peptides.

The delivery assay for anti-HER2 mAb conjugated to antimicrobial peptides, shown in Table 8, was carried out using the following method. 100 nM of anti-HER2 mAb (or the peptide-linked anti-HER2 mAb) and 100 nM of Z-GFP was added to the T47D cells sub-cultured to 80% confluency level in 48-well plates, and incubated at 37° C. incubator for 4 hours. The plates were then removed from the incubator, and the culturing media was removed from the adherent cells. The adherent cells were washed gently with an equal volume of ice-cold PBS. Then, the PBS wash was replaced 250 μl of fresh PBS for fluorescence microscope imaging. The delivery of anti-HER2 mAb was determined qualitatively by estimating the green fluorescence intensity emitted from Z-GFP bound to anti-HER2 mAb.

Experimental Procedures for Examples in FIG. 26

Anti-HER2 mAb, and the LL37-linked antibody were produced using the same procedure as provided above in Example 1. The MMAE-linked antibodies were produced by following the same method as provided above in Example 1.

Anti-HER2 mAb-MMAE and anti-HER2 mAb-PEP6-MMAE were produced using the same methods as provided in Example 2 above.

Anti-HER2 mAb-PEP55-MMAE, anti-HER2 mAb-PEP36-MMAE, anti-HER2 mAb-PEP38-MMAE: The anti-HER2 mAb-PEP #55, anti-HER2 mAb-PEP #36, and anti-HER2 mAb-PEP #38 were produced using the same method as described above for in Table 7. The MMAE-linked anti-HER2 mAb-PEP #55, -PEP #36, and -PEP #38 were produced by reacting the VcMMAE to the TCEP-reduced anti-HER2 mAb-PEP #55, -PEP #36, and -PEP #38, respectively, and the method of conjugation and purification were the same as provided in Example 2 above.

Cell viability assay with XTT was performed using the same method as in Example 3 (above).

Example 6. Ratio of LL37-Derived Peptides Per Antibody Monomer

LL37 enhances antibody delivery and improves the targeted killing efficiency with anti-HER2 antibodies and ADCs. In the foregoing examples, all LL37-linked antibodies have the LL37 peptide covalently linked to both light chains or to both heavy chains at a specific amino acid sequence, retaining/maintaining the symmetrical and homodimeric mAb structures of an antibody monomer.

Figure 27A:
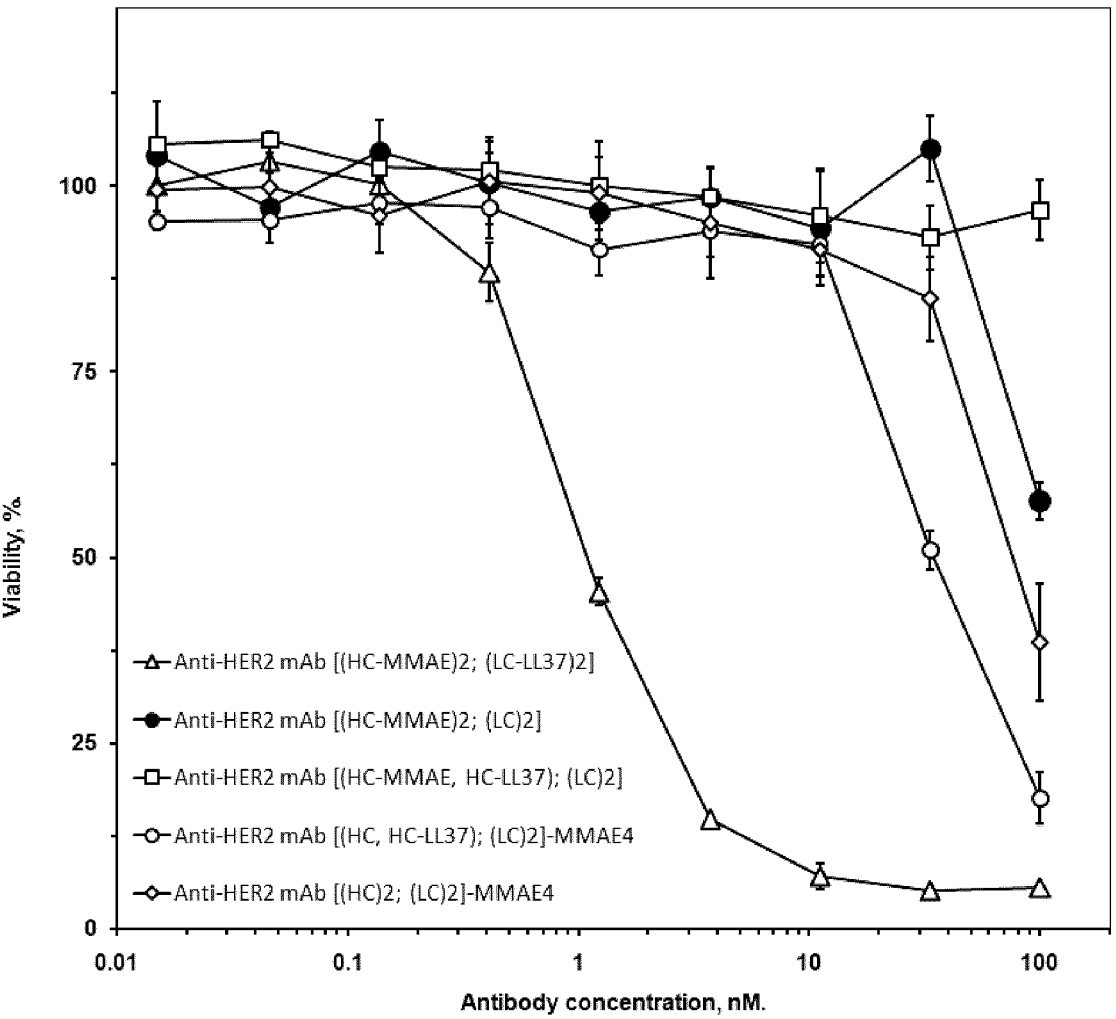
FIGS. 27A, 27B and 27C show the viabilities of Rt4v6 cells (FIG. 27A), PC3 cells (FIG. 27B), and OV CAR3 cells (FIG. 27C), respectively, after 72 hrs treatment with the HER2-specific ADCs that have one LL37 covalently linked in a mAb (i.e., anti-HER2 nAB [(HC, HC-LL37); (LC)2]-MMAE4, and anti-HER2 mAb [(HC-MMAE, HC-LL37)
Figure 27B:
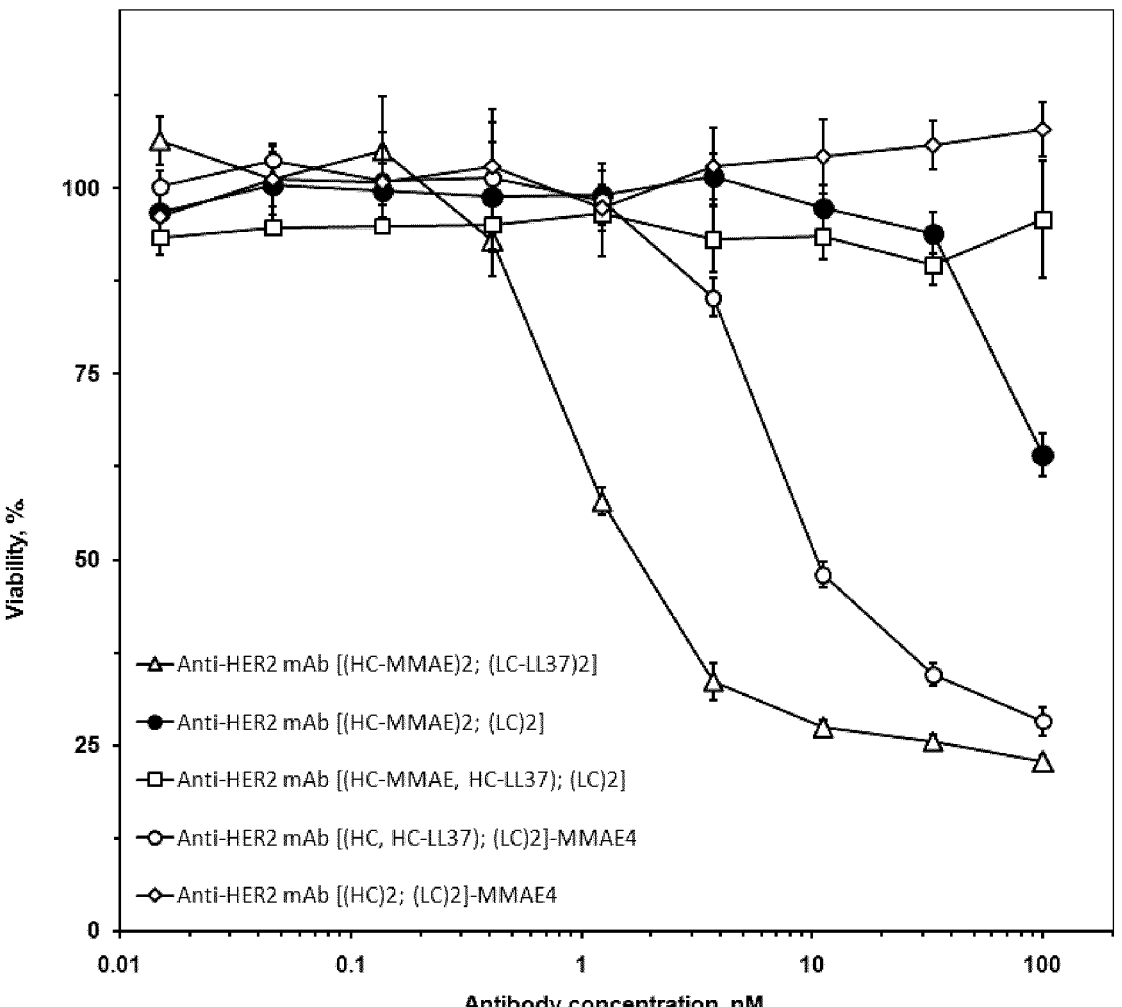
Figure 27C:
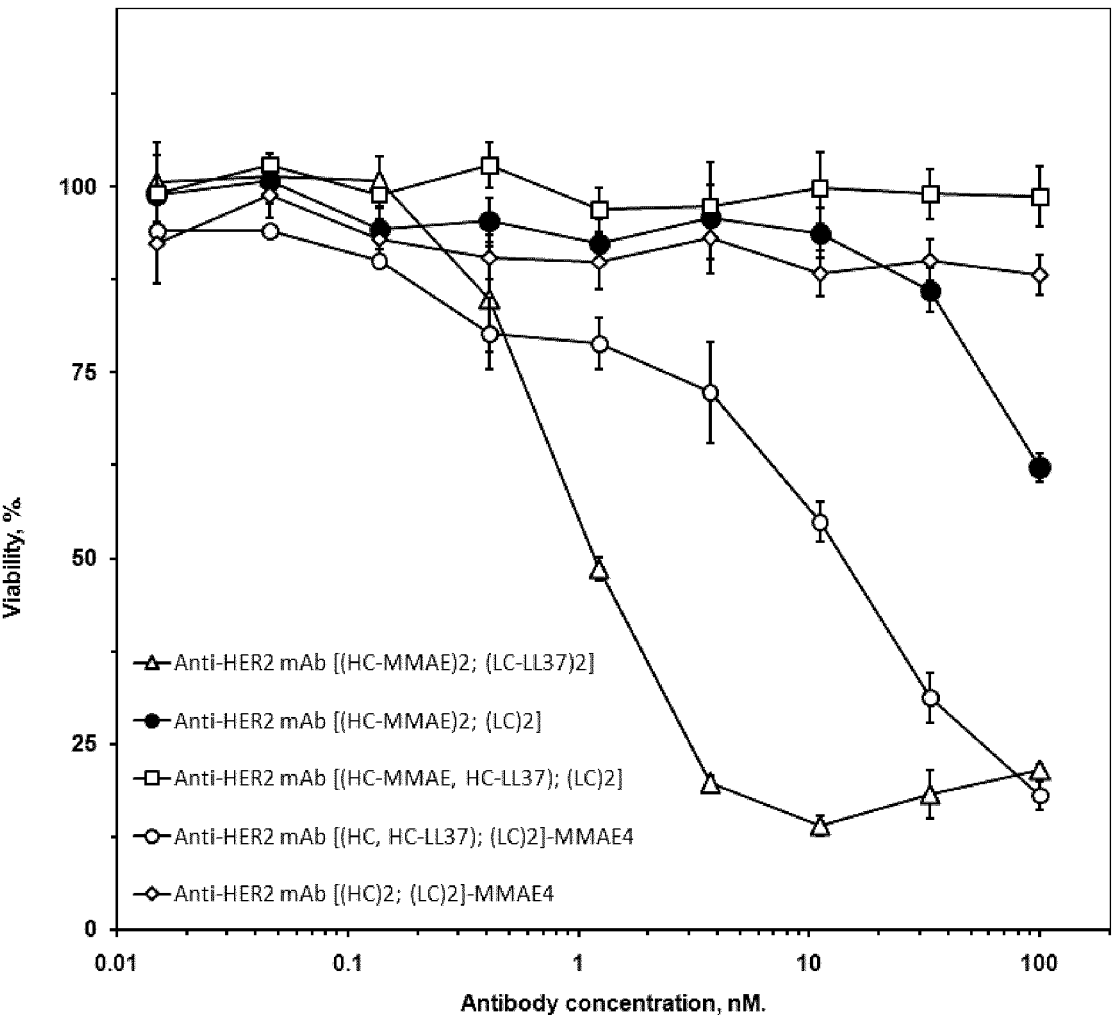

FIGS. 27A, 27B and 27C show that an anti-HER2 ADC with a single LL37 peptide per antibody monomer does not enhance delivery as well as the ADC with two LL37 peptides per antibody monomer, and the anti-HER2 ADC with one LL37 covalently linked to one of the heavy chains in the antibody monomer (regardless of the number of MMAE molecules they carry) are less efficient than the double/dual LL37-linked HER2-specific ADC that has LL37 covalently linked to both light chains in the antibody monomer.

FIG. 28 shows that an anti-HER2 antibody with four LL37 peptides per monomer enhances delivery of the antibody even more than the anti-HER2 antibody with only two LL37 peptides per monomer, and further confirms that the anti-HER2 antibody with two LL37 peptides per monomer enhances delivery of the antibody better than the anti-HER2 antibody with only one LL37 peptide per antibody monomer. It was observed that the antibody with four covalently linked LL37 peptides per monomer was much more insoluble than antibodies with four LL37 peptides per monomer. Antibodies with only two LL37 peptides per monomer are therefore preferred over antibodies with four LL37 peptides for many applications.

Referring to FIGS. 27A, 27B, 27C and 28, it is noted that the two or four LL37 peptides per antibody monomer in these examples are symmetrical in geometry and orientation in the antibody monomer structure, which may be a preferred orientation (or one example of a preferred orientation) for optimal delivery enhancement when multiple LL37 peptides are attached (at multiple sites on the antibody monomer structure) by maximizing distance between the LL37 peptide groups and permitting multimerization of LL37-conjugated antibodies/ADCs at target cell surfaces (see Example 11).

This example also demonstrates attachment of LL37 peptides (or LL37-derived peptides) can be attached and covalently linked to the glycosylations in the Fc fragment of an antibody or ADC.

Experimental Procedures for FIGS. 27A, 27B and 27C

Production of Anti-HER2 mAb [(HC-MMAE)2, (LC)2], and anti-HER2 mAb [(HC-MJAE)2, (LC-LL37)2]. Anti-HER2 mAb [(HC-azide)2, (LC)2] was generated from Anti-HER2 mAb by following the methods described by Boeggeman et al. 2009 Bioconjugate Chem., 20, 1228 with the following modifications that create two reactive azides per mAb. Briefly, anti-HER2mAb was buffer-exchanged from PBS to 25 mM Tris-HCl (pH 8.0). 16 units of Endoglycosidase, Endo S (NEB Catalog Number P0741), was added to 4 mg of anti-HER2 mAb to partially trim the glycosylation site in the heavy chain at 37 degree C. for 4 hours (see., Collin and Olsen, 2001, EMBO J., 20, 3046). The completed reaction mixture, which was verified by a down-shifted heavy chain band on SDS-PAGE, was buffer-exchanged to 10 mM MnCl2 and 25 mM Tris-HCl (pH 8.0) and concentrated to about 10 mg/ml in a 30 kD MWCO concentrator. 0.4 mM of UDP-GalNAz (Carbosynth Catalog Number NU30954) and 0.1 mg/ml of GalT (R&D System Catalog Number 7040-GT) were added to covalently link the Gal-NAz to the trimmed glycosylation site in the heavy chain of anti-HER2 mAb (~10 mg/ml) at 30 degree C. for 16 hours (see., Ramakrishnan and Qasba, 2002, J. Biol. Chem. 277, 20833). The Anti-HER2 mAb [(HC-azide)2, (LC)2] was purified on Protein A affinity chromatography, and then dialyzed into PBS. DBCO-PEG12-MMAE (Click Chemistry Tools, Catalog Number 1226-5) was added to the azide-modified anti-HER2 mAb at 25 degree C. overnight. The Anti-HER2 mAb [(HC-MMAE)2, (LC)2] was purified on PD10 desalting column (Sephadex G25) equilibrated in PBS. The final product of anti-HER2 mAb [(HC-MMAE)2, (LC)2] was verified on SDS-PAGE (i.e., upshift of the heavy chain band). LL37 was ligated to the C-terminus of light chains using the sortase reaction according to the method described above. The final product of anti-HER2 mAb [(HC-MMAE)2, (LC-LL37)2] was verified on SDS-PAGE. LL37 was covalently linked to both light chains in the mAb monomer structure.

Production of Anti-HER2 mAb [(HC-MJAE, HC-LL37), (LC)2], and Anti-HER2 mAb [(HC, HC-LL37), (LC2)]-MJAE4. Anti-HER2 mAb [(HC-azide)2, (LC)2] was generated from anti-HER2 mAb as described above. DBCO-PEG4-Maleimide-LL37 was made from reacting 2.5 mM of DBCO-PEG4-Maleimide (Sigma Catalog Number 760676) dissolved in DMSO to 3 mM of a LL37-Cys peptide (SEQ ID No. 35) dissolved in PBS in a thiol-maleimide reaction incubated overnight (i.e., 16 hours) at 4 degree C. The reaction mixture was used directly as a source of DBCO-PEG4-Maleimide-LL37 (concentration of 2.5 mM), and reacted with anti-HER2 mAb [(HC-azide)2, (LC)2] to produce anti-HER2 mAb [(HC, HC-LL37), (LC)2]. On SDS-PAGE, about 50% of heavy chain has the covalently linked DBCO-PEG4-Maleimide-LL37, corresponding to 1 LL37 per anti-HER2 mAb (i.e. one LL37 per antibody monomer). Anti-HER2 mAb [(HC, HC-LL37), (LC)2] was purified on Protein A chromatography, and then dialyzed into PBS. For production of anti-HER2 mAb [(HC-MMAE, HC-LL37), (LC)2], the purified anti-HER2 mAb [(HC, HC-LL37), (LC)2] with one unreacted azide was further treated with DBCO-PEG12-MMAE (Click Chemistry Tools, Catalog Number 1226-5) to produce anti-HER2 mAb [(HC-MMAE, HC-LL37), (LC)2]. The MMAE content was estimated from its UV absorbance at 250 nm and 280 nm, and verified to have at least 1 MMAE per anti-HER2 mAb.

For production of anti-HER2 mAb [(HC, HC-LL37), (LC)2]-MMAE4, the purified anti-HER2 mAb [(HC, HC-LL37), (LC)2] was partially reduced with 2 molar equivalent of TCEP to generate 4 free thiols from the main chain cysteines in the mAb using the method as described above, and reacted with maleimide-Vc-MMAE (Medchem Express Catalog Number HY-15575) to produce the anti-HER2 mAb [(HC, HC-LL37), (LC)2]-MMAE4. The final product was purified and buffer exchanged into PBS on PD-10 desalting chromatography (Sephadex G25). The MMAE content was determined from its UV absorbance at 250 nm and 280 nm, and verified to have about 4 MMAE per anti-HER2 mAb.

For production of anti-HER2 mAb [(HC)2, (LC)2]-MMAE4, the anti-HER2 mAb was partially reduced with 2 molar equivalent of TCEP to generate 4 free thiols from the main chain cysteines in the mAb using the method as described above, and reacted with maleimide-Vc-MMAE (Medchem Express Catalog Number HY-15575) to produce the anti-HER2 mAb-MMAE4, which is also anti-HER2 mAb [(HC)2, (LC)2]-MMAE4. The final product was purified and buffer exchanged into PBS on PD-10 desalting chromatography (Sephadex G25). The MMAE content was determined from its UV absorbance at 250 nm and 280 nm, and verified to have about 4 MMAE per anti-HER2 mAb.

Cell viability assay was carried out with XTT as described above.

Experimental Procedures for FIG. 28

Z-FRP, and anti-HER2 mAb [(HC)2; (LC-LL37)2], which is also labeled as anti-HER2 mAb-LL37 (i.e., HC, LC-LL37), were produced by following the same method as described (above).

Production of Anti-HER2 mAb [HC, HC-LL37; (LC)2]. Anti-HER2 mAb [HC, HC-LL37; (LC)2], was generated from Anti-HER2 mAb by following the methods described by Boeggeman et al. 2009 Bioconjugate Chem., 20, 1228 with the following modifications that create two reactive azides per mAb. Briefly, anti-HER2 mAb was buffer-exchanged from PBS to 25 mM Tris-HCl (pH 8.0). 16 units of Endoglycosidase, Endo S (NEB Catalog Number P0741), were added to 4 mg of anti-HER2 mAb to partially trim the glycosylation site in the heavy chain at 37 degree C. for 4 hours (see., Collin and Olsen, 2001, EMBO J., 20, 3046). The completed reaction mixture, which was verified by a down-shifted heavy chain band on SDS-PAGE, was buffer-exchanged to 10 mM MnCl2 and 25 mM Tris-HCl (pH 8.0) and concentrated to about 10 mg/ml in a 30 kD MWCO concentrator. 0.4 mM of UDP-GalNAz (Carbosynth Catalog Number NU30954) and 0.1 mg/ml of GalT (R&D System Catalog Number 7040-GT) were added to covalently link the GalNAz to the trimmed glycosylation site in the heavy chain of anti-HER2 mAb (~10 mg/ml) at 30 degree C. for 16 hours (see., Ramakrishnan and Qasba, 2002, J. Biol. Chem. 277, 20833). The Anti-HER2 mAb [(HC-azide)2; (LC)2] was purified on Protein A affinity chromatography, and then dialyzed into PBS. DBCO-PEG4-MAL-LL37 was made by reacting 2.5 mM of DBCO-PEG4-Maleimide (Sigma Catalog Number 760676) dissolved in DMSO to 3 mM of LL37-Cys (SEQ ID NO: 35) dissolved in PBS for 16 hours at 4 degree C., and the completed reaction mixture was used directly as a source of DBCO-PEG4-MAL-LL37 (~2.5 mM) without purification. 400 μM of the crude DBCO-PEG4-MAL-LL37 (~2.5 mM stock) was added to 3 mg/ml of the anti-HER2 mAb [(HC-azide)2; (LC)2] at 25 degree C. for overnight, and the completed reaction mixture was verified on SDS-PAGE, and about 50% of heavy chain has the covalently linked LL37. The anti-HER2 mAb [HC, HC-LL37; (LC)2] was purified on a Protein A chromatography column, and buffer-exchanged in PBS. The final product of anti-HER2 mAb [HC, HC-LL37; (LC)2] was verified on SDS-PAGE, and 50% of heavy chain had the covalently linked LL37.

Production of Anti-HER2 mAb [(HC-LL37)2, (LC-LL37) 2]. The structural gene encoding the anti-HER2 mAb heavy chain with C-terminal (G4S)2-LPMTGGHHHHHH (SEQ ID NO: 117) was PCR amplified from the anti-HER2 mAb heavy chain (SEQ ID NO: 8) plasmid template with forward and reverse primers (SEQ ID NO: 118 and 119), and subcloned into the EcoRI-BamHI sites of pTT5 plasmid vector. The structural gene encoding the anti-HER2 mAb light chain with C-terminal (G4S)2-LAETGGHHHHHH (SEQ ID NO: 120) was PCR amplified from the anti-HER2 mAb light chain (SEQ ID NO: 9) plasmid template with forward and reverse primers (SEQ ID NO: 121 and 122), and subcloned into the EcoRI-BamHI sites of pTT5 plasmid vector. Expression of the above anti-HER2 mAb (SEQ ID NOs: 123 and 124) with sortase recognition sequences in heavy and light chains was done by transient transfection co-delivering both the heavy and light chains (SEQ ID NOs: 117 and 120) in pTT5 plasmids (mixed in an optimized ratio) into CHO cells. At the end of cell growth, the culture media was harvested, and the secreted antibody was purified (purity of >99%) from the clear supernatant of the culture media by Protein A binding chromatography in phosphate buffered saline (PBS). Anti-HER2 mAb [(HC-LL37)2; (LC-LL37)2] was made by sortase-catalyzed ligation to LL37 peptide (SEQ ID NO: 2) in a reaction mixture that contains 720 μM of GG-LL37 peptide (SEQ ID NO: 2), 80 μM of sortase recognition sequence (i.e., equivalent to 20 μM of Anti-HER2 mAb), 1 μM sortase that is specific for LPMTG sequence, 1 μM sortase that is specific for LAETG sequence, 1 mM TCEP, and 5 mM CaCl₂), in a buffered solution (20 mM Tris-HCl, pH 7.5, 150 mM NCl). The reaction was incubated inside a 37° C. incubator for 16 hours. Ligation of LL37 to both heavy and light chains were verified on SDS-PAGE (i.e., an up-shift of the light and heavy chains), and greater than 95% of antibody heavy and light chains carry the covalently linked LL37. Anti-HER2 mAb [(HC-LL37)2; (LC-LL37)2] was then purified by Protein A affinity chromatography, and buffer-exchanged to phosphate buffer saline with addition of 0.7% (w/v) CHAPS. Precipitation of anti-HER2 mAb [(HC-LL37)2; (LC-LL37)2] persisted even after addition of CHAPS and salt (i.e., increase in ionic strength). The purity of Anti-HER2 mAb [(HC-LL37)2, (LC-LL37)2] was greater than 95% as verified on SDS-PAGE.

Delivery assay: Anti-HER2 mAbs and equimolar amount of Z-RFP (prepared at 4 nM, 20 nM, and 100 nM), were added to Rt4v6 cells sub-cultured to 80% confluency level in 48-well plate, and incubated at 37° C. incubator for 3 hours. The plate was then removed from the incubator, and the culturing media was removed from the adherent Rt4v6. First, the adherent Rt4v6 was gently washed twice with ice cold PBS. Cells were treated with trypsin, and neutralized with DMEM+10% FBS. Cells were washed with FACS buffer (2% FBS, 0.05% sodium azide, 2 mM EDTA in PBS), and stained with e780 viability dye for 30 minutes at 4° C. Cells were washed twice with FACS buffer (2% FBS, 0.05% sodium azide, 2 mM EDTA in PBS), and resuspended in FACS buffer for analysis. The FACS samples were stored on ice until flow cytometry analysis on a LSRII-561 machine. The delivery of anti-HER2 mAbs was quantitated by measuring the red fluorescence intensity (i.e., PE-Texas Red color channel in the FACS detector) emitted from Z-RFP bound to anti-HER2 mAb.

Example 7. Rapid Delivery of Antibody Drug by LL37

FIG. 29 shows that the LL37-enhanced delivery of antibody is a rapid process, evidenced by a rapid decay in Z-RFP-bound antibody fluorescence shortly after incubation begins. As shown in FIG. 29 (Panel A), fluorescent signal for anti-HER2 mAb-LL37 rapidly increases in the first 30-60 minutes of incubation with the target cell BT474 (high level of HER2+) and then rapidly decays by 4 hours of incubation. FIG. 29 (Panel B) shows the same experiment with anti-EGFR mAb-LL37 and the target cell MDA-MB468. The delivery of antibody was quantitated by measuring the red fluorescence intensity (i.e., PE-Texas Red color channel in the FACS detector) emitted from Z-RFP bound to antibody mAbs.

This rapid increase and decay in antibody delivery suggests that most of the delivery was completed within 3-4 hours of administering the LL37-enhanced antibody drug to the target cells. This interpretation is consistent with timing of the enhanced killing of target cancer cells with LL37- conjugated antibodies observed in the earlier examples. For example, in 3 hours of incubation (i.e., treatment) the LL37-enhanced anti-HER2 mAb-Taxol wiped out more than 75% of OVCAR3 cells (as shown in FIG. 16). Similarly, the LL37-enhanced anti-HER2 mAb-MMAE killed ~90% of AGS cells and RT4v6 cells (as shown in FIG. 20 Panel A and B) in just 3 hours of drug incubation (i.e., treatment). FIG. 22 also shows that in just 3 hours of drug incubation, the LL37-enhanced anti-folate receptor mAb-MMAE had already wiped out ~75% of OVCAR3 cells (as shown in FIG. 22 Panel A).

Experimental Procedures for Examples in FIG. 29

Z-RFP, anti-HER2 mAb, anti-HER2 mAb-LL37, anti-EGFR mAb, anti-EGFR mAb-LL37 were produced using the same procedure as described above. Delivery assay were carried out using the same procedures as described in Example 1 above. Briefly, 100 nM of antibody and 100 nM of Z-FRP were added to their respective target cells, incubated for the specified duration of time, and analyzed by FACS. For anti-HER2 mAb and anti-HER2 mAb-LL37, the target cell is BT474 cells. For anti-EGFR mAb and anti-EGFR mAb-LL37, the target cell is MDA-MB468.

Example 8—LL37 Enhances Delivery to Other Cell Types (i.e., Non-Cancerous, Normal Cells)

LL37 also can be used to enhance specific delivery of antibody (or ADC) to other cell types (i.e., non-cancerous normal human cells, stem cells, etc. . . . ) displaying the target antigens. FIG. 30 Panel A shows a comparison of anti-HER2 mAb and the covalently linked anti-HER2 mAb-LL37 conjugate, and shows that LL37 strongly enhances the delivery of an HER2-specific antibody (i.e, anti-HER2 mAb-LL37) to HEK293 cells that display a recombinantly expressed HER2 extracellular domain. FIG. 30 Panel B shows a comparison of anti-CD30 mAb and anti-CD30 mAb:Z-RFP-LL37 complex, and shows that LL37 also strongly enhances the delivery of anti-CD30 mAb to the human induced pluripotent stem cells (iPSC). FIG. 30 Panel C shows that covalently linked anti-HER2 mAb-LL37 conjugate is more efficient than anti-HER2 mAb at delivering cytotoxic payload to isolated human fibroblast cells. FIG. 30 Panel D shows that covalently linked anti-CD20 mAb-LL37 (i.e., Ofatumumab-LL37) is more efficient than anti-CD20 mAb (i.e., Ofatumumab) at targeted delivery to CD20-positive RL cells (i.e. human B lymphoblast cells). FIG. 30 Panel E shows that covalently linked anti-CD3e mAb-LL37 (i.e., Foralumab-LL37) is more efficient than anti-CD3e mAb (i.e., Foralumab) at targeted delivery to the CD3-positive Jurkat cells.

Experimental Procedures for Examples in FIG. 30

Z-FRP, anti-HER2 mAb, anti-HER2 mAb-LL37, anti-HER2 mAb-MMAE, and anti-HER2 mAb-LL37-MMAE, were produced using the same procedure as described above.

HEK293 cells expressing the recombinant HER2 extracellular domain (ECD) were made by transfecting HEK293 with a plasmid that encodes the expression of human HER2ECD structural gene (SEQ ID NO: 128).

The structural gene sequence of Z-RFP-LL37 (SEQ ID NO: 125) is subcloned from Z-RFP (SEQ ID NO: 7) by inserting the LL37 sequence with Quick Change mutagenesis primers (SEQ ID NO: 126 and 127). The sequence was confirmed by sequencing analysis of the entire Z-RFP-LL37 structural gene (SEQ ID NO: 125).

Z-RFP-LL37 is highly expressed in *Escherichia coli* BL21(DE3) in LB media following induction with IPTG and overnight incubation at room temperature (18° C.).

The bright red fluorescent *E. coli* cells containing the expressed Z-RFP-LL37 were harvested, and lysed by sonication in a buffer that contains 40 mM Tris-HCl (pH 8.0), 1% CHAPS (w/v), 500 mM NaCl, and 2 mM beta-mercaptoethanol (50% duty cycle per pulse, 30-second sonication pulse for 10 times, cooling the sonicator probe on ice between pulses). The lysate was clarified by centrifugation (15,000×g, 60 minutes, 4° C.) to remove insoluble cell debris. The clear supernatant containing the expressed Z-RFP-LL37 was isolated on a Nickel-NTA chromatography resin, and was purified using an imidazole elution gradient. Sample fractions containing the majority of Z-RFP-LL37 were combined and dialyzed in 20 mM Tris-HCl (pH 8.0), 480 mM NaCl, and 2 mM beta-mercaptoethanol overnight. The buffer-exchanged Z-RFP-LL37 was concentrated in a centrifugal diafiltration device to finalize the purification. High purity Z-RFP-LL37 (>90% purity as judged from SDS-PAGE with Coomassie Blue staining) was obtained using this method.

Delivery assays were carried out using the same procedures as described above. Briefly, for FIG. 30 Panel A, 100 nM of antibody and 100 nM of Z-RFP were added to the HEK293 cells expressing the recombinant HER2 extracellular domain (SEQ ID No. 128), incubated for 4 hours. Culture media was removed, and the cells were gently washed with ice-cold 1×PBS. Cells were treated with trypsin, and then neutralized and resuspended with FACS buffer (1×PBS, 2% FBS, 1 mM EDTA, 0.02% sodium azide) for analysis by FACS (Texas Red channel).

For FIG. 30 Panel B, anti-CD30 mAb, Brentuximab (R&D System Catalog No. MAB9576), and equimolar number of Z-RFP or Z-RFP-LL37 were added to Gibco Episomal hiPSC cells (ThermoFisher Catalog No. A18945) at described final concentrations (i.e., 8 nM, 40 nM, and 200 nM) and incubated for 3 hours. Culture media was removed, and the cells were gently washed with 1×PBS. Cells were further washed with Versene for 3 minutes at 37 degree Celsius, and then washed and resuspended in FACS buffer (1×PBS, 2% FBS, 1 mM EDTA, 0.02% sodium azide) for analysis by FACS (Texas Red channel).

For FIG. 30 Panel C, antibody drug conjugates were added to fibroblast cells at described final concentrations, and incubated for 72 hours, Culture media was removed, and replaced with DMEM complete media. XTT-PMS solution was added to the culturing media, and incubated for 4 hours at 37 degree Celsius. Absorbance at 475 nm was measured, and % viability was calculated with respect to the cells that receive no treatment.

For FIG. 30 Panel D, Ofatumumab-LL37 was made from Ofatumumab (SEQ ID NOs: 40 and 41) in a sortase-catalyzed reaction to GG-LL37 peptide (SEQ ID NO: 2), and purified on Protein A chromatography. For cell delivery assay, Ofatumumab/Ofatumumab-LL37 and equimolar number of Z-RFP were added to RL cells at described final concentration (i.e., 0.5 nM, 5 nM, and 50 nM) and incubated for 30 minutes. The liquid suspension culture was gently spun in a microcentrifuge at 2000 rpm for 4 minutes, and the clear supernatant was removed, and the cell pellet was washed in PBS and resuspended in FACS buffer (1×PBS, 2% FBS, 1 mM EDTA, 0.02% sodium azide) for analysis by FACS (Texas Red channel).

For FIG. 30 Panel E, Foralumab-LL37 was made from Foralumab (SEQ ID NOs: 129 and 130) in a sortase-catalyzed reaction to GG-LL37 peptide (SEQ ID NO: 2), and purified on Protein A chromatography. For cell delivery assay, Foralumab/Foralumab-LL37 and equimolar number of Z-RFP were added to Jurkat cells at described final concentration (i.e, 1 nM, 10 nM, and 100 nM) and incubated for 30 minutes. The liquid suspension culture was gently spun in a microcentrifuge at 2000 rpm for 4 minutes, and the clear supernatant was removed, and the cell pellet was washed in PBS and resuspended in FACS buffer (1×PBS, 2% FBS, 1 mM EDTA, 0.02% sodium azide) for analysis by FACS (Texas Red channel).

Example 9—Dimerization of LL37

As shown in FIG. 31, size exclusion chromatography in combination with multi-angle static light scattering (SEC-MALS) analysis indicates that anti-HER2 mAb-LL37, an antibody construct with 2 symmetrical LL37 peptides per antibody monomer, forms a stable tetravalent dimer in solution with an estimated molecular size of 360-430 kD (compared to the 140-150 kD anti-HER2 mAb for a bivalent monomer). This result contrasts with the observation in Example 6 that anti-HER2 antibody with four covalently linked LL37 peptides per monomer (i.e., Anti-HER2 mAb [(HC-LL37)2, (LC-LL37)2]) has increased insolubility (i.e., precipitation) as a result of aggregation although the delivery enhancement can be significantly enhanced (see FIG. 28 and discussion in Example 6).

Experimental Procedures for Examples in FIG. 31

To determine the molecular mass distributions, size, and composition independent of column calibration by reference standards, SEC-MALS was used. Briefly, anti-HER2 mAb and the covalently conjugated anti-HER2 mAb-LL37 were buffer-exchanged and diluted to 2.0 mg/ml in D-PBS (pH 7.2) supplemented with 0.2M Arginine and 0.01% (w/v) Polysorbate 20, and spun at 20,000×g for 10 minutes at 4 degree Celcius. After preparation, 10 μl (~20 μg) of Anti-HER2 mAb and the covalently conjugated anti-HER2 mAb-LL37 were injected onto a size exclusion column, GE Healthcare Superdex200 (5×150 mm), operated at 0.25 ml/min and at 22-25 degree Celcius in an HPLC system, which is also equipped with an online multi-angle static light scattering (MALS) detector for absolute characterization of the molar mass and size of macromolecules and nanoparticles in solution. Data were acquired and processed using the ASTRA software from Wyatt Technologies.

Example 10 In Vivo Safety and Efficacy

For demonstration of in vivo safety with LL37-enhanced antibody delivery in live animals, a comparison of biodistribution was performed between anti-HER2 mAb-MMAE8 (ADC) and anti-HER2 mAb-LL37-MMAE8 (LL37-enhanced ADC) after injection in mice bearing JIMT1 xenograft tumors, which are negative for binding to HER2-specific antibody. As shown in FIG. 32 Panel A, conjugation of LL37 was not observed to significantly increase non-specific ADC delivery/effects.

For demonstration of the enhanced in vivo efficacy with LL37, a comparison of biodistribution was performed between anti-HER2 mAb-MMAE8 (ADC) and the anti-HER2 mAb-LL37-MMAE8 (LL37-enhanced ADC) after injection in live mice bearing the RT4v6 xenograft tumors, which bind to HER2-specific antibody. As shown in FIG. 32 Panel B, conjugation with LL37 more than doubles (i.e., increases by 100%) the delivery and retainment of anti-HER2 mAb to the RT4v6-grafted mice.

From the above examples, it is expected that covalently conjugating LL37 peptides to antibodies or ADCs would not negatively impact the safety of the antibodies/ADCs. In vivo toxicology experiments (as shown in FIGS. 33-37) confirmed that conjugating LL37 (2 per antibody monomer) to anti-HER2 ADC (MMAE DAR 8) did not significantly change the safety and toxicology profiles of the ADC with respect to pharmacokinetic endpoints, biochemistry, hematology, and cell differentials.

Experimental Procedures for Examples in FIG. 32

Radiolabeling: ADC and LL37-ADC were first treated with 100 mM Diethylenetriaminepentaacetic Acid (DTPA), and then buffer exchanged to 100 mM HEPES (pH 7.0) for radiolabeling. Isotope In-111 (indium trichloride, 900 μCi, 2.5 μL in 0.1 N HCl) was added to the antibody solution (100 μg/100 μl) and the solution was mixed at room temperature for 1 h. ITLC showed excellent labelling efficiency (>95%). The experiment was performed with 3-4 aliquots of 200 μg each antibody for 4 times. Results were consistent. About 100 μg of each antibody was used per injection.

For the JIMT1 tumor graft, three groups of three immunocompromised NRG female mice (~25 g) bearing HER-2 (+) JIMT-1 tumours on their back were anaesthetized, and then injected with 80 μL of 11In-mAb in PBS administered via tail vein. Average injected activities were 426 μCi (15.76 MBq). For RT4v6 tumor graft, another three groups of three immunocompromised NODSIC female mice (~25 g) bearing rt4v6 tumours on their back were anaesthetized, and then injected with 80 μL of 11In-mAb in PBS administered via tail vein. Average injected activities were 194 μCi (7.2 MBq).

Immediately after injection, dynamic whole-body images were acquired using a multimodal SPECT/CT scanner (VECTor/CT, MILabs, The Netherlands), equipped with a XUHS-2 mm mouse pinhole collimator. Thereafter, acquisitions were done at 24 and 48 h post-injection. Throughout each scanning procedure, the mouse was kept under isoflurane anesthesia and constant body temperature was maintained using a heating pad. The average organ activity per volume was obtained from the SPECT images and the Standardized Uptake Value (SUVs) was extracted from each organ. In order to relate the scanner units (counts/pixel) to radioactivity concentration (MBq/mL), a calibration factor was determined scanning a source with a known concentration of 111In. Mice were sacrificed for ex vivo biodistribution and the radioactivity in diverse organs was determined by γ-counting. For post-mortem biodistribution of 111In-mAb, a full biodistribution was conducted (blood, urine, heart, liver, kidneys, lungs, small intestine, large intestine, brain, bladder, muscle, spleen, stomach, bone, tumour, pancreas, and feces) following the last scan at 48 h post-injection. Organs were cleaned from blood and weighed, and the activity was determined using a γ-counter (Packard Cobra II autogamma counter, PerkinElmer, Waltham, MA, USA). The calibration factor for 37 kBq of 111In was 463,606 cpm (instrument specific). Total organ weights were used for the calculations of injected dose per gram of tissue (% ID/g organ) except for blood, muscle, and bone where average literature values were used.

Experimental Procedures for Examples in FIGS.
33-37

Six female cynomolgus monkeys from the Lovelace Biomedical colony were randomized into two groups of three based on their body weight. Animals assigned to group one received 1 mg/kg of ADC [i.e., anti-HER2 mAb-(MMAE)s, DAR of 8], and the other three assigned to group two received 1 mg/kg of LL37-ADC [i.e., anti-HER2 mAb-LL37-(MMAE)s, DAR of 8] administered by a single intravenous (IV) injection. Blood samples for clinical chemistry, hematology and additional analysis were collected at defined time points for up to 30 days after treatment. Animals did not show any signs of distress or health issues during daily treatment regimen and sample collections. During the study duration there were not any side effects or major changes in body weights due to antibody treatment, and treatment of monkeys with ADC and LL37-ADC at 1 mg/kg induced similar changes in clinical chemistry, cell differentials, and hematology parameters.

Example 11—Multimerization and Phosphatidylserine

FIG. 38 shows three graphs (Panels A, B and C) comparing the relative level of phosphatidylserine (PS) on various cell types, measured using the fluorescent labeled PS-binding protein, Annexin V-AlexaFluor488, in a fluorescence-activated cell sorting (FACS) instrument. Using this information, the level of improvement in ADC drug efficacy (IC50) with and without LL37 conjugation was compared for various cell types rated as undetectable, low, medium, or high in cell surface PS (see Tables 9A, 9B and 9C) These tables also compare the level of ADC-specific antigen expression on the cell surface (e.g. HER2 expression is indicated in FIG. 1 Panels C, D and E). Table 9A shows that low-HER2 expressing cells (such as PC3, LnCap, T47D, and RT4v6) are more efficiently targeted by LL37-conjugated ADC than by ADC not conjugated with LL37 (i.e., anti-HER2 mAb-MMAE8), and the cytotoxic effects of ADC [i.e., IC50) were vastly improved by at least 32-fold to 155-fold depending on the level of cell surface phosphatidylserine (PS)]. In contrast, Tables 9A, 9B and 9C also show that the cytotoxic effects of ADC (i.e., IC50) is less sensitive to LL37 (i.e., little or insignificant enhancement) for the cells that display low-level of cell surface phosphatidylserine (such as OVCAR3, AGS, Ramos, RL).

TABLE 9A

Comparison of the level of improvement in anti-HER2 (Trastuzumab) ADC drug efficacy (IC50) by LL37 to the level of phosphatidylserine and level of HER2 on the target cell surface.

| Cell line | Phosphatidylserine (PS) level on cell surface | HER2 level on cell surface | Anti-HER2 mAb-MMAE$_8$, IC50 (nM) | Anti-HER2 mAb-LL37-MMAE$_8$, IC50 (nM) | Improvement in IC50 by LL37 |
|---|---|---|---|---|---|
| PC3 | +++ | + | 46.12 | 0.33 | 138.8-fold |
| LnCap | +++ | + | 14.15 | 0.36 | 38.3-fold |
| T47D | ++ | + | 89.0 | 2.70 | 32.0-fold |
| RT4v6 | +++ | + | 45.49 | 0.29 | 155.9-fold |

TABLE 9A-continued

Comparison of the level of improvement in anti-HER2 (Trastuzumab) ADC drug efficacy (IC50) by LL37 to the level of phosphatidylserine and level of HER2 on the target cell surface.

| Cell line | Phosphatidylserine (PS) level on cell surface | HER2 level on cell surface | Anti-HER2 mAb-MMAE$_8$, IC50 (nM) | Anti-HER2 mAb-LL37-MMAE$_8$, IC50 (nM) | Improvement in IC50 by LL37 |
|---|---|---|---|---|---|
| OVCAR3 | + | +++ | 0.27 | 0.13 | 1.1-fold |
| AGS | + | + | 4.84 | 1.53 | 2.2-fold |
| CHO | ++ | – | >100 | 12.0 | >7.333-fold |

Legend:
High level (+++),
Medium level (++),
Low level (+),
None (–)

TABLE 9B

Comparison of the level of improvement in anti-CD20 (Ofatumumab) ADC drug efficacy (IC50) by LL37 to the level of phosphatidylserine and level of CD20 on the target cell surface.

| Cell line | Phosphatidylserin (PS) level on cell surface | CD20 level on cell surface | Anti-CD20 mAb-MMAE$_8$, IC50 (nM) | Anti-CD20 mAb-LL37-MMAE$_8$, IC50 (nM) | Improvement in IC50 by LL37 |
|---|---|---|---|---|---|
| Ramos | + | +++ | 0.135 | 0.058 | 1.3-fold |
| RL | + | ++ | 0.676 | 0.70 | Insignificant |

Legend:
High level (+++),
Medium level (++),
Low level (+),
None (–)

TABLE 9C

Comparison of the level of improvement in anti-CD22 (Inotuzumab) ADC drug efficacy (IC50) by LL37 to the level of phosphatidylserine and level of CD22 on the target cell surface.

| Cell line | Phosphatidylserin (PS) level on cell surface | CD22 level on cell surface | Anti-CD22 mAb-MMAE$_8$, IC50 (nM) | Anti-CD22 mAb-LL37-MMAE$_8$, IC50 (nM) | Improvement in IC50 by LL37 |
|---|---|---|---|---|---|
| Ramos | + | ++ | 0.04 | 0.035 | Insignificant |
| RL | + | ++ | 0.26 | 0.235 | Insignificant |

Legend:
High level (+++),
Medium level (++),
Low level (+),
None (–)

Phosphatidylserine (PS), normally constrained to the intracellular surface, is exposed on the external surface of tumors and most tumorigenic cell lines (see., De et al., 2018, Mol. Ther. Nucleic Acids., 10, 9), as well as other unhealthy cells. LL37 has been reported to bind outer leaflet phosphatidylserine through its positively charged and hydrophobic side chains, and to oligomerize on the cell surface (see., Sancho-Vaello et al., 2017, Sci. Rep. 7, 15371). To demonstrate that the delivery and efficacy enhancements observed for LL37 conjugates in the examples above are not merely a result of binding to phosphatidylserine, covalent conjugates of phosphatidylserine (PS)-specific binding proteins (i.e., Annexin V and Evectin2) linked to anti-HER2 mAb or to its ADC (i.e., anti-HER2 mAb-MMAE8) were prepared and evaluated. FIG. 39 panel A shows that with the covalently linked PS-specific binding proteins (i.e., Annexin V, Evectin2), the antibody-protein conjugates have enhanced binding to phosphatidylserine when compared to antibody or ADC (i.e., anti-HER2 mAb, or anti-HER2 mAb-MMAE8). However, FIG. 39 panel B shows that these PS-specific binding proteins have only minimally improved (i.e., comparable) drug efficacy when compared to anti-HER2 mAb-MMAE8. This result therefore further supports the notion that multimerization of LL37 is responsible for the exceptional enhancement in antibody delivery and therapeutic efficacy of the LL37-linked ADC conjugates.

Without wishing to be bound by theory, the exceptional enhancement of LL37 in promoting the antibody delivery to target cells is likely the direct result of LL37 multimerization due to the higher concentration of LL37 at the cell surface and interaction with phosphatidylserine embedded in the outer leaflet of the target cells. Example 2 supports this notion as it shows that LL37 can deliver antibodies/ADCs in excess of the number of antigenic receptors (i.e. beyond the saturation limit) in the target cells (see FIG. 8). This is shown schematically in FIG. 40A, where antibodies in excess of the number of epitope sites are shown clustered at the cell surface due to intermolecular association between LL37-derived polypeptides. This notion is further supported by FIG. 40B, which shows an oversaturation of bound antibodies stained with red fluorescent protein.

Experimental Procedures for Examples in FIG. 38

Delivery assay: For the comparison shown in FIG. 38 (Panels A, B, and C), the adherent cells were washed with PBS and detached from culturing plate into suspension with trypsin treatment, and then neutralized in 10% FBS containing media. Cells were washed twice with PBS in microcentrifuge tubes (spun at 2,000 rpm for 5 minutes), and then washed and resuspended with 1× Annexin-binding buffer (10 mM HEPES, pH 7.4, 140 mM NaCl, and 2.5 mM Calcium chloride). 0.1 million cells in 100 µl (density of 1 million cells per ml) were stained with 5 µl of Annexin V-AlexaFluor488 (Thermo Fisher Scientific, Catalog No. A13201), protected from light, and incubated for 15 minutes at 23 degree Celsius. Cells were washed twice with 1× Annexin-binding buffer (10 mM HEPES, pH 7.4, 140 mM NaCl, and 2.5 mM Calcium chloride), spun (at 2,000 rpm for 5 minutes in microcentrifuge tubes), and resuspended in 200 µl of Annexin V binding buffer containing propidium iodide (PI) dye for FACS measurement (for P1, excitation and emission wavelengths were 535 nm and 617 nm, respectively; for AlexaFluor488, 490 nm was used for excitation and 525 nm was used for emission detection). Propidium iodide was used to exclude the dead cell pollution, so only the live cells (i.e., PI signal of zero) with the bound Annexin V-AlexaFluor488 were counted.

Experimental Procedures for Examples in Tables 9A, 9B and 9C

Cell viability assay with XTT. For the comparison shown in Tables 9A, 9B, and 9C, cell assay was done by treating/ incubating the cells with antibody drug conjugates (0.01 nM to 100 nM concentration) for 72 hours in the 37 degree C. tissue culture incubator. For Table 9A, the anti-HER2 mAb-MMAE8 and anti-HER2-LL37-MMAE8 were made as described above. For Table 9B, the anti-CD20 mAb-MMAE8 and anti-CD20 mAb-LL37-MMAE8 were made from Ofatumumab (SEQ ID NOs: 40 and 41) using the same reaction procedures described above. For Table 9C, the anti-CD22 mAb-MMAE8 and anti-CD22 mAb-LL37-MMAE8 were made from Inotuzumab (SEQ ID NOs: 131 and 132) using the same procedures described above. After treatment, cell viability was determined by XTT assay as described above. The viability values for antibody concentrations (0.01 nM to 100 nM) tested were plotted, and curve fit was done in GraphPad Prism to calculate IC50.

Experimental Procedures for Examples in FIG. 39

Anti-HER2 mAb, Anti-HER2 mAb-MMAE (MMAE DAR of 8), Anti-HER2 mAb-LL37, and Anti-HER2 mAb-MMAE-LL37 (MMAE DAR of 8) were produced using the same methods as provided above in Example 1 and 2. The Annexin V (SEQ ID NO: 133) was produced as a recombinant fusion protein expressed and purified from E. coli, and was linked enzymatically to the C-terminus of light chain in Anti-HER2 mAb/Anti-HER2 mAb-MMAE. The covalent conjugate of Annexin V to Anti-HER2 mAb or to Anti-HER2 mAb-MMAE was purified from the reaction mixture on Protein A affinity chromatography, and then buffer-exchanged into PBS. The purified Anti-HER2 mAb-Annexin5 and Anti-HER2 mAb-MMAE-Annexin5 were verified on SDS-PAGE. Similarly, Evectin2 (SEQ ID NO: 134) was produced as a recombinant fusion protein expressed and purified from E. coli, and was linked enzymatically to the C-terminus of light chain in Anti-HER2 mAb/Anti-HER2 mAb-MMAE. The covalent conjugate of Evectin2 to Anti-HER2 mAb or to Anti-HER2 mAb-MMAE was purified from the reaction mixture on Protein A affinity chromatography, and then buffer-exchanged into PBS. The purified Anti-HER2 mAb-Evectin2 and Anti-HER2 mAb-MMAE-Evectin2 were verified on SDS-PAGE.

Phosphatidylserine (PS)-binding assay: To quantitate the PS-binding shown in FIG. 39 panel A, sample wells in the 96-wells plate were coated with 10 µg/ml of PS diluted in ethanol, and were dried at 21 degree Celsius (i.e., room temperature) in an air-circulating incubator for at least 15 hours (i.e., overnight). On the following day, the PS-coated wells were further treated (i.e. blocking step) with 5% skimmed milk at 21 degree Celsius in a 300-rpm shaking incubator for 1 hour. The wells were rinsed (i.e., washing step) with phosphate buffer saline (i.e., PBS) 3 times. 100 ul of sample containing the PS-specific protein-antibody conjugate diluted in 5% skimmed milk was added to the appropriate wells and incubated at 21 degree Celsius in a 300-rpm shaking incubator for 1 hour. The sample wells were washed 5 times with PBS (0.2 ml per wash), and immediately treated and incubated with the secondary antibody, goat anti-human IgG-HRP (100 ul per well, prepared in 1-in-5000 dilution in 5% skimmed milk) at 21 degree Celsius in a 300-rpm shaking incubator for 1 hour. The sample wells were washed 5 times with PBS (0.2 ml per wash), and immediately treated with TMB substrate (100 ul per well) wrapped in aluminum foil (i.e., to keep dark for light sensitive substrate/reaction) and incubated at 21 degree Celsius for 5-7 minutes. The reaction was stopped by the addition of 100 ul 250 nM $H_2SO_4$, and the amount of the lipid-bound bi-specific antibodies was quantitated by measuring the spectral absorbance at 450 nm and 620 nm.

Viability assay: Cell viability assay with XTT was performed using the same method as in Example 3 (above).

Figure 40A:
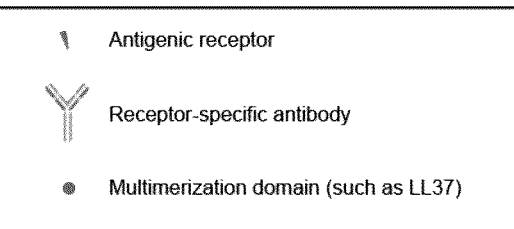
Figure 40B:
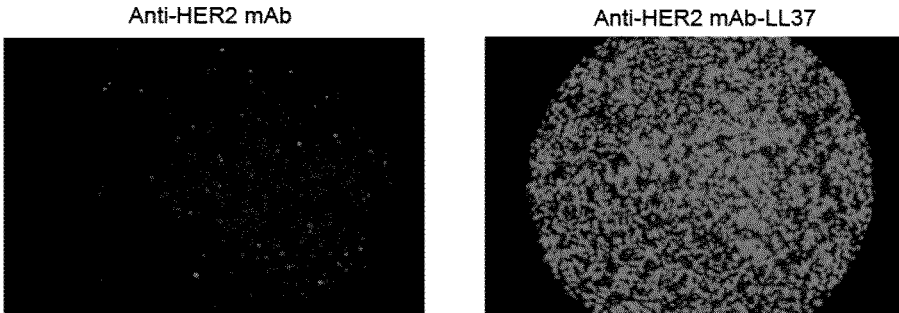

Experimental Procedures for Examples in FIG. 40

Z-RFP, anti-HER2 mAb, and the LL37-linked antibody were produced using the same procedure as described above in FIG. 8 (Example 2). Briefly, anti-HER2 mAb (or the LL37-linked anti-HER2 mAb, also represented as anti-HER2 mAb-LL37) and equal molar amount of Z-RFP were added to OVCAR3 cells sub-cultured to 80% confluency level at 100 nM in 48-well plate, and incubated at 37 degree C. incubator for 3 hours. The plate was then removed from the incubator, and the culturing media was removed from the adherent OVCAR3. The adherent OVCAR3 were washed gently with an equal volume of PBS, and were directly visualized on a fluorescent microscope.

All citations are hereby incorporated by reference in their entirety. Where any definition of any term, expression or phrase defined herein is in conflict with any term, expression or phrase provided in an incorporated reference, the definition as defined herein shall govern.

The present invention has been described with regard to one or more embodiments. However, it will be apparent to persons skilled in the art that a number of variations and modifications can be made without departing from the scope of the invention as defined in the claims.

---

What is claimed is:

1. A covalent conjugate comprising:

an antibody that specifically binds to a cell surface epitope of a human cell, or an antibody derivative, the antibody derivative comprising: an antibody variable domain that specifically binds to the cell surface epitope of the human cell, and a hinge region coupling two heavy chains or two heavy chain fragments;

a payload comprising: a small molecule drug of less than 3 kDa that is toxic to human cells, or a plurality of small molecule drugs that are each less than 3 kDa and which are toxic to human cells; or a peptide or protein of less than 100 kDa, wherein the peptide or protein comprises: a transcription factor, a bacterial toxin, a viral toxin, a protease, an RNAse, a DNAse, a proteolysis targeting chimera (PROTAC), or a fluorescent or colorimetric marker; and a first LL37-derived polypeptide and a second LL37-derived polypeptide, the first LL37-derived polypeptide and the second LL37-derived polypeptide each comprising an LL37-derived amino acid sequence or sequences, wherein each of the LL37-derived amino acid sequence or sequences independently comprise:

SEQ ID NO: 14 (IGKEFKRIVQRIKD-FLRNLVPRTES);

or SEQ ID NO: 111 (SETRPVLNRLFDKIRQ-VIRKFEKGI);

or a fragment of SEQ ID NO: 14 or 111 having consecutive deletions at either or both of the N- and C-termini up to a total deletion of at most 8 amino acids;

or a plurality of fragments of SEQ ID NO: 14 and/or SEQ ID NO: 111, each fragment of the plurality of fragments independently having consecutive deletions at either or both of the N- and C-termini up to a total deletion of at most 10 amino acids;

wherein each Lys and Arg residue in each fragment is independently substituted or not substituted with a conservative substitute amino acid residue selected from the group consisting of: Lys, Orn (ornithine), DBu (2,4-diaminobutanoate), Dpr (2,3-diaminopropionate), Hyl (hydroxylysine), aHyl (allo-hydroxylysine), MeLys (6-N-methyllysine), Arg, Cit (citrulline), and 2-amino-3-guanidinopropionate;

wherein 0, 1, 2, 3, 4 or 5 amino acid residues, selected from the group consisting of Gly, Asp, Glu, Asn, Gln, Ile, Leu, Val, Phe, Ser, Thr, Pro, and a combination thereof, in each fragment are each independently substituted with a conservative substitute amino acid residue selected from within its Group, $X^1$, $X^2$, $X^3$, $X^4$, $X^5$, or $X^6$ as defined below:

(Group $X^1$) Ala, Gly;

(Group $X^2$) Asp, Glu, bAad (3-aminoadipic acid), Apm (2-aminopimelic acid);

(Group $X^3$) Asn, Gln;

(Group $X^4$) Ile, Leu, Met, Val, Phe, Tyr, Trp, Abu (2-aminobutyric acid), Ahe (2-aminoheptanoic acid), aIle (allo-isoleucine), Nva (norvaline), Nle (norleucine);

(Group $X^5$) Ser, Thr, Tyr;

(Group $X^6$) Pro, 3Hyp (3-hydroxyproline), 4Hyp (4-hydroxyproline); and wherein 0, 1 or 2 amino acid residues, selected from the group consisting of Lys, Arg, Gly, Asp, Glu, Asn, Gln, Ile, Leu, Val, Phe, Ser, Thr, Pro, and a combination thereof, in each fragment are each independently substituted with a non-conservative substitute a amino acid residue.

2. The covalent conjugate of claim 1, wherein the LL37-derived amino a acid sequence or sequences comprise SEQ ID NO: 16 or SEQ ID NO: 74.

3. The covalent conjugate of claim 1, wherein each fragment of the plurality of fragments independently comprises SEQ ID NO: 51 or the inverse sequence of SEQ ID NO: 51, or wherein the plurality of fragments comprise a pair of palindromic sequences.

4. The covalent conjugate of claim 1, wherein:

the antibody or the antibody derivative comprises a first heavy chain constant region and a second heavy chain constant region, wherein the first LL37-derived polypeptide is coupled directly or indirectly to the first heavy chain constant region and the second LL37-derived polypeptide is coupled directly or indirectly to the same amino acid residue in the second heavy chain constant region;

the antibody or the antibody derivative comprises a first light chain constant region and a second light chain constant region, wherein the first LL37-derived polypeptide is coupled directly or indirectly to the first light chain constant region and the second LL37-derived polypeptide is coupled directly or indirectly to the same amino acid residue in the second light chain constant region the antibody or the antibody derivative comprises a first heavy chain constant region and a second heavy chain constant region, wherein the first LL37-derived polypeptide is coupled directly or indirectly to a C-terminus of the first heavy chain constant region and the second LL37-derived polypeptide is coupled directly or indirectly to a C-terminus of the second heavy chain constant region; or the antibody or the antibody derivative comprises a first light chain constant region and a second light chain constant region, wherein the first LL37-derived polypeptide is coupled directly or indirectly to a C-terminus of the first light chain constant region and the second LL37-derived polypeptide is coupled directly or indirectly to a C-terminus of the second light chain constant region.

5. The covalent conjugate of claim 1, wherein a ratio of LL37-derived polypeptides per antibody monomer in the covalent conjugate is exactly 2:1, exactly 4:1, exactly 6:1 or exactly 8:1.

6. The covalent conjugate of claim 1, wherein the first LL37-derived polypeptide and the second LL37-derived polypeptide form a covalent conjugate with the antibody or with the antibody derivative through: peptide bonds; disulfide linkages; isopeptide bonds; and/or 1,2,3-triazole linkages.

7. The covalent conjugate of claim 1, wherein the covalent conjugate comprises: 18V4F, 4R34.1.19, A-803, Abagovomab, Abciximab, Abituzumab, Abrezekimab, Abrilumab, Adalimumab, ADCPF-06688992, Adecatumumab, Adotrastuzumab, Afelimomab, Afutuzumab, AGS16F, Alacizumab, Alemtuzumab, Alirocumab, ALKS4230, Altumomab, Amatuximab, AMG191, AMG531, Anatumomab, Andecaliximab, Anetumab, Anifrolumab, Anti-HMI.24, Apolizumab, Aprutumab, Arcitumomab, ARDS, Aselizumab, ASG-15ME, Atezolizumab, Atinumab, AUTO2, Avelumab, Azintuxizumab, B-701, Basiliximab, Bavituximab, BAY1179470, Bectumomab, Begelomab, Belantamab, Belimumab, Bemarituzumab, Benralizumab, Bersanlimab, Bertilimumab, Bevacizumab, BI-505, Biciromab, BIIB023, Bimagrumab, Bimekizumab, BION-1301, Bivatuzumab, Bleselumab, Blinatumomab, Blontuvetmab, Blosozumab, BMS-986148, BMS-986156, BMS-986179, Brentuximab, Brodalumab, Brolucizumab, Brontictuzumab, BTH1704, Burosumab, C7-FcDT, Cabiralizumab, Camidanlumab, Camrelizumab, CAN04, Canakinumab, Cantuzumab, CAP-100, Caplacizumab, capromab, Carotuximab, Catumaxomab, CC-90002, CD133KDEL, CD147-CART, CD96-S32F, CDX-1401, Cedelizumab, Cemiplimab, Cergutuzumab, Cetrelimab, Cetuximab, Cibisatamab, Citatuzumab, Cixutumumab, Claudiximab, Clenoliximab, Clivatuzumab, Codrituzumab, Cofetuzumab, Coltuximab, COM701, COM902, Conatumumab, Crizanlizumab, Crotedumab, CSL324, Cusatuzumab, Dacetuzumab, Daclizumab, Dalotuzumab, Dapirolizumab, Daratumumab, Darleukin, DCR2, Dectrekumab, Demcizumab, Denintuzumab, Denosumab, Depatuxizumab, Derlotuxizumab, Detumomab, Dinutuximab, Dorlimomab, Drozitumab, Duligotuzumab, Dupilumab, Durvalumab, Duvortuxizumab, Ecromeximab, Eculizumab, Edrecolomab, Efalizumab, EGFR806, EJ212_007-C12-5, ELB01101, Elgemtumab, Elotuzumab, Elsilimomab, Emactuzumab, Emapalumab, EMD525797, Emibetuzumab, Enapotamab, Enavatuzumab, Enfortumab, Enoblituzumab, Enoticumab, EOL4G8, Epratuzumab, Ertumaxomab, Etaracizumab, Evolocumab, Fanolesomab, Faralimomab, Farletuzumab, Fezakinumab, Fibatuzumab, Ficlatuzumab, Flanvotumab, Flotetuzumab, FLYSYN, Foralumab, Galiximab, Gancotamab, Ganitumab, Gatipotuzumab, Gavilimomab, GD2Bi-aATC, Gemtuzumab, GI-270384, Gilvetmab, Girentuximab, Glembatumumab, Golimumab, Gomiliximab, GSK2849330, Guselkumab, HB-n1, HFE7A, HLX20, HS-110, Hu3S193, Ibalizumab, Ibritumomab, Icrucumab, Ifabotuzumab, Igovomab, Imalumab, Imaprelimab, IMC-CS4, Imgatuzumab, Inclacumab, Indatuximab, Indusatumab, Inebilizumab, Infliximab, Inotuzumab, Intetumumab, Iomab-B, iPH5401, Ipilimumab, Iratumumab, Isatuximab, Iscalimab, Istiratumab, Itolizumab, Ixekizumab, Keliximab, KH7B9, KTN0182A, KU42.33C, Labetuzumab, Ladiratuzumab, Lanadelumab, Lanalumab, Laprituximab, Lemalesomab, Leronlimab, Letolizumab, Lexatumumab, Lifastuzumab, Lilotomab, Lintuzumab, Lirilumab, Lokivetmab, Loncastuximab, Lorvotuzumab, Losatuxizumab, Lucatumumab, Lulizumab, Lumretuzumab, Lupartumab, Lutikizumab, LY3321367, LY3435151, M290, Mapatumumab, Margetuximab, Maslimomab, Matuzumab, Mavrilimumab, MBG453, MCLA-117, MEDI3617, MEDI3622, MEN1112, Mepolizumab, Milatuzumab, Minretumomab, Mirvetuximab, Mitumomab, MLS102, MM-111, MMP9, MNRP1685A, Modotuximab, Mogamulizumab, Monalizumab, Moxetumomab, MOXR0916, Muromonab, MVT-5873, Nacolomab, Naptumomab, Naratuximab, Narnatumab, Natalizumab, Navicixizumab, Necitumumab, Nerelimomab, Nesvacumab, Netakimab, NI-0101, Nimotuzumab, Nivolumab, NNC0151-00000000, Nofetumomab, Obinutuzumab, Ocaratuzumab, Ocrelizumab, Odulimomab, Ofatumumab, Olaratumab, Oleclumab, olokizumab, Omalizumab, Onartuzumab, Ontuxizumab, Onvatilimab, Opicinumab, Oportuzumab, Oregovomab, Otelixizumab, Otlertuzumab, Oxelumab, Pamrevlumab, Panitumumab, Pankomab, Parsatuzumab, Pasotuxizumab, Patritumab, PD-0360324, PDR00I, Pembrolizumab, Pemtumomab, Pertuzumab, PF-00547659, PF-03446962, PF-04518600, PF-06650808, Pidilizumab, Pinatuzumab, Pintumomab, Plozalizumab, Polatuzumab, Prezalumab, Priliximab, Pritumumab, PTK7-ADC, Quilizumab, Radretumab, Ramucirumab, Ranibizumab, Ravagalimab, Refanezumab, REGN2176, Relatlimab, Reslizumab, RG7287, Rilotumumab, Rinucumab, Risankizumab, Rituximab, RO-001, R06958688, Robatumumab, Romilkimab, Romosozumab, Rovalpituzumabtesirine, Rovelizumab, Rozanolixizumab, Ruplizumab, Sacituzumab, Samalizumab, Samrotamab, SAR252067, SAR408701, Sarilumab, Satralizumab, Satumomab, Secukinumab, Selicrelumab, Seribantumab, Setrusumab, SGN-15, SGN-CD123A, SGN-CD228A, SGN-CD352A, SGN-CD47M, SGN-CD48A, SGN-CD70A, SGN-LIVIA, SHP647, Siamab.com, Sibrotuzumab, Siltuximab, Simtuzumab, Sirtratumab, SL-279252, Sofituzumab, Solitomab, Sonepcizumab, Sontuzumab, Spartalizumab, Sphingomab, SS1 (dsFv) PE38 (CAT-5001), Sulesomab, TAB004, Tabalumab, Tacatuzumab, Tadocizumab, Talacotuzumab, Tamtuvetmab, Taplitumomab, Tarextumab, Telimomab, Telisotuzumab, Tenatumomab, Teneliximab, Teplizumab, Tepoditamab, Teprotumumab, Theralizumab, Tigatuzumab, Tildrakizumab, Timigutuzumab, Timolumab, Tiragotumab, Tislelizumab, Tisotumab, TKH2, Tocilizumab, Tomuzotuximab, Tositumomab, Trastuzumab, Tregalizumab, Tremelimumab, TSR-022, TTX-030, Tucotuzumab, Ublituximab, Ulocuplumab, Urelumab, Ustekinumab, Ustekinumab, Vadastuximab, Vanalimab, Vapaliximab, Varlilumab, Vatelizumab, Vedolizumab, Vepalimomab, Vesencumab, Visilizumab, Vobarilizumab, Vofatamab, Vociximab, Vonrolizumab, Vopratelimab, Vorsetuzumab, Votumumab, Vunakizumab, VXIS/2503, Y-443, Zalutumumab, Zanolimumab, Zenocutuzumab, Ziralimumab, or Zolbetuzumab; or wherein the covalent conjugate comprises: A-803, ADCPF-06688992, Afutuzumab, Alemtuzumab, AMG191, AMG531, Anti-HMI.24, Apolizumab, Atezolizumab, AUTO2, Avelumab, Azintuxizumab, Basiliximab, Bectumomab, Belantamab, Bersanlimab, BI-505, BION-1301, Bleselumab, Blinatumomab, Blontuvetmab, Brentuximab, Cabiralizumab, Camidanlumab, Camrelizumab, CAN04, CAP-100, CC-90002, CD133KDEL, CD96-S32F, CDX-1401, Cedelizumab, Cemiplimab, Cetrelimab, Cixutumumab, Clenoliximab, Codrituzumab, Coltuximab, Com902, Conatumumab, Crotedumab, Cusatuzumab, Dacetuzumab, Daclizumab, Dalotuzumab, Dapirolizumab, Daratumumab, Darleukin, DCR2, Dectrekumab, Denintuzumab, Detumomab, Drozitumab, Durvalumab, Duvortuxizumab, Efalizumab, EJ212007-C12-5, ELB01101, Elotuzumab, Elsilimomab, Emactuzumab, Emibetuzumab, Enapotamab, Epratuzumab, Fanolesomab, Fibatuzumab, Ficlatuzumab, Flotetuzumab, FLYSYN, Foralumab, Galiximab, Ganitumab, Gemtuzumab, GI-270384, Gilvetmab, Gomiliximab, HFE7A, Hu3S193, Ibalizumab, Ibritumomab, Ifabotuzumab, IMC-CS4, Inebilizumab, Inotuzumab, Iomab-B, Ipilimumab, Iratumumab, Isatuximab, Iscalimab, Istiratumab, Itolizumab, Keliximab, KTN0182A, Leronlimab, Letolizumab, Lexatumumab, Lilotomab, Lintuzumab, Lirilumab, Loncastuximab, Lucatumumab, Lulizumab, Lutikizumab, Maslimomab, MCLA-117, MEN1112, Milatuzumab, Mitumomab, Mogamulizumab, Monalizumab, Moxetumomab, Muromonab, Nacolomab, Naratuximab, Natalizumab, NI-0101, Nivolumab, Nofetumomab, Obinutuzumab, Ocaratuzumab, Ocrelizumab, Odulimomab, Ofatumumab, Olokizumab, Onartuzumab, Otelixizumab, Otlertuzumab, Oxelumab, PD-0360324, PDR00I, Pembrolizumab, Pidilizumab, Pinatuzumab, Polatuzumab, Priliximab, Radretumab, Ravagalimab, REGN2176, Relatlimab, Rilotumumab, Rinucumab, Rituximab, RO-001, Robatumumab, Romilkimab, Rovelizumab, Ruplizumab, Samalizumab, Sarilumab, Satralizumab, Selicrelumab, SGN-15, SGN-CD123A, SGN-CD352A, SGN-CD47M, SGN-CD48A, SGN-CD70A, Siltuximab, SL-279252, Sontuzumab, Spartalizumab, Tabalumab, Talacotuzumab, Tamtuvetmab, Taplitumomab, Telimomab, Telisotuzumab, Teneliximab, Teplizumab, Tepoditamab, Teprotumumab, Theralizumab, Tigatuzumab, Tiragotumab, Tislelizumab, Tocilizumab, Tositumomab, Tregalizumab, Tremelimumab, TTX-030, Ublituximab, Ulocuplumab, Vadastuximab, Vanalimab, Varlilumab, Visilizumab, Vobarilizumab, Vorsetuzumab, or Zanolimumab; or wherein the covalent conjugate comprises: SB1(MVT-5873), Abagovomab, Abituzumab, Abrezekimab, ADCPF-06688992, Adecatumumab, AGS16F, Alacizumab, ALKS4230, Altumomab, Amatuximab, AMG191, Anatumomab, Andecaliximab, Anetumab, Anti-HMI.24, Aprutumab, Arcitumomab, ASG-15ME, Atezolizumab, Atinumab, Avelumab, B-701, Bavituximab, BAY1179470, Bemarituzumab, Bersanlimab, Bevacizumab, BI-505, Bivatuzumab, Bleselumab, BMS-986148SS1, BMS-986156, BMS-986179, Brolucizumab, Brontictuzumab, BTH1704Pemtumomab, Cabiralizumab, Camrelizumab, CAN04, Cantuzumab, Carotuximab, Catumaxomab, CC-90002, CD133KDEL, CD147-CART, CDX-1401, Cemiplimab, Cergutuzumab, Cetrelimab, Cetuximab, Cibisatamab, Citatuzumab, Cixutumumab, Claudiximab, Clivatuzumab, Codrituzumab, Cofetuzumab, COM701, Com902, Conatumumab, Crizanlizumab, Crotedumab, Cusatuzumab, Dacetuzumab, Dalotuzumab, Dectrekumab, Demcizumab, Depatuxizumab, Derlotuximab, dinutuximab, Drozitumab, Duligotuzumab, Durvalumab, Ecromeximab, Edrecolomab, EGFR806, Elgemtumab, Emactuzumab, EMD525797, Emibetuzumab, Enapotamab, Enavatuzumab, Enfortumab, Enoblituzumab, Enoticumab, EOL4G8, Ertumaxomab, Etaracizumab, Fanolesomab, Farletuzumab, Fibatuzumab, Ficlatuzumab, Flanvotumab, Gancotamab, Ganitumab, Gatipotuzumab, Gavilimomab, GD2Bi-aATC, GI-270384, Gilvetmab, Girentuximab, Glembatumumab, GSK2849330, HLX20, HS-110, Hu3S193, Icrucumab, Ifabotuzumab, Igovomab, Imalumab, Imaprelimab, IMC-CS4, Imgatuzumab, Inclacumab, Indatuximab, Indusatumab, Intetumumab, iPH5401, Ipilimumab, Iscalimab, Istiratumab, KH7B9, KTN0182A, KU42.33C, Labetuzumab, Ladiratuzumab, Laprituximab, Leronlimab, Lexatumumab, Lifastuzumab, Lirilumab, Lorvotuzumab, Losatuxizumab, Lucatumumab, Lulizumab, Lumretuzumab, Lupartumab Lutikizumab, LY3321367, LY3435151, Mapatumumab, Margetuximab, C7-FcDT, Matuzumab, MBG453, MEDI3617, MEDI3622, Milatuzumab, Minretumomab, Mirvetuximab, Mitumomab, MLS102, MM-111, MMP9, MNRP1685A, Modotuximab, Monalizumab, MOXR0916, Nacolomab, Naptumomab, Namatumab, Navicixizumab, Necitumumab, Nesvacumab, Nimotuzumab, Nivolumab, NNC0151-00000000, Nofetumomab, Olaratumab, Oleclumab, Onartuzumab, Ontuxizumab, Onvatilimab, Oportuzumab, Oregovomab, Oxelumab, Pamrevlumab, Panitumumab, Pankomab, Parsatuzumab, Pasotuxizumab, Patritumab, PD-0360324, PDR00I, PE38 (CAT-5001), Pembrolizumab, Pertuzumab, PF-03446962, PF-04518600, PF-06650808, Pidilizumab, Pintumomab, Pritumumab, PTK7-ADC, Ramucirumab, Ranibizumab, Ravagalimab, Relatlimab, RG7287, Rilotumumab, RO-001, R06958688, Robatumumab, Romilkimab, Rovalpituzumab, Sacituzumab, Samrotamab, SAR408701, Sarilumab, Satralizumab, Satumomab, Selicrelumab, Seribantumab, SGN-15, SGN-CD228A, SGN-CD47M, SGN-CD70A, SGN-LIVIA, Sibrotuzumab, Sirtratumab, SL-279252, Sofituzumab, Solitomab, Sonepcizumab, Sontuzumab, Spartalizumab, Sphingomab, TAB004, Tacatuzumab, Tarextumab, Telisotuzumab, Tenatumomab, Teneliximab, Teprotumumab, Theralizumab, Tigatuzumab, Timigutuzumab, Timolumab, Tiragotumab, Tislelizumab, Tisotumab, TKH2HB-n1, Tocilizumab, Tomuzotuximab, Trastuzumab, Tremelimumab, TSR-022, TTX-030, Tucotuzumab, Urelumab, Vanalimab, Vapaliximab, Varlilumab, Vatelizumab, Vepalimomab, Vesencumab, Vobarilizumab, Vofatamab, Volociximab, Volociximab, Vonlerolizumab, Vopratelimab, Vorsetuzumab, Votumumab, VXIS/2503, Y-443, Zalutumumab, Zenocutuzumab, Ziralimumab, or Zolbetuximab; or wherein the covalent conjugate comprises: ALKS4230, Atezolizumab, Avelumab, Bleselumab, Cabiralizumab, Camrelizumab, CDX-1401, Cemiplimab, Cetrelimab, COM701, Com902, Dacetuzumab, Durvalumab, EGFR806, Elsilimomab, Emactuzumab, Enoblituzumab, Gilvetmab, HLX20, HS-110, Imalumab, IMC-CS4, Ipilimumab, Iscalimab, Lucatumumab, Lulizumab, MEDI3622, Monalizumab, MOXR0916, Nivolumab, Olokizumab, Oxelumab, PD-0360324, PDROOI, Pembrolizumab, PF-04518600, Pidilizumab, Ravagalimab, Relatlimab, Samalizumab, Selicrelumab, Siltuximab, SL-279252, Spartalizumab, TAB004, Teneliximab, Theralizumab, Tiragotumab, Tislelizumab, Tremelimumab, Urelumab, Vanalimab, Varlilumab, Vonlerolizumab, or Vopratelimab; or wherein the covalent conjugate comprises: Adalimumab, Afelimomab, ARDS, BIIB023, Cedelizumab, Clenoliximab, Com902, CSL324, Faralimomab, Golimumab, Ibalizumab, Infliximab, Iomab-B, Keliximab, Nerelimomab, Priliximab, SAR252067, Tenatumomab, Tiragotumab, Tregalizumab, Ustekinumab, Y-443, or Zanolimumab; or wherein the covalent conjugate comprises: 18V4F, 4R34.1.19, Abciximab, Abrilumab, Adalimumab, ADF-06688992, Afelimomab, Alirocumab, Andecaliximab, Anifrolumab, Aselizumab, Basiliximab, Begelomab, Belimumab, Benralizumab, Bersanlimab, Bertilimumab, BI-505, BIIB023, Bimagrumab, Bimekizumab, Bleselumab, Blosozumab, Brodalumab, Burosumab, Camidanlumab, Canakinumab, CD147-CART, Cedelizumab, Clenoliximab, Crotedumab, Dacetuzumab, Daclizumab, Dapirolizumab, Daratumumab, Dectrekumab, Denosumab, Dorlimomab, Dupilumab, Efalizumab, Emapalumab, Etaracizumab, Evolocumab, Fezakinumab, Flotetuzumab, Gavilimomab, GI-270384, Glembatumumab, Golimumab, Guselkumab, HFE7A, Hu3S193, Ibalizumab, Infliximab, iPH5401, Isatuximab, Iscalimab, Ixekizumab, Keliximab, Lanalumab, Lemalesomab, Letolizumab, Lokivetmab, Lucatumumab, Lutikizumab, LY3321367, M290, Mavrilimumab, MBG453, Mepolizumab, Milatuzumab, Mitumomab, MMP9, Natalizumab, Nerelimomab, Netakimab, NI-0101, NNC0151-00000000, Odulimomab, Omalizumab, Opicinumab, Oxelumab, Pamrevlumab, PF-00547659, Plozalizumab, Prezalumab, Priliximab, Quilizumab, Ravagalimab, REGN2176, Reslizumab, Rinucumab, Risankizumab, RO-001, Romilkimab, Romosozumab, Rozanolixizumab, Ruplizumab, SAR2S2067, Sarilumab, Satralizumab, Secukinumab, Selicrelumab, Setrusumab, SGN-IS, SGN-CD123A, SHP647, Simtuzumab, SL-2792S2, Sonepcizumab, Sulesomab, Tabalumab, Tadocizumab, Talacotuzumab, Tamtuvetmab, Telimomab, Tenatumomab, Teneliximab, Tildrakizumab, Timolumab, Tisotumab, Tocilizumab, Tregalizumab, TSR-022, Ustekinumab, Ustekinumab, Vanalimab, Vapaliximab, Vatelizumab, Vedolizumab, Vepalimomab, Vobarilizumab, Vunakizumab, VXIS/2503, Zanolimumab, or Ziralimumab; or wherein the covalent conjugate comprises: Trastuzumab, Mirvetuximab, Panitumumab, Lifastuzumab, Labetuzumab, Citatuzumab, Foralumab, Brentuximab, Rituximab, Ofatumumab, Vadastuximab, Vofatamab, or hjS91; or wherein the covalent conjugate comprises Trastuzumab.

8. The covalent conjugate of claim 1, wherein the cell surface epitope forms part of: SAC (Mucin SAC), ST4, activin receptor-like kinase 1, ACVR2B, adenocarcinoma antigen, alpha-fetoprotein, AOC3, AXL, c-Met, C242 antigen (CanAg) novel glycoform of MUCI, CA-12S, *Canis lupus familiaris* IL31, tumor-associated glycoprotein 72 antigen, Addressin, Angiopoietin-2, CS, CA19-9, Carbonic anhydrase 9 (CA-IX), CCL11, CD3, CD1a, CD1b, CD1c, CD1d, CD1e, CD2, CD3d, CD3e, CD3g, CD4, CDS, CD6, CD7, CD8a, CD8b, CD9, CDI0, CDI 1a, CDI 1b, CDI 1e, CDI Id, CD13, CD14, CDISs, CDISsu, CD ISu, CD16a, CD16b, CDI 7, CD18, CD19, CD20, CD21, CD22, CD23, CD24, CD2S, CD26, CD27, CD28, CD29, CD30, CD31, CD32A, CD32B, CD32C, CD33, CD34, CD3S, CD36, CD37, CD38, CD39, CD40, CD41, CD42a, CD42b, CD42c, CD42d, CD43, CD44, CD44v6, CD4S, CD46, CD47, CD48, CD49a, CD49b, CD49c, CD49d, CD49e, CD49f, CDS0, CDSI, CDS2, CDS3, CDS4, CDSS, CDS6, CDS7, CDS8, CDS9, CD60a, CD60b, CD60c, CD61, CD62E, CD62L, CD62P, CD63, CD64a, CD6S, CD6Ss, CD66a, CD66b, CD66c, CD66d, CD66e, CD66f, CD68, CD69, CD70, CD71, CD72, CD73, CD74, CD7S, CD7Ss, CD77, CD79A, CD79B, CD80, CD81, CD82, CD83, CD84, CD8SA, CD8SB, CD8SC, CD8SD, CD8SF, CD8SG, CD8SH, CD8SI, CD8SJ, CD8SK, CD8SM, CD86, CD87, CD88, CD89, CD90, CD91, CD92, CD93, CD94, CD9S, CD96, CD97, CD97B, CD98, CD99, CD99R, CDI00, CDI0I, CD102, CD103, CD104, CDIOS, CD106, CD107a, CD107b, CD108, CD109, CD110, CD111, CD112, CD112R, CD113, CD114, CDI 15, CDI 16, CDI 17, CDI 18, CDI 19, CD120a, CD120b, CD121a, CD121b, CD122, CD123, CD124, CD125, CD126, CD127, CD129, CD130, CD131, CD132, CD133, CD134, CD135, CD136, CD137, CD138, CD140A, CD140B, CD141, CD142, CD143, CD144, CD146, CD147, CD148, CD150, CD151, CD152, CD153, CD154, CD155, CD156a, CD156b, CD156c, CD157, CD158a, CD158B1, CD158B2, CD158C, CD158D, CD158E1, CD158E2, CD158F1, CD158F2, CD158G, CD158H, CD158I, CD158J, CD158K, CD159a, CD159c, CD160, CD161, CD162, CD163, CD164, CD165, CD166, CD167a, CD167b, CD168, CD169, CDI 70, CDI 71, CDI 72a, CDI 72b, CDI 72g, CDI 73, CDI 74, CDI 75, CDI 75s, CDI 76, CDI 77, CDI 78, CDI 79a, CDI 79b, CD180, CD181, CD182, CD183, CD184, CD185, CD186, CD191, CD192, CD193, CD194, CD195, CD196, CD197, CD198w, CD199, CD200, CD201, CD202b, CD203c, CD204, CD205, CD206, CD207, CD208, CD209, CD210, CD212, CD213a1, CD213a2, CD215, CD217, CD218a, CD218b, CD220, CD221, CD222, CD223, CD224, CD225, CD226, CD227, CD228, CD229, CD230, CD231, CD232, CD233, CD234, CD235a, CD235b, CD236, CD236R, CD238, CD239, CD240CE, CD240D, CD241, CD242, CD243, CD244, CD246, CD247, CD248, CD249, CD252, CD253, CD254, CD256, CD257, CD258, CD261, CD262, CD263, CD264, CD265, CD266, CD267, CD268, CD269, CD270, CD271, CD272, CD273, CD274, CD275, CD276, CD277, CD278, CD279, CD280, CD281, CD282, CD283, CD284, CD286, CD288, CD289, CD290, CD292, CD293w, CD294, CD295, CD296, CD297, CD298, CD299, CD300A, CD300C, CD300E, CD300F, CD301, CD302, CD303, CD304, CD305, CD306, CD307a, CD307b, CD307c, CD307d, CD307e, CD309, CD312, CD314, CD315, CD316, CD317, CD318, CD319, CD320, CD321, CD322, CD324, CD325, CD326, CD327, CD328, CD329, CD331, CD332, CD333, CD334, CD335, CD336, CD337, CD338, CD339, CD340, CD344, CD349, CD350, CD351, CD352, CD353, CD354, CD355, CD357, CD358, CD360, CD361, CD362, CD363, CD364, CD365, CD366, CD367, CD368, CD369, CD370, CD371, CD66, CTGF, Cytokeratin, DLLI, DLL3, DLL4, EGFL7, EGFR, EPHA3, FAP, FcRn, FGF23, Fibrin, Fibronectin, FRalpha, Ganglioside D2, gp75, GPC3, Guanylate cyclase 2C, Hematopoietin 1, Hepatocyte growth factor, Her3, Histone HI, HLA-DR, IgE, IL-13, IL-17, IL-18, IL-2, IL-22, IL-31, IL-5, IL-6, ILIRAP, IL23, INFAI, Integrin beta-7, Interferon receptor, IL-I, Inter-leukin 23, KLKBI, LEC, Leucine-rich repeat-containing protein 15, LINGO-I, LIVIA, Lysyl oxidase homolog 2, Mesothelin, MIF, MMP9, Myelin-associated glycoprotein, Nectin-4, NOTCH!, NOTCH2, Notch3, PCSK9, PS, PSMA (GCPII), PTK7, Reticulon 4 (NOGO), Sclerostin, SLITRK6, Sodium-dependent phosphate transport protein 2B (NaPi2b), Sphingosine-1-phosphate (SIP), STEAPI, TcRa, Tenascin C (TN-C), TIGIT, TROP-2, Tumor necrosis factor, TWEAK, VEGFA, VEGFR1, VEGFR2, VEGRFI, Vimentin, VISTA, or von Willebrand factor; or wherein the cell surface epitope forms part of: AXL, c-Met, C242 antigen (CanAg) novel glycoform of MUC1, *Canis lupus familiaris* IL31, CD3, CD1a, CD1b, CD1c, CD1d, CD1e, CD2, CD3d, CD3e, CD3g, CD4, CDS, CD6, CD8a, CD8b, CD9, CD11a, CD11b, CD11c, CD11d, CD13, CD15s, CD15u, CD16a, CD16b, CDI 7, CD18, CD19, CD20, CD21, CD22, CD23, CD24, CD25, CD27, CD28, CD30, CD32A, CD32B, CD32C, CD33, CD34, CD37, CD38, CD39, CD40, CD43, CD44, CD45, CD47, CD48, CD49d, CD50, CD52, CD53, CD54, CD60a, CD62E, CD63, CD64a, CD65, CD65s, CD68, CD69, CD70, CD71, CD72, CD74, CD75, CD77, CD79A, CD79B, CD80, CD83, CD84, CD85A, CD85B, CD85C, CD85D, CD85F, CD85G, CD85H, CD85I, CD85J, CD85K, CD85M, CD86, CD90, CD92, CD93 CD94 CD95 CD96 CD97B CD99 CD99R CDI06 CDI08 CD110 CD115 CDI 17, CD123, CD126, CD130, CD131, CD132, CD133, CD135, CD140B, CD143, CD148, CD150, CD152, CD153, CD154, CD157, CD158a, CD158B1, CD158B2, CD158C, CD158D, CD158E1, CD158E2, CD158F1, CD158F2, CD158G, CD158H, CD158I, CD158J, CD158K, CD159a, CD159c, CD160, CD161, CD162, CD164, CD165, CD166, CD169, CD170, CD172a, CD174, CD175, CD177, CD178, CD179a, CD179b, CD180, CD181, CD182, CD183, CD184, CD185, CD194, CD195, CD197, CD198w, CD200, CD204, CD205, CD206, CD207, CD209, CD210, CD212, CD213a1, CD215, CD218a, CD218b, CD221, CD223, CD229, CD231, CD233, CD236R, CD244, CD247, CD252, CD256, CD262, CD267, CD268, CD269, CD273, CD279, CD280, CD281, CD282, CD283, CD284, CD286, CD288, CD289, CD290, CD296, CD300A, CD300C, CD300E, CD300F, CD303, CD305, CD306, CD307a, CD307b, CD307c, CD307d, CD307e, CD312, CD314, CD317, CD319, CD320, CD321, CD322, CD325, CD327, CD328, CD329, CD334, CD335, CD336, CD337, CD352, CD353, CD355, CD361, CD367, CD368, CD369, CD370, CD371, DLLI, EPHA3, Fibronectin, GPC3, Hepatocyte growth factor, HLA-DR, IL-13, IL-6, ILIRAP, TcRa, or TIGIT; or wherein the cell surface epitope forms part of: SAC (Mucin SAC), 5T4, activin receptor-like kinase 1, adenocarcinoma antigen, alpha-fetoprotein, AOC3, AXL, c-Met, C242 antigen (CanAg) novel glycoform of MUC1, CA-125, *Canis lupus familiaris* IL31, tumor-associated glycoprotein 72 antigen, Angiopoietin-2, CA19-9, Carbonic anhydrase 9 (CA-IX), CD1d, CDS, CD7, CD9, CDI0, CD13, CD14, CD15s, CD15su, CD15u, CD24, CD27, CD29, CD39, CD40, CD44, CD44v6, CD46, CD47, CD49b, CD49e, CD49f, CD50, CD51, CD54, CD56, CD57, CD58, CD60a, CD60b, CD60c, CD61, CD62P, CD66a, CD66c, CD66e, CD68, CD70, CD73, CD81, CD87, CD88, CD91, CD99, CD99R, CDI00, CD102, CD105, CD106, CD109, CDI 12, CDI 12R, CDI 15, CDI 17, CD126, CD133, CD134, CD136, CD137, CD138, CD140A, CD141, CD142, CD144, CD146, CD147, CD151, CD152, CD156a, CD156b, CD158a, CD159a, CD164, CD167a, CD168, CDI 71, CDI 74, CDI 75, CDI 75s, CDI 76, CDI 78, CD195, CD201, CD203c, CD205, CD206, CD213a2, CD220, CD221, CD223, CD224, CD225, CD226, CD227, CD228, CD233, CD239, CD243, CD243, CD246, CD248, CD252, CD253, CD254, CD261, CD262, CD266, CD271, CD272, CD274, CD276, CD278, CD279, CD280, CD295, CD299, CD301, CD302, CD304, CD309, CD317, CD318, CD324, CD326, CD331, CD332, CD333, CD334, CD338, CD339, CD340, CD344, CD349, CD350, CD354, CD357, CD358, CD360, CD363, CD366, CD66, CTGF, Cytokeratin, DLLI, DLL3, DLL4, EGFL7, EGFR, EPHA3, FAP, FRalpha, Ganglioside D2, gp75, GPC3, Guanylate cyclase 2C, Hematopoietin 1, Hepatocyte growth factor, Her3, Histone HI, IL-13, ILIRAP, Leucine-rich repeat-containing protein 15, LIVIA, Mesothelin, MIF, MMP9, Nectin-4, NOTCH!, NOTCH2, Notch3, PS, PSMA (GCPII), PTK7, Reticulon 4 (NOGO), SLITRK6, Sodium-dependent phosphate transport protein 2B (NaPi2b), Sphingosine-1-phosphate (SIP), STEAPI, Tenascin C (TN-C), TIGIT, TROP-2, VEGFA, VEGFR1, VEGFR2, VEGRFI, Vimentin, or VISTA; or wherein the cell surface epitope forms part of: CD27, CD40, CD81, CD86, CD90, CD112R, CDI 15, CD134, CD137, CD152, CD153, CD156b, CD159a, CD162, CDI 78, CD200, CD205, CD223, CD252, CD272, CD274, CD276, CD278, CD279, CD360, CD369, IL-6, MIF, PSMA (GCPII), or TIGIT; or wherein the cell surface epitope forms part of: CD4, CD31, CD32A, CD32B, CD32C, CD34, CD45, CD55, CD59, CD66d, CD81, CD111, CD112, CD113, CD114, CD155, CDI 78, CD212, CD232, CD234, CD258, CD270, CD289, CD321, CD365, Interferon receptor, Tenascin C (TN-C), TIGIT, or Tumor necrosis factor; or wherein the cell surface epitope forms part of: ACVR2B, AOC3, Addressin, CCLI 1, CD4, CDS, CD11a, CD11b, CD25, CD26, CD31, CD35, CD36, CD38, CD40, CD41, CD49b, CD49c, CD49d, CD54, CD60a, CD61, CD62L, CD66b, CD66d, CD74, CD83, CD86, CD88, CD89, CD90, CD95, CD97, CD100, CD103, CD104, CD106, CD107a, CD107b, CD116, CD119, CD122, CD123, CD124, CD125, CD126, CD127, CD140B, CD142, CD147, CD154, CD162, CD174, CD178, CD191, CD192, CD193, CD196, CD202b, CD208, CD210, CD217, CD220, CD252, CD254, CD257, CD258, CD265, CD268, CD270, CD275, CD284, CD294, CD295, CD329, CD363, CD366, CTGF, FcRn, FGF23, Hematopoietin 1, IgE, IL-13, IL-17, IL-18, IL-22, IL-31, IL-5, IL23, INFAI, Integrin beta-7, IL-1, Interleukin 23, LEC, LINGO-I, Lysyl oxidase homolog 2, MMP9, PCSK9, Sclerostin, Tenascin C (TN-C), Tumor necrosis factor, or TWEAK; or wherein the cell surface epitope forms part of: HER2, folate receptor, EGFR, CD20, CD30, CD3e, FGFR3, Napi2b, CD33A, CEACAM5, EPCAM, or PSMA; or wherein the cell surface epitope forms part of HER2.

9. The covalent conjugate of any one of claim 1, wherein the payload comprises the small molecule drug, wherein the small molecule drug is a V-ATPase inhibitor, a HSP90 inhibitor, an ion channel inhibitor, an IAP inhibitor, an mTor inhibitor, a microtubule stabilizer, a microtubule destabilizer, a dolastatin, a methionine aminopeptidase, an inhibitor of nuclear export of proteins, a DPPIV inhibitor, an inhibitor of phosphoryl transfer reactions in mitochondria, a protein synthesis inhibitor, a kinase inhibitor, a CDK2 inhibitor, a CDK9 inhibitor, a proteasome inhibitor, a kinesin inhibitor, an HDAC inhibitor, a DNA damaging agent, a DNA alkylating agent, a DNA intercalator, a DNA minor groove binder or a DHFR inhibitor, a radionuclide-containing compound, a chemotherapeutic moiety, an anti-cancer drug, an antimitotic compound, an inhibitor of DNA replication, an inhibitor of protein synthesis, cyclophosphamide, vincristine, prednisolone, cyclophosphamide, methotrexate, 5-fluorouracil, a DNA cleaving compound, a chalicheamicin, SN-38, irinotecan, camptothecin, D6.5, a duocarmycin, an auristatin, a maytansine, a maytansinoid, an amatoxin, durcomycin, doxorubicin, a pyrrolbenzodiazepine (PBD), an anthracycline, paclitaxel, a fungal toxin, or a derivative, analogue or prodrug thereof, or wherein the payload comprises the small molecule drug, wherein the small molecule drug is MMAE, MMAF, DMI, DM2, DM3, DM4, SN38, doxorubicin, pyrrolbenzodiazepine (PBD), duocarmycin, tubulysin, chalicheamicin, anthracycline, paclitaxel, vinblastine, alpha-amanitin, or a derivative, analogue or prodrug thereof; or wherein the payload comprises the small molecule drug, wherein the small molecule drug is MMAE, DMI, doxorubicin, duocarmycin, paclitaxel or a derivative, analogue or prodrug thereof, or wherein the payload comprises the peptide or protein.

10. The covalent conjugate of claim 1, wherein the covalent conjugate comprises the antibody, optionally wherein the covalent conjugate comprises an anti-HER2 antibody, and the payload is MMAE.

11. The covalent conjugate of claim 1, wherein the human cell has outer leaflet phosphatidylserine; and/or wherein the human cell is: a cancer cell; a pathogen-infected cell; or an immune cell responsible for an autoimmune condition or disease.

12. A covalent conjugate comprising:

an antibody that specifically binds to a cell surface epitope of a human cell that has outer leaflet phosphatidylserine, or an antibody derivative, the antibody derivative comprising: an antibody variable domain that specifically binds to the cell surface epitope of the human cell, and a hinge region coupling two heavy chains or two heavy chain fragments;

a payload comprising: a small molecule drug of less than 3 kDa that is toxic to human cells, or a plurality of small molecule drugs that are each less than 3 kDa and which are toxic to human cells; or a peptide or protein of less than 100 kDa, wherein the peptide or protein comprises: a transcription factor, a bacterial toxin, a viral toxin, a protease, an RNAse, a DNAse, a proteolysis targeting chimera (PROTAC), or a fluorescent or colorimetric marker; and a first LL37-derived polypeptide and a second LL37-derived polypeptide, the first LL37-derived polypeptide, the first LL37-derived polypeptide and the second LL37-derived polypeptide each comprising an LL37-derived amino acid sequence or sequences, wherein each of the LL37-derived amino acid sequence or sequences independently comprise:

SEQ ID NO: 14 (IGKEFKRIVQRIKD-FLRNLVPRTES);

or SEQ ID NO: 111 (SETRPVLNRLFDKIRQ-VIRKFEKGI);

or a fragment of SEQ ID NO: 14 or 111 having consecutive deletions at either or both of the N- and C-termini up to a total deletion of at most 8 amino acids;

or a plurality of fragments of SEQ ID NO: 14 and/or SEQ ID NO: 111, each fragment of the plurality of fragments independently having consecutive deletions at either or both of the N- and C-termini up to a total deletion of at most 10 amino acids;

wherein each Lys and Arg residue in each fragment is independently substituted or not substituted with a conservative substitute amino acid residue selected from the group consisting of: Lys, Orn (ornithine), DBu (2,4-diaminobutanoate), Dpr (2,3-diaminopropionate), Hyl (hydroxylysine), aHyl (allo-hydroxylysine), MeLys (6-N-methyllysine), Arg, Cit (citrulline), and 2-amino-3-guanidinopropionate;

wherein 0, 1, 2, 3, 4 or 5 amino acid residues, selected from the group consisting of Gly, Asp, Glu, Asn, Gln, Ile, Leu, Val, Phe, Ser, Thr, Pro, and a combination thereof, in each fragment are each independently substituted with a conservative substitute amino acid residue selected from within its Group, $X^1$, $X^1$, $X^3$, $X^4$, $X^5$, or $X^6$ as defined below:

(Group $X^1$) Ala, Gly;

(Group $X^2$) Asp, Glu, bAad (3-aminoadipic acid), Apm (2-aminopimelic acid);

(Group $X^3$) Asn, Gln;

(Group $X^4$) Ile, Leu, Met, Val, Phe, Tyr, Trp, Abu (2-aminobutyric acid), Ahe (2-aminoheptanoic acid), alle (allo-isoleucine), Nva (norvaline), Nle (norleucine);

(Group $X^5$) Ser, Thr, Tyr;

(Group $X^6$) Pro, 3Hyp (3-hydroxyproline), 4Hyp (4-hydroxyproline); and wherein 0, 1 or 2 amino acid residues, selected from the group consisting of Lys, Arg, Gly, Asp, Glu, Asn, Gln, Ile, Leu, Val, Phe, Ser, Thr, Pro, and a combination thereof, in each fragment are each independently substituted with a non-conservative substitute amino acid residue.

13. A covalent conjugate comprising:

an antibody that specifically binds to a cell surface epitope of a human cell, or an antibody derivative, the antibody derivative comprising: an antibody variable domain that specifically binds to the cell surface epitope of the human cell, and a hinge region coupling two heavy chains or two heavy chain fragments;

a payload comprising: a small molecule drug of less than 3 kDa that is toxic to human cells, or a plurality of small molecule drugs that are each less than 3 kDa and which are toxic to human cells; or a peptide or protein of less than 100 kDa, wherein the peptide or protein comprises: a transcription factor, a bacterial toxin, a viral toxin, a protease, an RNAse, a DNAse, a proteolysis targeting chimera (PROTAC), or a fluorescent or colorimetric marker; and a first LL37-derived polypeptide and a second LL37-derived polypeptide, the first LL37-derived polypeptide, the first LL37-derived polypeptide and the second LL37-derived polypeptide each comprising an LL37-derived amino acid sequence or sequences, wherein each of the LL37-derived amino acid sequence or sequences independently comprise:

SEQ ID NO: 14 (IGKEFKRIVQRIKD-FLRNLVPRTES);

or SEQ ID NO: 111 (SETRPVLNRLFDKIRQ-VIRKFEKGI);

or a fragment of SEQ ID NO: 14 or 111 having consecutive deletions at either or both of the N- and C-termini up to a total deletion of at most 8 amino acids;

or a plurality of fragments of SEQ ID NO: 14 and/or SEQ ID NO: 111, each fragment of the plurality of fragments independently having consecutive deletions at either or both of the N- and C-termini up to a total deletion of at most 10 amino acids;

wherein each Lys and Arg residue in each fragment is independently substituted or not substituted with a conservative substitute amino acid residue selected from the group consisting of: Lys, Orn (ornithine), DBu (2,4-diaminobutanoate), Dpr (2,3-diaminopropionate), Hyl (hydroxylysine), aHyl (allo-hydroxylysine), MeLys (6-N-methyllysine), Arg, Cit (citrulline), and 2-amino-3-guanidinopropionate;

wherein 0, 1, 2, 3, 4 or 5 amino acid residues, selected from the group consisting of Gly, Asp, Glu, Asn, Gln, Ile, Leu, Val, Phe, Ser, Thr, Pro, and a combination thereof, in each fragment are each independently substituted with a conservative substitute amino acid residue selected from within its Group, $X^1$, $X^2$, $X^3$, $X^4$, $X^5$, or $X^6$ as defined below:

(Group $X^1$) Ala, Gly;

(Group $X^2$) Asp, Glu, bAad (3-aminoadipic acid), Apm (2-aminopimelic acid);

(Group $X^3$) Asn, Gln;

(Group $X^4$) Ile, Leu, Met, Val, Phe, Tyr, Trp, Abu (2-aminobutyric acid), Ahe (2-aminoheptanoic acid), aIle (allo-isoleucine), Nva (norvaline), Ne (norleucine);

(Group $X^5$) Ser, Thr, Tyr;

(Group $X^6$) Pro, 3Hyp (3-hydroxyproline), 4Hyp (4-hydroxyproline);

wherein 0, 1 or 2 amino acid residues, selected from the group consisting of Lys, Arg, Gly, Asp, Glu, Asn, Gln, Ile, Leu, Val, Phe, Ser, Thr, Pro, and a combination thereof, in each fragment are each independently substituted with a non-conservative substitute amino acid residue; and wherein the human cell is: a cancer cell; a pathogen-infected cell; or an immune cell responsible for an autoimmune condition or disease.

* * * * *

```
                        SEQUENCE LISTING

<160> NUMBER OF SEQ ID NOS: 134

<210> SEQ ID NO 1
<211> LENGTH: 37
<212> TYPE: PRT
<213> ORGANISM: homo sapiens
<220> FEATURE:
<221> NAME/KEY: MISC_FEATURE
<223> OTHER INFORMATION: full length LL37

<400> SEQUENCE: 1

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
        35

<210> SEQ ID NO 2
<211> LENGTH: 39
<212> TYPE: PRT
<213> ORGANISM: artificial
<220> FEATURE:
<223> OTHER INFORMATION: GG-LL37

<400> SEQUENCE: 2

Gly Gly Leu Leu Gly Asp Phe Phe Arg Lys Ser Lys Glu Lys Ile Gly
1               5                   10                  15

Lys Glu Phe Lys Arg Ile Val Gln Arg Ile Lys Asp Phe Leu Arg Asn
            20                  25                  30

Leu Val Pro Arg Thr Glu Ser
        35

<210> SEQ ID NO 3
<211> LENGTH: 469
<212> TYPE: PRT
<213> ORGANISM: artificial
<220> FEATURE:
<223> OTHER INFORMATION: Anti-HER2 mAb (Trastuzumab) heavy chain;
      Secretory signal peptide at 1-19

<400> SEQUENCE: 3

Met Asp Trp Thr Trp Arg Ile Leu Phe Leu Val Ala Ala Ala Thr Gly
1               5                   10                  15

Ala His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Asn Ile
        35                  40                  45
```

```
Lys Asp Thr Tyr Ile His Trp Val Arg Gln Ala Pro Gly Lys Gly Leu
    50                  55                  60

Glu Trp Val Ala Arg Ile Tyr Pro Thr Asn Gly Tyr Thr Arg Tyr Ala
65                  70                  75                  80

Asp Ser Val Lys Gly Arg Phe Thr Ile Ser Ala Asp Thr Ser Lys Asn
                85                  90                  95

Thr Ala Tyr Leu Gln Met Asn Ser Leu Arg Ala Glu Asp Thr Ala Val
            100                 105                 110

Tyr Tyr Cys Ser Arg Trp Gly Gly Asp Gly Phe Tyr Ala Met Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
            165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
            245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
            325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Asp Glu Leu Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
            405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460
```

```
Leu Ser Pro Gly Lys
465

<210> SEQ ID NO 4
<211> LENGTH: 246
<212> TYPE: PRT
<213> ORGANISM: artificial
<220> FEATURE:
<223> OTHER INFORMATION: Anti-HER2 mAb (Trastuzumab) light chain;
      Secretory signal peptide at 1-19

<400> SEQUENCE: 4

Met Leu Pro Ser Gln Leu Ile Gly Phe Leu Leu Leu Trp Val Pro Ala
1               5                   10                  15

Ser Arg Gly Asp Ile Gln Met Thr Gln Ser Pro Ser Ser Leu Ser Ala
                20                  25                  30

Ser Val Gly Asp Arg Val Thr Ile Thr Cys Arg Ala Ser Gln Asp Val
                35                  40                  45

Asn Thr Ala Val Ala Trp Tyr Gln Gln Lys Pro Gly Lys Ala Pro Lys
    50                  55                  60

Leu Leu Ile Tyr Ser Ala Ser Phe Leu Tyr Ser Gly Val Pro Ser Arg
65                  70                  75                  80

Phe Ser Gly Ser Arg Ser Gly Thr Asp Phe Thr Leu Thr Ile Ser Ser
                85                  90                  95

Leu Gln Pro Glu Asp Phe Ala Thr Tyr Tyr Cys Gln Gln His Tyr Thr
            100                 105                 110

Thr Pro Pro Thr Phe Gly Gln Gly Thr Lys Leu Glu Ile Lys Arg Thr
            115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
            165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
            195                 200                 205

Lys Val Tyr Ala Cys Glu Val Thr His Gln Gly Leu Ser Ser Pro Val
    210                 215                 220

Thr Lys Ser Phe Asn Arg Gly Glu Cys Gly Gly Gly Ser Leu Pro
225                 230                 235                 240

Met Thr Gly Gly His Gly
                245

<210> SEQ ID NO 5
<211> LENGTH: 55
<212> TYPE: DNA
<213> ORGANISM: artificial
<220> FEATURE:
<223> OTHER INFORMATION: forward PCR primer

<400> SEQUENCE: 5
ctgggtcacc gtggtagcgg ctcttgactc gagcaccacc accaccacca ctgag          55

<210> SEQ ID NO 6
<211> LENGTH: 57
<212> TYPE: DNA
<213> ORGANISM: artificial
```

<220> FEATURE:
<223> OTHER INFORMATION: reverse PCR primer

<400> SEQUENCE: 6
agagccgcta ccacggtgac ccagtttttga cggcagatca cagtagcggg caaccgc          57

<210> SEQ ID NO 7
<211> LENGTH: 990
<212> TYPE: DNA
<213> ORGANISM: artificial
<220> FEATURE:
<223> OTHER INFORMATION: structural gene sequence of Z-RFP

<400> SEQUENCE: 7
atgggcagca gccatcacca ccatcatcac catcacagcg gcagcgatta caaggatgac          60
gacgacaagg ctggcagcca tatggctagc gtggacaaca aattcaacaa agaacaacaa          120
aacgcgttct atgagatctt acatttacct aacttaaacg aagaacaacg aaacgccttc          180
atccaaagtt taaagatgaa cccaagccaa agcgctaacc ttttagcaga agctaaaaag          240
ctaaacgacg ctcaggcgcc gaaaggtacc ggatccgaat tcatggttag cgaactgatt          300
aaggaaaata tgcacatgaa actgtatatg gaaggcaccg tcaacaatca tcactttaaa          360
tgcacgagtg aaggtgaagg caagccgtat gaaggcaccc agacgatgcg tattaaagca          420
gtggaaggcg gtccgctgcc gtttgcattc gatattctgg ccaccagttt tatgtacggt          480
tccaaaacct tcattaacca tacgcagggc atcccggatt tctttaaaca aagtttttccg          540 gaaggtttca cctgggaacg tgtgaccacg tatgaagacg gcggtgttct gaccgccacg          600
caggatacgt ccctgcaaga cggctgtctg atttacaatg ttaaaatccg cggtgtcaac          660
ttcccgagca atggcccggt tatgcagaaa aagaccctgg gttgggaagc atctaccgaa          720
acgctgtatc cggctgatgg tggtctggaa ggtcgtgcag acatggctct gaaactggtg          780
ggcggtggcc atctgatttg caacctgaag accacgtacc gttctaaaaa gccggcgaaa          840
aatctgaaga tgccgggtgt ctattacgtg gatcgtcgcc tggaacgcat caaagaagcc          900
gacaaggaaa cctatgttga acagcatgaa gtggcggttg cccgctactg tgatctgccg          960
tcaaaactgg gtcaccgtgg tagcggctct                                           990

<210> SEQ ID NO 8
<211> LENGTH: 1407
<212> TYPE: DNA
<213> ORGANISM: artificial
<220> FEATURE:
<223> OTHER INFORMATION: cDNA of heavy chain for anti-HER2 mAb
     (Trastuzumab); 1-57 encodes the N-terminal secretory signal
     peptide

<400> SEQUENCE: 8
atggattgga catggaggat tctgttcctg gtggctgcag ctactggagc tcattctgag          60
gtgcagctgg tggaatcagg aggaggactg gtgcagccag gaggatctct gagactgtct          120
tgcgccgcca gcggcttcaa catcaaggac acctacatcc attgggtccg gcaggctcca          180
ggaaaaggac tggaatgggt ggctaggatc tacccacca acggctacac ccgatacgca          240
gacagcgtga agggcaggtt caccatcagc gccgatacca gcaagaacac cgcctacctg          300
cagatgaaca gcctgagagc cgaggacacc gccgtgtact attgtagccg gtggggagga          360
gacggcttct acgctatgga ttattggggc caggaacac tggtgacagt gtctagcgct          420
agcaccaagg gacctagcgt gtttcctctg gcccccttcta gcaagagcac aagcggagga          480

-continued

```
acagccgctc tgggctgtct ggtgaaagac tacttccccg agccagtgac cgtgtcttgg      540
aactcaggag ccctgacaag cggagtgcac acatttccag ccgtgctgca gagcagcgga      600
ctgtactctc tgagcagcgt ggtgaccgtg ccttcttctt ctctgggcac ccagacctac      660
atctgcaacg tgaaccacaa gcccagcaac accaaggtgg acaagaaggt ggagcccaag      720
tcttgcgaca aaacacatac ttgccctcca tgtccagctc cagaactgct gggaggacca      780
agcgtgttcc tgttccctcc taagcccaag gacaccctga tgatcagccg gacccccagaa     840 gtgacttgcg tggtggtgga cgtgtcccac gaagaccccg aggtcaagtt caattggtac      900
gtggacggag tggaggtgca caacgctaag accaagcccg gggaggagca gtacaacagc      960
acctacaggg tggtgtccgt gctgacagtg ctgcaccagg attggctgaa cggcaaggag     1020
tacaagtgca aggtgtccaa caaggccctg ccagctccca tcgagaagac catcagcaag     1080
gccaagggac agcctagaga gcctcaggtg tacaccctgc ctccttctag ggacgagctg     1140
accaagaacc aggtgtccct gacttgcctc gtgaagggct ctacccccag cgacatcgca     1200
gtggagtggg aaagcaacgg tcagccagag aacaactaca gaccaccccc cccagtgctg     1260
gacagcgacg gcagcttctt cctgtacagc aagctgaccg tggacaaaag ccgctggcag     1320
cagggcaacg tgttctcttg cagcgtgatg cacgaggccc tgcacaacca ctacacccag     1380
aagagcctga gcctgagccc aggaaag                                          1407
```

<210> SEQ ID NO 9
<211> LENGTH: 738
<212> TYPE: DNA
<213> ORGANISM: artificial
<220> FEATURE:
<223> OTHER INFORMATION: cDNA of light chain for anti-HER2 mAb
      (Trastuzumab); 1-57 encodes the N-terminal secretory signal
      peptide

<400> SEQUENCE: 9

```
atgctgccca gccagctgat cggctttctg ctgctgtggg tgcctgcctc cagaggcgac       60
atccagatga cccagagccc atccagcctg tctgcctccg tgggcgacag agtgaccatc      120
acatgccgcg cttctcagga tgtgaacaca gccgtggctt ggtaccagca gaagcctggc      180
aaggccccaa agctgctgat ctactccgcc tctttcctgt attccggcgt gccaagcagg      240
ttttccggca gccggtctgg aaccgacttc accctgacaa tctcttccct gcagcccgag      300
gattttgcca catactattg ccagcagcac tataccacac ccctaccttc ggccagggc       360 acaaagctgg agatcaagag gaccgtggcc gctcctagcg tgttcatctt ccacccctct      420
gacgagcagc tgaagtctgg cacagcttcc gtggtgtgcc tgctgaacaa cttctaccca      480
cgggaggcca aggtgcagtg gaaggtggat aacgctctgc agtccggcaa tagccaggag      540
tctgtgaccg agcaggactc caaggatagc acatattctc tgagctctac cctgacactg      600
tccaaggccg attacgagaa gcacaaggtg tatgcttgcg aggtgaccca tcagggcctg      660
tccagccccg tgacaaagtc tttcaatagg ggagagtgtg aggaggagg ctccctgcct       720 atgaccggcg gccatggc                                                     738
```

<210> SEQ ID NO 10
<211> LENGTH: 42
<212> TYPE: DNA
<213> ORGANISM: artificial
<220> FEATURE:
<223> OTHER INFORMATION: forward-direction PCR primer

<400> SEQUENCE: 10

-continued

```
actgacgaat tcatggtgag caagggcgag gagctgttca cc                            42

<210> SEQ ID NO 11
<211> LENGTH: 43
<212> TYPE: DNA
<213> ORGANISM: artificial
<220> FEATURE:
<223> OTHER INFORMATION: reverse-direction PCR primer

<400> SEQUENCE: 11
actgacctcg agttacttgt acagctcgtc catgccgaga gtg                           43

<210> SEQ ID NO 12
<211> LENGTH: 999
<212> TYPE: DNA
<213> ORGANISM: artificial
<220> FEATURE:
<223> OTHER INFORMATION: structural gene sequence of Z-GFP

<400> SEQUENCE: 12
atgggcagca gccatcacca ccatcatcac catcacagcg gcagcgatta caaggatgac         60
gacgacaagg ctggcagcca tatggctagc gtggacaaca aattcaacaa agaacaacaa        120
aacgcgttct atgagatctt acatttacct aacttaaacg aagaacaacg aaacgccttc        180
atccaaagtt aaaagatga cccaagccaa agcgctaacc tttttagcaga agctaaaaag        240 ctaaacgacg ctcaggcgcc gaaaggtacc ggatccgaat tcatggtgag caagggcgag       300
gagctgttca ccggggtggt gcccatcctg gtcgagctgg acggcgacgt aaacggccac       360
aagttcagcg tgtccggcga gggcgagggc gatgccacct acggcaagct gaccctgaag       420
ttcatctgca ccaccggcaa gctgcccgtg ccctggccca ccctcgtgac caccctgacc       480
tacggcgtgc agtgcttcag ccgctacccc gaccacatga gcagcacga  cttcttcaag       540 tccgccatgc ccgaaggcta cgtccaggag cgcaccatct tcttcaagga cgacggcaac       600
tacaagaccc gcgccgaggt gaagttcgag ggcgacaccc tggtgaaccg catcgagctg       660
aagggcatcg acttcaagga ggacggcaac atcctggggc acaagctgga gtacaactac       720
aacagccaca cgtctatat catggccgac aagcagaaga acggcatcaa ggtgaacttc        780
aagatccgcc acaacatcga ggacggcagc gtgcagctcg ccgaccacta ccagcagaac       840
acccccatcg gcgacggccc cgtgctgctg cccgacaacc actacctgag cacccagtcc       900
gccctgagca agacccccaa cgagaagcgc gatcacatgg tcctgctgga gttcgtgacc       960
gccgccggga tcactctcgg catggacgag ctgtacaag                              999

<210> SEQ ID NO 13
<211> LENGTH: 25
<212> TYPE: PRT
<213> ORGANISM: homo sapiens
<220> FEATURE:
<221> NAME/KEY: MISC_FEATURE
<223> OTHER INFORMATION: PEP#35 fragment of LL37

<400> SEQUENCE: 13

Leu Leu Gly Asp Phe Phe Arg Lys Ser Lys Glu Lys Ile Gly Lys Glu
1               5                   10                  15

Phe Lys Arg Ile Val Gln Arg Ile Lys
            20                  25

<210> SEQ ID NO 14
<211> LENGTH: 25
```

-continued

```
<212> TYPE: PRT
<213> ORGANISM: homo sapiens
<220> FEATURE:
<221> NAME/KEY: MISC_FEATURE
<223> OTHER INFORMATION: PEP#36 fragment of LL37

<400> SEQUENCE: 14

Ile Gly Lys Glu Phe Lys Arg Ile Val Gln Arg Ile Lys Asp Phe Leu
1               5                   10                  15

Arg Asn Leu Val Pro Arg Thr Glu Ser
            20                  25

<210> SEQ ID NO 15
<211> LENGTH: 19
<212> TYPE: PRT
<213> ORGANISM: homo sapiens
<220> FEATURE:
<221> NAME/KEY: MISC_FEATURE
<223> OTHER INFORMATION: PEP#37 fragment of LL37

<400> SEQUENCE: 15

Leu Leu Gly Asp Phe Phe Arg Lys Ser Lys Glu Lys Ile Gly Lys Glu
1               5                   10                  15

Phe Lys Arg

<210> SEQ ID NO 16
<211> LENGTH: 18
<212> TYPE: PRT
<213> ORGANISM: homo sapiens
<220> FEATURE:
<221> NAME/KEY: MISC_FEATURE
<223> OTHER INFORMATION: PEP#38 fragment of LL37

<400> SEQUENCE: 16

Ile Val Gln Arg Ile Lys Asp Phe Leu Arg Asn Leu Val Pro Arg Thr
1               5                   10                  15

Glu Ser

<210> SEQ ID NO 17
<211> LENGTH: 13
<212> TYPE: PRT
<213> ORGANISM: homo sapiens
<220> FEATURE:
<221> NAME/KEY: MISC_FEATURE
<223> OTHER INFORMATION: PEP#39 fragment of LL37

<400> SEQUENCE: 17

Leu Leu Gly Asp Phe Phe Arg Lys Ser Lys Glu Lys Ile
1               5                   10

<210> SEQ ID NO 18
<211> LENGTH: 12
<212> TYPE: PRT
<213> ORGANISM: homo sapiens
<220> FEATURE:
<221> NAME/KEY: MISC_FEATURE
<223> OTHER INFORMATION: PEP#40 fragment of LL37

<400> SEQUENCE: 18

Ile Gly Lys Glu Phe Lys Arg Ile Val Gln Arg Ile
1               5                   10

<210> SEQ ID NO 19
<211> LENGTH: 13
<212> TYPE: PRT
<213> ORGANISM: homo sapiens
```

-continued

```
<220> FEATURE:
<221> NAME/KEY: MISC_FEATURE
<223> OTHER INFORMATION: PEP#41 fragment of LL37

<400> SEQUENCE: 19

Lys Asp Phe Leu Arg Asn Leu Val Pro Arg Thr Glu Ser
1               5                   10

<210> SEQ ID NO 20
<211> LENGTH: 15
<212> TYPE: PRT
<213> ORGANISM: homo sapiens
<220> FEATURE:
<221> NAME/KEY: MISC_FEATURE
<223> OTHER INFORMATION: PEP#42 fragment of LL37

<400> SEQUENCE: 20

Lys Ser Lys Glu Lys Ile Gly Lys Glu Phe Lys Arg Ile Val Gln
1               5                   10                  15

<210> SEQ ID NO 21
<211> LENGTH: 15
<212> TYPE: PRT
<213> ORGANISM: homo sapiens
<220> FEATURE:
<221> NAME/KEY: MISC_FEATURE
<223> OTHER INFORMATION: PEP#43 fragment of LL37

<400> SEQUENCE: 21

Arg Ile Lys Asp Phe Leu Arg Asn Leu Val Pro Arg Thr Glu Ser
1               5                   10                  15

<210> SEQ ID NO 22
<211> LENGTH: 8
<212> TYPE: PRT
<213> ORGANISM: artificial
<220> FEATURE:
<223> OTHER INFORMATION: Sortase recognition sequence

<400> SEQUENCE: 22

Leu Pro Met Thr Gly Gly His Gly
1               5

<210> SEQ ID NO 23
<211> LENGTH: 5
<212> TYPE: PRT
<213> ORGANISM: artificial
<220> FEATURE:
<223> OTHER INFORMATION: SrtA recognition sequence derived from
      Staphylococcus aureus
<220> FEATURE:
<221> NAME/KEY: MISC_FEATURE
<222> LOCATION: (3)..(3)
<223> OTHER INFORMATION: Xaa can be any amino acid

<400> SEQUENCE: 23

Leu Pro Xaa Thr Gly
1               5

<210> SEQ ID NO 24
<211> LENGTH: 5
<212> TYPE: PRT
<213> ORGANISM: artificial
<220> FEATURE:
<223> OTHER INFORMATION: Srt A recognition sequence derived from
      Streptococcus pyogenes
<220> FEATURE:
<221> NAME/KEY: MISC_FEATURE
<222> LOCATION: (3)..(3)
```

-continued

```
<223> OTHER INFORMATION: Xaa can be any amino acid
<220> FEATURE:
<221> NAME/KEY: MISC_FEATURE
<222> LOCATION: (5)..(5)
<223> OTHER INFORMATION: Xaa can be Ala or Gly

<400> SEQUENCE: 24

Leu Pro Xaa Thr Xaa
1               5

<210> SEQ ID NO 25
<211> LENGTH: 5
<212> TYPE: PRT
<213> ORGANISM: artificial
<220> FEATURE:
<223> OTHER INFORMATION: Sortase recognition sequence derived from
      Clostridium difficile
<220> FEATURE:
<221> NAME/KEY: MISC_FEATURE
<222> LOCATION: (1)..(1)
<223> OTHER INFORMATION: Xaa can be Ser or Pro
<220> FEATURE:
<221> NAME/KEY: MISC_FEATURE
<222> LOCATION: (3)..(3)
<223> OTHER INFORMATION: Xaa can be any amino acid

<400> SEQUENCE: 25

Xaa Pro Xaa Thr Gly
1               5

<210> SEQ ID NO 26
<211> LENGTH: 5
<212> TYPE: PRT
<213> ORGANISM: Streptococcus pyogenes
<220> FEATURE:
<221> NAME/KEY: MISC_FEATURE
<223> OTHER INFORMATION: SrtC recognition sequence

<400> SEQUENCE: 26

Gln Val Pro Thr Gly
1               5

<210> SEQ ID NO 27
<211> LENGTH: 5
<212> TYPE: PRT
<213> ORGANISM: artificial
<220> FEATURE:
<223> OTHER INFORMATION: Engineered sortase recognition sequence
<220> FEATURE:
<221> NAME/KEY: MISC_FEATURE
<222> LOCATION: (3)..(3)
<223> OTHER INFORMATION: Xaa can be any amino acid

<400> SEQUENCE: 27

Leu Ala Xaa Thr Gly
1               5

<210> SEQ ID NO 28
<211> LENGTH: 5
<212> TYPE: PRT
<213> ORGANISM: artificial
<220> FEATURE:
<223> OTHER INFORMATION: Engineered sortase recognition sequence
<220> FEATURE:
<221> NAME/KEY: MISC_FEATURE
<222> LOCATION: (3)..(3)
<223> OTHER INFORMATION: Xaa can be any amino acid

<400> SEQUENCE: 28

Leu Pro Xaa Ser Gly
```

1               5

<210> SEQ ID NO 29
<211> LENGTH: 508
<212> TYPE: PRT
<213> ORGANISM: artificial
<220> FEATURE:
<223> OTHER INFORMATION: Anti-HER2 (scFv)-Fc; Secretory signal peptide
      at 1-19

<400> SEQUENCE: 29

Met Gly Ser Thr Ala Ile Leu Ala Leu Leu Leu Ala Val Leu Gln Gly
1               5                   10                  15

Val Cys Ser Gln Val Gln Leu Leu Gln Ser Gly Ala Glu Leu Lys Lys
                20                  25                  30

Pro Gly Glu Ser Leu Lys Ile Ser Cys Lys Gly Ser Gly Tyr Ser Phe
            35                  40                  45

Thr Ser Tyr Trp Ile Ala Trp Val Arg Gln Met Pro Gly Lys Gly Leu
        50                  55                  60

Glu Tyr Met Gly Leu Ile Tyr Pro Gly Asp Ser Asp Thr Lys Tyr Ser
65                  70                  75                  80

Pro Ser Phe Gln Gly Gln Val Thr Ile Ser Val Asp Lys Ser Val Ser
                85                  90                  95

Thr Ala Tyr Leu Gln Trp Ser Ser Leu Lys Pro Ser Asp Ser Ala Val
            100                 105                 110

Tyr Phe Cys Ala Arg His Asp Val Gly Tyr Cys Thr Asp Arg Thr Cys
        115                 120                 125

Ala Lys Trp Pro Glu Trp Leu Asp Asn Trp Gly Gln Gly Thr Leu Val
    130                 135                 140

Thr Val Ser Ser Gly Gly Gly Gly Ser Gly Gly Gly Gly Ser Gly Gly
145                 150                 155                 160

Gly Gly Ser Gln Ser Val Leu Thr Gln Pro Pro Ser Val Ser Ala Ala
                165                 170                 175

Pro Gly Gln Lys Val Thr Ile Ser Cys Ser Gly Ser Ser Ser Asn Ile
            180                 185                 190

Gly Asn Asn Tyr Val Ser Trp Tyr Gln Gln Leu Pro Gly Thr Ala Pro
        195                 200                 205

Lys Leu Leu Ile Tyr Gly His Thr Asn Arg Pro Ala Gly Val Pro Asp
    210                 215                 220

Arg Phe Ser Gly Ser Lys Ser Gly Thr Ser Ala Ser Leu Ala Ile Ser
225                 230                 235                 240

Gly Phe Arg Ser Glu Asp Glu Ala Asp Tyr Tyr Cys Ala Ser Trp Asp
                245                 250                 255

Tyr Thr Leu Ser Gly Trp Val Phe Gly Gly Gly Thr Lys Leu Thr Val
            260                 265                 270

Leu Gly Gly Ser Glu Pro Lys Ser Cys Asp Lys Thr His Thr Cys Pro
        275                 280                 285

Pro Cys Pro Ala Pro Glu Leu Leu Gly Gly Pro Ser Val Phe Leu Phe
    290                 295                 300

Pro Pro Lys Pro Lys Asp Thr Leu Met Ile Ser Arg Thr Pro Glu Val
305                 310                 315                 320

Thr Cys Val Val Val Asp Val Ser His Glu Asp Pro Glu Val Lys Phe
                325                 330                 335

Asn Trp Tyr Val Asp Gly Val Glu Val His Asn Ala Lys Thr Lys Pro
            340                 345                 350

-continued

```
Arg Glu Glu Gln Tyr Asn Ser Thr Tyr Arg Val Val Ser Val Leu Thr
        355                 360                 365

Val Leu His Gln Asp Trp Leu Asn Gly Lys Glu Tyr Lys Cys Lys Val
    370                 375                 380

Ser Asn Lys Ala Leu Pro Ala Pro Ile Glu Lys Thr Ile Ser Lys Ala
385                 390                 395                 400

Lys Gly Gln Pro Arg Glu Pro Gln Val Tyr Thr Leu Pro Pro Ser Arg
                405                 410                 415

Asp Glu Leu Thr Lys Asn Gln Val Ser Leu Thr Cys Leu Val Lys Gly
                420                 425                 430

Phe Tyr Pro Ser Asp Ile Ala Val Glu Trp Glu Ser Asn Gly Gln Pro
            435                 440                 445

Glu Asn Asn Tyr Lys Thr Thr Pro Pro Val Leu Asp Ser Asp Gly Ser
    450                 455                 460

Phe Phe Leu Tyr Ser Lys Leu Thr Val Asp Lys Ser Arg Trp Gln Gln
465                 470                 475                 480

Gly Asn Val Phe Ser Cys Ser Val Met His Glu Ala Leu His Asn His
                485                 490                 495

Tyr Thr Gln Lys Ser Leu Ser Leu Ser Pro Gly Lys
                500                 505
```

```
<210> SEQ ID NO 30
<211> LENGTH: 1524
<212> TYPE: DNA
<213> ORGANISM: artificial
<220> FEATURE:
<223> OTHER INFORMATION: cDNA of Anti-HER2 (scFv)-Fc; nucleotides 1-57
      encode the N-terminal secretory signal peptide

<400> SEQUENCE: 30
atgggctcta cagccatcct ggcactgctg ctggccgtgc tgcaggggggt gtgctctcag       60 gtgcagctgc tgcagagcgg agccgagctg aagaagcccg cgagagcct gaagatcagc       120 tgcaagggca gcggctacag cttcaccagc tactggatcg cctgggtccg gcagatgcct       180
ggcaagggcc tggaatacat gggcctgatc taccccggcg atagcgacac caagtacagc       240
cccagcttcc agggccaggt caccatcagc gtggacaaga gcgtgtccac cgcctacctg       300
cagtggagca gcctgaagcc cagcgacagc gccgtgtact tctgcgccag acacgacgtg       360
ggctactgca ccgacagaac ctgcgccaag tggcccgagt ggctggataa ttggggccag       420
ggcaccctgg tcacagtgtc ctctggcggc ggaggaagtg gaggggggagg aagcggagga       480 gggggcagcc agtctgtcct gacccagccc ccttctgtgt ctgccgcccc tggccagaaa       540
gtgaccatca gctgctccgg ctccagcagc aacatcggca caaactacgt gtcctggtat       600
cagcagctgc ccggcacagc ccccaagctg ctgatctacg ccacaccaa cagacctgcc       660 ggcgtgcccg atagattcag cggcagcaag agcggcacca cgccagcct ggccatcagc       720 ggcttcagaa gcgaggacga ggccgactac tactgcgcca gctgggacta cacactgagc       780 ggctggggtgt cggcggagg gaccaagctg accgtcctgg gcggatccga acccaagagc       840
tgcgacaaga cccacacctg ccccccttgt cctgctccgg agctgctggg cggacccagc       900
gtgttcctgt tcccccccaa gcccaaggac accctgatga tcagccggac ccccgaagtg       960
acctgcgtgg tggtggacgt gtcccacgag gaccctgaag tgaagttcaa ttggtacgtg      1020
gacggcgtgg aggtgcacaa cgccaagacc aagcccgggg aggaacagta caacagcacc      1080
taccgggtgg tgtccgtgct gacagtgctg caccaggact ggctgaacgg caaagaatac      1140
```

-continued

```
aagtgcaagg tgtccaacaa ggccctgcct gcacccatcg agaaaaccat cagcaaggcc      1200
aagggccagc ccagagaacc ccaggtgtac accctgccac ccagcagaga tgagctgacc      1260
aagaaccagg tgtcactgac ctgcctcgtg aagggcttct accccagcga tatcgccgtg      1320
gagtgggaga gcaacggcca gcctgagaac aactacaaga ccacccccc tgtgctggac        1380 agcgacggca gcttcttcct gtacagcaag ctgacagtgg acaagtcccg gtggcagcag      1440
ggcaacgtgt tctcttgctc cgtgatgcac gaggccctgc acaaccacta cacccagaag      1500
tccctaagct tgagccccgg caag                                             1524
```

<210> SEQ ID NO 31
<211> LENGTH: 511
<212> TYPE: PRT
<213> ORGANISM: artificial
<220> FEATURE:
<223> OTHER INFORMATION: Anti-HER2 mAb heavy chain-LL37 fusion;
      secretory signal peptide at 1-19

<400> SEQUENCE: 31

```
Met Asp Trp Thr Trp Arg Ile Leu Phe Leu Val Ala Ala Ala Thr Gly
1               5                   10                  15

Ala His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Asn Ile
        35                  40                  45

Lys Asp Thr Tyr Ile His Trp Val Arg Gln Ala Pro Gly Lys Gly Leu
    50                  55                  60

Glu Trp Val Ala Arg Ile Tyr Pro Thr Asn Gly Tyr Thr Arg Tyr Ala
65                  70                  75                  80

Asp Ser Val Lys Gly Arg Phe Thr Ile Ser Ala Asp Thr Ser Lys Asn
                85                  90                  95

Thr Ala Tyr Leu Gln Met Asn Ser Leu Arg Ala Glu Asp Thr Ala Val
            100                 105                 110

Tyr Tyr Cys Ser Arg Trp Gly Gly Asp Gly Phe Tyr Ala Met Asp Tyr
            115                 120                 125

Trp Gly Gln Gly Thr Leu Val Thr Val Ser Ser Ala Ser Thr Lys Gly
        130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
            195                 200                 205

Thr Val Pro Ser Ser Ser Leu Gly Thr Gln Thr Tyr Ile Cys Asn Val
        210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
            275                 280                 285
```

```
Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
                340                 345                 350

Pro Ile Glu Lys Thr Ile Ser Lys Ala Lys Gly Gln Pro Arg Glu Pro
            355                 360                 365

Gln Val Tyr Thr Leu Pro Pro Ser Arg Asp Glu Leu Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
                420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
    450                 455                 460

Leu Ser Pro Gly Lys Gly Gly Gly Gly Ser Leu Leu Gly Asp Phe Phe
465                 470                 475                 480

Arg Lys Ser Lys Glu Lys Ile Gly Lys Glu Phe Lys Arg Ile Val Gln
                485                 490                 495

Arg Ile Lys Asp Phe Leu Arg Asn Leu Val Pro Arg Thr Glu Ser
                500                 505                 510
```

<210> SEQ ID NO 32
<211> LENGTH: 1533
<212> TYPE: DNA
<213> ORGANISM: artificial
<220> FEATURE:
<223> OTHER INFORMATION: cDNA of Anti-HER2 mAb heavy chain-LL37 fusion;
     nucleotides 1-57 encode the N-terminal secretory signal peptide

<400> SEQUENCE: 32

```
atggattgga catggaggat tctgttcctg gtggctgcag ctactggagc tcattctgag      60
gtgcagctgg tggaatcagg aggaggactg gtgcagccag gaggatctct gagactgtct     120
tgcgccgcca gcggcttcaa catcaaggac acctacatcc attgggtccg gcaggctcca     180
ggaaaaggac tggaatgggt ggctaggatc tacccacca acggctacac ccgatacgca      240
gacagcgtga agggcaggtt caccatcagc gccgatacca gcaagaacac cgcctacctg     300
cagatgaaca gcctgagagc cgaggacacc gccgtgtact attgtagccg gtggggagga     360
gacggcttct acgctatgga ttattgggc agggaacac tggtgacagt gtctagcgct       420
agcaccaagg gacctagcgt gtttcctctg gcccttcta gcaagagcac aagcggagga      480
acagccgctc tgggctgtct ggtgaaagac tacttccccg agccagtgac cgtgtcttgg     540
aactcaggag ccctgacaag cggagtgcac acatttccag ccgtgctgca gagcagcgga     600
ctgtactctc tgagcagcgt ggtgaccgtg ccttcttctt ctctgggcac ccagacctac     660
atctgcaacg tgaaccacaa gcccagcaac accaaggtgg acaagaaggt ggagcccaag     720
tcttgcgaca aaacacatac ttgccctcca tgtccagctc cagaactgct gggaggacca     780
```

-continued

```
agcgtgttcc tgttccctcc taagcccaag gacaccctga tgatcagccg gaccccagaa      840
gtgacttgcg tggtggtgga cgtgtcccac gaagaccccg aggtcaagtt caattggtac      900
gtggacggag tggaggtgca caacgctaag accaagccca gggaggagca gtacaacagc      960
acctacaggt tggtgtccgt gctgacagtg ctgcaccagg attggctgaa cggcaaggag     1020
tacaagtgca aggtgtccaa caaggccctg ccagctccca tcgagaagac catcagcaag     1080
gccaagggac agcctagaga gcctcaggtg tacaccctgc ctccttctag ggacgagctg     1140
accaagaacc aggtgtccct gacttgcctc gtgaagggct tctaccccag cgacatcgca     1200
gtggagtggg aaagcaacgg tcagccagag aacaactaca agaccacccc cccagtgctg     1260
gacagcgacg gcagcttctt cctgtacagc aagctgaccg tggacaaaag ccgctggcag     1320
cagggcaacg tgttctcttg cagcgtgatg cacgaggccc tgcacaacca ctacacccag     1380
aagagcctga gcctgagccc aggaaaggga ggaggaggct ccctgctcgg cgacttcttc     1440
cggaagtcca aggagaagat tggcaaggag ttcaagcgca tcgtgcagag aatcaaggac     1500
ttcctgcgga atctggtgcc tagaaccgaa agc                                  1533
```

```
<210> SEQ ID NO 33
<211> LENGTH: 275
<212> TYPE: PRT
<213> ORGANISM: artificial
<220> FEATURE:
<223> OTHER INFORMATION: Anti-HER2 mAb Light chain-LL37 fusion;
      secretory signal peptide at 1-19

<400> SEQUENCE: 33

Met Leu Pro Ser Gln Leu Ile Gly Phe Leu Leu Leu Trp Val Pro Ala
1               5                   10                  15

Ser Arg Gly Asp Ile Gln Met Thr Gln Ser Pro Ser Ser Leu Ser Ala
                20                  25                  30

Ser Val Gly Asp Arg Val Thr Ile Thr Cys Arg Ala Ser Gln Asp Val
            35                  40                  45

Asn Thr Ala Val Ala Trp Tyr Gln Gln Lys Pro Gly Lys Ala Pro Lys
        50                  55                  60

Leu Leu Ile Tyr Ser Ala Ser Phe Leu Tyr Ser Gly Val Pro Ser Arg
65                  70                  75                  80

Phe Ser Gly Ser Arg Ser Gly Thr Asp Phe Thr Leu Thr Ile Ser Ser
                85                  90                  95

Leu Gln Pro Glu Asp Phe Ala Thr Tyr Tyr Cys Gln Gln His Tyr Thr
            100                 105                 110

Thr Pro Pro Thr Phe Gly Gln Gly Thr Lys Leu Glu Ile Lys Arg Thr
            115                 120                 125

Val Ala Ala Pro Ser Val Phe Ile Phe Pro Pro Ser Asp Glu Gln Leu
        130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
        210                 215                 220
```

```
Thr Lys Ser Phe Asn Arg Gly Glu Cys Gly Gly Gly Gly Ser Leu Leu
225                 230                 235                 240

Gly Asp Phe Phe Arg Lys Ser Lys Glu Lys Ile Gly Lys Glu Phe Lys
                245                 250                 255

Arg Ile Val Gln Arg Ile Lys Asp Phe Leu Arg Asn Leu Val Pro Arg
                260                 265                 270

Thr Glu Ser
        275

<210> SEQ ID NO 34
<211> LENGTH: 825
<212> TYPE: DNA
<213> ORGANISM: artificial
<220> FEATURE:
<223> OTHER INFORMATION: cDNA of Anti-HER2 mAb Light chain-LL37 fusion;
      nucleotides 1-57 encode the N-terminal secretory signal peptide

<400> SEQUENCE: 34
atgctgccca gccagctgat cggctttctg ctgctgtggg tgcctgcctc cagaggcgac      60
atccagatga cccagagccc atccagcctg tctgcctccg tgggcgacag agtgaccatc     120
acatgccgcg cttctcagga tgtgaacaca gccgtggctt ggtaccagca gaagcctggc     180
aaggccccaa agctgctgat ctactccgcc tctttcctgt attccggcgt gccaagcagg     240
ttttccggca gccggtctgg aaccgacttc accctgacaa tctcttccct gcagcccgag     300
gattttgcca catactattg ccagcagcac tataccacac ccctaccctt cggccagggc     360
acaaagctgg agatcaagag gaccgtggcc gctcctagcg tgttcatctt tccaccctct     420
gacgagcagc tgaagtctgg cacagcttcc gtggtgtgcc tgctgaacaa cttctaccca     480
cgggaggcca aggtgcagtg gaaggtggat aacgctctgc agtccggcaa tagccaggag     540
tctgtgaccg agcaggactc caaggatagc acatattctc tgagctctac cctgacactg     600
tccaaggccg attacgagaa gcacaaggtg tatgcttgcg aggtgaccca tcagggcctg     660
tccagccccg tgacaaagtc tttcaatagg ggagagtgtg gaggaggagg ctccctgctc     720
ggcgacttct ccggaagtc caaggagaag attggcaagg agttcaagcg catcgtgcag     780
agaatcaagg acttcctgcg gaatctggtg cctagaaccg aaagc                     825

<210> SEQ ID NO 35
<211> LENGTH: 38
<212> TYPE: PRT
<213> ORGANISM: artificial
<220> FEATURE:
<223> OTHER INFORMATION: PEP#94 LL37 derived peptide

<400> SEQUENCE: 35

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
                20                  25                  30

Pro Arg Thr Glu Ser Cys
        35

<210> SEQ ID NO 36
<211> LENGTH: 448
<212> TYPE: PRT
<213> ORGANISM: artificial
<220> FEATURE:
<223> OTHER INFORMATION: Anti-Folate receptor mAb heavy chain; secretory
      signal peptide is removed from N-terminus
```

-continued

```
<400> SEQUENCE: 36

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
                20                  25                  30

Phe Met Asn Trp Val Lys Gln Ser Pro Gly Gln Ser Leu Glu Trp Ile
            35                  40                  45

Gly Arg Ile His Pro Tyr Asp Gly Asp Thr Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415
```

-continued

```
Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 37
<211> LENGTH: 231
<212> TYPE: PRT
<213> ORGANISM: artificial
<220> FEATURE:
<223> OTHER INFORMATION: Anti-Folate receptor mAb light chain; secretory
      signal peptide is removed from N-terminus

<400> SEQUENCE: 37

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys Gly Gly Gly Gly Ser Leu
    210                 215                 220

Pro Glu Thr Gly Gly His Gly
225                 230

<210> SEQ ID NO 38
<211> LENGTH: 465
<212> TYPE: PRT
<213> ORGANISM: artificial
<220> FEATURE:
<223> OTHER INFORMATION: Anti-EGFR mAb (Panitumumab) heavy chain;
      secretory signal peptide at 1-16

<400> SEQUENCE: 38

Met Pro Leu Leu Leu Leu Leu Pro Leu Leu Trp Ala Gly Ala Leu Ala
1               5                   10                  15

Gln Val Gln Leu Gln Glu Ser Gly Pro Gly Leu Val Lys Pro Ser Glu
            20                  25                  30
```

```
Thr Leu Ser Leu Thr Cys Thr Val Ser Gly Gly Ser Val Ser Ser Gly
        35                  40                  45

Asp Tyr Tyr Trp Thr Trp Ile Arg Gln Ser Pro Gly Lys Gly Leu Glu
        50                  55                  60

Trp Ile Gly His Ile Tyr Tyr Ser Gly Asn Thr Asn Tyr Asn Pro Ser
65                  70                  75                  80

Leu Lys Ser Arg Leu Thr Ile Ser Ile Asp Thr Ser Lys Thr Gln Phe
            85                  90                  95

Ser Leu Lys Leu Ser Ser Val Thr Ala Ala Asp Thr Ala Ile Tyr Tyr
            100                 105                 110

Cys Val Arg Asp Arg Val Thr Gly Ala Phe Asp Ile Trp Gly Gln Gly
            115                 120                 125

Thr Met Val Thr Val Ser Ser Ala Ser Thr Lys Gly Pro Ser Val Phe
        130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
            165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
            195                 200                 205

Ser Ser Leu Gly Thr Gln Thr Tyr Ile Cys Asn Val Asn His Lys Pro
        210                 215                 220

Ser Asn Thr Lys Val Asp Lys Arg Val Glu Pro Lys Ser Cys Asp Lys
225                 230                 235                 240

Thr His Thr Cys Pro Pro Cys Pro Ala Pro Glu Leu Leu Gly Gly Pro
            245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Lys Phe Asn Trp Tyr Val Asp Gly Val Glu Val His Asn
        290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
            325                 330                 335

Tyr Lys Cys Lys Val Ser Asn Lys Ala Leu Pro Ala Pro Ile Glu Lys
            340                 345                 350

Thr Ile Ser Lys Ala Lys Gly Gln Pro Arg Glu Pro Gln Val Tyr Thr
            355                 360                 365

Leu Pro Pro Ser Arg Glu Glu Met Thr Lys Asn Gln Val Ser Leu Thr
        370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
            405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445
```

-continued

```
Ala Leu His Asn His Tyr Thr Gln Lys Ser Leu Ser Leu Ser Pro Gly
    450                 455                 460

Lys
465
```

```
<210> SEQ ID NO 39
<211> LENGTH: 247
<212> TYPE: PRT
<213> ORGANISM: artificial
<220> FEATURE:
<223> OTHER INFORMATION: Anti-EGFR mAb (Panitumumab) light chain;
      secretory signal peptide at 1-20

<400> SEQUENCE: 39
```

```
Met Arg Leu Pro Ala Gln Leu Leu Gly Leu Leu Met Leu Trp Val Ser
1               5                   10                  15

Gly Ser Ser Gly Asp Ile Gln Met Thr Gln Ser Pro Ser Ser Leu Ser
            20                  25                  30

Ala Ser Val Gly Asp Arg Val Thr Ile Thr Cys Gln Ala Ser Gln Asp
        35                  40                  45

Ile Ser Asn Tyr Leu Asn Trp Tyr Gln Gln Lys Pro Gly Lys Ala Pro
    50                  55                  60

Lys Leu Leu Ile Tyr Asp Ala Ser Asn Leu Glu Thr Gly Val Pro Ser
65                  70                  75                  80

Arg Phe Ser Gly Ser Gly Ser Gly Thr Asp Phe Thr Phe Thr Ile Ser
                85                  90                  95

Ser Leu Gln Pro Glu Asp Ile Ala Thr Tyr Phe Cys Gln His Phe Asp
            100                 105                 110

His Leu Pro Leu Ala Phe Gly Gly Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys Gly Gly Gly Ser Leu
225                 230                 235                 240

Pro Met Thr Gly Gly His Gly
                245
```

```
<210> SEQ ID NO 40
<211> LENGTH: 468
<212> TYPE: PRT
<213> ORGANISM: artificial
<220> FEATURE:
<223> OTHER INFORMATION: Anti-CD20 mAb (Ofatumumab)  heavy chain;
      secretory signal peptide at 1-16

<400> SEQUENCE: 40
```

```
Met Pro Leu Leu Leu Leu Leu Pro Leu Leu Trp Ala Gly Ala Leu Ala
1               5                   10                  15
```

-continued

```
Glu Val Gln Leu Val Glu Ser Gly Gly Gly Leu Val Gln Pro Gly Arg
        20                  25                  30

Ser Leu Arg Leu Ser Cys Ala Ala Ser Gly Phe Thr Phe Asn Asp Tyr
        35                  40                  45

Ala Met His Trp Val Arg Gln Ala Pro Gly Lys Gly Leu Glu Trp Val
    50                  55                  60

Ser Thr Ile Ser Trp Asn Ser Gly Ser Ile Gly Tyr Ala Asp Ser Val
65                  70                  75                  80

Lys Gly Arg Phe Thr Ile Ser Arg Asp Asn Ala Lys Lys Ser Leu Tyr
                85                  90                  95

Leu Gln Met Asn Ser Leu Arg Ala Glu Asp Thr Ala Leu Tyr Tyr Cys
            100                 105                 110

Ala Lys Asp Ile Gln Tyr Gly Asn Tyr Tyr Tyr Gly Met Asp Val Trp
        115                 120                 125

Gly Gln Gly Thr Thr Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Arg Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Glu Glu Met Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
```

-continued

```
            435                 440                 445
Met His Glu Ala Leu His Asn His Tyr Thr Gln Lys Ser Leu Ser Leu
    450                 455                 460

Ser Pro Gly Lys
465

<210> SEQ ID NO 41
<211> LENGTH: 247
<212> TYPE: PRT
<213> ORGANISM: artificial
<220> FEATURE:
<223> OTHER INFORMATION: Anti-CD20 mAb (Ofatumumab)  light chain;
      secretory signal peptide at 1-20

<400> SEQUENCE: 41

Met Arg Leu Pro Ala Gln Leu Leu Gly Leu Leu Met Leu Trp Val Ser
1               5                   10                  15

Gly Ser Ser Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Ser Tyr Leu Ala Trp Tyr Gln Gln Lys Pro Gly Gln Ala Pro
    50                  55                  60

Arg Leu Leu Ile Tyr Asp Ala Ser Asn Arg Ala Thr Gly Ile Pro Ala
65                  70                  75                  80

Arg Phe Ser Gly Ser Gly Ser Gly Thr Asp Phe Thr Leu Thr Ile Ser
            85                  90                  95

Ser Leu Glu Pro Glu Asp Phe Ala Val Tyr Tyr Cys Gln Gln Arg Ser
            100                 105                 110

Asn Trp Pro Ile Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
            195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys Gly Gly Gly Ser Leu
225                 230                 235                 240

Pro Met Thr Gly Gly His Gly
                245

<210> SEQ ID NO 42
<211> LENGTH: 466
<212> TYPE: PRT
<213> ORGANISM: artificial
<220> FEATURE:
<223> OTHER INFORMATION: Anti-Napi2b mAb (Lifastuzumab) heavy chain;
      secretory signal peptide at 1-16

<400> SEQUENCE: 42

Met Pro Leu Leu Leu Leu Leu Pro Leu Leu Trp Ala Gly Ala Leu Ala
```

-continued

```
1            5              10             15

Glu Val Gln Leu Val Glu Ser Gly Gly Gly Leu Val Gln Pro Gly Gly
             20             25             30

Ser Leu Arg Leu Ser Cys Ala Ala Ser Gly Phe Ser Phe Ser Asp Phe
             35             40             45

Ala Met Ser Trp Val Arg Gln Ala Pro Gly Lys Gly Leu Glu Trp Val
     50             55             60

Ala Thr Ile Gly Arg Val Ala Phe His Thr Tyr Tyr Pro Asp Ser Met
65                70             75             80

Lys Gly Arg Phe Thr Ile Ser Arg Asp Asn Ser Lys Asn Thr Leu Tyr
             85             90             95

Leu Gln Met Asn Ser Leu Arg Ala Glu Asp Thr Ala Val Tyr Tyr Cys
             100            105            110

Ala Arg His Arg Gly Phe Asp Val Gly His Phe Asp Phe Trp Gly Gln
             115            120            125

Gly Thr Leu Val Thr Val Ser Ser Ala Ser Thr Lys Gly Pro Ser Val
     130            135            140

Phe Pro Leu Ala Pro Ser Ser Lys Ser Thr Ser Gly Gly Thr Ala Ala
145            150            155            160

Leu Gly Cys Leu Val Lys Asp Tyr Phe Pro Glu Pro Val Thr Val Ser
             165            170            175

Trp Asn Ser Gly Ala Leu Thr Ser Gly Val His Thr Phe Pro Ala Val
             180            185            190

Leu Gln Ser Ser Gly Leu Tyr Ser Leu Ser Ser Val Val Thr Val Pro
             195            200            205

Ser Ser Ser Leu Gly Thr Gln Thr Tyr Ile Cys Asn Val Asn His Lys
     210            215            220

Pro Ser Asn Thr Lys Val Asp Lys Arg Val Glu Pro Lys Ser Cys Asp
225            230            235            240

Lys Thr His Thr Cys Pro Pro Cys Pro Ala Pro Glu Leu Leu Gly Gly
             245            250            255

Pro Ser Val Phe Leu Phe Pro Pro Lys Pro Lys Asp Thr Leu Met Ile
             260            265            270

Ser Arg Thr Pro Glu Val Thr Cys Val Val Val Asp Val Ser His Glu
     275            280            285

Asp Pro Glu Val Lys Phe Asn Trp Tyr Val Asp Gly Val Glu Val His
     290            295            300

Asn Ala Lys Thr Lys Pro Arg Glu Glu Gln Tyr Asn Ser Thr Tyr Arg
305            310            315            320

Val Val Ser Val Leu Thr Val Leu His Gln Asp Trp Leu Asn Gly Lys
             325            330            335

Glu Tyr Lys Cys Lys Val Ser Asn Lys Ala Leu Pro Ala Pro Ile Glu
             340            345            350

Lys Thr Ile Ser Lys Ala Lys Gly Gln Pro Arg Glu Pro Gln Val Tyr
             355            360            365

Thr Leu Pro Pro Ser Arg Glu Glu Met Thr Lys Asn Gln Val Ser Leu
     370            375            380

Thr Cys Leu Val Lys Gly Phe Tyr Pro Ser Asp Ile Ala Val Glu Trp
385            390            395            400

Glu Ser Asn Gly Gln Pro Glu Asn Asn Tyr Lys Thr Thr Pro Pro Val
             405            410            415

Leu Asp Ser Asp Gly Ser Phe Phe Leu Tyr Ser Lys Leu Thr Val Asp
             420            425            430
```

-continued

```
Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465
```

```
<210> SEQ ID NO 43
<211> LENGTH: 252
<212> TYPE: PRT
<213> ORGANISM: artificial
<220> FEATURE:
<223> OTHER INFORMATION: Anti-Napi2b mAb (Lifastuzumab) light chain;
      Secretory signal peptide at 1-20

<400> SEQUENCE: 43

Met Arg Leu Pro Ala Gln Leu Leu Gly Leu Leu Met Leu Trp Val Ser
1               5                  10                  15

Gly Ser Ser Gly Asp Ile Gln Met Thr Gln Ser Pro Ser Ser Leu Ser
        20                  25                  30

Ala Ser Val Gly Asp Arg Val Thr Ile Thr Cys Arg Ser Ser Glu Thr
        35                  40                  45

Leu Val His Ser Ser Gly Asn Thr Tyr Leu Glu Trp Tyr Gln Gln Lys
    50                  55                  60

Pro Gly Lys Ala Pro Lys Leu Leu Ile Tyr Arg Val Ser Asn Arg Phe
65                  70                  75                  80

Ser Gly Val Pro Ser Arg Phe Ser Gly Ser Gly Ser Gly Thr Asp Phe
            85                  90                  95

Thr Leu Thr Ile Ser Ser Leu Gln Pro Glu Asp Phe Ala Thr Tyr Tyr
            100                 105                 110

Cys Phe Gln Gly Ser Phe Asn Pro Leu Thr Phe Gly Gln Gly Thr Lys
        115                 120                 125

Val Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
            165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys Gly
225                 230                 235                 240

Gly Gly Gly Ser Leu Pro Met Thr Gly Gly His Gly
            245                 250
```

```
<210> SEQ ID NO 44

<400> SEQUENCE: 44

000

<210> SEQ ID NO 45
```

```
<400> SEQUENCE: 45

000

<210> SEQ ID NO 46
<211> LENGTH: 463
<212> TYPE: PRT
<213> ORGANISM: artificial
<220> FEATURE:
<223> OTHER INFORMATION: Anti-CD33A mAb (Vadastuximab) heavy chain;
      secretory signal peptide at 1-16

<400> SEQUENCE: 46

Met Pro Leu Leu Leu Leu Pro Leu Leu Trp Ala Gly Ala Leu Ala
1               5                   10                  15

Gln Val Gln Leu Val Gln Ser Gly Ala Glu Val Lys Lys Pro Gly Ala
            20                  25                  30

Ser Val Lys Val Ser Cys Lys Ala Ser Gly Tyr Thr Phe Thr Asn Tyr
        35                  40                  45

Asp Ile Asn Trp Val Arg Gln Ala Pro Gly Gln Gly Leu Glu Trp Ile
    50                  55                  60

Gly Trp Ile Tyr Pro Gly Asp Gly Ser Thr Lys Tyr Asn Glu Lys Phe
65                  70                  75                  80

Lys Ala Lys Ala Thr Leu Thr Ala Asp Thr Ser Thr Ser Thr Ala Tyr
                85                  90                  95

Met Glu Leu Arg Ser Leu Arg Ser Asp Asp Thr Ala Val Tyr Tyr Cys
                100                 105                 110

Ala Ser Gly Tyr Glu Asp Ala Met Asp Tyr Trp Gly Gln Gly Thr Thr
            115                 120                 125

Val Thr Val Ser Ser Ala Ser Thr Lys Gly Pro Ser Val Phe Pro Leu
    130                 135                 140

Ala Pro Ser Ser Lys Ser Thr Ser Gly Gly Thr Ala Ala Leu Gly Cys
145                 150                 155                 160

Leu Val Lys Asp Tyr Phe Pro Glu Pro Val Thr Val Ser Trp Asn Ser
                165                 170                 175

Gly Ala Leu Thr Ser Gly Val His Thr Phe Pro Ala Val Leu Gln Ser
                180                 185                 190

Ser Gly Leu Tyr Ser Leu Ser Ser Val Val Thr Val Pro Ser Ser Ser
            195                 200                 205

Leu Gly Thr Gln Thr Tyr Ile Cys Asn Val Asn His Lys Pro Ser Asn
    210                 215                 220

Thr Lys Val Asp Lys Arg Val Glu Pro Lys Ser Cys Asp Lys Thr His
225                 230                 235                 240

Thr Cys Pro Pro Cys Pro Ala Pro Glu Leu Leu Gly Gly Pro Ser Val
                245                 250                 255

Phe Leu Phe Pro Pro Lys Pro Lys Asp Thr Leu Met Ile Ser Arg Thr
                260                 265                 270

Pro Glu Val Thr Cys Val Val Val Asp Val Ser His Glu Asp Pro Glu
            275                 280                 285

Val Lys Phe Asn Trp Tyr Val Asp Gly Val Glu Val His Asn Ala Lys
    290                 295                 300

Thr Lys Pro Arg Glu Glu Gln Tyr Asn Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Lys Val Ser Asn Lys Ala Leu Pro Ala Pro Ile Glu Lys Thr Ile
```

-continued

```
                340                 345                 350

Ser Lys Ala Lys Gly Gln Pro Arg Glu Pro Gln Val Tyr Thr Leu Pro
        355                 360                 365

Pro Ser Arg Glu Glu Met Thr Lys Asn Gln Val Ser Leu Thr Cys Leu
        370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Tyr Ser Lys Leu Thr Val Asp Lys Ser Arg
                420                 425                 430

Trp Gln Gln Gly Asn Val Phe Ser Cys Ser Val Met His Glu Ala Leu
        435                 440                 445

His Asn His Tyr Thr Gln Lys Ser Leu Ser Leu Ser Pro Gly Lys
        450                 455                 460
```

<210> SEQ ID NO 47
<211> LENGTH: 247
<212> TYPE: PRT
<213> ORGANISM: artificial
<220> FEATURE:
<223> OTHER INFORMATION: Anti-CD33A mAb (Vadastuximab) light chain;
      secretory signal peptide at 1-20

<400> SEQUENCE: 47

```
Met Arg Leu Pro Ala Gln Leu Leu Gly Leu Leu Met Leu Trp Val Ser
1               5                   10                  15

Gly Ser Ser Gly Asp Ile Gln Met Thr Gln Ser Pro Ser Ser Leu Ser
                20                  25                  30

Ala Ser Val Gly Asp Arg Val Thr Ile Asn Cys Lys Ala Ser Gln Asp
            35                  40                  45

Ile Asn Ser Tyr Leu Ser Trp Phe Gln Gln Lys Pro Gly Lys Ala Pro
        50                  55                  60

Lys Thr Leu Ile Tyr Arg Ala Asn Arg Leu Val Asp Gly Val Pro Ser
65                  70                  75                  80

Arg Phe Ser Gly Ser Gly Ser Gly Gln Asp Tyr Thr Leu Thr Ile Ser
                85                  90                  95

Ser Leu Gln Pro Glu Asp Phe Ala Thr Tyr Tyr Cys Leu Gln Tyr Asp
            100                 105                 110

Glu Phe Pro Leu Thr Phe Gly Gly Gly Thr Lys Val Glu Ile Lys Arg
        115                 120                 125

Thr Val Ala Ala Pro Ser Val Phe Ile Phe Pro Pro Ser Asp Glu Gln
        130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
                180                 185                 190

Tyr Ser Leu Ser Ser Thr Leu Thr Leu Ser Lys Ala Asp Tyr Glu Lys
            195                 200                 205

His Lys Val Tyr Ala Cys Glu Val Thr His Gln Gly Leu Ser Ser Pro
        210                 215                 220

Val Thr Lys Ser Phe Asn Arg Gly Glu Cys Gly Gly Gly Gly Ser Leu
225                 230                 235                 240
```

```
Pro Met Thr Gly Gly His Gly
            245

<210> SEQ ID NO 48
<211> LENGTH: 465
<212> TYPE: PRT
<213> ORGANISM: artificial
<220> FEATURE:
<223> OTHER INFORMATION: Anti-CEACAM5 mAb (Labetuzumab) heavy chain;
      secretory signal peptide at 1-16

<400> SEQUENCE: 48

Met Pro Leu Leu Leu Leu Leu Pro Leu Leu Trp Ala Gly Ala Leu Ala
1               5                   10                  15

Glu Val Gln Leu Val Glu Ser Gly Gly Gly Val Val Gln Pro Gly Arg
                20                  25                  30

Ser Leu Arg Leu Ser Cys Ser Ala Ser Gly Phe Asp Phe Thr Thr Tyr
            35                  40                  45

Trp Met Ser Trp Val Arg Gln Ala Pro Gly Lys Gly Leu Glu Trp Ile
    50                  55                  60

Gly Glu Ile His Pro Asp Ser Ser Thr Ile Asn Tyr Ala Pro Ser Leu
65                  70                  75                  80

Lys Asp Arg Phe Thr Ile Ser Arg Asp Asn Ala Lys Asn Thr Leu Phe
                85                  90                  95

Leu Gln Met Asp Ser Leu Arg Pro Glu Asp Thr Gly Val Tyr Phe Cys
            100                 105                 110

Ala Ser Leu Tyr Phe Gly Phe Pro Trp Phe Ala Tyr Trp Gly Gln Gly
            115                 120                 125

Thr Pro Val Thr Val Ser Ser Ala Ser Thr Lys Gly Pro Ser Val Phe
    130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
            195                 200                 205

Ser Ser Leu Gly Thr Gln Thr Tyr Ile Cys Asn Val Asn His Lys Pro
    210                 215                 220

Ser Asn Thr Lys Val Asp Lys Arg Val Glu Pro Lys Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
                260                 265                 270

Arg Thr Pro Glu Val Thr Cys Val Val Val Asp Val Ser His Glu Asp
            275                 280                 285

Pro Glu Val Lys Phe Asn Trp Tyr Val Asp Gly Val Glu Val His Asn
    290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
            325                 330                 335

Tyr Lys Cys Lys Val Ser Asn Lys Ala Leu Pro Ala Pro Ile Glu Lys
            340                 345                 350
```

-continued

Thr Ile Ser Lys Ala Lys Gly Gln Pro Arg Glu Pro Gln Val Tyr Thr
        355              360              365

Leu Pro Pro Ser Arg Glu Glu Met Thr Lys Asn Gln Val Ser Leu Thr
        370              375              380

Cys Leu Val Lys Gly Phe Tyr Pro Ser Asp Ile Ala Val Glu Trp Glu
385              390              395              400

Ser Asn Gly Gln Pro Glu Asn Asn Tyr Lys Thr Thr Pro Pro Val Leu
                405              410              415

Asp Ser Asp Gly Ser Phe Phe Leu Tyr Ser Lys Leu Thr Val Asp Lys
                420              425              430

Ser Arg Trp Gln Gln Gly Asn Val Phe Ser Cys Ser Val Met His Glu
        435              440              445

Ala Leu His Asn His Tyr Thr Gln Lys Ser Leu Ser Leu Ser Pro Gly
        450              455              460

Lys
465

<210> SEQ ID NO 49
<211> LENGTH: 246
<212> TYPE: PRT
<213> ORGANISM: artificial
<220> FEATURE:
<223> OTHER INFORMATION: Anti-CEACAM5 mAb (Labetuzumab) light chain;
      secretory signal peptide at 1-20

<400> SEQUENCE: 49

Met Arg Leu Pro Ala Gln Leu Leu Gly Leu Leu Met Leu Trp Val Ser
1               5               10              15

Gly Ser Ser Gly Asp Ile Gln Leu Thr Gln Ser Pro Ser Ser Leu Ser
                20              25              30

Ala Ser Val Gly Asp Arg Val Thr Ile Thr Cys Lys Ala Ser Gln Asp
        35              40              45

Val Gly Thr Ser Val Ala Trp Tyr Gln Gln Lys Pro Gly Lys Ala Pro
        50              55              60

Lys Leu Leu Ile Tyr Trp Thr Ser Thr Arg His Thr Gly Val Pro Ser
65              70              75              80

Arg Phe Ser Gly Ser Gly Ser Gly Thr Asp Phe Thr Phe Thr Ile Ser
                85              90              95

Ser Leu Gln Pro Glu Asp Ile Ala Thr Tyr Tyr Cys Gln Gln Tyr Ser
        100             105             110

Leu Tyr Arg Ser Phe Gly Gln Gly Thr Lys Val Glu Ile Lys Arg Thr
        115             120             125

Val Ala Ala Pro Ser Val Phe Ile Phe Pro Pro Ser Asp Glu Gln Leu
        130             135             140

Lys Ser Gly Thr Ala Ser Val Val Cys Leu Leu Asn Asn Phe Tyr Pro
145             150             155             160

Arg Glu Ala Lys Val Gln Trp Lys Val Asp Asn Ala Leu Gln Ser Gly
                165             170             175

Asn Ser Gln Glu Ser Val Thr Glu Gln Asp Ser Lys Asp Ser Thr Tyr
                180             185             190

Ser Leu Ser Ser Thr Leu Thr Leu Ser Lys Ala Asp Tyr Glu Lys His
        195             200             205

Lys Val Tyr Ala Cys Glu Val Thr His Gln Gly Leu Ser Ser Pro Val
        210             215             220

Thr Lys Ser Phe Asn Arg Gly Glu Cys Gly Gly Gly Gly Ser Leu Pro

-continued

```
225               230               235               240
Met Thr Gly Gly His Gly
                  245

<210> SEQ ID NO 50
<211> LENGTH: 462
<212> TYPE: PRT
<213> ORGANISM: artificial
<220> FEATURE:
<223> OTHER INFORMATION: Anti-EpCAM mAb (Citatuzumab); heavy chain;
      secretory peptide at 1-16

<400> SEQUENCE: 50

Met Pro Leu Leu Leu Leu Leu Pro Leu Leu Trp Ala Gly Ala Leu Ala
1               5                   10                  15

Glu Val Gln Leu Val Gln Ser Gly Pro Gly Leu Val Gln Pro Gly Gly
                20                  25                  30

Ser Val Arg Ile Ser Cys Ala Ala Ser Gly Tyr Thr Phe Thr Asn Tyr
            35                  40                  45

Gly Met Asn Trp Val Lys Gln Ala Pro Gly Lys Gly Leu Glu Trp Met
        50                  55                  60

Gly Trp Ile Asn Thr Tyr Thr Gly Glu Ser Thr Tyr Ala Asp Ser Phe
65                  70                  75                  80

Lys Gly Arg Phe Thr Phe Ser Leu Asp Thr Ser Ala Ser Ala Ala Tyr
                85                  90                  95

Leu Gln Ile Asn Ser Leu Arg Ala Glu Asp Thr Ala Val Tyr Tyr Cys
                100                 105                 110

Ala Arg Phe Ala Ile Lys Gly Asp Tyr Trp Gly Gln Gly Thr Leu Leu
            115                 120                 125

Thr Val Ser Ser Ala Ser Thr Lys Gly Pro Ser Val Phe Pro Leu Ala
        130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
            195                 200                 205

Gly Thr Gln Thr Tyr Ile Cys Asn Val Asn His Lys Pro Ser Asn Thr
        210                 215                 220

Lys Val Asp Lys Arg Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
                260                 265                 270

Glu Val Thr Cys Val Val Val Asp Val Ser His Glu Asp Pro Glu Val
            275                 280                 285

Lys Phe Asn Trp Tyr Val Asp Gly Val Glu Val His Asn Ala Lys Thr
        290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335
```

```
Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
            355                 360                 365

Ser Arg Glu Glu Met Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
            435                 440                 445

Asn His Tyr Thr Gln Lys Ser Leu Ser Leu Ser Pro Gly Lys
    450                 455                 460
```

```
<210> SEQ ID NO 51
<211> LENGTH: 252
<212> TYPE: PRT
<213> ORGANISM: artificial
<220> FEATURE:
<223> OTHER INFORMATION: Anti-EpCAM mAb (Citatuzumab) light chain;
      secretory peptide at 1-20

<400> SEQUENCE: 51
```

```
Met Arg Leu Pro Ala Gln Leu Leu Gly Leu Leu Met Leu Trp Val Ser
1               5                   10                  15

Gly Ser Ser Gly Asp Ile Gln Met Thr Gln Ser Pro Ser Ser Leu Ser
            20                  25                  30

Ala Ser Val Gly Asp Arg Val Thr Ile Thr Cys Arg Ser Thr Lys Ser
            35                  40                  45

Leu Leu His Ser Asn Gly Ile Thr Tyr Leu Tyr Trp Tyr Gln Gln Lys
    50                  55                  60

Pro Gly Lys Ala Pro Lys Leu Leu Ile Tyr Gln Met Ser Asn Leu Ala
65                  70                  75                  80

Ser Gly Val Pro Ser Arg Phe Ser Ser Ser Gly Ser Gly Thr Asp Phe
                85                  90                  95

Thr Leu Thr Ile Ser Ser Leu Gln Pro Glu Asp Phe Ala Thr Tyr Tyr
            100                 105                 110

Cys Ala Gln Asn Leu Glu Ile Pro Arg Thr Phe Gly Gln Gly Thr Lys
            115                 120                 125

Val Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
            195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys Gly
225                 230                 235                 240
```

```
Gly Gly Gly Ser Leu Pro Met Thr Gly Gly His Gly
                245                 250

<210> SEQ ID NO 52

<400> SEQUENCE: 52

000

<210> SEQ ID NO 53

<400> SEQUENCE: 53

000

<210> SEQ ID NO 54

<400> SEQUENCE: 54

000

<210> SEQ ID NO 55

<400> SEQUENCE: 55

000

<210> SEQ ID NO 56

<400> SEQUENCE: 56

000

<210> SEQ ID NO 57

<400> SEQUENCE: 57

000

<210> SEQ ID NO 58

<400> SEQUENCE: 58

000

<210> SEQ ID NO 59

<400> SEQUENCE: 59

000

<210> SEQ ID NO 60

<400> SEQUENCE: 60

000

<210> SEQ ID NO 61

<400> SEQUENCE: 61

000

<210> SEQ ID NO 62
<211> LENGTH: 475
<212> TYPE: PRT
<213> ORGANISM: artificial
```

<220> FEATURE:
<223> OTHER INFORMATION: Anti-FGFR3 mAb (Vofatamab) heavy chain;
      secretory peptide at 1-19

<400> SEQUENCE: 62

```
Met Asp Trp Thr Trp Arg Ile Leu Phe Leu Val Ala Ala Ala Thr Gly
1               5                   10                  15

Ala His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Thr Ser Thr Gly Ile Ser Trp Val Arg Gln Ala Pro Gly Lys Gly Leu
    50                  55                  60

Glu Trp Val Gly Arg Ile Tyr Pro Thr Asn Gly Ser Thr Asn Tyr Ala
65                  70                  75                  80

Asp Ser Val Gly Arg Phe Thr Ile Ser Ala Asp Thr Ser Lys Asn Thr
                85                  90                  95

Ala Tyr Leu Gln Met Asn Ser Leu Arg Ala Glu Asp Thr Ala Val Tyr
            100                 105                 110

Tyr Cys Ala Arg Thr Tyr Gly Ile Tyr Asp Leu Tyr Val Asp Tyr Thr
        115                 120                 125

Glu Tyr Val Met Asp Tyr Trp Gly Gln Gly Thr Leu Val Thr Val Ser
    130                 135                 140

Ser Ala Ser Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Ser Leu Gly Thr Gln
    210                 215                 220

Thr Tyr Ile Cys Asn Val Asn His Lys Pro Ser Asn Thr Lys Val Asp
225                 230                 235                 240

Lys Lys Val Glu Pro Lys Ser Cys Asp Lys Thr His Thr Cys Pro Pro
                245                 250                 255

Cys Pro Ala Pro Glu Leu Leu Gly Gly Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser
            340                 345                 350

Asn Lys Ala Leu Pro Ala Pro Ile Glu Lys Thr Ile Ser Lys Ala Lys
        355                 360                 365

Gly Gln Pro Arg Glu Pro Gln Val Tyr Thr Leu Pro Pro Ser Arg Asp
    370                 375                 380

Glu Leu Thr Lys Asn Gln Val Ser Leu Thr Cys Leu Val Lys Gly Phe
```

```
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
                420                 425                 430

Phe Leu Tyr Ser Lys Leu Thr Val Asp Lys Ser Arg Trp Gln Gln Gly
                435                 440                 445

Asn Val Phe Ser Cys Ser Val Met His Glu Ala Leu His Asn His Tyr
    450                 455                 460

Thr Gln Lys Ser Leu Ser Leu Ser Pro Gly Lys
465                 470                 475
```

```
<210> SEQ ID NO 63
<211> LENGTH: 1425
<212> TYPE: DNA
<213> ORGANISM: artificial
<220> FEATURE:
<223> OTHER INFORMATION: cDNA of Anti-FGFR3 mAb (Vofatamab) heavy chain;
      secretory signal peptide sequence (nucleotides 1-57) included at
      5' end

<400> SEQUENCE: 63
atggattgga catggaggat tctgttcctg gtggctgcag ctactggagc tcattctgag      60
gtgcagctgg tggaatcagg aggaggactg gtgcagccag gaggatctct gagactgtct     120
tgcgccgcca gcggcttcac ctttacctct accggcatct cttgggtgag acaggcccct     180
ggcaagggcc tggagtgggt gggcagaatc taccctacaa acggatctac caactacgcc     240
gattctgtgg gcagattcac aatctctgcc gatacatcta gaacacagc ttacctgcag     300 atgaactctc tgagagctga ggatacagct gtgtactatt gtgctagaac atacggcatc     360
tacgatctgt acgtggatta tacagagtac gtgatggatt attggggcca gggaacactg     420
gtgacagtgt ctagcgctag caccaaggga cctagcgtgt tcctctggc cccttctagc     480 aagagcacaa gcggaggaac agccgctctg ggctgtctgg tgaaagacta cttccccgag     540
ccagtgaccg tgtcttggaa ctcaggagcc ctgacaagcg gagtgcacac atttccagcc     600
gtgctgcaga gcagcggact gtactctctg agcagcgtgg tgaccgtgcc ttcttcttct     660
ctgggcaccc agacctacat ctgcaacgtg aaccacaagc ccagcaacac caaggtggac     720
aagaaggtgg agcccaagtc ttgcgacaaa acacatactt gccctccatg tccagctcca     780
gaactgctgg gaggaccaag cgtgttcctg ttccctccta gcccaaggga caccctgatg     840
atcagccgga ccccagaagt gacttgcgtg gtggtggacg tgtcccacga agaccccgag     900
gtcaagttca attggtacgt ggacggagtg gaggtgcaca acgctaagac caagcccagg     960
gaggagcagt acaacagcac ctacagggtg gtgtccgtgc tgacagtgct gcaccaggat    1020
tggctgaacg gcaaggagta caagtgcaag gtgtccaaca aggccctgcc agctcccatc    1080
gagaagacca tcagcaaggc caagggacag cctagagagc ctcaggtgta caccctgcct    1140
ccttctaggg acgagctgac caagaaccag gtgtccctga cttgcctcgt gaagggcttc    1200
taccccagcg acatcgcagt ggagtgggaa agcaacggtc agccagagaa caactacaag    1260
accacccccc cagtgctgga cagcgacggc agcttcttcc tgtacagcaa gctgaccgtg    1320
gacaaaagcc gctggcagca gggcaacgtg ttctcttgca gcgtgatgca cgaggccctg    1380
cacaaccact acacccagaa gagcctgagc ctgagcccag gaaag                     1425
```

```
<210> SEQ ID NO 64
```

-continued

```
<211> LENGTH: 246
<212> TYPE: PRT
<213> ORGANISM: artificial
<220> FEATURE:
<223> OTHER INFORMATION: Anti-FGFR3 mAb (Vofatamab) light chain;
      secretory signal peptide at 1-19

<400> SEQUENCE: 64

Met Leu Pro Ser Gln Leu Ile Gly Phe Leu Leu Leu Trp Val Pro Ala
1               5                   10                  15

Ser Arg Gly Asp Ile Gln Met Thr Gln Ser Pro Ser Ser Leu Ser Ala
            20                  25                  30

Ser Val Gly Asp Arg Val Thr Ile Thr Cys Arg Ala Ser Gln Asp Val
        35                  40                  45

Ser Thr Ala Val Ala Trp Tyr Gln Gln Lys Pro Gly Lys Ala Pro Lys
    50                  55                  60

Leu Leu Ile Tyr Ser Ala Ser Phe Leu Tyr Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Ser Tyr Thr
            100                 105                 110

Thr Pro Pro Thr Phe Gly Gln Gly Thr Lys Val Glu Ile Lys Arg Thr
            115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
            165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
            195                 200                 205

Lys Val Tyr Ala Cys Glu Val Thr His Gln Gly Leu Ser Ser Pro Val
    210                 215                 220

Thr Lys Ser Phe Asn Arg Gly Glu Cys Gly Gly Gly Ser Leu Pro
225                 230                 235                 240

Met Thr Gly Gly His Gly
                245

<210> SEQ ID NO 65
<211> LENGTH: 738
<212> TYPE: DNA
<213> ORGANISM: artificial
<220> FEATURE:
<223> OTHER INFORMATION: cDNA of Anti-FGFR3 mAb (Vofatamab) light chain;
      secretory signal peptide sequence (nucleotide# 1-57) included at
      5' end

<400> SEQUENCE: 65
atgctgccca gccagctgat cggctttctg ctgctgtggg tgcctgcctc cagaggcgac        60
atccagatga cccagagccc atccagcctg tctgcctccg tgggcgacag agtgaccatc       120
acatgccgcg cttctcagga tgtgtccaca gctgtggcct ggtaccagca gaagcctggc       180 aaggcccta agctgctgat ctactctgct tcttttctgt attctggcgt gccttctaga       240
ttttctggct ctggcagcgg cacagatttt acactgacaa tctcttctct gcagcctgag       300
```

-continued

```
gattttgcta catattactg tcagcagtct tacacaacac ctcctacatt tggccagggc      360
acaaaggtgg agatcaagag gaccgtggcc gctcctagcg tgttcatctt tccaccctct      420
gacgagcagc tgaagtctgg cacagcttcc gtggtgtgcc tgctgaacaa cttctaccca      480
cgggaggcca aggtgcagtg gaaggtggat aacgctctgc agtccggcaa tagccaggag      540
tctgtgaccg agcaggactc caaggatagc acatattctc tgagctctac cctgacactg      600
tccaaggccg attacgagaa gcacaaggtg tatgcttgcg aggtgaccca tcagggcctg      660
tccagccccg tgacaaagtc tttcaatagg ggagagtgtg aggaggagg ctccctgcct      720 atgaccggcg gccatggc                                                    738
```

```
<210> SEQ ID NO 66
<211> LENGTH: 463
<212> TYPE: PRT
<213> ORGANISM: artificial
<220> FEATURE:
<223> OTHER INFORMATION: Anti-PSMA mAb, hj591 heavy chain; secretory
      signal peptide at 1-19

<400> SEQUENCE: 66

Met Asp Trp Thr Trp Arg Ile Leu Phe Leu Val Ala Ala Ala Thr Gly
1               5                   10                  15

Ala His Ser Glu Val Gln Leu Val Gln Ser Gly Pro Glu Val Lys Lys
                20                  25                  30

Pro Gly Ala Thr Val Lys Ile Ser Cys Lys Thr Ser Gly Tyr Thr Phe
            35                  40                  45

Thr Glu Tyr Thr Ile His Trp Val Lys Gln Ala Pro Gly Lys Gly Leu
        50                  55                  60

Glu Trp Ile Gly Asn Ile Asn Pro Asn Asn Gly Gly Thr Thr Tyr Asn
65                  70                  75                  80

Gln Lys Phe Glu Asp Lys Ala Thr Leu Thr Val Asp Lys Ser Thr Asp
                85                  90                  95

Thr Ala Tyr Met Glu Leu Ser Ser Leu Arg Ser Glu Asp Thr Ala Val
                100                 105                 110

Tyr Tyr Cys Ala Ala Gly Trp Asn Phe Asp Tyr Trp Gly Gln Gly Thr
            115                 120                 125

Leu Leu Thr Val Ser Ser Ala Ser Thr Lys Gly Pro Ser Val Phe Pro
        130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
            195                 200                 205

Ser Leu Gly Thr Gln Thr Tyr Ile Cys Asn Val Asn His Lys Pro Ser
        210                 215                 220

Asn Thr Lys Val Asp Lys Lys Val Glu Pro Lys Ser Cys Asp Lys Thr
225                 230                 235                 240

His Thr Cys Pro Pro Cys Pro Ala Pro Glu Leu Leu Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
```

```
                275                280                285

Glu Val Lys Phe Asn Trp Tyr Val Asp Gly Val Glu Val His Asn Ala
    290                295                300

Lys Thr Lys Pro Arg Glu Glu Gln Tyr Asn Ser Thr Tyr Arg Val Val
305                310                315                320

Ser Val Leu Thr Val Leu His Gln Asp Trp Leu Asn Gly Lys Glu Tyr
                325                330                335

Lys Cys Lys Val Ser Asn Lys Ala Leu Pro Ala Pro Ile Glu Lys Thr
                340                345                350

Ile Ser Lys Ala Lys Gly Gln Pro Arg Glu Pro Gln Val Tyr Thr Leu
                355                360                365

Pro Pro Ser Arg Asp Glu Leu Thr Lys Asn Gln Val Ser Leu Thr Cys
    370                375                380

Leu Val Lys Gly Phe Tyr Pro Ser Asp Ile Ala Val Glu Trp Glu Ser
385                390                395                400

Asn Gly Gln Pro Glu Asn Asn Tyr Lys Thr Thr Pro Pro Val Leu Asp
                405                410                415

Ser Asp Gly Ser Phe Phe Leu Tyr Ser Lys Leu Thr Val Asp Lys Ser
                420                425                430

Arg Trp Gln Gln Gly Asn Val Phe Ser Cys Ser Val Met His Glu Ala
                435                440                445

Leu His Asn His Tyr Thr Gln Lys Ser Leu Ser Leu Ser Pro Gly
    450                455                460
```

<210> SEQ ID NO 67
<211> LENGTH: 1389
<212> TYPE: DNA
<213> ORGANISM: artificial
<220> FEATURE:
<223> OTHER INFORMATION: cDNA of Anti-PSMA mAb, hj591 heavy chain;
      secretory signal peptide sequence (nucleotide# 1-57) included at
      5' end

<400> SEQUENCE: 67

```
atggattgga catggaggat tctgttcctg gtggctgcag ctactggagc tcattctgag      60
gtgcagctgg tgcagtctgg acctgaggtg aagaagcctg gcgccactgt gaagatttct     120
tgtaagacat ctggatatac tttcactgaa tacactattc attgggtgaa gcaggcccct     180
ggcaagggcc tggagtggat cggtaacatt aatcctaaca acggcggcac tacatataat     240
cagaagtttg aggataaggc tacactgaca gtggataaaa gcacagatac agcttacatg     300
gagctgtctt ctctgagatc tgaagatacc gctgtgtatt attgtgccgc cggatggaat     360
tttgactact ggggtcaggg cactttactg actgtgtcct ccgcaagcac taagggacct     420
tctgtgtttc ctctggctcc tagctctaag tccacatctg gcggaaccgc tgctctggga     480
tgtctggtga agattatttt ccctgagcct gtgacagtga gttggaactc tggcgccctg     540
actagcggcg tgcatacctt tcctgccgtg ctgcagtctc tggcctgta ttctctgtct     600 tctgtggtga ccgtgccatc tagctctctg ggaacacaga catacatctg taatgttaat     660
cataagcctt ctaatacaaa ggttgataag aaagtggagc ctaagagctg tgataagact     720
cacacctgcc ctccttgtcc tgcccctgaa ctgctgggag ccctagtgt gttcctgttt     780 cctccaaagc caaggatac actgatgatc tctagaaccc ctgaggtgac atgtgtggtg     840
gtggatgtgt cacatgaaga tcctgaggtg aagtttaatt ggtatgtgga tggagtggaa     900
gtgcataatg ctaagaccaa gcctagagag gagcagtata attctaccta tagagtggtg     960
```

```
tctgtgctga cagtgctgca ccaggattgg ctgaatggaa aggaatacaa gtgtaaagtg   1020
agtaataagg ccctgcctgc tcctattgag aaaacaattt ctaaggctaa gggacagcct   1080
agagagccac aggtgtacac actgcctcct agtagagatg aactgacaaa gaaccaggtg   1140
tctctgacat gtctggtgaa gggcttttat ccatctgata ttgccgtgga gtgggagtct   1200
aatgggcagc ctgaaaacaa ttataaaact acacctcctg tgctggatag tgatggctct   1260
ttctttctgt actctaagct gactgtggat aagtctaggt ggcagcaggg caacgtgttt   1320
agctgtagcg tgatgcatga ggccctccat aaccactata cgcagaagtc actgagcctg   1380
agcccagga                                                          1389
```

```
<210> SEQ ID NO 68
<211> LENGTH: 246
<212> TYPE: PRT
<213> ORGANISM: artificial
<220> FEATURE:
<223> OTHER INFORMATION: Anti-PSMA mAb, hj591 light chain; secretory
      signal peptide at 1-19

<400> SEQUENCE: 68

Met Leu Pro Ser Gln Leu Ile Gly Phe Leu Leu Leu Trp Val Pro Ala
1               5                   10                  15

Ser Arg Gly Asp Ile Gln Met Thr Gln Ser Pro Ser Ser Leu Ser Thr
            20                  25                  30

Ser Val Gly Asp Arg Val Thr Leu Thr Cys Lys Ala Ser Gln Asp Val
        35                  40                  45

Gly Thr Ala Val Asp Trp Tyr Gln Gln Lys Pro Gly Pro Ser Pro Lys
    50                  55                  60

Leu Leu Ile Tyr Trp Ala Ser Thr Arg His Thr Gly Ile Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Asp Tyr Tyr Cys Gln Gln Tyr Asn Ser
            100                 105                 110

Tyr Pro Leu Thr Phe Gly Pro Gly Thr Lys Val Asp Ile Lys Arg Thr
            115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
            165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
            195                 200                 205

Lys Val Tyr Ala Cys Glu Val Thr His Gln Gly Leu Ser Ser Pro Val
    210                 215                 220

Thr Lys Ser Phe Asn Arg Gly Glu Cys Gly Gly Gly Ser Leu Pro
225                 230                 235                 240

Met Thr Gly Gly His Gly
                245
```

```
<210> SEQ ID NO 69
<211> LENGTH: 738
<212> TYPE: DNA
```

<213> ORGANISM: artificial
<220> FEATURE:
<223> OTHER INFORMATION: cDNA of Anti-PSMA mAb, hj591 light chain;
      secretory signal peptide sequence (nucleotides 1-57) included at
      5' end

<400> SEQUENCE: 69
atgctgccca gccagctgat cggctttctg ctgctgtggg tgcctgcctc cagaggcgat       60
atccagatga cacagtctcc tagctctctg agcacctctg tgggagatag agtgaccctg      120
acatgtaagg cctctcagga tgtgggcact gccgtggatt ggtatcagca gaagcctggc      180
ccttctccta agctgctgat ctattgggct tctactagac atacaggcat cccttctagg      240
ttcagcggct ctggctctgg aactgatttt acactgacca tctcttctct gcagcctgag      300
gattttgctg attactactg tcagcagtat aatagctacc ctctgacctt cggccctggc      360
acaaaggtgg acatcaagag gaccgtggcc gctcctagcg tgttcatctt ccaccctct       420 gacgagcagc tgaagtctgg cacagcttcc gtggtgtgcc tgctgaacaa cttctaccca      480
cgggaggcca aggtgcagtg gaaggtggat aacgctctgc agtccggcaa tagccaggag      540
tctgtgaccg agcaggactc caaggatagc acatattctc tgagctctac cctgacactg      600
tccaaggccg attacgagaa gcacaaggtg tatgcttgcg aggtgaccca tcagggcctg      660
tccagccccg tgacaaagtc tttcaatagg ggagagtgtg gaggaggagg ctccctgcct      720
atgaccggcg gccatggc                                                    738

<210> SEQ ID NO 70

<400> SEQUENCE: 70

000

<210> SEQ ID NO 71

<400> SEQUENCE: 71

000

<210> SEQ ID NO 72

<400> SEQUENCE: 72

000

<210> SEQ ID NO 73

<400> SEQUENCE: 73

000

<210> SEQ ID NO 74
<211> LENGTH: 32
<212> TYPE: PRT
<213> ORGANISM: artificial
<220> FEATURE:
<223> OTHER INFORMATION: PEP#48 LL37 derived peptide

<400> SEQUENCE: 74

Phe Arg Lys Ser Lys Glu Lys Ile Gly Lys Phe Phe Lys Arg Ile Val
1               5                   10                  15

Gln Arg Ile Phe Asp Phe Leu Arg Asn Leu Val Met Met Trp Leu Leu
            20                  25                  30

-continued

<210> SEQ ID NO 75
<211> LENGTH: 37
<212> TYPE: PRT
<213> ORGANISM: artificial
<220> FEATURE:
<223> OTHER INFORMATION: PEP#49 LL37 derived peptide

<400> SEQUENCE: 75

Leu Leu Gly Asp Phe Phe Arg Gln Ser Lys Glu Lys Ile Gly Lys Glu
1               5                   10                  15

Phe Gln Gln Ile Val Gln Gln Ile Lys Asp Phe Leu Gln Asn Leu Val
            20                  25                  30

Pro Gln Thr Glu Ser
        35

<210> SEQ ID NO 76
<211> LENGTH: 37
<212> TYPE: PRT
<213> ORGANISM: artificial
<220> FEATURE:
<223> OTHER INFORMATION: PEP#50 LL37 derived peptide

<400> SEQUENCE: 76

Leu Leu Gly Asp Phe Phe Arg Ala Ser Lys Glu Lys Ile Gly Lys Glu
1               5                   10                  15

Phe Ala Ala Ile Val Gln Ala Ile Lys Asp Phe Leu Ala Asn Leu Val
            20                  25                  30

Pro Ala Thr Glu Ser
        35

<210> SEQ ID NO 77
<211> LENGTH: 36
<212> TYPE: PRT
<213> ORGANISM: artificial
<220> FEATURE:
<223> OTHER INFORMATION: PEP#55 LL37 derived peptide

<400> SEQUENCE: 77

Lys Glu Phe Lys Arg Ile Val Gln Arg Ile Lys Asp Phe Leu Arg Gly
1               5                   10                  15

Gly Gly Gly Ser Arg Leu Phe Asp Lys Ile Arg Gln Val Ile Arg Lys
            20                  25                  30

Phe Glu Lys Gly
        35

<210> SEQ ID NO 78
<211> LENGTH: 26
<212> TYPE: PRT
<213> ORGANISM: Styela clava
<220> FEATURE:
<221> NAME/KEY: MISC_FEATURE
<223> OTHER INFORMATION: PEP#86, Clavanin B, an alpha-helical
      antimicrobial peptide

<400> SEQUENCE: 78

Gly Gly Ser Val Phe Gln Phe Leu Gly Arg Ile Ile His His Val Gly
1               5                   10                  15

Asn Phe Val His Gly Phe Ser His Val Phe
            20                  25

<210> SEQ ID NO 79
<211> LENGTH: 13
<212> TYPE: PRT
<213> ORGANISM: artificial

<220> FEATURE:
<223> OTHER INFORMATION: PEP#98, an antimicrobial anti-inflammatory
      peptide alpha-melanocyte-stimulating hormone(MSH)

<400> SEQUENCE: 79

Ser Tyr Ser Met Glu His Phe Arg Trp Gly Lys Pro Val
1               5                   10

<210> SEQ ID NO 80
<211> LENGTH: 19
<212> TYPE: PRT
<213> ORGANISM: homo sapiens
<220> FEATURE:
<221> NAME/KEY: MISC_FEATURE
<223> OTHER INFORMATION: PEP#99,Keratin-derived antimicrobial peptide
      (KDAMP)

<400> SEQUENCE: 80

Arg Ala Ile Gly Gly Gly Leu Ser Ser Val Gly Gly Gly Ser Ser Thr
1               5                   10                  15

Ile Lys Tyr

<210> SEQ ID NO 81

<400> SEQUENCE: 81

000

<210> SEQ ID NO 82
<211> LENGTH: 35
<212> TYPE: PRT
<213> ORGANISM: homo sapiens
<220> FEATURE:
<221> NAME/KEY: MISC_FEATURE
<223> OTHER INFORMATION: PEP#102, human beta-defensin 1, hBD1

<400> SEQUENCE: 82

Asp His Tyr Asn Cys Val Ser Ser Gly Gly Gln Cys Leu Tyr Ser Ala
1               5                   10                  15

Cys Pro Ile Phe Lys Ile Gln Gly Thr Cys Tyr Arg Gly Lys Ala Lys
            20                  25                  30

Cys Cys Lys
        35

<210> SEQ ID NO 83

<400> SEQUENCE: 83

000

<210> SEQ ID NO 84
<211> LENGTH: 33
<212> TYPE: PRT
<213> ORGANISM: homo sapiens
<220> FEATURE:
<221> NAME/KEY: MISC_FEATURE
<223> OTHER INFORMATION: PEP#104, human neutrophil peptide 4(HNP4), an
      alpha defensin

<400> SEQUENCE: 84

Val Cys Ser Cys Arg Leu Val Phe Cys Arg Arg Thr Glu Leu Arg Val
1               5                   10                  15

Gly Asn Cys Leu Ile Gly Gly Val Ser Phe Thr Tyr Cys Cys Thr Arg
            20                  25                  30

Val

<210> SEQ ID NO 85

<400> SEQUENCE: 85

000

<210> SEQ ID NO 86

<400> SEQUENCE: 86

000

<210> SEQ ID NO 87

<400> SEQUENCE: 87

000

<210> SEQ ID NO 88

<400> SEQUENCE: 88

000

<210> SEQ ID NO 89

<400> SEQUENCE: 89

000

<210> SEQ ID NO 90

<400> SEQUENCE: 90

000

<210> SEQ ID NO 91

<400> SEQUENCE: 91

000

<210> SEQ ID NO 92

<400> SEQUENCE: 92

000

<210> SEQ ID NO 93

<400> SEQUENCE: 93

000

<210> SEQ ID NO 94
<211> LENGTH: 451
<212> TYPE: PRT
<213> ORGANISM: artificial
<220> FEATURE:
<223> OTHER INFORMATION: Anti-CD20 mAb (Rituximab) heavy chain;
      secretory signal peptide is removed from N-terminus

<400> SEQUENCE: 94

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr

```
                   20                  25                  30

Asn Met His Trp Val Lys Gln Thr Pro Gly Arg Gly Leu Glu Trp Ile
         35                  40                  45

Gly Ala Ile Tyr Pro Gly Asn Gly Asp Thr Ser Tyr Asn Gln Lys Phe
     50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                 85                  90                  95

Ala Arg Ser Thr Tyr Tyr Gly Gly Asp Trp Tyr Phe Asn Val Trp Gly
             100                 105                 110

Ala Gly Thr Thr Val Thr Val Ser Ala Ala Ser Thr Lys Gly Pro Ser
             115                 120                 125

Val Phe Pro Leu Ala Pro Ser Ser Lys Ser Thr Ser Gly Gly Thr Ala
         130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                 165                 170                 175

Val Leu Gln Ser Ser Gly Leu Tyr Ser Leu Ser Ser Val Val Thr Val
             180                 185                 190

Pro Ser Ser Ser Leu Gly Thr Gln Thr Tyr Ile Cys Asn Val Asn His
             195                 200                 205

Lys Pro Ser Asn Thr Lys Val Asp Lys Lys Ala Glu Pro Lys Ser Cys
     210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                 245                 250                 255

Ile Ser Arg Thr Pro Glu Val Thr Cys Val Val Val Asp Val Ser His
             260                 265                 270

Glu Asp Pro Glu Val Lys Phe Asn Trp Tyr Val Asp Gly Val Glu Val
         275                 280                 285

His Asn Ala Lys Thr Lys Pro Arg Glu Glu Gln Tyr Asn Ser Thr Tyr
     290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
             325                 330                 335

Glu Lys Thr Ile Ser Lys Ala Lys Gly Gln Pro Arg Glu Pro Gln Val
             340                 345                 350

Tyr Thr Leu Pro Pro Ser Arg Asp Glu Leu Thr Lys Asn Gln Val Ser
             355                 360                 365

Leu Thr Cys Leu Val Lys Gly Phe Tyr Pro Ser Asp Ile Ala Val Glu
     370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                 405                 410                 415

Asp Lys Ser Arg Trp Gln Gln Gly Asn Val Phe Ser Cys Ser Val Met
             420                 425                 430

His Glu Ala Leu His Asn His Tyr Thr Gln Lys Ser Leu Ser Leu Ser
     435                 440                 445
```

-continued

Pro Gly Lys
    450

<210> SEQ ID NO 95
<211> LENGTH: 226
<212> TYPE: PRT
<213> ORGANISM: artificial
<220> FEATURE:
<223> OTHER INFORMATION: Anti-CD20 mAb (Rituximab) light chain;
      secretory signal peptide is removed from N-terminus

<400> SEQUENCE: 95

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
                100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys Gly Gly Gly Gly Ser Leu Pro Met Thr Gly Gly
    210                 215                 220

His Gly
225

<210> SEQ ID NO 96
<211> LENGTH: 5
<212> TYPE: PRT
<213> ORGANISM: artificial
<220> FEATURE:
<223> OTHER INFORMATION: PEP#47

<400> SEQUENCE: 96

Met Met Trp Leu Leu
1               5

<210> SEQ ID NO 97
<211> LENGTH: 15
<212> TYPE: PRT
<213> ORGANISM: homo sapiens
<220> FEATURE:

-continued

```
<221> NAME/KEY: MISC_FEATURE
<223> OTHER INFORMATION: PEP#51 fragment of LL37

<400> SEQUENCE: 97

Lys Glu Phe Lys Arg Ile Val Gln Arg Ile Lys Asp Phe Leu Arg
1               5                   10                  15

<210> SEQ ID NO 98

<400> SEQUENCE: 98

000

<210> SEQ ID NO 99

<400> SEQUENCE: 99

000

<210> SEQ ID NO 100

<400> SEQUENCE: 100

000

<210> SEQ ID NO 101

<400> SEQUENCE: 101

000

<210> SEQ ID NO 102

<400> SEQUENCE: 102

000

<210> SEQ ID NO 103
<211> LENGTH: 5
<212> TYPE: PRT
<213> ORGANISM: homo sapiens
<220> FEATURE:
<221> NAME/KEY: MISC_FEATURE
<223> OTHER INFORMATION: PEP#58 fragment of LL37

<400> SEQUENCE: 103

Val Gln Arg Ile Lys
1               5

<210> SEQ ID NO 104
<211> LENGTH: 7
<212> TYPE: PRT
<213> ORGANISM: homo sapiens
<220> FEATURE:
<221> NAME/KEY: MISC_FEATURE
<223> OTHER INFORMATION: PEP#59 fragment of LL37

<400> SEQUENCE: 104

Ile Val Gln Arg Ile Lys Asp
1               5

<210> SEQ ID NO 105
<211> LENGTH: 11
<212> TYPE: PRT
<213> ORGANISM: homo sapiens
<220> FEATURE:
<221> NAME/KEY: MISC_FEATURE
<223> OTHER INFORMATION: PEP#60 fragment of LL37
```

<400> SEQUENCE: 105

Lys Arg Ile Val Gln Arg Ile Lys Asp Phe Leu
1               5                   10

<210> SEQ ID NO 106
<211> LENGTH: 10
<212> TYPE: PRT
<213> ORGANISM: homo sapiens
<220> FEATURE:
<221> NAME/KEY: MISC_FEATURE
<223> OTHER INFORMATION: PEP#61 fragment of LL37

<400> SEQUENCE: 106

Glu Phe Lys Arg Ile Val Gln Arg Ile Lys
1               5                   10

<210> SEQ ID NO 107
<211> LENGTH: 10
<212> TYPE: PRT
<213> ORGANISM: homo sapiens
<220> FEATURE:
<221> NAME/KEY: MISC_FEATURE
<223> OTHER INFORMATION: PEP#62 fragment of LL37

<400> SEQUENCE: 107

Val Gln Arg Ile Lys Asp Phe Leu Arg Asn
1               5                   10

<210> SEQ ID NO 108
<211> LENGTH: 20
<212> TYPE: PRT
<213> ORGANISM: homo sapiens
<220> FEATURE:
<221> NAME/KEY: MISC_FEATURE
<223> OTHER INFORMATION: PEP#63 fragment of LL37

<400> SEQUENCE: 108

Glu Lys Ile Gly Lys Glu Phe Lys Arg Ile Val Gln Arg Ile Lys Asp
1               5                   10                  15

Phe Leu Arg Asn
            20

<210> SEQ ID NO 109
<211> LENGTH: 20
<212> TYPE: PRT
<213> ORGANISM: homo sapiens
<220> FEATURE:
<221> NAME/KEY: MISC_FEATURE
<223> OTHER INFORMATION: PEP#64 fragment of LL37

<400> SEQUENCE: 109

Glu Phe Lys Arg Ile Val Gln Arg Ile Lys Asp Phe Leu Arg Asn Leu
1               5                   10                  15

Val Pro Arg Thr
            20

<210> SEQ ID NO 110
<211> LENGTH: 19
<212> TYPE: PRT
<213> ORGANISM: artificial
<220> FEATURE:
<223> OTHER INFORMATION: PEP#66 LL37 derived peptide

<400> SEQUENCE: 110

Gly Ser Ile Gly Lys Glu Phe Lys Arg Ile Val Gln Arg Ile Lys Asp

-continued

```
1               5               10              15

Phe Leu Arg

<210> SEQ ID NO 111
<211> LENGTH: 25
<212> TYPE: PRT
<213> ORGANISM: artificial
<220> FEATURE:
<223> OTHER INFORMATION: Reverse sequence of residues 13-37 of LL37

<400> SEQUENCE: 111

Ser Glu Thr Arg Pro Val Leu Asn Arg Leu Phe Asp Lys Ile Arg Gln
1               5               10              15

Val Ile Arg Lys Phe Glu Lys Gly Ile
            20              25

<210> SEQ ID NO 112

<400> SEQUENCE: 112

000

<210> SEQ ID NO 113
<211> LENGTH: 21
<212> TYPE: DNA
<213> ORGANISM: artificial
<220> FEATURE:
<223> OTHER INFORMATION: Forward qRT-PCR primer (5' to 3') for surviving

<400> SEQUENCE: 113
aaggaccacc gcatctctac a                                           21

<210> SEQ ID NO 114
<211> LENGTH: 22
<212> TYPE: DNA
<213> ORGANISM: artificial
<220> FEATURE:
<223> OTHER INFORMATION: Reverse qRT-PCR primer (5' to 3') for surviving

<400> SEQUENCE: 114
ccaagtctgg ctcgttctca gt                                          22

<210> SEQ ID NO 115
<211> LENGTH: 19
<212> TYPE: DNA
<213> ORGANISM: artificial
<220> FEATURE:
<223> OTHER INFORMATION: Forward qRT-PCR primer (5' to 3') for GAPDH

<400> SEQUENCE: 115
gaaggtgaag gtcggagtc                                              19

<210> SEQ ID NO 116
<211> LENGTH: 20
<212> TYPE: DNA
<213> ORGANISM: artificial
<220> FEATURE:
<223> OTHER INFORMATION: Reverse qRT-PCR primer (5' to 3') for GAPDH

<400> SEQUENCE: 116
gaagatggtg atgggatttc                                             20

<210> SEQ ID NO 117
<211> LENGTH: 1470
<212> TYPE: DNA
```

<213> ORGANISM: artificial
<220> FEATURE:
<223> OTHER INFORMATION: cDNA of heavy chain for anti-HER2 mAb
      (Trastuzumab)-(G4S)2-LPMTGGHHHHHH; 1-57 encodes the N-terminal
      secretory signal peptide

<400> SEQUENCE: 117
atggattgga catggaggat tctgttcctg gtggctgcag ctactggagc tcattctgag        60
gtgcagctgg tggaatcagg aggaggactg gtgcagccag gaggatctct gagactgtct       120
tgcgccgcca gcggcttcaa catcaaggac acctacatcc attgggtccg gcaggctcca       180
ggaaaaggac tggaatgggt ggctaggatc tacccacca acggctacac ccgatacgca        240
gacagcgtga agggcaggtt caccatcagc gccgatacca gcaagaacac cgcctacctg       300
cagatgaaca gcctgagagc cgaggacacc gccgtgtact attgtagccg gtggggagga       360
gacggcttct acgctatgga ttattgggc cagggaacac tggtgacagt gtctagcgct        420
agcaccaagg gacctagcgt gtttcctctg gccccttcta gcaagagcac aagcggagga       480
acagccgctc tgggctgtct ggtgaaagac tacttcccg agccagtgac cgtgtcttgg        540
aactcaggag ccctgacaag cggagtgcac acatttccag ccgtgctgca gagcagcgga       600
ctgtactctc tgagcagcgt ggtgaccgtg ccttcttctt ctctgggcac ccagacctac       660
atctgcaacg tgaaccacaa gcccagcaac accaaggtgg acaagaaggt ggagcccaag       720
tcttgcgaca aaacacatac ttgccctcca tgtccagctc cagaactgct gggaggacca       780
agcgtgttcc tgttccctcc taagcccaag gacaccctga tgatcagccg gacccccagaa      840 gtgacttgcg tggtggtgga cgtgtcccac gaagacccg aggtcaagtt caattggtac        900
gtggacggag tggaggtgca caacgctaag accaagccca gggaggagca gtacaacagc       960
acctacaggg tggtgtccgt gctgacagtg ctgcaccagg attggctgaa cggcaaggag      1020
tacaagtgca aggtgtccaa caaggccctg ccagctccca tcgagaagac catcagcaag      1080
gccaagggac agcctagaga gcctcaggtg tacaccctgc ctccttctag ggacgagctg      1140
accaagaacc aggtgtccct gacttgcctc gtgaagggct tctaccccag cgacatcgca      1200
gtggagtggg aaagcaacgg tcagccagag aacaactaca agaccacccc cccagtgctg      1260
gacagcgacg gcagcttctt cctgtacagc aagctgaccg tggacaaaag ccgctggcag      1320
cagggcaacg tgttctcttg cagcgtgatg cacgaggccc tgcacaacca ctacacccag      1380
aagagcctga gcctgagccc caggaggagga ggaggctccg gcggcggcgg aagcctgcct    1440
atgaccggag gccatcacca ccatcatcac                                        1470

<210> SEQ ID NO 118
<211> LENGTH: 56
<212> TYPE: DNA
<213> ORGANISM: artificial
<220> FEATURE:
<223> OTHER INFORMATION: Forward PCR primer (5' to 3'), EcoRI site at
      position 7-12

<400> SEQUENCE: 118
actgacgaat cggccggcc gccaccatgg attggacatg gaggattctg ttcctg              56

<210> SEQ ID NO 119
<211> LENGTH: 121
<212> TYPE: DNA
<213> ORGANISM: artificial
<220> FEATURE:
<223> OTHER INFORMATION: Reverse PCR primer (5' to 3'), BamHI site at
      position 7-12

<400> SEQUENCE: 119
actgacggat ccctcgagtc agtgatgatg gtggtgatgg cctccggtca taggcaggct          60
tccgccgccg ccggagcctc ctcctcctcc tgggctcagg ctcaggctct tctgggtgta         120
g                                                                          121

<210> SEQ ID NO 120
<211> LENGTH: 765
<212> TYPE: DNA
<213> ORGANISM: artificial
<220> FEATURE:
<223> OTHER INFORMATION: cDNA of light chain for anti-HER2 mAb
      (Trastuzumab)-(G4S)2-LAETGGHHHHHH; 1-57 encodes the N-terminal
      secretory signal peptide

<400> SEQUENCE: 120
atgctgccca gccagctgat cggctttctg ctgctgtggg tgcctgcctc cagaggcgac          60
atccagatga cccagagccc atccagcctg tctgcctccg tgggcgacag agtgaccatc         120
acatgccgcg cttctcagga tgtgaacaca gccgtggctt ggtaccagca gaagcctggc         180
aaggccccaa agctgctgat ctactccgcc tctttcctgt attccggcgt gccaagcagg         240
ttttccggca gccggtctgg aaccgacttc accctgacaa tctcttccct gcagcccgag         300
gattttgcca catactattg ccagcagcac tataccacac ccctaccctt cggccagggc         360
acaaagctgg agatcaagag gaccgtggcc gctcctagcg tgttcatctt ccaccctct          420 gacgagcagc tgaagtctgg cacagcttcc gtggtgtgcc tgctgaacaa cttctaccca         480
cgggaggcca aggtgcagtg gaaggtggat aacgctctgc agtccggcaa tagccaggag         540
tctgtgaccg agcaggactc caaggatagc acatattctc tgagctctac cctgacactg         600
tccaaggccg attacgagaa gcacaaggtg tatgcttgcg aggtgaccca tcagggcctg         660
tccagccccg tgacaaagtc tttcaatagg ggagagtgtg gaggaggagg ctccggcggc         720
ggcggaagcc tggccgagac cggaggccat caccaccatc atcac                         765

<210> SEQ ID NO 121
<211> LENGTH: 56
<212> TYPE: DNA
<213> ORGANISM: artificial
<220> FEATURE:
<223> OTHER INFORMATION: Forward PCR primer (5' to 3'), EcoRI site at
      position 7-12

<400> SEQUENCE: 121
actgacgaat tcggccggcc gccaccatgc tgcccagcca gctgatcggc tttctg             56

<210> SEQ ID NO 122
<211> LENGTH: 103
<212> TYPE: DNA
<213> ORGANISM: artificial
<220> FEATURE:
<223> OTHER INFORMATION: Reverse PCR primer (5' to 3'), BamHI site at
      position 7-12

<400> SEQUENCE: 122
actgacggat ccctcgagtc agtgatgatg gtggtgatgg cctccggtct cggccaggct          60
tccgccgccg ccggagcctc ctcctccaca ctctcccta ttg                           103

<210> SEQ ID NO 123
<211> LENGTH: 490
<212> TYPE: PRT

```
<213> ORGANISM: artificial
<220> FEATURE:
<223> OTHER INFORMATION: Anti-HER2 mAb heavy chain-(G4S)2-LPMTGGHHHHHH;
      fusion; secretory signal peptide at 1-19

<400> SEQUENCE: 123

Met Asp Trp Thr Trp Arg Ile Leu Phe Leu Val Ala Ala Ala Thr Gly
1               5                   10                  15

Ala His Ser Glu Val Gln Leu Val Glu Ser Gly Gly Gly Leu Val Gln
                20                  25                  30

Pro Gly Gly Ser Leu Arg Leu Ser Cys Ala Ala Ser Gly Phe Asn Ile
            35                  40                  45

Lys Asp Thr Tyr Ile His Trp Val Arg Gln Ala Pro Gly Lys Gly Leu
    50                  55                  60

Glu Trp Val Ala Arg Ile Tyr Pro Thr Asn Gly Tyr Thr Arg Tyr Ala
65                  70                  75                  80

Asp Ser Val Lys Gly Arg Phe Thr Ile Ser Ala Asp Thr Ser Lys Asn
                85                  90                  95

Thr Ala Tyr Leu Gln Met Asn Ser Leu Arg Ala Glu Asp Thr Ala Val
            100                 105                 110

Tyr Tyr Cys Ser Arg Trp Gly Gly Asp Gly Phe Tyr Ala Met Asp Tyr
            115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
            165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
            195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
            245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
            275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
            325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
            355                 360                 365

Gln Val Tyr Thr Leu Pro Pro Ser Arg Asp Glu Leu Thr Lys Asn Gln
    370                 375                 380
```

```
Val Ser Leu Thr Cys Leu Val Lys Gly Phe Tyr Pro Ser Asp Ile Ala
385             390             395             400

Val Glu Trp Glu Ser Asn Gly Gln Pro Glu Asn Asn Tyr Lys Thr Thr
                405             410             415

Pro Pro Val Leu Asp Ser Asp Gly Ser Phe Phe Leu Tyr Ser Lys Leu
            420             425             430

Thr Val Asp Lys Ser Arg Trp Gln Gln Gly Asn Val Phe Ser Cys Ser
            435             440             445

Val Met His Glu Ala Leu His Asn His Tyr Thr Gln Lys Ser Leu Ser
        450             455             460

Leu Ser Pro Gly Gly Gly Gly Ser Gly Gly Gly Gly Ser Leu Pro
465             470             475             480

Met Thr Gly Gly His His His His His His
            485             490
```

```
<210> SEQ ID NO 124
<211> LENGTH: 255
<212> TYPE: PRT
<213> ORGANISM: artificial
<220> FEATURE:
<223> OTHER INFORMATION: Anti-HER2 mAb Light chain-(G4S)2-LAETGGHHHHHH
      fusion; secretory signal peptide at 1-19

<400> SEQUENCE: 124
```

```
Met Leu Pro Ser Gln Leu Ile Gly Phe Leu Leu Leu Trp Val Pro Ala
1               5               10              15

Ser Arg Gly Asp Ile Gln Met Thr Gln Ser Pro Ser Ser Leu Ser Ala
            20              25              30

Ser Val Gly Asp Arg Val Thr Ile Thr Cys Arg Ala Ser Gln Asp Val
            35              40              45

Asn Thr Ala Val Ala Trp Tyr Gln Gln Lys Pro Gly Lys Ala Pro Lys
        50              55              60

Leu Leu Ile Tyr Ser Ala Ser Phe Leu Tyr Ser Gly Val Pro Ser Arg
65              70              75              80

Phe Ser Gly Ser Arg Ser Gly Thr Asp Phe Thr Leu Thr Ile Ser Ser
                85              90              95

Leu Gln Pro Glu Asp Phe Ala Thr Tyr Tyr Cys Gln Gln His Tyr Thr
            100             105             110

Thr Pro Pro Thr Phe Gly Gln Gly Thr Lys Leu Glu Ile Lys Arg Thr
            115             120             125

Val Ala Ala Pro Ser Val Phe Ile Phe Pro Pro Ser Asp Glu Gln Leu
        130             135             140

Lys Ser Gly Thr Ala Ser Val Val Cys Leu Leu Asn Asn Phe Tyr Pro
145             150             155             160

Arg Glu Ala Lys Val Gln Trp Lys Val Asp Asn Ala Leu Gln Ser Gly
            165             170             175

Asn Ser Gln Glu Ser Val Thr Glu Gln Asp Ser Lys Asp Ser Thr Tyr
            180             185             190

Ser Leu Ser Ser Thr Leu Thr Leu Ser Lys Ala Asp Tyr Glu Lys His
            195             200             205

Lys Val Tyr Ala Cys Glu Val Thr His Gln Gly Leu Ser Ser Pro Val
        210             215             220

Thr Lys Ser Phe Asn Arg Gly Glu Cys Gly Gly Gly Gly Ser Gly Gly
225             230             235             240

Gly Gly Ser Leu Ala Glu Thr Gly Gly His His His His His His
            245             250             255
```

-continued

```
<210> SEQ ID NO 125
<211> LENGTH: 1119
<212> TYPE: DNA
<213> ORGANISM: artificial
<220> FEATURE:
<223> OTHER INFORMATION: Structural gene sequence of Z-RFP-LL37 (5' to
      3')

<400> SEQUENCE: 125
atgggcagca gccatcacca ccatcatcac catcacagcg gcagcgatta caaggatgac      60
gacgacaagg ctggcagcca tatggctagc gtggacaaca aattcaacaa agaacaacaa     120
aacgcgttct atgagatctt acatttacct aacttaaacg aagaacaacg aaacgccttc     180
atccaaagtt taaaagatga cccaagccaa agcgctaacc ttttagcaga agctaaaaag     240
ctaaacgacg ctcaggcgcc gaaaggtacc ggatccgaat tcatggttag cgaactgatt     300
aaggaaaata tgcacatgaa actgtatatg gaaggcaccg tcaacaatca tcactttaaa     360
tgcacgagtg aaggtgaagg caagccgtat gaaggcaccc agacgatgcg tattaaagca     420
gtggaaggcg gtccgctgcc gtttgcattc gatattctgg ccaccagttt tatgtacggt     480
tccaaaacct tcattaacca tacgcagggc atcccggatt tctttaaaca aagttttccg     540
gaaggtttca cctgggaacg tgtgaccacg tatgaagacg gcggtgttct gaccgccacg     600
caggatacgt ccctgcaaga cggctgtctg atttacaatg ttaaaatccg cggtgtcaac     660
ttcccgagca atggcccggt tatgcagaaa aagaccctgg gttgggaagc atctaccgaa     720
acgctgtatc cggctgatgg tggtctggaa ggtcgtgcag acatggctct gaaactggtg     780
ggcggtggcc atctgatttg caacctgaag accacgtacc gttctaaaaa gccggcgaaa     840
aatctgaaga tgccgggtgt ctattacgtg gatcgtcgcc tggaacgcat caaagaagcc     900
gacaaggaaa cctatgttga acagcatgaa gtggcggttg cccgctactg tgatctgccg     960
tcaaaactgg tcaccgtgc ggccgcaggc agcctgctgg gcgacttctt ccgcaaaagc    1020
aaagagaaga ttggcaaaga atttaagcgc attgtgcagc gtattaagga tttcctgcgc    1080
aatctggtgc cgcgtaccga aagcggtagc ggctcttga                           1119

<210> SEQ ID NO 126
<211> LENGTH: 94
<212> TYPE: DNA
<213> ORGANISM: artificial
<220> FEATURE:
<223> OTHER INFORMATION: forward-direction PCR primer (5' to 3')

<400> SEQUENCE: 126
ggcaaagaat ttaagcgcat tgtgcagcgt attaaggatt tcctgcgcaa tctggtgccg      60
cgtaccgaaa gcggtagcgg ctcttgactc gagc                                  94

<210> SEQ ID NO 127
<211> LENGTH: 92
<212> TYPE: DNA
<213> ORGANISM: artificial
<220> FEATURE:
<223> OTHER INFORMATION: reverse-direction PCR primer (5' to 3')

<400> SEQUENCE: 127
gcttaaattc tttgccaatc ttctctttgc ttttgcggaa gaagtcgccc agcaggctgc      60
ctgcggccgc acggtgaccc agttttgacg gc                                    92
```

US 12,643,944 B2

-continued

```
<210> SEQ ID NO 128
<211> LENGTH: 2112
<212> TYPE: DNA
<213> ORGANISM: homo sapiens
<220> FEATURE:
<221> NAME/KEY: misc_feature
<223> OTHER INFORMATION: Structural gene sequence of human HER2
      extracellular domain (5' to 3'); 1-66 encodes the N-terminal
      secretory signal peptide.

<400> SEQUENCE: 128
atggagctgg cggccttgtg ccgctggggg ctcctcctcg ccctcttgcc ccccggagcc        60
gcgagcaccc aagtgtgcac cggcacagac atgaagctgc ggctccctgc cagtcccgag       120
acccacctgg acatgctccg ccacctctac cagggctgcc aggtggtgca gggaaacctg       180
gaactcacct acctgcccac caatgccagc ctgtccttcc tgcaggatat ccaggaggtg       240
cagggctacg tgctcatcgc tcacaaccaa gtgaggcagg tcccactgca gaggctgcgg       300
attgtgcgag gcacccagct ctttgaggac aactatgccc tggccgtgct agacaatgga       360
gacccgctga caataccac ccctgtcaca ggggcctccc aggaggcct gcgggagctg        420 cagcttcgaa gcctcacaga gatcttgaaa ggaggggtct tgatccagcg gaaccccag       480 ctctgctacc aggacacgat tttgtggaag gacatcttcc acaagaacaa ccagctggct       540
ctcacactga tagacaccaa ccgctctcgg gcctgccacc cctgttctcc gatgtgtaag       600
ggctcccgct gctggggaga gagttctgag gattgtcaga gcctgacgcg cactgtctgt       660
gccggtggct gtgcccgctg caaggggcca ctgcccactg actgctgcca tgagcagtgt       720
gctgccggct gcacgggccc caagcactct gactgcctgg cctgcctcca cttcaaccac       780
agtggcatct gtgagctgca ctgcccagcc ctggtcacct acaacacaga cacgtttgag       840
tccatgccca tcccgaggg ccggtataca ttcggcgcca gctgtgtgac tgcctgtccc        900
tacaactacc tttctacgga cgtgggatcc tgcacccctcg tctgcccct gcacaaccaa       960 gaggtgacag cagaggatgg aacacagcgg tgtgagaagt gcagcaagcc ctgtgcccga      1020
gtgtgctatg gtctgggcat ggagcacttg cgagaggtga gggcagttac cagtgccaat      1080
atccaggagt ttgctggctg caagaagatc tttgggagcc tggcatttct gccggagagc      1140
tttgatgggg acccagcctc caacactgcc ccgctccagc cagagcagct ccaagtgttt      1200
gagactctgg aagagatcac aggttaccta tacatctcag catggccgga cagcctgcct      1260
gacctcagcg tcttccagaa cctgcaagta atccggggac gaattctgca caatggcgcc      1320
tactcgctga ccctgcaagg gctgggcatc agctggctgg ggctgcgctc actgagggaa      1380
ctgggcagtg gactggccct catccaccat aacacccacc tctgcttcgt gcacacggtg      1440
ccctgggacc agctctttcg gaacccgcac aagctctgc tccacactgc caaccggcca       1500
gaggacgagt gtgtgggcga gggcctggcc tgccaccagc tgtgcgcccg agggcactgc      1560
tggggtccag gcccacccca gtgtgtcaac tgcagccagt ccttcggg ccaggagtgc        1620 gtggaggaat gccgagtact gcaggggctc cccagggagt atgtgaatgc caggcactgt      1680
ttgccgtgcc accctgagtg tcagccccag aatggctcag tgacctgttt tggaccggag      1740
gctgaccagt gtgtggcctg tgcccactat aaggaccctc ccttctgcgt ggcccgctgc      1800
cccagcggtg tgaaacctga cctctcctac atgcccatct ggaagtttcc agatgaggag      1860
ggcgcatgcc agccttgccc catcaactgc acccactcct gtgtggacct ggatgacaag      1920
ggctgccccg ccgagcagag agccagccct ctgacgacgc gtgctgtggg ccaggacacg      1980
caggaggtca tcgtggtgcc acactccttg cccctttaagg tggtggtgat ctcagccatc      2040
```

```
ctggccctgg tggtgctcac catcatctcc cttatcatcc tcatcatgct ttggcagaag     2100
aagccacgtt ag                                                         2112

<210> SEQ ID NO 129
<211> LENGTH: 464
<212> TYPE: PRT
<213> ORGANISM: artificial
<220> FEATURE:
<223> OTHER INFORMATION: Anti-CD3e mAb (Foralumab) heavy chain
      (artificial); secretory signal peptide at 1-16

<400> SEQUENCE: 129

Met Pro Leu Leu Leu Leu Leu Pro Leu Leu Trp Ala Gly Ala Leu Ala
1               5                   10                  15

Gln Val Gln Leu Val Glu Ser Gly Gly Gly Val Val Gln Pro Gly Arg
            20                  25                  30

Ser Leu Arg Leu Ser Cys Ala Ala Ser Gly Phe Lys Phe Ser Gly Tyr
        35                  40                  45

Gly Met His Trp Val Arg Gln Ala Pro Gly Lys Gly Leu Glu Trp Val
    50                  55                  60

Ala Val Ile Trp Tyr Asp Gly Ser Lys Lys Tyr Tyr Val Asp Ser Val
65                  70                  75                  80

Lys Gly Arg Phe Thr Ile Ser Arg Asp Asn Ser Lys Asn Thr Leu Tyr
                85                  90                  95

Leu Gln Met Asn Ser Leu Arg Ala Glu Asp Thr Ala Val Tyr Tyr Cys
            100                 105                 110

Ala Arg Gln Met Gly Tyr Trp His Phe Asp Leu Trp Gly Arg Gly Thr
            115                 120                 125

Leu Val Thr Val Ser Ser Ala Ser Thr Lys Gly Pro Ser Val Phe Pro
        130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
            195                 200                 205

Ser Leu Gly Thr Gln Thr Tyr Ile Cys Asn Val Asn His Lys Pro Ser
        210                 215                 220

Asn Thr Lys Val Asp Lys Arg Val Glu Pro Lys Ser Cys Asp Lys Thr
225                 230                 235                 240

His Thr Cys Pro Pro Cys Pro Ala Pro Glu Leu Leu Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
            275                 280                 285

Glu Val Lys Phe Asn Trp Tyr Val Asp Gly Val Glu Val His Asn Ala
    290                 295                 300

Lys Thr Lys Pro Arg Glu Glu Gln Tyr Asn Ser Thr Tyr Arg Val Val
305                 310                 315                 320

Ser Val Leu Thr Val Leu His Gln Asp Trp Leu Asn Gly Lys Glu Tyr
                325                 330                 335
```

```
Lys Cys Lys Val Ser Asn Lys Ala Leu Pro Ala Pro Ile Glu Lys Thr
            340             345             350

Ile Ser Lys Ala Lys Gly Gln Pro Arg Glu Pro Gln Val Tyr Thr Leu
        355             360             365

Pro Pro Ser Arg Glu Glu Met Thr Lys Asn Gln Val Ser Leu Thr Cys
    370             375             380

Leu Val Lys Gly Phe Tyr Pro Ser Asp Ile Ala Val Glu Trp Glu Ser
385             390             395             400

Asn Gly Gln Pro Glu Asn Asn Tyr Lys Thr Thr Pro Pro Val Leu Asp
                405             410             415

Ser Asp Gly Ser Phe Phe Leu Tyr Ser Lys Leu Thr Val Asp Lys Ser
            420             425             430

Arg Trp Gln Gln Gly Asn Val Phe Ser Cys Ser Val Met His Glu Ala
        435             440             445

Leu His Asn His Tyr Thr Gln Lys Ser Leu Ser Leu Ser Pro Gly Lys
    450             455             460

<210> SEQ ID NO 130
<211> LENGTH: 248
<212> TYPE: PRT
<213> ORGANISM: artificial
<220> FEATURE:
<223> OTHER INFORMATION: Anti-CD3e mAb (Foralumab)  light chain
      (artificial); secretory signal peptide at 1-20

<400> SEQUENCE: 130

Met Arg Leu Pro Ala Gln Leu Leu Gly Leu Leu Met Leu Trp Val Ser
1               5               10              15

Gly Ser Ser Gly Glu Ile Val Leu Thr Gln Ser Pro Ala Thr Leu Ser
            20              25              30

Leu Ser Pro Gly Glu Arg Ala Thr Leu Ser Cys Arg Ala Ser Gln Ser
        35              40              45

Val Ser Ser Tyr Leu Ala Trp Tyr Gln Gln Lys Pro Gly Gln Ala Pro
    50              55              60

Arg Leu Leu Ile Tyr Asp Ala Ser Asn Arg Ala Thr Gly Ile Pro Ala
65              70              75              80

Arg Phe Ser Gly Ser Gly Ser Gly Thr Asp Phe Thr Leu Thr Ile Ser
            85              90              95

Ser Leu Glu Pro Glu Asp Phe Ala Val Tyr Tyr Cys Gln Gln Arg Ser
        100             105             110

Asn Trp Pro Pro Leu Thr Phe Gly Gly Gly Thr Lys Val Glu Ile Lys
        115             120             125

Arg Thr Val Ala Ala Pro Ser Val Phe Ile Phe Pro Pro Ser Asp Glu
    130             135             140

Gln Leu Lys Ser Gly Thr Ala Ser Val Val Cys Leu Leu Asn Asn Phe
145             150             155             160

Tyr Pro Arg Glu Ala Lys Val Gln Trp Lys Val Asp Asn Ala Leu Gln
                165             170             175

Ser Gly Asn Ser Gln Glu Ser Val Thr Glu Gln Asp Ser Lys Asp Ser
            180             185             190

Thr Tyr Ser Leu Ser Ser Thr Leu Thr Leu Ser Lys Ala Asp Tyr Glu
        195             200             205

Lys His Lys Val Tyr Ala Cys Glu Val Thr His Gln Gly Leu Ser Ser
    210             215             220

Pro Val Thr Lys Ser Phe Asn Arg Gly Glu Cys Gly Gly Gly Gly Ser
225             230             235             240
```

Leu Pro Met Thr Gly Gly His Gly
            245

<210> SEQ ID NO 131
<211> LENGTH: 467
<212> TYPE: PRT
<213> ORGANISM: artificial
<220> FEATURE:
<223> OTHER INFORMATION: Anti-CD22 mAb (Inotuzumab) heavy chain;
      secretory signal peptide at 1-16

<400> SEQUENCE: 131

Met Pro Leu Leu Leu Leu Leu Pro Leu Leu Trp Ala Gly Ala Leu Ala
1               5                   10                  15

Glu Val Gln Leu Val Gln Ser Gly Ala Glu Val Lys Lys Pro Gly Ala
            20                  25                  30

Ser Val Lys Val Ser Cys Lys Ala Ser Gly Tyr Arg Phe Thr Asn Tyr
            35                  40                  45

Trp Ile His Trp Val Arg Gln Ala Pro Gly Gln Gly Leu Glu Trp Ile
    50                  55                  60

Gly Gly Ile Asn Pro Gly Asn Asn Tyr Ala Thr Tyr Arg Arg Lys Phe
65                  70                  75                  80

Gln Gly Arg Val Thr Met Thr Ala Asp Thr Ser Thr Ser Thr Val Tyr
            85                  90                  95

Met Glu Leu Ser Ser Leu Arg Ser Glu Asp Thr Ala Val Tyr Tyr Cys
            100                 105                 110

Thr Arg Glu Gly Tyr Gly Asn Tyr Gly Ala Trp Phe Ala Tyr Trp Gly
            115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
            165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
            195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Arg Val Glu Pro Lys Ser Cys
225                 230                 235                 240

Asp Lys Thr His Thr Cys Pro Pro Cys Pro Ala Pro Glu Leu Leu Gly
            245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
            275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
            325                 330                 335

Lys Glu Tyr Lys Cys Lys Val Ser Asn Lys Ala Leu Pro Ala Pro Ile

-continued

```
                 340              345              350

Glu Lys Thr Ile Ser Lys Ala Lys Gly Gln Pro Arg Glu Pro Gln Val
        355              360              365

Tyr Thr Leu Pro Pro Ser Arg Glu Glu Met Thr Lys Asn Gln Val Ser
    370              375              380

Leu Thr Cys Leu Val Lys Gly Phe Tyr Pro Ser Asp Ile Ala Val Glu
385              390              395              400

Trp Glu Ser Asn Gly Gln Pro Glu Asn Asn Tyr Lys Thr Thr Pro Pro
                405              410              415

Val Leu Asp Ser Asp Gly Ser Phe Phe Leu Tyr Ser Lys Leu Thr Val
                420              425              430

Asp Lys Ser Arg Trp Gln Gln Gly Asn Val Phe Ser Cys Ser Val Met
        435              440              445

His Glu Ala Leu His Asn His Tyr Thr Gln Lys Ser Leu Ser Leu Ser
    450              455              460

Pro Gly Lys
465
```

```
<210> SEQ ID NO 132
<211> LENGTH: 252
<212> TYPE: PRT
<213> ORGANISM: artificial
<220> FEATURE:
<223> OTHER INFORMATION: Anti-CD22 mAb (Inotuzumab) light chain;
      secretory signal peptide at 1-20

<400> SEQUENCE: 132

Met Arg Leu Pro Ala Gln Leu Leu Gly Leu Leu Met Leu Trp Val Ser
1               5               10               15

Gly Ser Ser Gly Asp Val Gln Val Thr Gln Ser Pro Ser Ser Leu Ser
                20               25               30

Ala Ser Val Gly Asp Arg Val Thr Ile Thr Cys Arg Ser Ser Gln Ser
        35               40               45

Leu Ala Asn Ser Tyr Gly Asn Thr Phe Leu Ser Trp Tyr Leu His Lys
    50               55               60

Pro Gly Lys Ala Pro Gln Leu Leu Ile Tyr Gly Ile Ser Asn Arg Phe
65               70               75               80

Ser Gly Val Pro Asp Arg Phe Ser Gly Ser Gly Ser Gly Thr Asp Phe
                85               90               95

Thr Leu Thr Ile Ser Ser Leu Gln Pro Glu Asp Phe Ala Thr Tyr Tyr
                100              105              110

Cys Leu Gln Gly Thr His Gln Pro Tyr Thr Phe Gly Gln Gly Thr Lys
        115              120              125

Val Glu Ile Lys Arg Thr Val Ala Ala Pro Ser Val Phe Ile Phe Pro
    130              135              140

Pro Ser Asp Glu Gln Leu Lys Ser Gly Thr Ala Ser Val Val Cys Leu
145              150              155              160

Leu Asn Asn Phe Tyr Pro Arg Glu Ala Lys Val Gln Trp Lys Val Asp
                165              170              175

Asn Ala Leu Gln Ser Gly Asn Ser Gln Glu Ser Val Thr Glu Gln Asp
                180              185              190

Ser Lys Asp Ser Thr Tyr Ser Leu Ser Ser Thr Leu Thr Leu Ser Lys
        195              200              205

Ala Asp Tyr Glu Lys His Lys Val Tyr Ala Cys Glu Val Thr His Gln
    210              215              220
```

-continued

```
Gly Leu Ser Ser Pro Val Thr Lys Ser Phe Asn Arg Gly Glu Cys Gly
225                 230                 235                 240

Gly Gly Gly Ser Leu Pro Met Thr Gly Gly His Gly
                245                 250
```

<210> SEQ ID NO 133
<211> LENGTH: 320
<212> TYPE: PRT
<213> ORGANISM: homo sapiens
<220> FEATURE:
<221> NAME/KEY: MISC_FEATURE
<223> OTHER INFORMATION: Annexin V

<400> SEQUENCE: 133

```
Met Ala Gln Val Leu Arg Gly Thr Val Thr Asp Phe Pro Gly Phe Asp
1               5                   10                  15

Glu Arg Ala Asp Ala Glu Thr Leu Arg Lys Ala Met Lys Gly Leu Gly
                20                  25                  30

Thr Asp Glu Glu Ser Ile Leu Thr Leu Leu Thr Ser Arg Ser Asn Ala
            35                  40                  45

Gln Arg Gln Glu Ile Ser Ala Ala Phe Lys Thr Leu Phe Gly Arg Asp
        50                  55                  60

Leu Leu Asp Asp Leu Lys Ser Glu Leu Thr Gly Lys Phe Glu Lys Leu
65                  70                  75                  80

Ile Val Ala Leu Met Lys Pro Ser Arg Leu Tyr Asp Ala Tyr Glu Leu
                85                  90                  95

Lys His Ala Leu Lys Gly Ala Gly Thr Asn Glu Lys Val Leu Thr Glu
                100                 105                 110

Ile Ile Ala Ser Arg Thr Pro Glu Glu Leu Arg Ala Ile Lys Gln Val
            115                 120                 125

Tyr Glu Glu Glu Tyr Gly Ser Ser Leu Glu Asp Asp Val Val Gly Asp
        130                 135                 140

Thr Ser Gly Tyr Tyr Gln Arg Met Leu Val Val Leu Leu Gln Ala Asn
145                 150                 155                 160

Arg Asp Pro Asp Ala Gly Ile Asp Glu Ala Gln Val Glu Gln Asp Ala
                165                 170                 175

Gln Ala Leu Phe Gln Ala Gly Glu Leu Lys Trp Gly Thr Asp Glu Glu
                180                 185                 190

Lys Phe Ile Thr Ile Phe Gly Thr Arg Ser Val Ser His Leu Arg Lys
                195                 200                 205

Val Phe Asp Lys Tyr Met Thr Ile Ser Gly Phe Gln Ile Glu Glu Thr
        210                 215                 220

Ile Asp Arg Glu Thr Ser Gly Asn Leu Glu Gln Leu Leu Leu Ala Val
225                 230                 235                 240

Val Lys Ser Ile Arg Ser Ile Pro Ala Tyr Leu Ala Glu Thr Leu Tyr
                245                 250                 255

Tyr Ala Met Lys Gly Ala Gly Thr Asp Asp His Thr Leu Ile Arg Val
                260                 265                 270

Met Val Ser Arg Ser Glu Ile Asp Leu Phe Asn Ile Arg Lys Glu Phe
            275                 280                 285

Arg Lys Asn Phe Ala Thr Ser Leu Tyr Ser Met Ile Lys Gly Asp Thr
        290                 295                 300

Ser Gly Asp Tyr Lys Lys Ala Leu Leu Leu Leu Cys Gly Glu Asp Asp
305                 310                 315                 320
```

<210> SEQ ID NO 134

-continued

```
<211> LENGTH: 110
<212> TYPE: PRT
<213> ORGANISM: homo sapiens
<220> FEATURE:
<221> NAME/KEY: MISC_FEATURE
<223> OTHER INFORMATION: Evectin 2

<400> SEQUENCE: 134

Met Ala Phe Val Lys Ser Gly Trp Leu Leu Arg Gln Ser Thr Ile Leu
1               5                   10                  15

Lys Arg Trp Lys Lys Asn Trp Phe Asp Leu Trp Ser Asp Gly His Leu
            20                  25                  30

Ile Tyr Tyr Asp Asp Gln Thr Arg Gln Asn Ile Glu Asp Lys Val His
        35                  40                  45

Met Pro Met Asp Cys Ile Asn Ile Arg Thr Gly Gln Glu Cys Arg Asp
    50                  55                  60

Thr Gln Pro Pro Asp Gly Lys Ser Lys Asp Cys Met Leu Gln Ile Val
65                  70                  75                  80

Cys Arg Asp Gly Lys Thr Ile Ser Leu Cys Ala Glu Ser Thr Asp Asp
                85                  90                  95

Cys Leu Ala Trp Lys Phe Thr Leu Gln Asp Ser Arg Thr Asn
                100                 105                 110
```